United States Patent
Dusseaux

(10) Patent No.: US 10,709,775 B2
(45) Date of Patent: *Jul. 14, 2020

(54) CELLS FOR IMMUNOTHERAPY ENGINEERED FOR TARGETING CD38 ANTIGEN AND FOR CD38 GENE INACTIVATION

(71) Applicant: CELLECTIS, Paris (FR)

(72) Inventor: Mathilde Dusseaux, Maisons-Alfort (FR)

(73) Assignee: Cellectis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/751,472

(22) PCT Filed: Jul. 26, 2016

(86) PCT No.: PCT/EP2016/067800
§ 371 (c)(1),
(2) Date: Feb. 8, 2018

(87) PCT Pub. No.: WO2017/025323
PCT Pub. Date: Feb. 16, 2017

(65) Prior Publication Data
US 2018/0236053 A1 Aug. 23, 2018

(30) Foreign Application Priority Data

Aug. 11, 2015 (DK) .................................. 201570518
Jan. 25, 2016 (WO) .................. PCT/EP2016/051467

(51) Int. Cl.
| | |
|---|---|
| *A61K 39/00* | (2006.01) |
| *C07K 14/705* | (2006.01) |
| *C07K 16/28* | (2006.01) |
| *A61K 39/395* | (2006.01) |
| *C12N 5/0783* | (2010.01) |
| *A61P 35/00* | (2006.01) |

(52) U.S. Cl.
CPC .... *A61K 39/0011* (2013.01); *A61K 39/39558* (2013.01); *A61P 35/00* (2018.01); *C07K 14/70596* (2013.01); *C07K 16/2803* (2013.01); *C07K 16/2896* (2013.01); *C12N 5/0636* (2013.01); *A61K 2039/5158* (2013.01); *A61K 2039/55522* (2013.01); *C07K 2317/622* (2013.01); *C07K 2319/03* (2013.01); *C07K 2319/33* (2013.01)

(58) Field of Classification Search
None
See application file for complete search history.

(56) References Cited

U.S. PATENT DOCUMENTS

2017/0296623 A1* 10/2017 Juillerat ................ A61K 38/17
2018/0000914 A1* 1/2018 Valton ................ C07K 14/7051

FOREIGN PATENT DOCUMENTS

| WO | 2006/099875 A1 | 9/2006 |
|---|---|---|
| WO | WO 2013/074916 A1 | 5/2013 |
| WO | WO 2013/176915 A1 | 11/2013 |
| WO | WO 2014/039523 A1 | 3/2014 |
| WO | WO 2014/184143 A1 | 11/2014 |
| WO | WO 2014/191128 A1 | 12/2014 |
| WO | WO 2015/136001 A1 | 9/2015 |
| WO | WO 2015/140268 A1 | 9/2015 |

OTHER PUBLICATIONS

J Bhattacharyya et al.: "T-cell immunotherapy with a chimeric receptor against CD38 is effective in eradicating chemotherapy-resistant B-cell lymphoma cells overexpressing survivin induced by BMI-1", Blood Cancer Journal (2012) 2, e75 doi:10.1038/bcj.2012.21; published online Jun. 22, 2012 (Jun. 22, 2012).
K. Mihara et al.: "Activated T-cell-mediated Immunotherapy With a Chimeric Receptor Against CD38 in B-cell Non-Hodgkin Lymphoma." J. Immunother 2009;32: pp. 737-743 (Sep. 2009).
K. Mihara et al.: "T-cell immunotherapy with a chimeric receptor against CD38 is effective in eliminating myeloma cells." Leukemia (2012) 26, pp. 365-367; doi:10.1038/leu.2011.205; published online Aug. 12, 2011.
H. Torikai et al.: "A foundation for universal T-cell based immunotherapy: T cells engineered to express a CD19-specific chimeric-antigen-receptor and eliminate expression of endogenous TCR." Blood 2012 119: pp. 5697-5705 Prepublished online Apr. 24, 2012; doi :10.1182/blood-2012-01-405365.
K. Mihara et al.: "Synergistic and persistent effect of T-cell immunotherapy with anti-CD19 or anti-CD38 chimeric receptor in conjunction with rituximab on B-cell non-Hodgkin lymphoma." British Journal of Haematology 2010, 151, pp. 37-46 First published online Jul. 30, 2010 doi: 10.1111/j.1365-2141.2010_08297.x.
E. Drent et al.: CD38 Chimeric Antigen Receptor Engineered T Cells As Therapeutic Tools for Multiple Myeloma. Blood, vol. 124, Dec. 1, 2014 (Dec. 1, 2014), p. 4759.
M. Sadelain et al.: The Basic Principles of Chimeric Antigen Receptor Design , Cancer Discovery, vol. 3, No. 4, Apr. 1, 2013 (Apr. 1, 2013), pp. 388-398.
A. Garfall et al.: Immunotherapy with chimeric antigen receptors for multiple myeloma.: Discovery Medicine, vol. 17, No. 91, Jan. 1, 2014 (Jan. 1, 2014), pp. 37-46.
International-Type Search Report for DK application PA201570518, dated Dec. 1, 2015.

(Continued)

*Primary Examiner* — Peter J Reddig
(74) *Attorney, Agent, or Firm* — Arrigo, Lee, Guttman & Mouta-Bellum LLP

(57) ABSTRACT

Methods of developing genetically engineered immune cells for immunotherapy, which can be endowed with Chimeric Antigen Receptors targeting an antigen marker that is common to both the pathological cells and said CD38 immune by the fact that the genes encoding said markers are inactivated in said immune cells by a rare cutting endonuclease such as TALEN, Cas9 or argonaute.

15 Claims, 34 Drawing Sheets

Specification includes a Sequence Listing.

(56) References Cited

OTHER PUBLICATIONS

Garfall et al., Immunotherapy with Chimeric Antigen Receptors for Multiple Myeloma, Discovery Medicine 17 (91):37-46 (2014).
Mihara et al., T-cell immunotherapy with chimeric antigen receptor against CD38 is effective in eliminating myeloma cells. Leukemia (2012) 26, 365-367.

* cited by examiner

A

B

A

B

C

Figure 5:
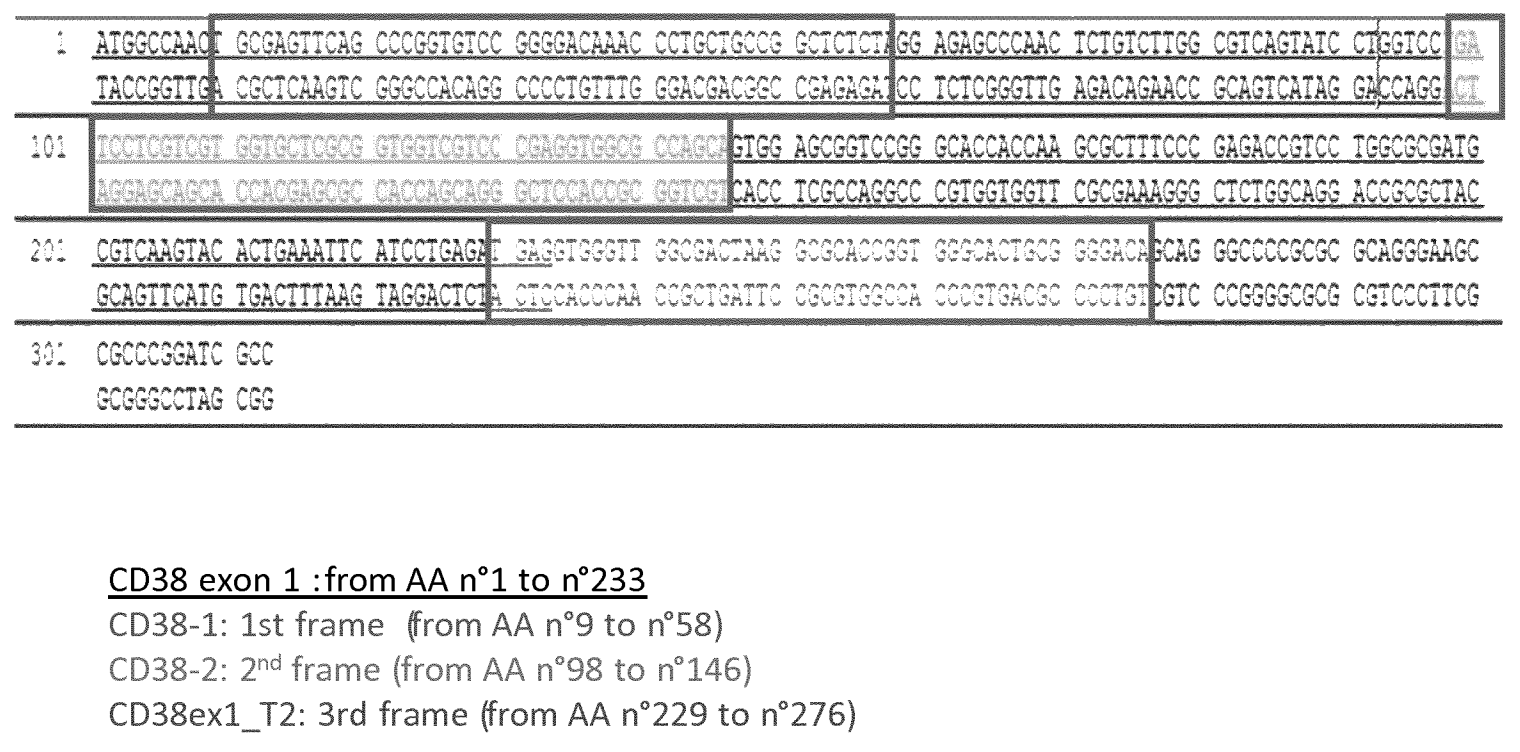

CD38 exon 1: from AA n°1 to n°233
CD38-1: 1st frame (from AA n°9 to n°58)
CD38-2: 2nd frame (from AA n°98 to n°146)
CD38ex1_T2: 3rd frame (from AA n°229 to n°276)

| Plasmid Name | Backbone | Sequence Name | Kd (nM) |
|---|---|---|---|
| pCLS27540 | pCLS9632 | 10F7-V1 | 30 |
| pCLS27541 | pCLS9632 | 10F7-V2 | |
| pCLS27542 | pCLS9632 | 10F7-V3 | |
| pCLS27543 | pCLS9632 | 13F11-V1 | 0,8 |
| pCLS27544 | pCLS9632 | 13F11-V2 | |
| pCLS27545 | pCLS9632 | 13F11-V3 | |
| pCLS27546 | pCLS9632 | 16B5-V1 | 3,2 |
| pCLS27547 | pCLS9632 | 16B5-V2 | |
| pCLS27548 | pCLS9632 | 16B5-V3 | |
| pCLS27549 | pCLS9632 | 25A10-V1 | 0,25 |
| pCLS27550 | pCLS9632 | 25A10-V2 | |
| pCLS27551 | pCLS9632 | 25A10-V3 | |
| pCLS27552 | pCLS9632 | 27B6-V1 | 2,2 |
| pCLS27553 | pCLS9632 | 27B6-V2 | |
| pCLS27554 | pCLS9632 | 27B6-V3 | |
| pCLS27555 | pCLS9632 | 28F5-V1 | unknown |
| pCLS27556 | pCLS9632 | 28F5-V2 | |
| pCLS27557 | pCLS9632 | 28F5-V3 | |
| pCLS27558 | pCLS9632 | 29B4-V1 | 0,52 |
| pCLS27559 | pCLS9632 | 29B4-V2 | |
| pCLS27560 | pCLS9632 | 29B4-V3 | |
| pCLS27561 | pCLS9632 | GMB005-V1 | 119 |
| pCLS27562 | pCLS9632 | GMB005-V2 | |
| pCLS27563 | pCLS9632 | GMB005-V3 | |

Native FcεRI

Structure of the polycistronic mcCAR construct

US 10,709,775 B2

CELLS FOR IMMUNOTHERAPY ENGINEERED FOR TARGETING CD38 ANTIGEN AND FOR CD38 GENE INACTIVATION

SEQUENCE LISTING

The instant application contains a Sequence Listing which has been submitted electronically in ASCII format and is hereby incorporated by reference in its entirety. Said ASCII copy, created on Dec. 3, 2018, is named DI201510US1_SL.txt and is 301,069 bytes in size.

FIELD OF THE INVENTION

The present invention relates to methods of developing genetically engineered, preferably non-alloreactive, immune cells for immunotherapy, which are endowed with Chimeric Antigen Receptors targeting the CD38 antigen marker that is common to both the pathological cells and the immune cells).

The method comprises expressing a CAR directed against said antigen marker and inactivating the genes in the immune cells contributing to the presence of said antigen marker on the surface of said immune cells. This inactivation is typically performed by using transgenes encoding RNA-guided endonucleases (ex: Cas9/CRISPR), meganucleases, Zinc-finger nucleases or TAL nucleases.

The engineered immune cells, preferably T-cells, direct their immune activity towards malignant, infected cells or defective immune cells, while avoiding their mutual destruction, auto-stimulation or aggregation. The invention opens the way to standard and affordable adoptive immunotherapy strategies using immune cells for treating cancer, infections and auto-immune diseases.

BACKGROUND OF THE INVENTION

Adoptive immunotherapy, which involves the transfer of autologous antigen-specific immune cells generated ex vivo, is a promising strategy to treat viral infections and cancer. The T cells used for adoptive immunotherapy, for instance, can be generated either by expansion of antigen-specific T-cells or redirection of T-cells through genetic engineering (Park, Rosenberg et al. 2011).

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous T-cell receptors (TCR) specificities may recognize the host tissue as foreign, resulting in graft versus host disease (GvHD), which can lead to serious tissue damage and death.

In order to provide allogeneic T-cells, the inventors previously disclosed a method to genetically engineer T-Cells, in which different effector genes, in particular those encoding T-cell receptors, were inactivated by using specific TAL-nucleases, better known under the trade mark TALEN™ (Cellectis, 8, rue de la Croix Jarry, 75013 PARIS). This method has proven to be highly efficiency in primary cells using RNA transfection as part of a platform allowing the mass production of allogeneic T-cells (WO 2013/176915).

CD38 (cluster of differentiation 38), also known as cyclic ADP ribose hydrolase is a glycoprotein found on the surface of many immune cells (white blood cells), in particular T-cells, including CD4+, CD8+, B lymphocytes and natural killer cells. CD38 also functions in cell adhesion, signal transduction and calcium signaling. Structural information about this protein can be found in the UniProtKB/Swiss-Prot database under reference P28907. In humans, the CD38 protein is encoded by the CD38 gene which located on chromosome 4. CD38 is a multifunctional ectoenzyme that catalyzes the synthesis and hydrolysis of cyclic ADP-ribose (cADPR) from NAD+ to ADP-ribose. These reaction products are deemed essential for the regulation of intracellular Ca2+. Also, loss of CD38 function was associated with impaired immune responses and metabolic disturbances (Malavasi F., et al. (2008). "Evolution and function of the ADP ribosyl cyclase/CD38 gene family in physiology and pathology". Physiol. Rev. 88(3): 841-86).

On another hand, CD38 protein is a marker of HIV infection, leukemias, myelomas, solid tumors, type II diabetes mellitus and bone metabolism, as well as some other genetically determined conditions. In particular, it has been used as a prognostic marker in leukemia (Ibrahim, S. et al. (2001) CD38 expression as an important prognostic factor in B-cell chronic lymphocytic leukemia. *Blood* 98:181-186).

Mihara et al (2009) describes an anti-CD38 chimeric antigen receptor based on the TBH-7 scFv. These engineered T-cells do not contain any other genetic modification. It is stressed in this publication that the recovery of viable cells was very low.

Although, cells expressing CD38 could be regarded as an attractive target for CARs, the fact that such antigen markers are also expressed at the surface of most T-cells, has hampered significantly the selection of these markers to perform immunotherapy.

The inventors here provide strategies for immunotherapy involving pathological cells expressing CD38 specific antigen marker also present at the surface of T-cells.

SUMMARY OF THE INVENTION

The present invention discloses methods to engineer T-cells intended to target pathological cells, whereas said pathological cells express CD38 marker that are also present on the surface of T-cells. By antigen marker is meant the whole protein of an immune-reactive fragment thereof.

More particularly, the engineered immune cells of the invention relate to anti-CD38 specific chimeric antigen receptors (anti-CD38 CARs) having specific architectures of versions V1, V2 and V3 such as illustrated in FIG. 8; this anti-CD38 CAR having as cytoplasmic domain the CD3 zeta signaling domain and a co-stimulatory domain from 4-1BB, and having VH and VL chains deriving from 25A10, 28F5, 13F11, 16B5, 10F7, 27B6 or 29B4 monoclonal antibodies.

According to the invention, the T-cells are preferably engineered in order to inactivate the expression of the gene encoding such CD38 antigen marker. This inactivation is preferably performed by a genome modification, more particularly through the expression in the T-cell of a specific rare-cutting endonuclease able to target a genetic locus directly or indirectly involved in the production or presentation of said CD38 antigen marker at the surface of the T-cell. Different types of rare-cutting endonucleases can be used, such as meganucleases, TAL-nucleases, zing-finger nucleases (ZFN), or RNA/DNA guided endonucleases like Cas9/CRISPR or argonaute (Ago). Here, the use of TALENs has been found particularly suitable to inactivate the CD38 gene. A schematic representation is presented in FIG. 1.

According to a preferred embodiment, the immune cells of the invention are engineered in order to inactivate the CD38 gene encoding for the CD38 surface antigen, and also to endow a specific anti-CD38 CAR, this double genetic modification aiming to specifically target cancerous CD38-expressing cells while reducing the risk for these anti-CD38 CAR immune cells to kill each other.

According to a still preferred embodiment, said double-genetically engineered anti-CD38 CAR cells have a CAR structure of V1, V2 or V3 such as presented in FIG. 8, this anti-CD38 CAR having as cytoplasmic domain the CD3 zeta signaling domain and a co-stimulatory domain from 4-1BB, and having VH and VL chains deriving from 25A10, 28F5, 13F11, 16B5, 10F7, 27B6 or 29B4 monoclonal antibodies.

According to another embodiment, the T-cells can be further engineered to make them allogeneic, especially by deleting genes involved into self-recognition, such as those, for instance, encoding components of T-cell receptors (TCR) or HLA complex.

According to another embodiment, the T-cells can be further engineered to integrate at least one epitope or mimotope in the extracellular binding domain of the chimeric antigen receptor in order to deplete in vivo such engineered T-cells in case of need.

The present invention encompasses the isolated cells or cell lines comprising the genetic modifications set forth in the detailed description, examples and figures, as well as any of the proteins, polypeptides or vectors useful to engineer said T-cells.

As a result of the invention, the engineered T-cells can be used as therapeutic products, ideally as an "off the shelf" product, in methods for treating or preventing cancer, infections or auto-immune disease. In particular, they are most suitable for the treatment of multiple myeloma (MM) or acute lymphoblastic lymphoma (ALL).

Preferred immune cells according to the present invention are the one resulting into the phenotype [CAR CD38]+ [CD38]−, preferably also [TCR] negative for their use as therapeutic products, preferably allogeneic ones.

BRIEF DESCRIPTION OF THE FIGURES

FIG. 5: Sequences of the Exon 1 of the CD38 antigen and of the 3 targets tested for CD38 KO by TALEN; the 3 targets CD38-1, CD38-2 and CD38ex1-T2 correspond to the successive framed parts. FIG. 5 discloses SEQ ID NO: 174.

Figure 8:
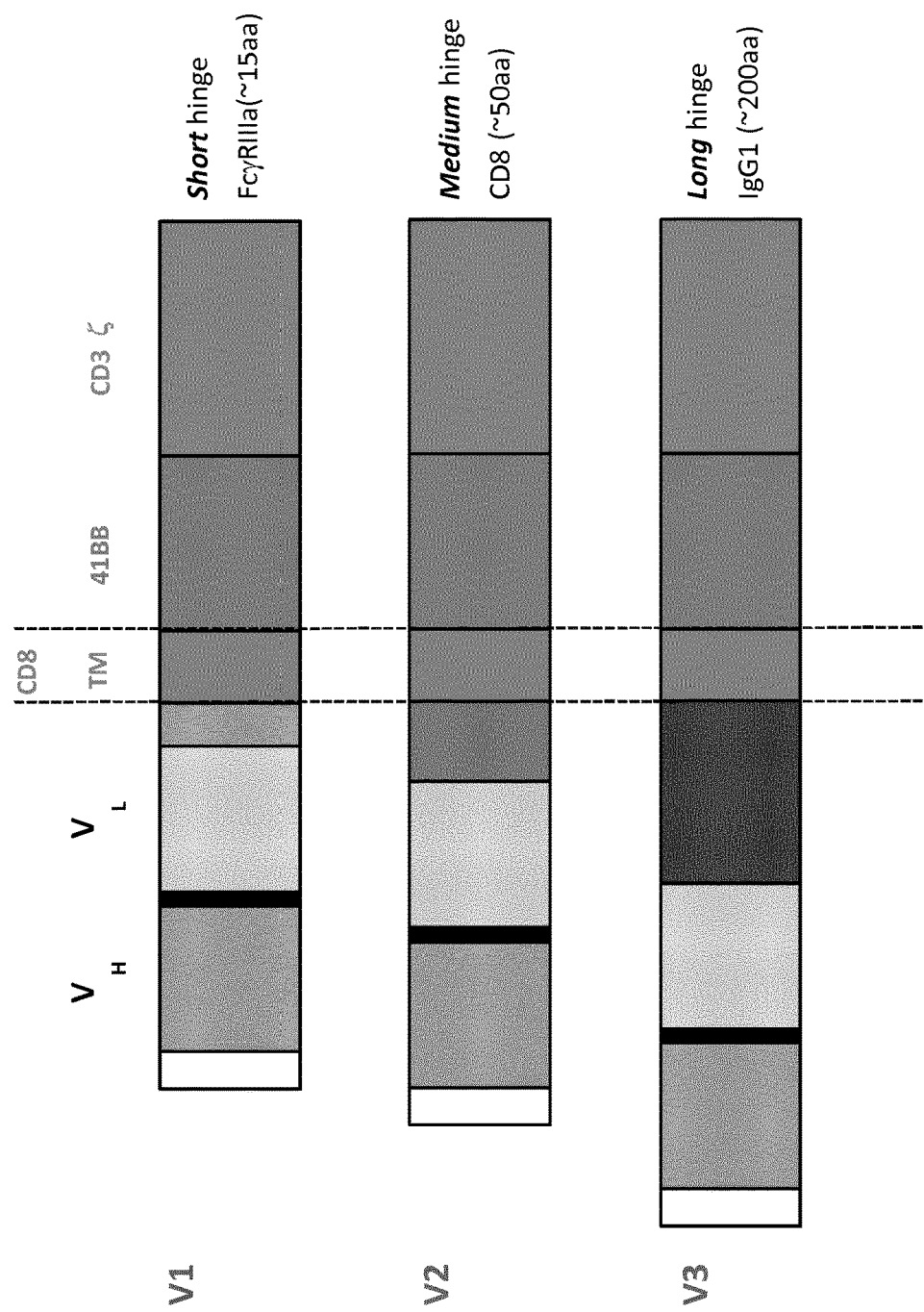

FIG. 8: Representation of the 3 versions (V1, V2 and V3) of designed and tested anti-CD38 CARs depending of the hinge used.

FIG. 9: Construct plasmids for subcloning of the anti-CD38 CARs, with the Kd (nM) of their respective scFvs.

Figure 10:
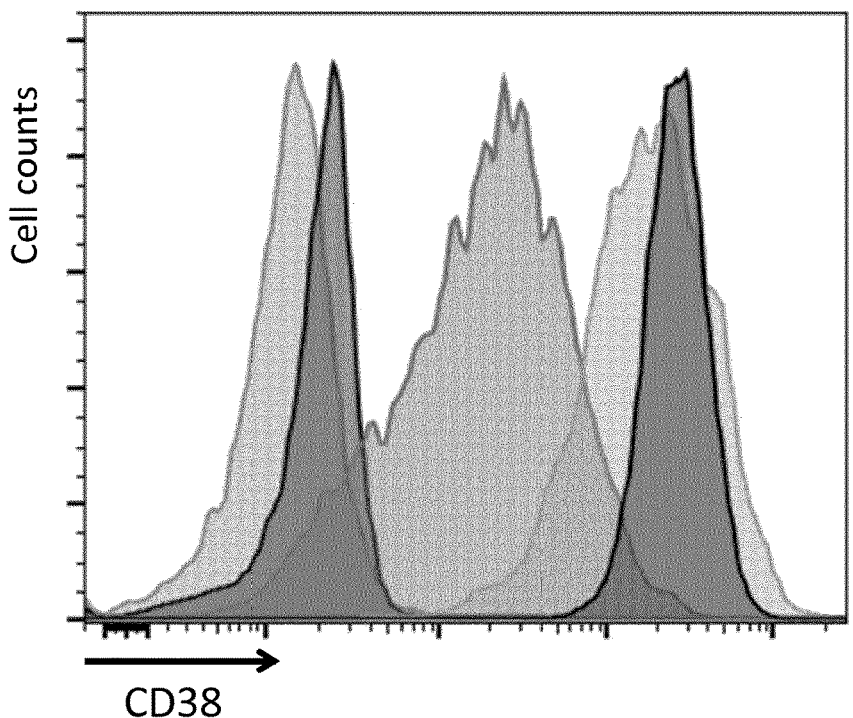

FIG. 10A-B: Testing of 5 cell lines (MOLP8, Daudi, U266 CD38+, U266 CD38- and K562) for quantitative expression of CD38 antigen using Kifikit method (Dako) A: FAC analysis; B: percentage of CD38 expression and number de CD38 antigens per cell.

Figure 11:
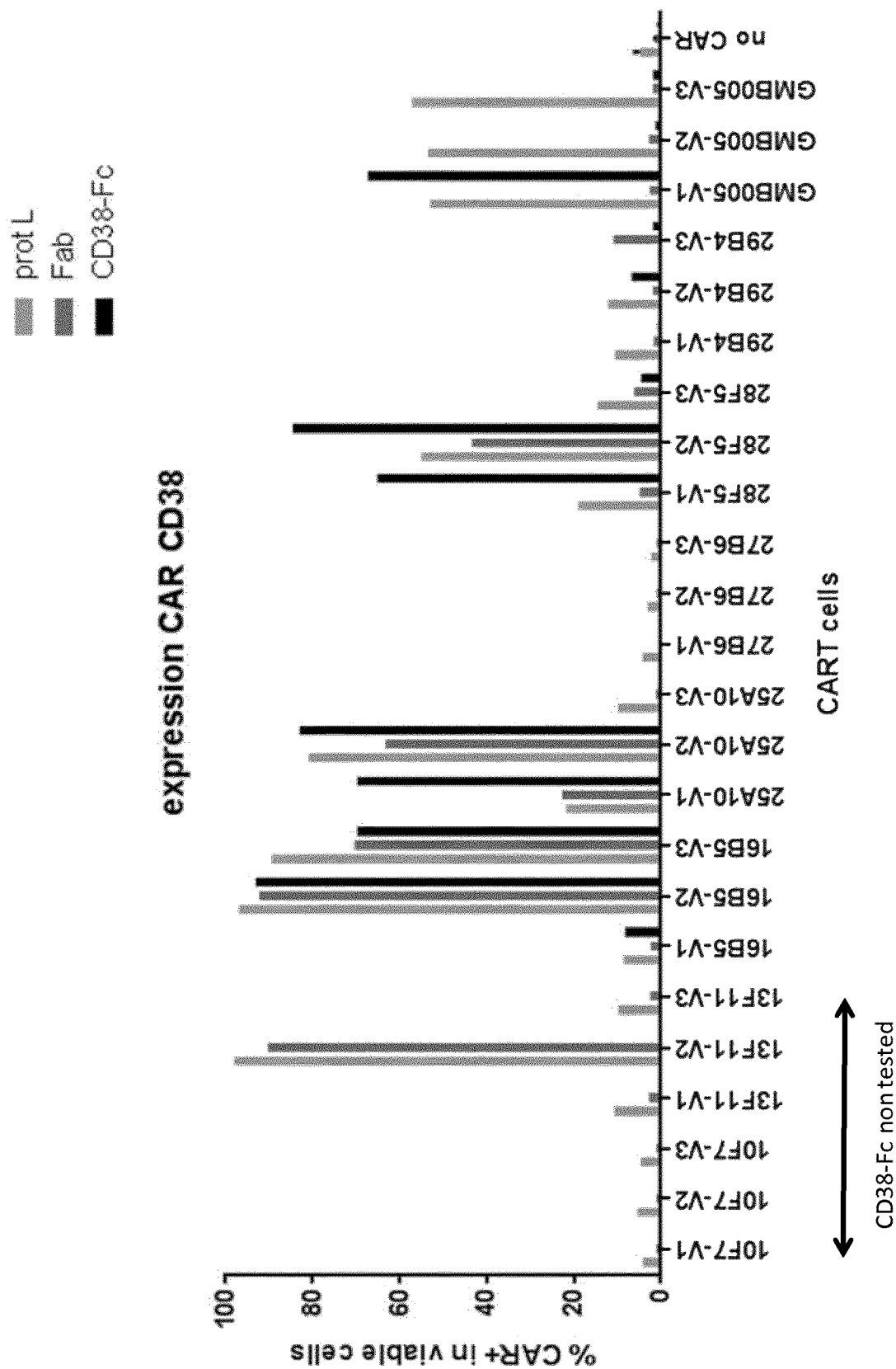

FIG. 11: Screening of all the 24 different CARs (8 pairs of scFvs×3 versions V1, V2 and V3) after transfection of the mRNAs encoding the CARs 5 days after freshly isolated T cells. CAR expression analysis by flow cytometry using protein L, anti-Fab or CD38-Fc (N=1)

Figure 12:
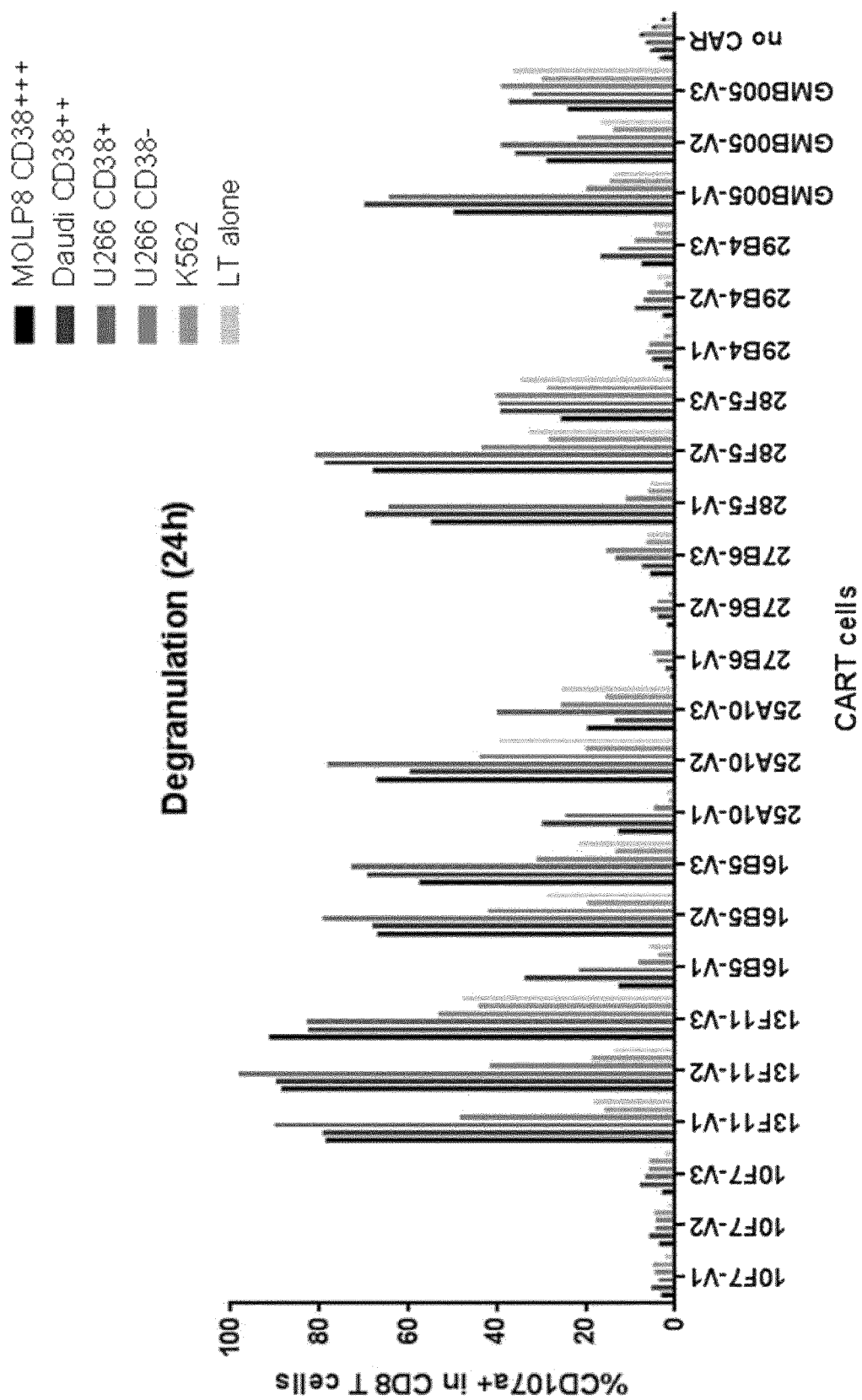

FIG. 12: Screening of all the 24 different CARs (8 pairs of scFvs×3 versions V1, V2 and V3) after transfection of the mRNAs encoding the CARs 5 days after activation of freshly isolated T cells. CD107a expression at the plasma membrane of T cells after incubation (5 hours) with target cell lines (N=1)

Figure 13:
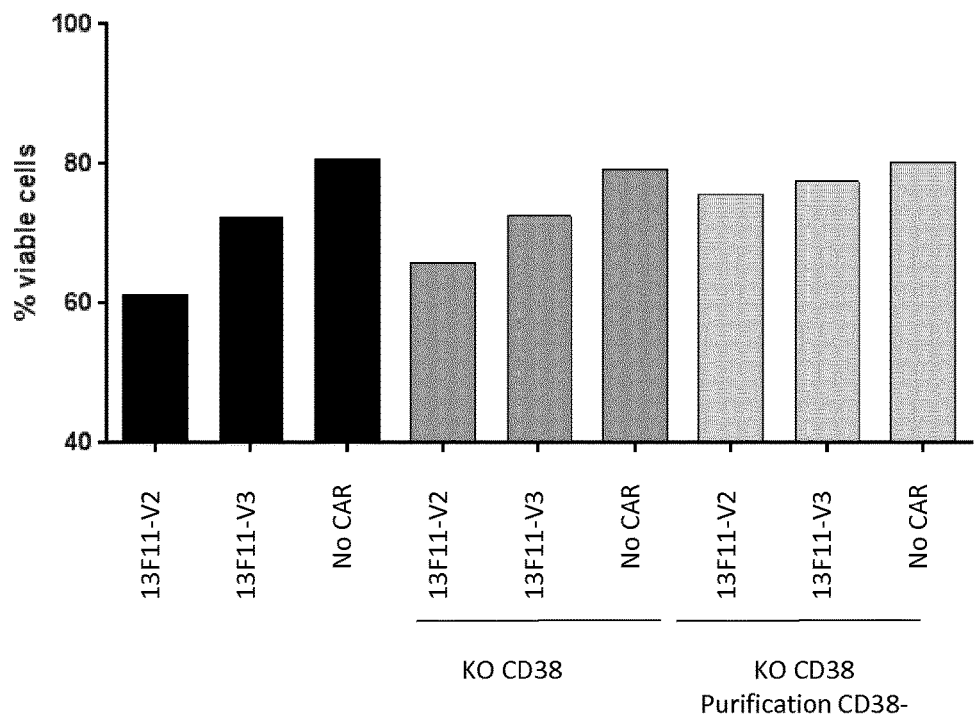
Figure 13:
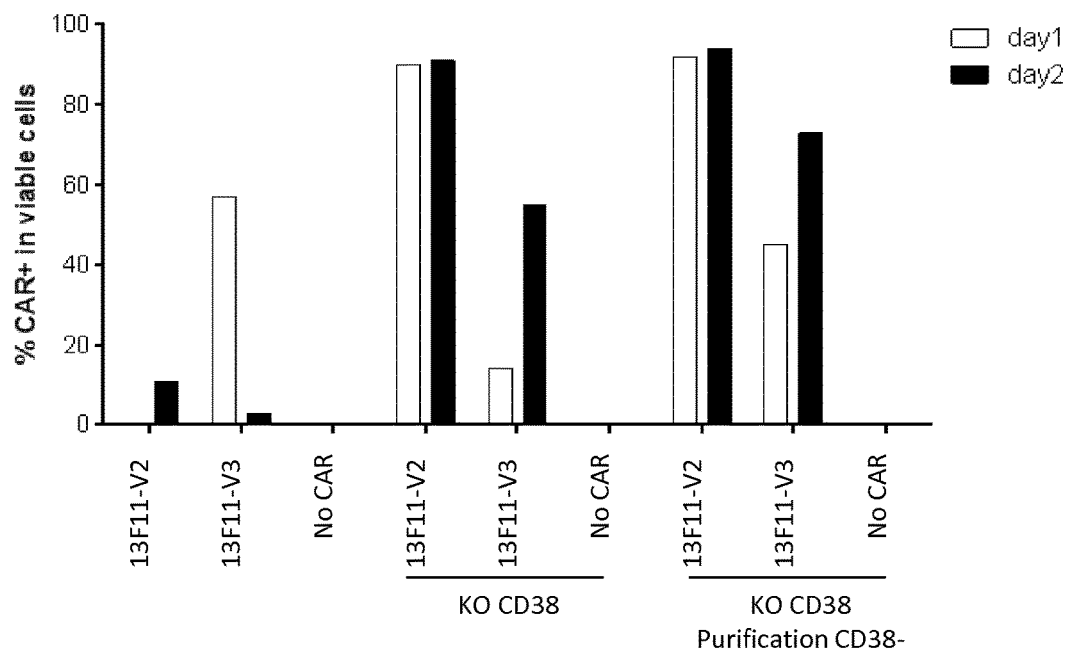

FIG. 13A-B: Comparison of wt, CD38-deficient, purified CD38-deficient anti-CD38 CAR T cells. A: T cells viability assessed by LUNA cell counter. B: CAR expression at day 1 and day 2 after mRNA transfection using CD38-Fc fusion protein (N=1).

Figure 14:
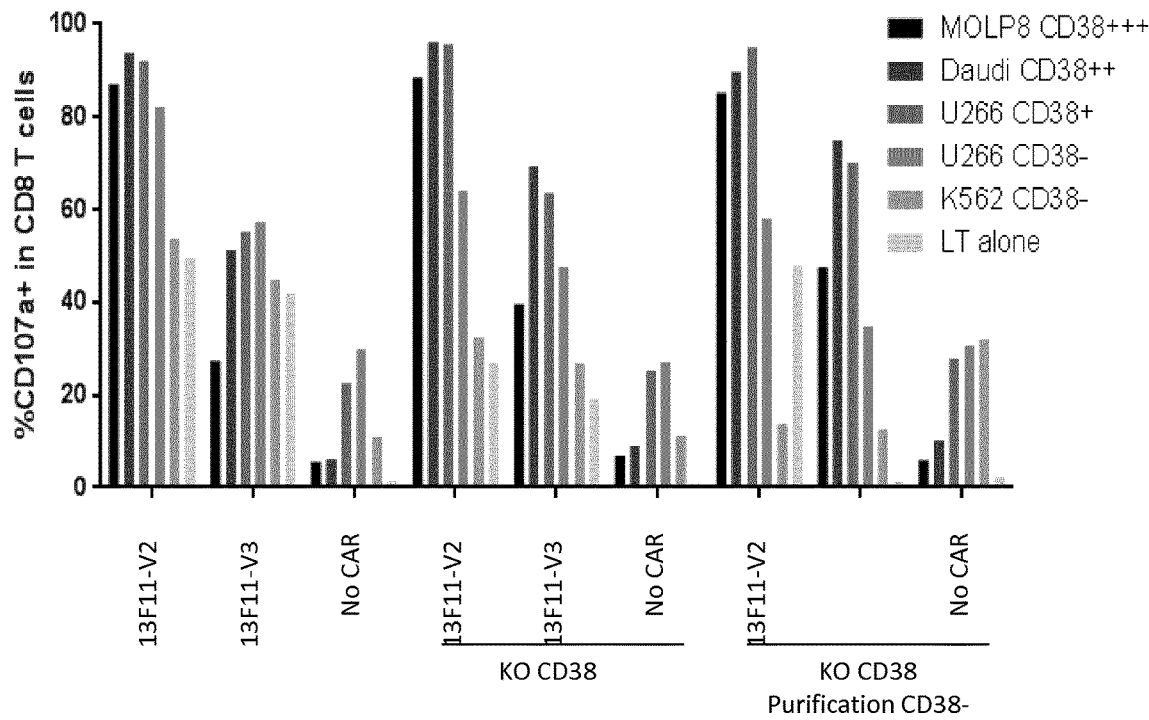
Figure 14:
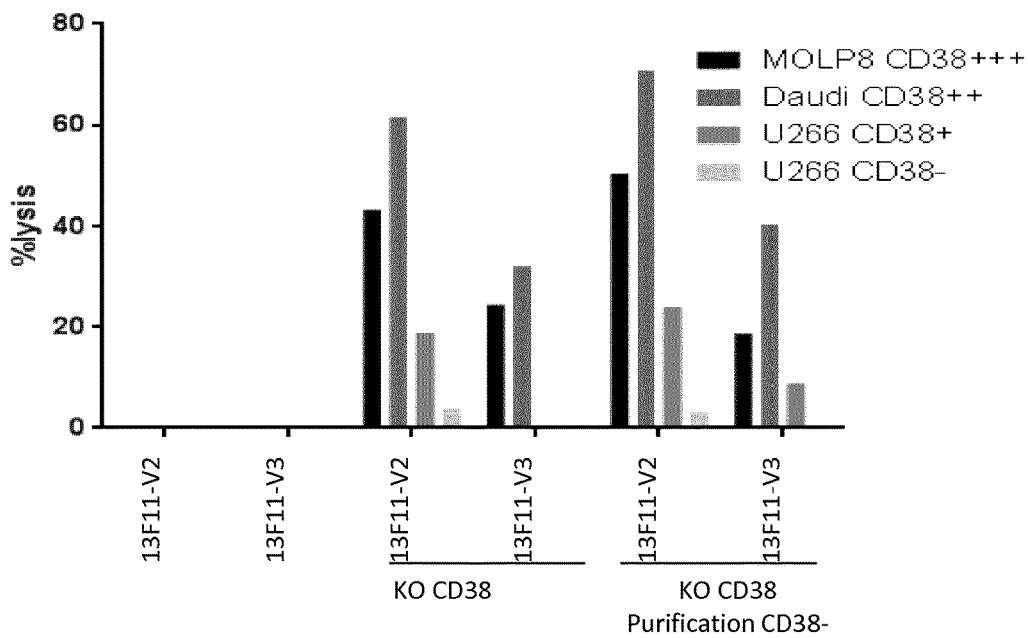

FIG. 14A-B: Comparison of wt, CD38-deficient, purified CD38-deficient anti-CD38 CAR T cells. A: Percentage of CD107a+CD8 T cells after T cells incubation with target cells. B: Target cells lysis normalized on no CAR T cells and K562 lysis. (N=1).

Figure 15:
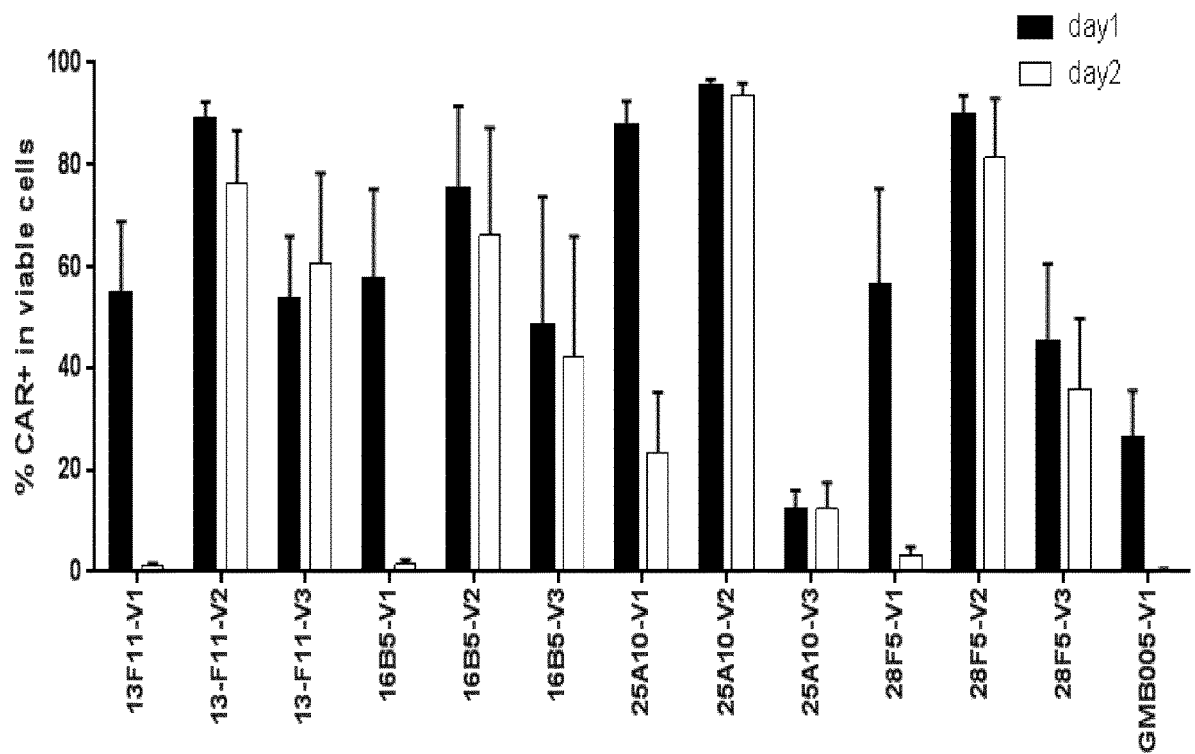

FIG. 15: CAR expression at day 1 and day 2 in purified CD38-deficient anti-CD38 CAR T cells after mRNA transfection using CD38-Fc fusion protein (N=3).

Figure 16:
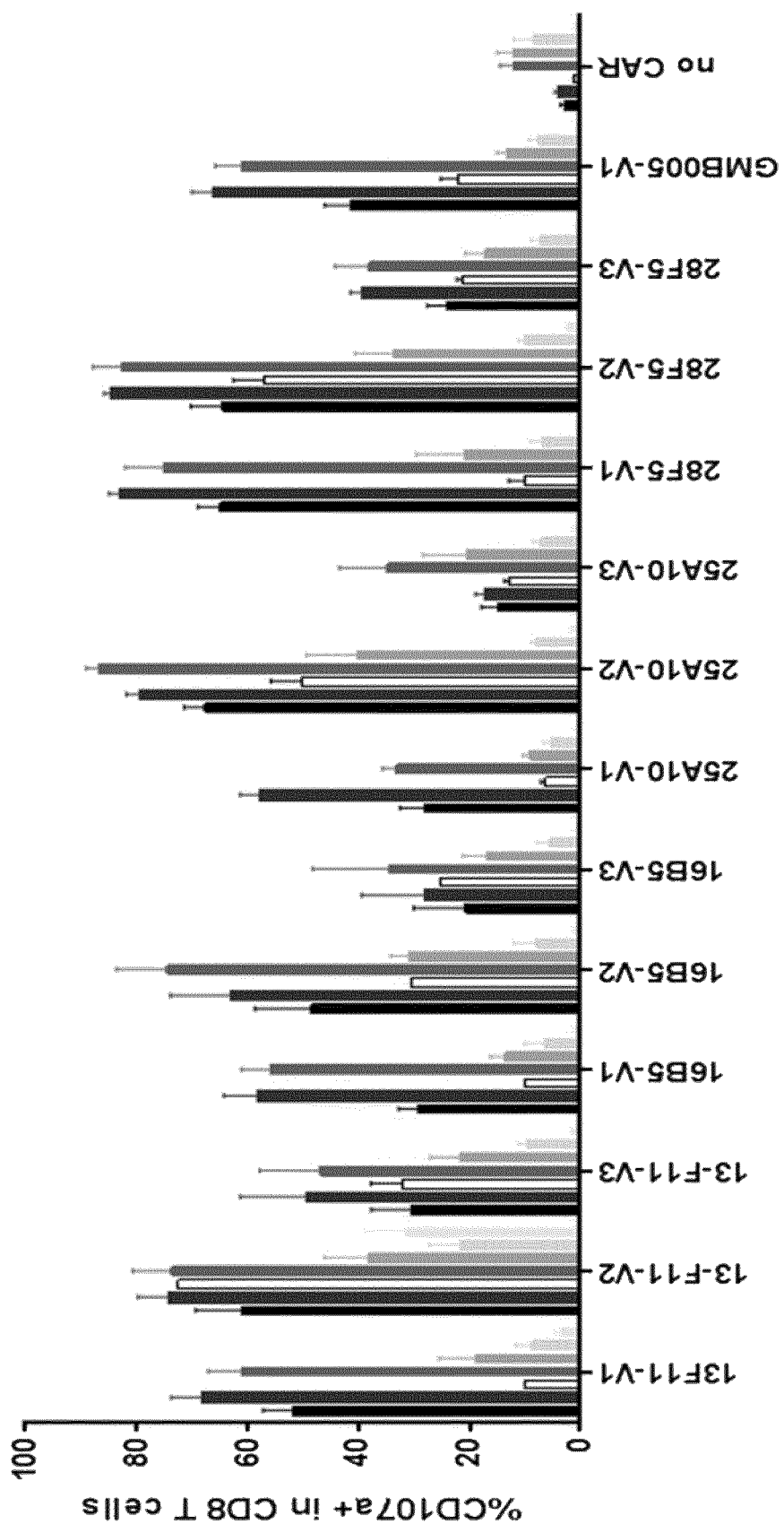

FIG. 16: Percentage of CD107a+CD8 T cells after T cells incubation with target cells (N=3, except for degranulation against autologous T cells (N=1 or 2)

Figure 17:
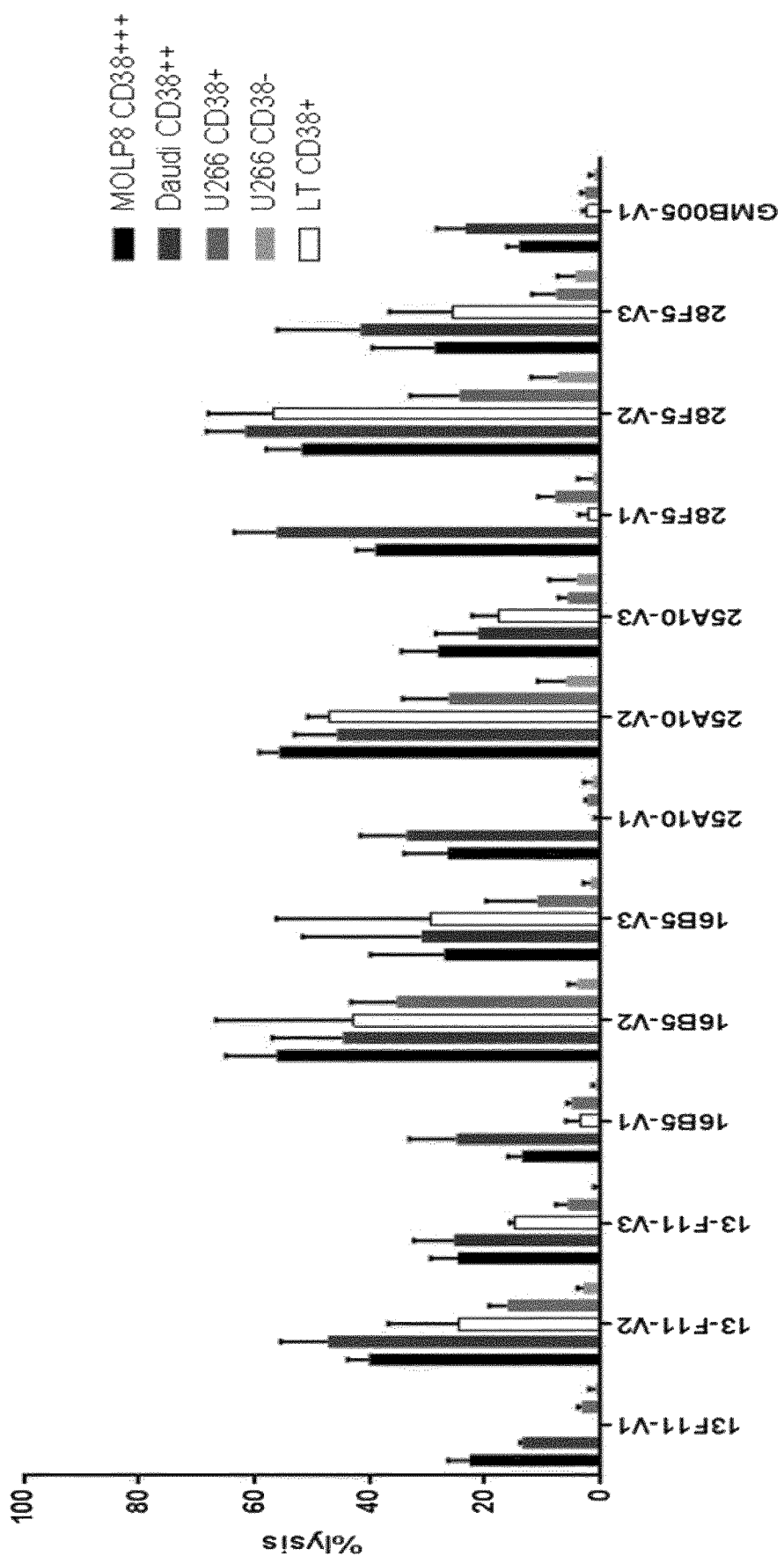

FIG. 17: Target cells lysis normalized on no-CAR T cells and K562 lysis (N=3, except for cytotoxicity against LT autologous N=1 or 2).

Figure 18:
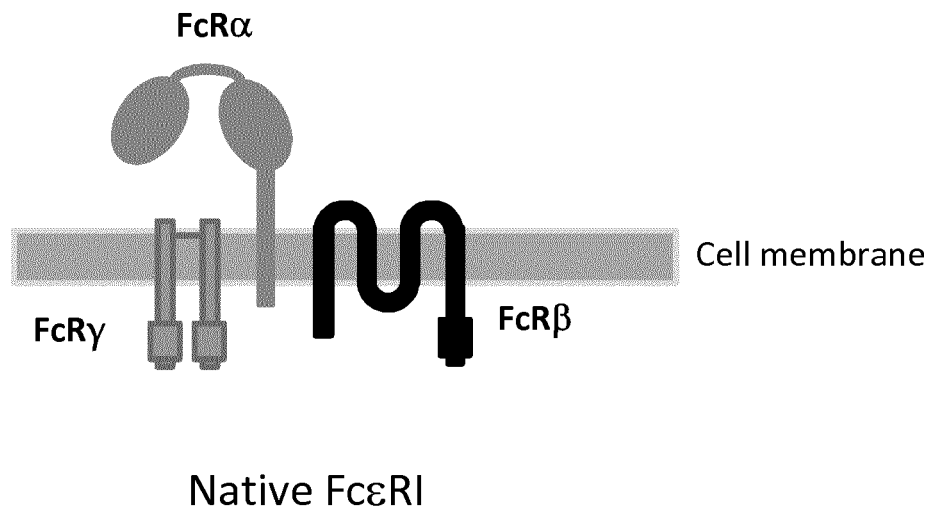

FIG. 18: Schematic representation of FcεRI from which derivate the multi-chain CAR architecture according to the invention.

Figure 19:
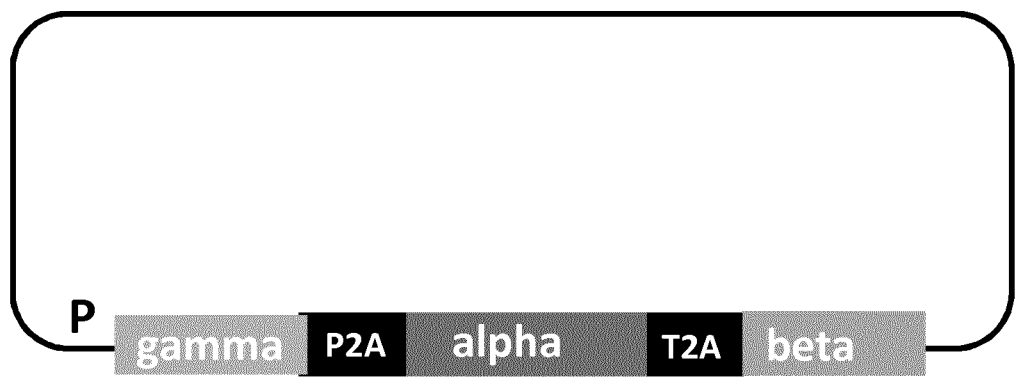

FIG. 19: General structure of the polycistronic construct encoding the CD38 multi-chain CAR according to the invention.

FIG. 20A-D: Different architectures of the CD38 specific multi-chain CAR according to the invention. From left to right: polypeptide gamma (fused to ITAM of CD3zeta), polypeptide alpha (fused to ScFv), polypeptide beta (fused to co-stimulatory domain from either CD28 or 41BB). A and B: polypeptide beta is fused to co-stimulatory domain from 41BB, VL and VH fragments being in opposite orders. C and D: polypeptide beta is fused to co-stimulatory domain from CD28, VL and VH fragments being in opposite orders.

Figure 21A:
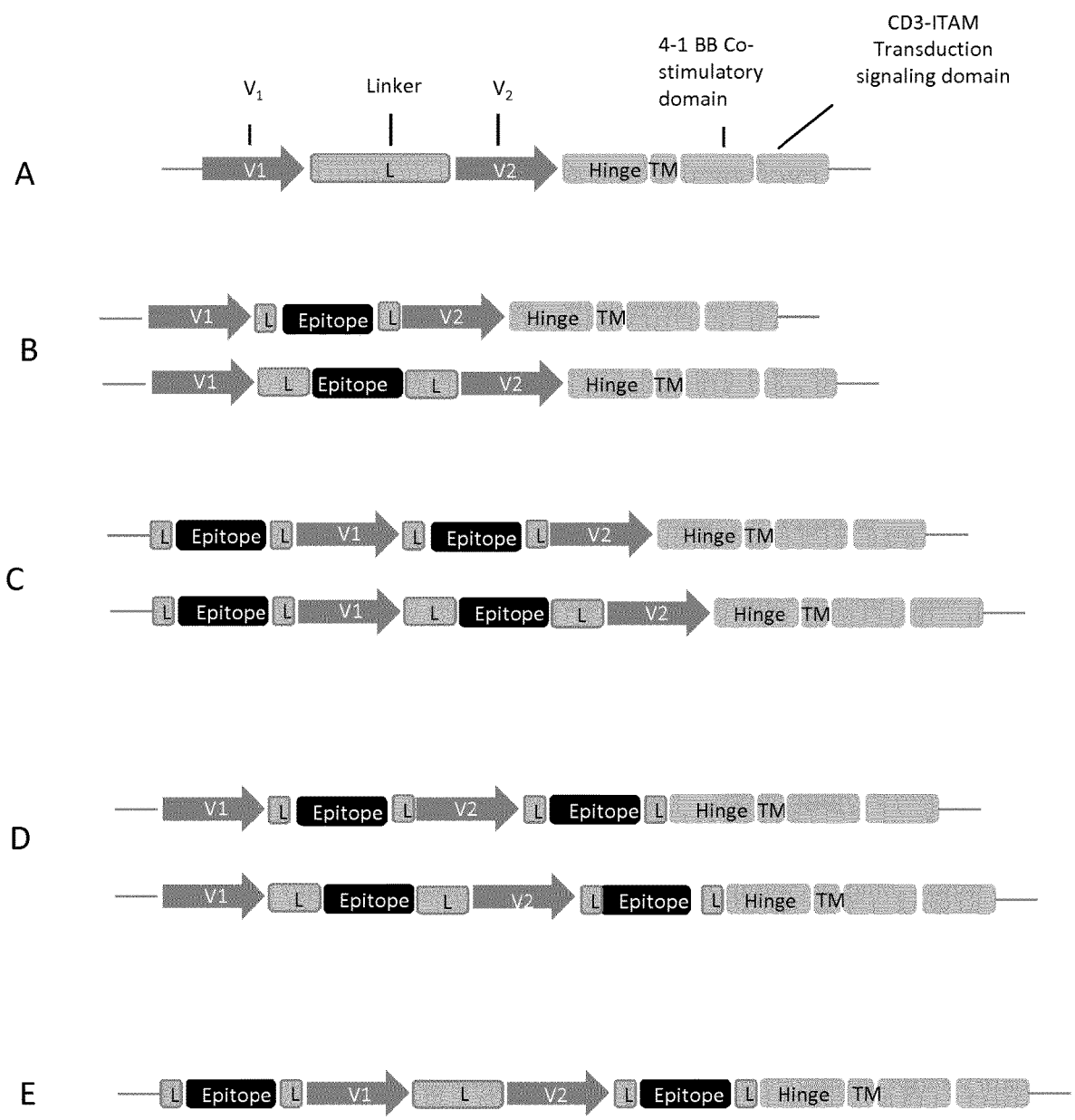
Figure 21B:
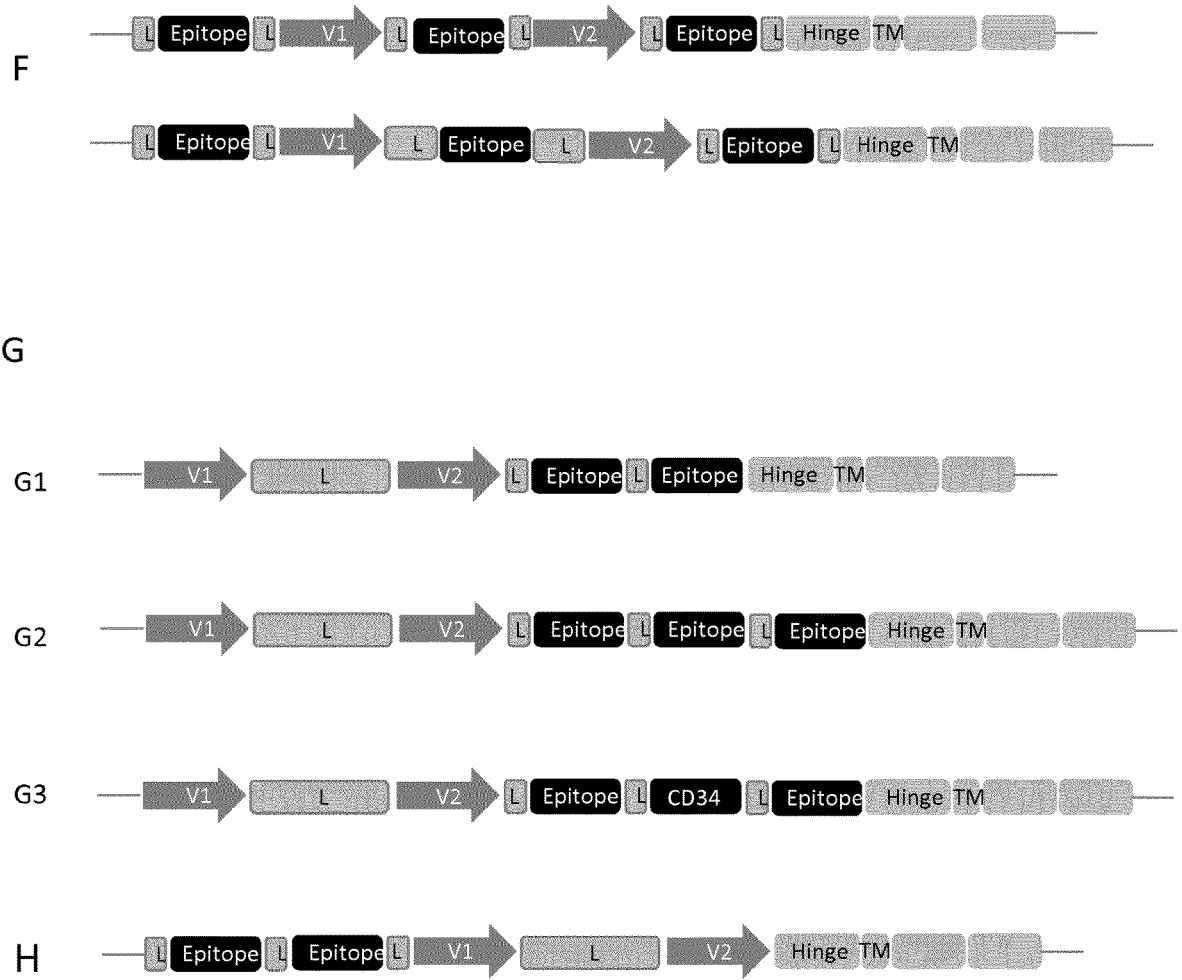

FIG. 21A and FIG. 21B: Schematic representation of exemplary anti-CD38 specific CARs according to the invention involving different mAb-epitope tagging for T cell depletion, especially CD20 mimotope(s), which are designed to mitigate possible side effects associated with CAR positive cells injection.

(A) anti-CD38 specific CAR prototype according to the present invention not involving an epitope tagging sequence for sorting or depleting cells: V1 and v2 represents either VH or VL chain respectively of an antibody binding CD38, TM: transmembrane domain, L: linker, TM: Transmembrane domain (preferably CD8α transmembrane domain), 4-1BB: intracellular co-stimulatory domain, CD3 ITAM: activation domain.

(B) anti-CD38 specific CAR architectures according to the invention further including at least one epitope inserted in the extracellular ligand binding domain of the CAR, wherein said epitope is inserted between the VH and VL chains; said epitope being bordered by different linkers.;

(C): anti-CD38 specific CAR architectures according to the invention, where two epitopes are inserted in the extracellular ligand binding domain of the CAR, one is inserted between the N-terminal end of the CAR and the VH chain, said epitope being bordered by at least one or two linkers; the second epitope is inserted between the VH and VL chains, said $2^{nd}$ epitope being also bordered by 2 at least one or two linkers. The architectures illustrated herein differ by the linkers used bordering the $2^{nd}$ epitope.

(D): anti-CD38 specific CAR architectures according to the invention, where two epitopes are inserted in the extracellular ligand binding domain of the CAR, one is inserted between the VH and VL chains; the other epitope is inserted between the VL chain and the hinge, each said epitope being also bordered by at least one or two linkers. The architectures illustrated herein differ by the linkers used bordering the $1^{st}$ epitope.

(E): anti-CD38 specific CAR architecture according to the invention, where two epitopes are inserted in the extracellular domain of the CAR, one is inserted between the N-terminal end of the CAR and the VH chain, said epitope being bordered by at least one or two linkers; the second epitope is inserted between the VL chain and the hinge, said $2^{nd}$ epitope being also bordered by such linkers.

(F): anti-CD38 specific CAR architectures according to the invention, where three epitopes are inserted in the extracellular domain of the CAR, one is inserted between the N-terminal end of the CAR and the VH chain, said epitope being bordered by at least one or two linkers; the second epitope is inserted between the VH and VL chains, said epitope being also bordered by such linkers, and the third epitope being inserted between the VL chain et the hinge. These two architectures differ by the linkers used bordering the $2^{nd}$ epitope.

(G): anti-CD38 specific CAR architectures according to the invention, where at least two epitopes (preferably CD20 epitopes) are inserted in the extracellular ligand binding domain between the hinge and the anti-CD38 VH and VL chains. In the third exemplary architecture, one CD34 epitope is included between two CD20 epitopes. Further architectures may be considered where CD34 replaces any other previous CD20 epitopes.

(H): anti-CD38 specific CAR architectures according to the invention, where at least two epitopes are inserted at the extremity of the extracellular ligand binding domain.

FIG. 22A-D: Evaluation of in vivo anti-tumor activity of T cells with CD38 knock out and endowing an anti CD19 CAR (CAR CD38-/- CAR-CD19 T cells); A) Timescale of the experiment; B) Bioluminescence imaging was assessed at Day 7, Day 14 and Day 21 in 4 groups of mice: no T cell was administrated, administration of T cells with KO CD38 and expressing RQR8 (CD38-/- RQR8), administration of T cells with KO CD38 and co-expressing CD19 CAR and RQR8, and administration of T cells WT CD38 and co-expressing CD19 CAR and RQR8. The missing mice at Day 14 and Day 21 are due to sacrificed ones for characterization purposes; C) Evaluation of the tumor progression by bioluminescence imaging at Day 7, Day 14 and Day 21 in the 4 above groups of mice: D) Evaluation of survival percentage in function of time in the 4 above groups of mice.

Figure 23:
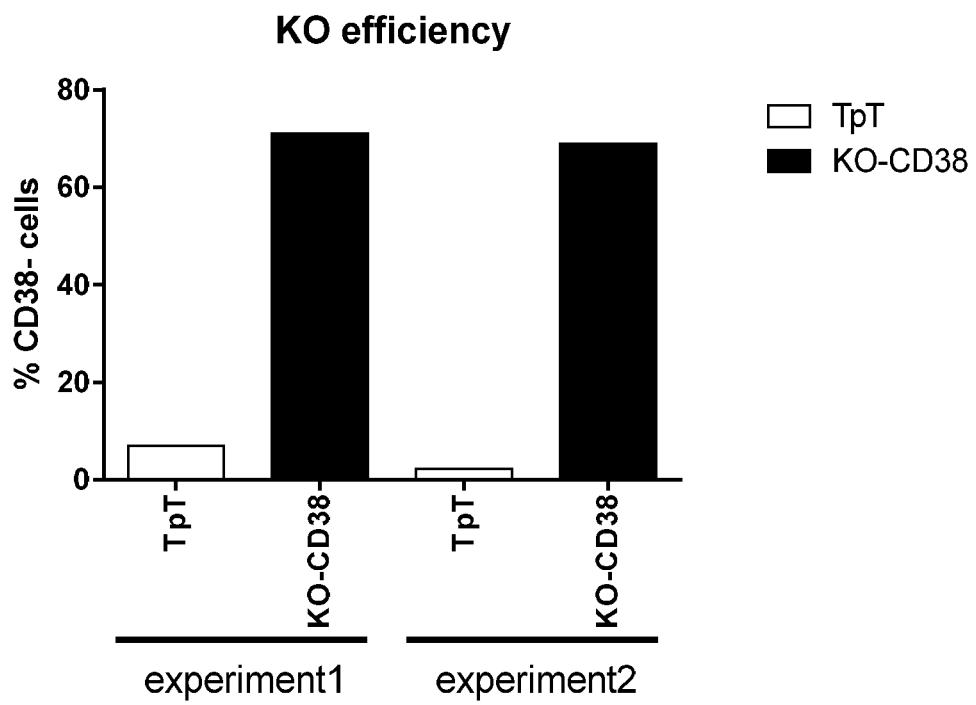

FIG. 23: Evaluation of CD38-KO efficacy in two independent experiments. The graph represents the % of CD38 negative cells 5 days after electroporation (TpT: buffer T=negative control).

Figures 24A, 24B:
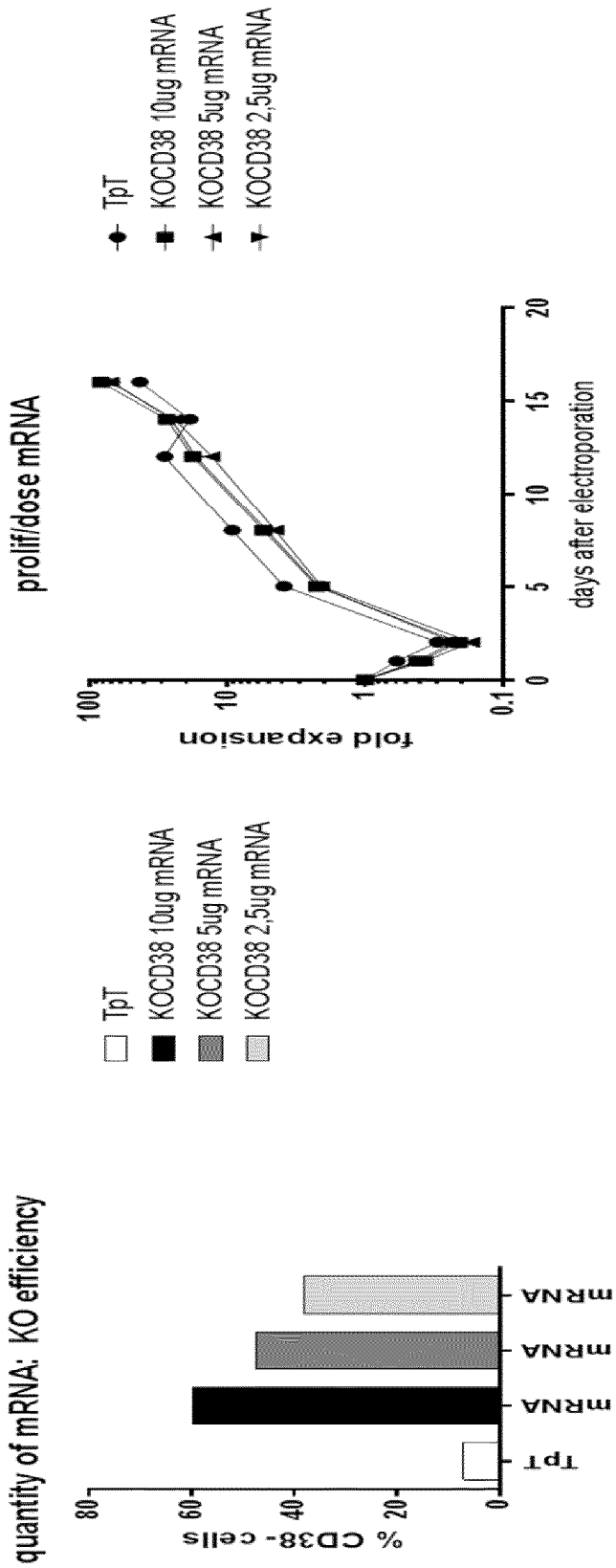

FIG. 24A-B: Evaluation of the effect of the amount of CD38 TALEN mRNA on the KO efficiency A) and T cell proliferation rate B). The quantity of mRNA in the graph corresponds to the mRNA total used (10 µg, 5 µg and 2.5 µg for each TALEN are equivalent to 2 µg, 1 µg and 0.5 µg of mRNA per $10^6$ cells).

Figures 25A, 25B:
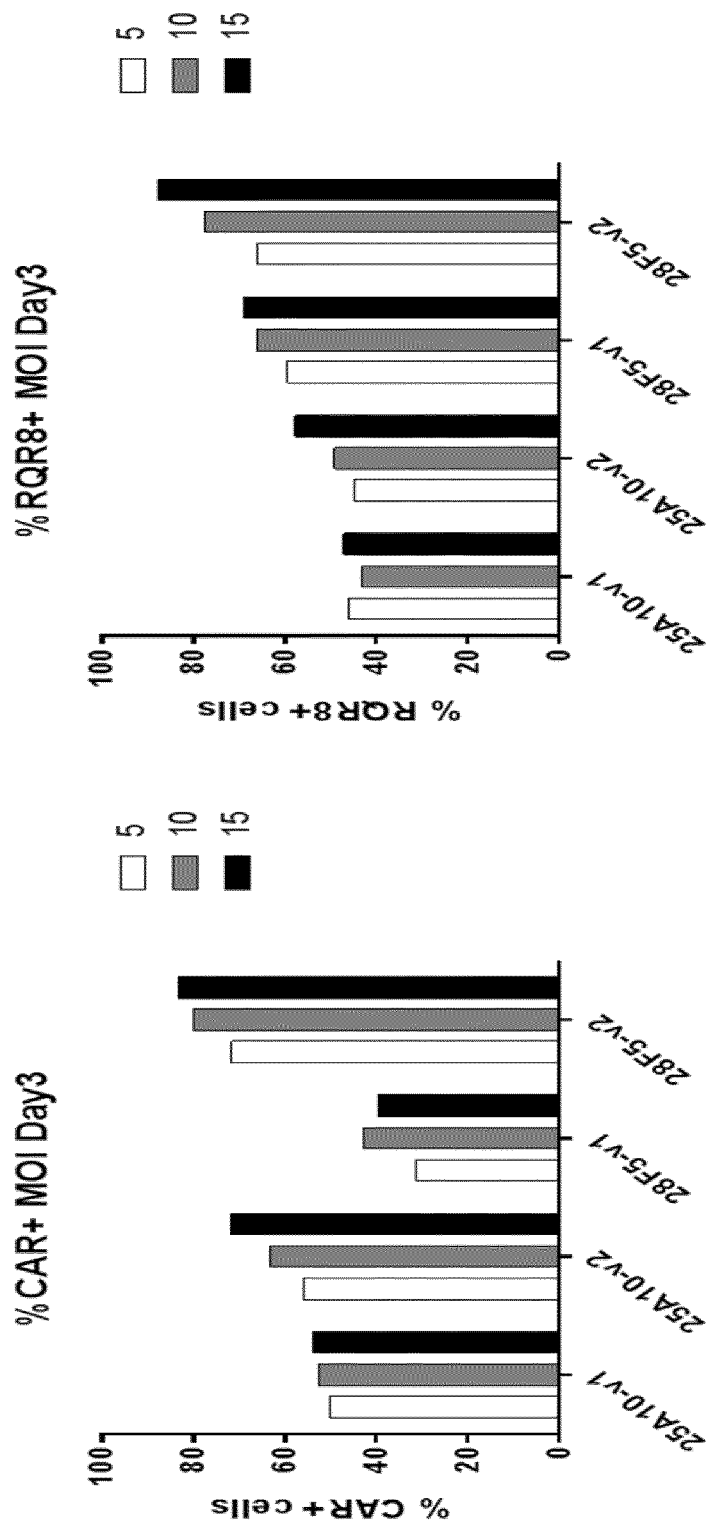

FIG. 25A-B: Evaluation of the transduction efficiency assessed by CD38-fc (A) or RQR8 (B) staining at Day 3 after transduction. Three MOIs (5, 10 and 15) for 4 different rLVs encoding for anti-CD38 CARs (25A10-V1 and V2, and 28F5 V1 and V2) were tested.

Figure 26:
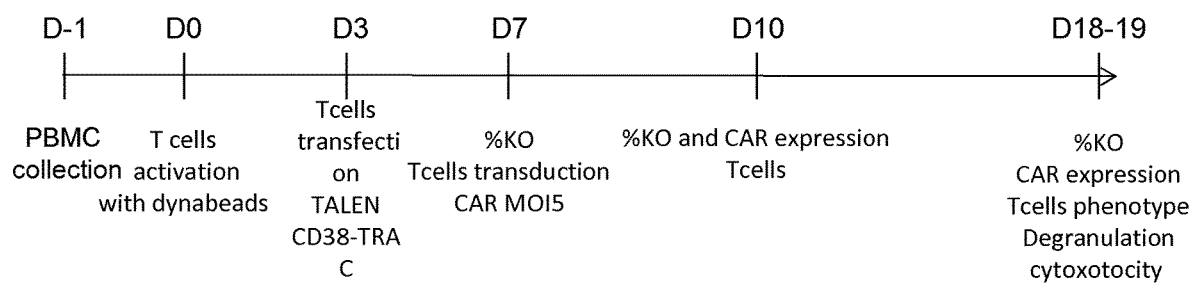

FIG. 26: Time scaling for the screening process of T cells having undergone CD38/TRAC double KO and anti-CD38 CAR transduction.

Figure 27A:
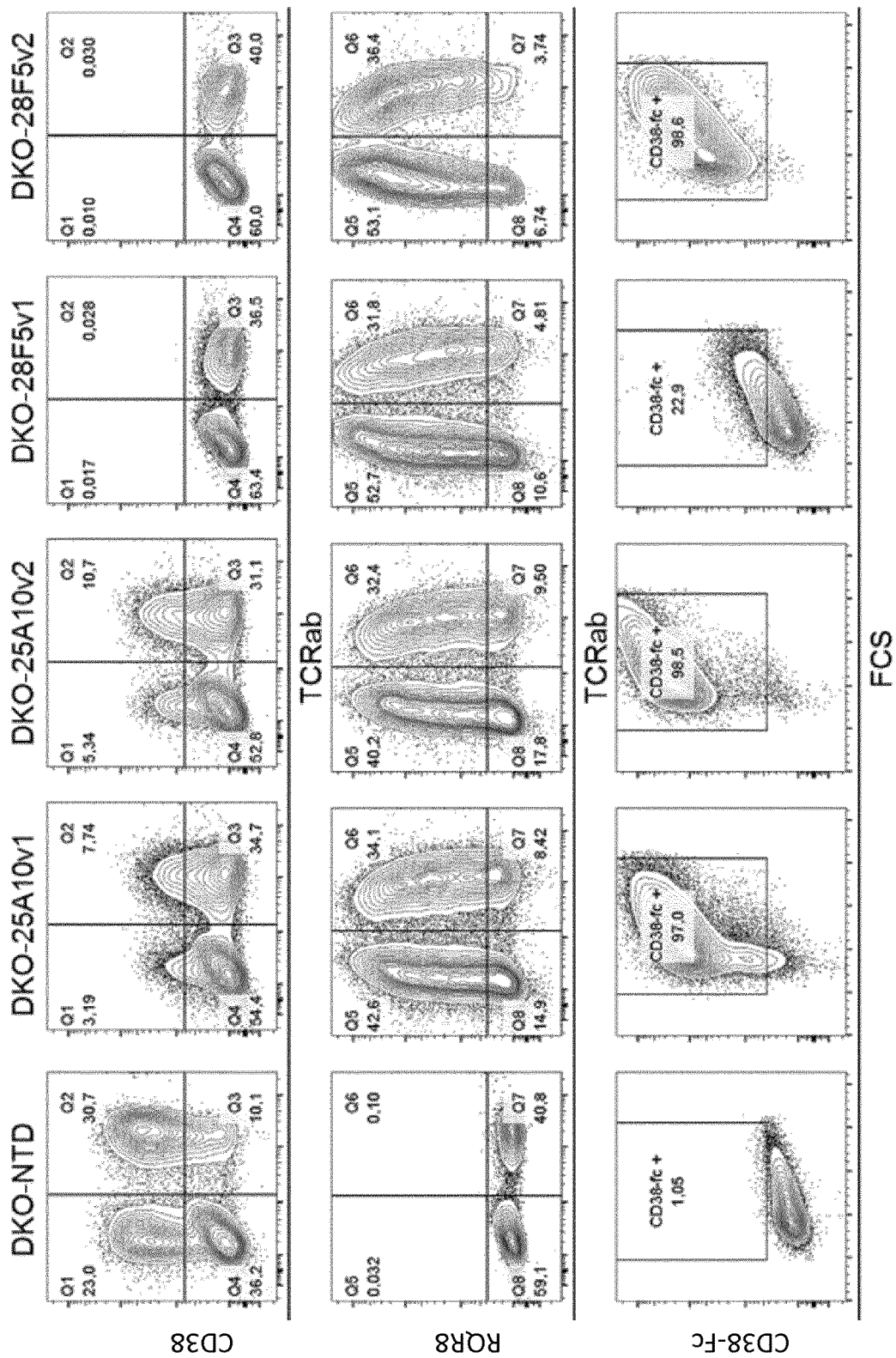
Figure 27B:
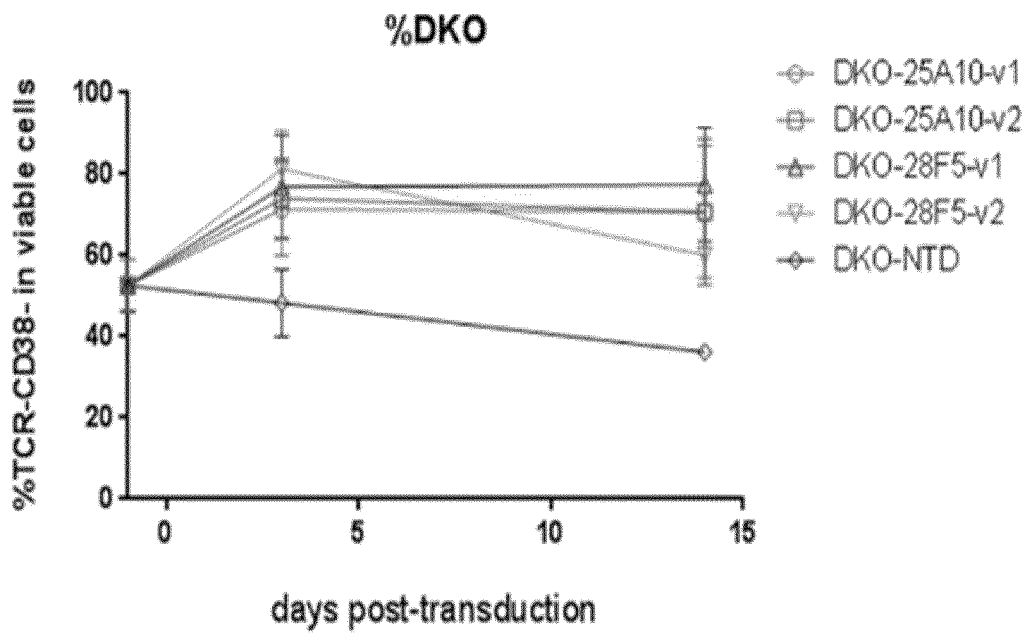
Figure 27C:
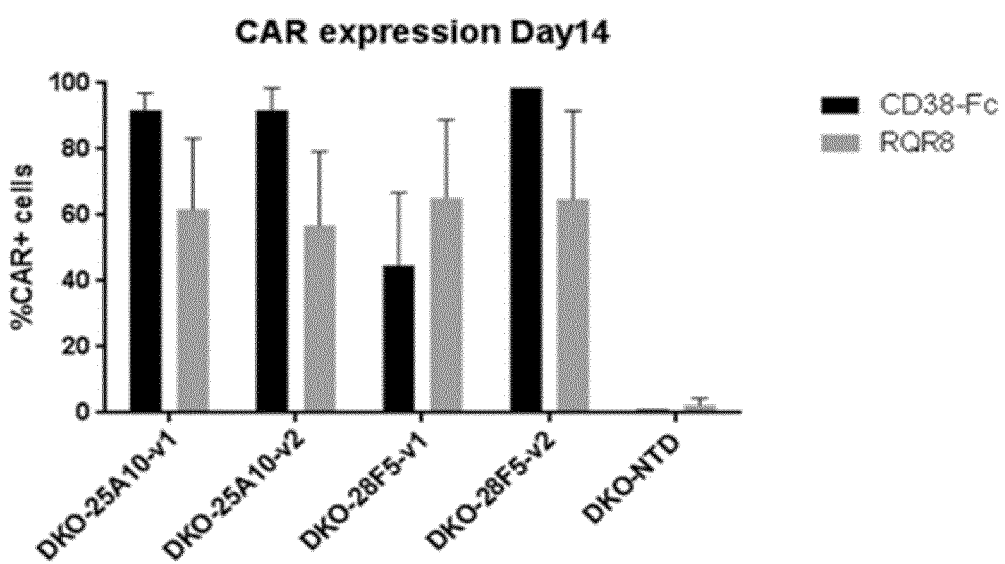

FIG. 27A-C: Evaluation of the efficiency of CD38/TRAC KO by TALEN mRNA electroporation in T cells, and of the CAR and RQR8 co-expression at the end of the culture process. A) three series of FACs corresponding to the expression of CD38 antigen and of anti-CD38 CAR-by RQR8 and CD38 Fc; these assays were performed on each of the 4 anti-CD38 CARs (25A10-V1 and V2, and 28F5 V1 and V2) which have undergone a CD38/TRAC double KO (DKO). B) Evaluation of the percentage of viable T cells having successfully undergone a CD38/TRAC double KO (DKO). C) Evaluation for the 4 above CARs of the anti-CD38 CAR expression based on RQR8 and CD38 Fc. NTD: non transduced.

Figures 28A, 28B:
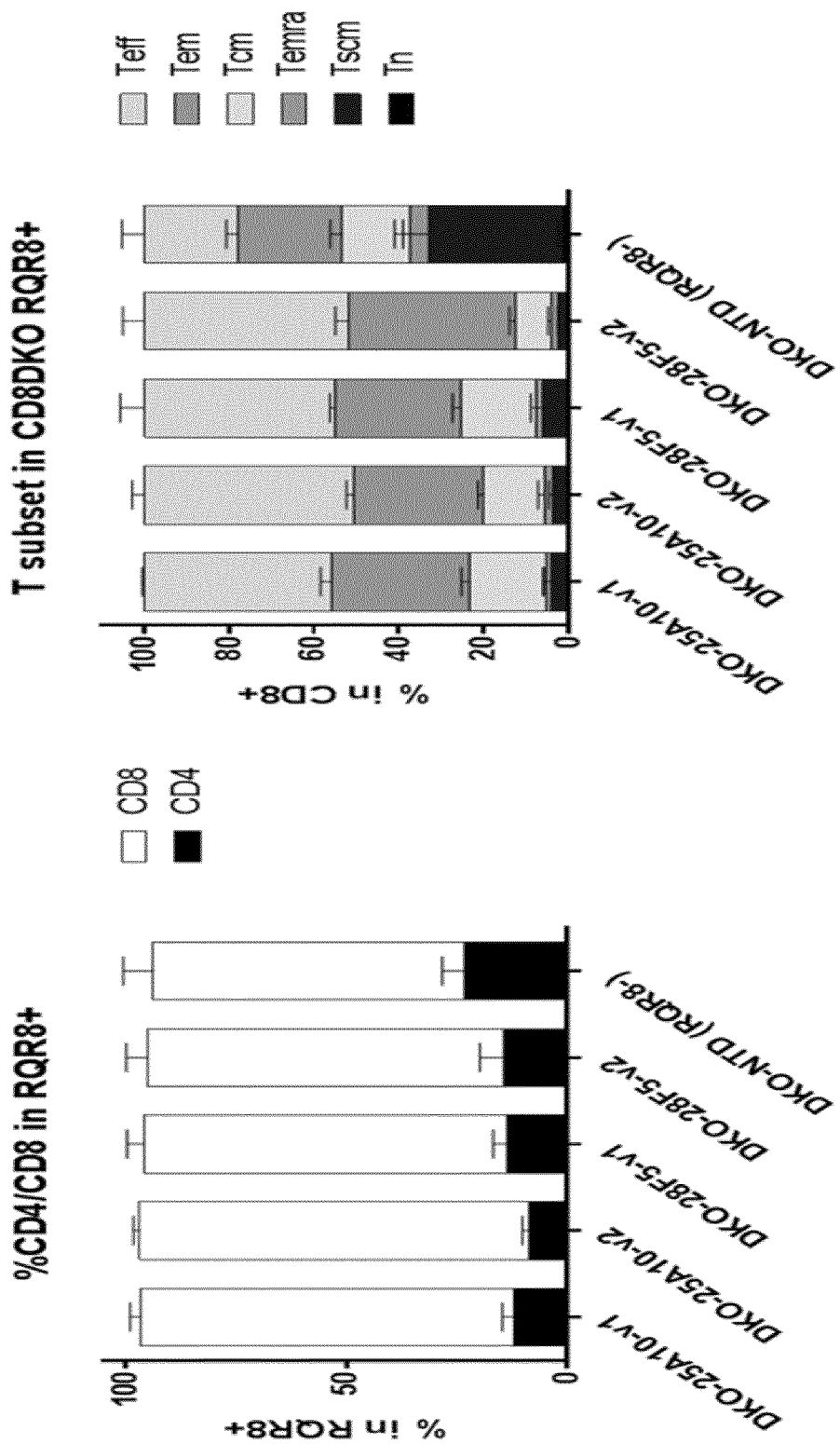

FIG. 28A-B: Characterization of the phenotype of T cells having successfully undergone a double CD38/TRAC KO and expressing anti-CD38 CAR. A) Determination of the ratio of CD4/CD8 in T cells expressing RQR8 for each one of the 4 above anti-CD38 CARs. B) Determination of the ratio of T cells subsets:effector T cell (Teff), memory effector T cell (Tem), central memory T cells (Tcm), stem cell memory T cells (Tscm), another category of memory T cells (Temra) and naïve T cells (Tn), for each one of the 4 above anti-CD38 CARs FIG. 29A-B: Evaluation of the activity for the 4 anti-CD38 CARs (25A10-V1 and V2, and 28F5 V1 and V2) A) Evaluation of their degranulation against MM cell lines: MOLP8, U266 (expressing or not CD38 antigen) and K562, against autologous T cells, and as positive control the case when no cell line was used (LT alone): B) Evaluation of their cytotoxicity against MM CD38 expressing cell lines, the values for U266 which is a MM expressing CD38 cell line was normalized to that of U266 not expressing CD38 cell line. For these 2 graphs: the legends next to them from top to the bottom correspond to the bars from left to right.

Figure 30:
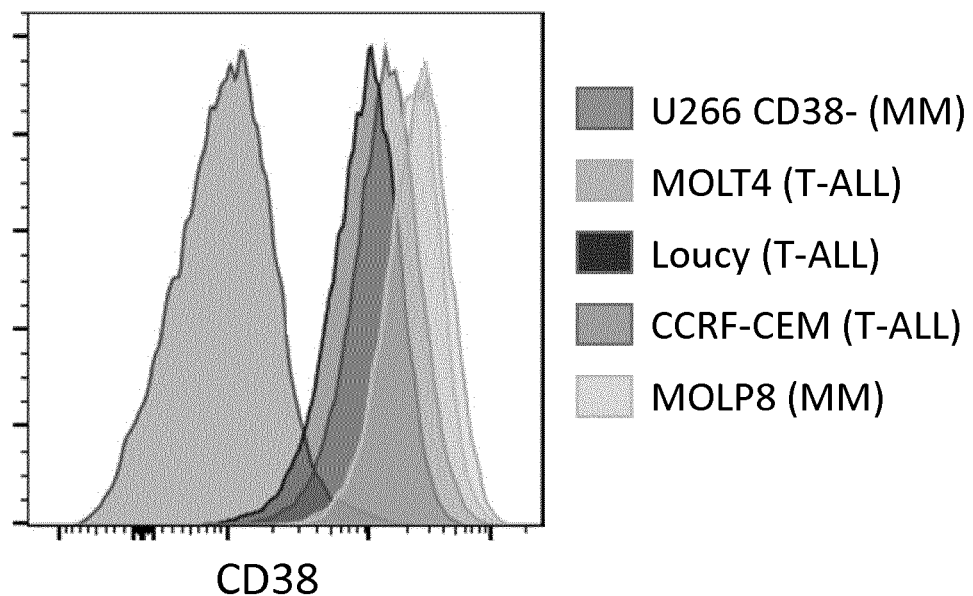

FIG. 30: Evaluation of the CD38 expression at the cell surface of three T acute lymphoblastic leukemia (T-ALL) cell lines (MOLT4, Loucy and CCFR-CEM), and of two MM cell lines (U266 CD38- and MOLP8).

Figure 31:
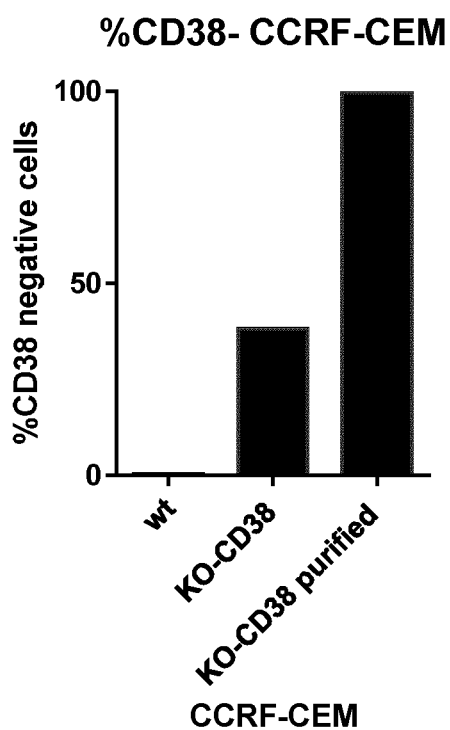

FIG. 31: Evaluation of the establishment of KO CD38 by determination of percentage of CD38 negative T cells in the CCRF-CEM (T-ALL) cell line before and after purification.

Figure 32A:
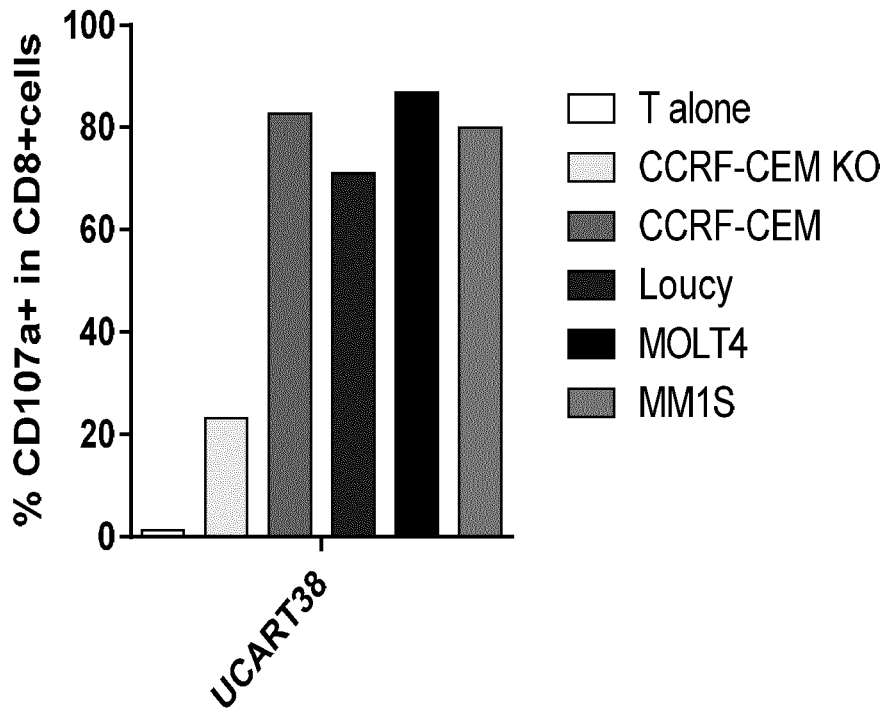
Figure 32B:
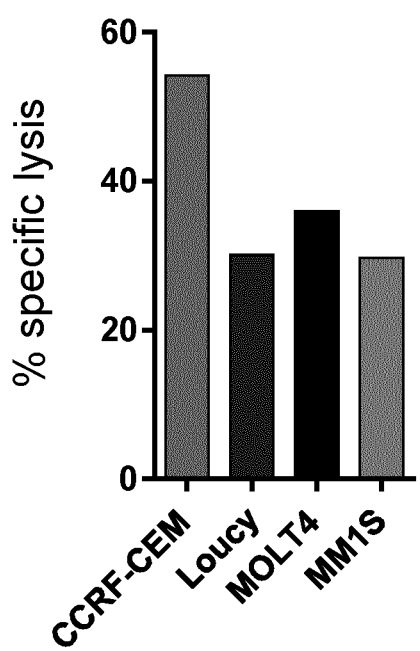

FIG. 32A-B: Evaluation of the a anti-CD38 CAR activity for the 25A10-V1 A) Evaluation of their degranulation against T ALL cell lines: CCRF-CEM original cell and the one KO CD38, Loucy and MOLT4,a MM1S MM cell line expressing CD38, and as positive control the case when no cell line was used (LT alone): B) Evaluation of their cytotoxicity against the above T ALL CD38 expressing cell lines (value for CCRF-CEM was normalized to the corresponding CD38 not expressing cell line). For these 2 graphs: the legends next to them from top to the bottom correspond to the bars from left to right.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The invention relates more particularly to anti-CD38 specific chimeric antigen receptors (anti-CD38 CARs) having one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4).

Engineered T-Cells Expressing Chimeric Antigen Receptors Against Pathological Cells The chimeric antigen receptors introduced into the T-cells according to the invention can adopt different design such as single-chain or multi-chain CARs. These different designs allow various strategies for improving specificity and binding efficiency towards the targeted pathological cells. Some of these strategies are illustrated in the figures of the present application. Single-chain CARs are the most classical version in the art. Multi-chain CAR architectures were developed by the applicant as allowing modulation of the activity of T-cells in terms of specificity and intensity. The multiple subunits can shelter additional co-stimulation domains or keep such domains at a distance, as well as other types of receptors, whereas classical single chain architecture can sometimes be regarded as too much sensitive and less permissive to multispecific interactions.

Single-Chain CAR

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity. However, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

According to one embodiment, the anti-CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4).

According to a preferred embodiment, the anti-CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10) and SEQ ID NO 62 and 58 (28F5).

According to a more preferred embodiment, the anti-CD38 specific chimeric antigen receptor (anti-CD38 CAR) has one of the polypeptide structure selected from V1 and V2 as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10) and, SEQ ID NO. 62 and 58 (28F5).

According to a preferred embodiment, said transmembrane domain of above anti-CD38 specific chimeric antigen receptor (anti-CD38 CAR) comprises a polypeptide sequence displaying at least 90%, at least 95%, at least 98% or at least 99% identity to SEQ ID NO.79 (CD8α TM).

According to a preferred embodiment, said $V_H$ and $V_L$ of above anti-CD38 specific chimeric antigen receptor (anti-CD38 CAR) comprise a polypeptide sequence displaying at least 90%, at least 95%, at least 98% or at least 99% identity to respectively SEQ ID NO. 14 and 10 (25A10) or SEQ ID NO. 62 and 58 (28F5).

According to a preferred embodiment, the CDRs sequences comprised in said $V_H$ and $V_L$ of said anti-CD38 specific chimeric antigen receptor (anti-CD38 CAR) are respectively SEQ ID NO.15-17 and SEQ ID NO.11-13; respectively SEQ ID NO.63-65 and SEQ ID NO.59-61; respectively SEQ ID NO.55-57 and SEQ ID NO.51-53; respectively SEQ ID NO.31-33 and SEQ ID NO.27-29; respectively SEQ ID NO.39-41 and SEQ ID NO.35-37; respectively SEQ ID NO.47-49 and SEQ ID NO.43-45; respectively SEQ ID NO.23-25 and SEQ ID NO.19-21.

According to a preferred embodiment, said hinge of above anti-CD38 specific chimeric antigen receptor (anti-CD38 CAR) comprises a sequence displaying at least 90%, at least 95%, at least 98% or at least 99% identity to one selected from SEQ ID NO. 76 (FcɛRIIIα), SEQ ID NO. 77 (CD8α) and SEQ ID NO. 78 (IgG1).

According to a more preferred embodiment, said hinge of above anti-CD38 specific chimeric antigen receptor (anti-CD38 CAR) comprises a sequence displaying at least 90%, at least 95%, at least 98% or at least 99% identity to SEQ ID NO. 77 (CD8α).

According to a preferred embodiment, said hinge of above anti-CD38 specific chimeric antigen receptor (anti-CD38 CAR) comprises a sequence displaying at least 90%, at least 95%, at least 98% or at least 99% identity to one selected from SEQ ID NO. 76 (FcɛRIIIα).

According to one embodiment, the anti-CD38 specific chimeric antigen receptor (anti-CD38 CAR) of the invention comprises a polypeptide sequence displaying at least 90%, at least 95%, at least 98% or at least 99% identity to one selected from SEQ ID NO. 82-84 (25A10), SEQ ID NO. 100-102 (28F5), SEQ ID NO. 97-99 (13F11), SEQ ID NO. 88-90 (16B5), SEQ ID NO. 91-93 (10F7), SEQ ID NO. 94-96 (27B6) and SEQ ID NO. 85-87 (29B4).

All above sequences of anti-CD38 CARs which are encompassed within the scope of the invention are presented in the following Table 1 (excepted the GMB005 CARs used as tool CAR for comparison). Are also disclosed sequences of the components which are used for their architectures (V1, V2 and V3 versions according to FIG. 8).

TABLE 1

Polypeptide sequences of anti-CD38 CARs based on the V1, V2 and V3 versions in FIG. 8, and of their corresponding components used to make them

| Name of CAR | SEQ ID # | Polypeptide sequence |
|---|---|---|
| CD8α-Signal peptide (SP) | 74 | MALPVTALLLPLALLLHAARP |
| FcεRIγ-signal peptide (SP) | 106 | MIPAVVLLLLLLVEQAAA |
| FcεRI?-signal peptide (SP) | 110 | MAPAMESPTLLCVALLFFAPDGVLA |
| GS linker | 75 | GGGGSGGGGSGGGGS |
| FCRIIIα hinge | 76 | GLAVSTISSFFPPGYQ |
| CD8α hinge | 77 | TTTPAPRPPTPAPTIASQPLSLRPEACRPAAGGAVHTRGLDFACD |
| IgG1 hinge | 78 | EPKSPDKTHTCPPCPAPPVAGPSVFLFPPKPKDTLMIARTPEVTCVVVDVSHEDPE VKFNWYVDGVEVHNAKTKPREEQYNSTYRVVSVLTVLHQDWLNGKEYKCKVSN KALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHY TQKSLSLSPGK |
| CD8α TM domain | 79 | IYIWAPLAGTCGVLLLSLVITLYC |
| 4-1 BB co-stimulatory domain | 80 | KRGRKKLLYIFKQPFMRPVQTTQEEDGCSCRFPEEEEGGCEL |
| CD28 co-stimulatory domain (CD28-IC) | 113 | RSKRSRGGHSDYMNMTPRRPGPTRKHYQPYAPPRDFAAYRS |
| CD3ζ activation domain | 81 | RVKFSRSADAPAYQQGQNQLYNELNLGRREEYDVLDKRRGRDPEMGGKPRRKN PQEGLYNELQKDKMAEAYSEIGMKGERRRGKGHDGLYQGLSTATKDTYDALHM QALPPR |
| Fc Receptor for IgE, alpha chain, transmembrane and intracellular domain (FcεRI?-TM-IC) | 111 | FFIPLLVVILFAVDTGLFISTQQQVTFLLKIKRTRKGFRLLNPHPKPNPKNN |
| Fc Receptor for IgE, gamma chain' without ITAM) (FcεRI γ-?ITAM) | 107 | LGEPQLCYILDAILFLYGIVLTLLYCRLKIQVRKAAITSYEKS |
| Receptor for IgE, beta chain, without ITAM (FcεRIγ-ΔITAM) | 112 | MDTESNRRANLALPQEPSSVPAFEVLEISPQEVSSGRLLKSASSPPLHTWLTVLKKE QEFLGVTQILTAMICLCFGTVVCSVLDISHIEGDIFSSFKAGYPFWGAIFFSISGMLSI ISERRNATYLVRGSLGANTASSIAGGTGITILIINLKKSLAYIHIHSCQKFFETKCFMAS FSTEIVVMMLFLTILGLGSAVSLTICGAGEELKGNKVPE |

TABLE 1-continued

Polypeptide sequences of anti-CD38 CARs based on the V1, V2 and V3 versions in FIG. 8, and of their corresponding components used to make them

| Name of CAR | SEQ ID # | Polypeptide sequence |
|---|---|---|
| GSG-P2A ribosomal skip peptide (GSG-P2A) | 108 | GSGATNFSLLKQAGDVEENPGP |
| GSG-T2A ribosomal skip peptide (GSG-T2A) | 109 | GSGEGRGSLLTCGDVEENPGP |
| 25A10-V1 CAR | 82 | MALPVTALLLPLALLLHAARPEVQLQQSGAELVRPGASVKLSCTASGFNIKDSLIH<br>WVKQRPEQGLEWIGWIDPEDDKTKYAPKFQDKATLTADTSSNTAYLQLSTLTSED<br>TAIYYCVSRYINYYFAYWGQGTTLTVSSGGGGSGGGGSGGGGSDIVMTQSPSSLT<br>VTAGEKVTMSCKSSQSLLHSGNQRNYLTWYQQKPGQPPKLLIYWASTRESGVPD<br>RFTGSGSGTDFTLTISSVQAEDLAVYYCQNDYDYPYTFGGGTKLEIKGLAVSTISSFF<br>PPGYQIYIWAPLAGTCGVLLLSLVITLYCKRGRKKLLYIFKQPFMRPVQTTQEEDGC<br>SCRFPEEEEGGCELRVKFSRSADAPAYQQGQNQLYNELNLGRREEYDVLDKRRGR<br>DPEMGGKPRRKNPQEGLYNELQKDKMAEAYSEIGMKGERRRGKGHDGLYQGLS<br>TATKDTYDALHMQALPPR |
| 25A10-V2 CAR | 83 | MALPVTALLLPLALLLHAARPEVQLQQSGAELVRPGASVKLSCTASGFNIKDSLIH<br>WVKQRPEQGLEWIGWIDPEDDKTKYAPKFQDKATLTADTSSNTAYLQLSTLTSED<br>TAIYYCVSRYINYYFAYWGQGTTLTVSSGGGGSGGGGSGGGGSDIVMTQSPSSLT<br>VTAGEKVTMSCKSSQSLLHSGNQRNYLTWYQQKPGQPPKLLIYWASTRESGVPD<br>RFTGSGSGTDFTLTISSVQAEDLAVYYCQNDYDYPYTFGGGTKLEIKTTTPAPRPPT<br>PAPTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAY<br>QQGQNQLYNELNLGRREEYDVLDKRRGRDPEMGGKPRRKNPQEGLYNELQKDK<br>MAEAYSEIGMKGERRRGKGHDGLYQGLSTATKDTYDALHMQALPPR |
| 25A10-V3 CAR | 84 | MALPVTALLLPLALLLHAARPEVQLQQSGAELVRPGASVKLSCTASGFNIKDSLIH<br>WVKQRPEQGLEWIGWIDPEDDKTKYAPKFQDKATLTADTSSNTAYLQLSTLTSED<br>TAIYYCVSRYINYYFAYWGQGTTLTVSSGGGGSGGGGSGGGGSDIVMTQSPSSLT<br>VTAGEKVTMSCKSSQSLLHSGNQRNYLTWYQQKPGQPPKLLIYWASTRESGVPD<br>RFTGSGSGTDFTLTISSVQAEDLAVYYCQNDYDYPYTFGGGTKLEIKEPKSPDKTHT<br>CPPCPAPPVAGPSVFLFPPKPKDTLMIARTPEVTCVVVDVSHEDPEVKFNWYVDG<br>VEVHNAKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK<br>IYIWAPLAGTCGVLLLSLVITLYCKRGRKKLLYIFKQPFMRPVQTTQEEDGCSCRFPE<br>EEEGGCELRVKFSRSADAPAYQQGQNQLYNELNLGRREEYDVLDKRRGRDPEMG<br>GKPRRKNPQEGLYNELQKDKMAEAYSEIGMKGERRRGKGHDGLYQGLSTATKDT<br>YDALHMQALPPR |
| 2964-V1 CAR | 85 | MALPVTALLLPLALLLHAARPEVQLVESGGGLVKPGGSLKLSCAASGFTFSDYFMY<br>WVRQTPEKRLEWVAIISDGGIYTYYPDSVKGRFTISRDNAKNNLYLQMSSLKSEDT<br>AMYYCARDGRDDYDGWYFDVWGAGTTVTVSSGGGGSGGGGSGGGGSDIVMT<br>QSHKFMSTSVGDRVNITCKASQDVNTAVAWYQQKPGQSPKLLIYWASTRHAGV<br>PDRFTGSGSGTDYALTISSVQAEDLALYYCQQHYSTPRTFGGGTKLEIKGLAVSTISS<br>FFPPGYQIYIWAPLAGTCGVLLLSLVITLYCKRGRKKLLYIFKQPFMRPVQTTQEED<br>GCSCRFPEEEEGGCELRVKFSRSADAPAYQQGQNQLYNELNLGRREEYDVLDKRR<br>GRDPEMGGKPRRKNPQEGLYNELQKDKMAEAYSEIGMKGERRRGKGHDGLYQ<br>GLSTATKDTYDALHMQALPPR |
| 2964-V2 CAR | 86 | MALPVTALLLPLALLLHAARPEVQLVESGGGLVKPGGSLKLSCAASGFTFSDYFMY<br>WVRQTPEKRLEWVAIISDGGIYTYYPDSVKGRFTISRDNAKNNLYLQMSSLKSEDT<br>AMYYCARDGRDDYDGWYFDVWGAGTTVTVSSGGGGSGGGGSGGGGSDIVMT<br>QSHKFMSTSVGDRVNITCKASQDVNTAVAWYQQKPGQSPKLLIYWASTRHAGV<br>PDRFTGSGSGTDYALTISSVQAEDLALYYCQQHYSTPRTFGGGTKLEIKTTTPAPRP<br>PTPAPTIASQPLSLRPEACRPAAGGAVHTRGLDFACDIYIWAPLAGTCGVLLLSLVI<br>TLYCKRGRKKLLYIFKQPFMRPVQTTQEEDGCSCRFPEEEEGGCELRVKFSRSADA<br>PAYQQGQNQLYNELNLGRREEYDVLDKRRGRDPEMGGKPRRKNPQEGLYNELQ<br>KDKMAEAYSEIGMKGERRRGKGHDGLYQGLSTATKDTYDALHMQALPPR |
| 2964-V3 CAR | 87 | MALPVTALLLPLALLLHAARPEVQLVESGGGLVKPGGSLKLSCAASGFTFSDYFMY<br>WVRQTPEKRLEWVAIISDGGIYTYYPDSVKGRFTISRDNAKNNLYLQMSSLKSEDT<br>AMYYCARDGRDDYDGWYFDVWGAGTTVTVSSGGGGSGGGGSGGGGSDIVMT<br>QSHKFMSTSVGDRVNITCKASQDVNTAVAWYQQKPGQSPKLLIYWASTRHAGV<br>PDRFTGSGSGTDYALTISSVQAEDLALYYCQQHYSTPRTFGGGTKLEIKEPKSPDKT<br>HTCPPCPAPPVAGPSVFLFPPKPKDTLMIARTPEVTCVVVDVSHEDPEVKFNWYV<br>DGVEVHNAKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQKSLSLSP<br>GKIYIWAPLAGTCGVLLLSLVITLYCKRGRKKLLYIFKQPFMRPVQTTQEEDGCSCR |

TABLE 1-continued

Polypeptide sequences of anti-CD38 CARs based on the V1, V2 and V3 versions
in FIG. 8, and of their corresponding components used to make them

| Name of CAR | SEQ ID # | Polypeptide sequence |
|---|---|---|
| | | FPEEEEGGCELRVKFSRSADAPAYQQGQNQLYNELNLGRREEYDVLDKRRGRDPE<br>MGGKPRRKNPQEGLYNELQKDKMAEAYSEIGMKGERRRGKHDGLYQGLSTAT<br>KDTYDALHMQALPPR |
| 16135-V1 CAR | 88 | MALPVTALLLPLALLLHAARPQAYLQQSGAELVRSGASVKMSCKASGYTFTSYNLH<br>WVKQTPGQGLEWIGYIYPGNGGTNYNQKFKGKATLTADTSSSTAYMQISSLTSED<br>SAVYFCARGGIYYYGSSLDYWGQTTLTVSSGGGGSGGGGSGGGGSNIVLTQSP<br>ASLAVSLGQRATISCRASESVDNYGTTFMYWYQQKPGQPPKLLIYLASNLESGVPA<br>RFSGSGSGTDFTLTIDPVEADDAATYYCQQNKEDPWTFGGGTKLEIKGLAVSTISS<br>FFPPGYQIYIWAPLAGTCGVLLLSLVITLYCKRGRKKLLYIFKQPFMRPVQTTQEED<br>GCSCRFPEEEEGGCELRVKFSRSADAPAYQQGQNQLYNELNLGRREEYDVLDKRR<br>GRDPEMGGKPRRKNPQEGLYNELQKDKMAEAYSEIGMKGERRRGKHDGLYQ<br>GLSTATKDTYDALHMQALPPR |
| 1665-V2 CAR | 89 | MALPVTALLLPLALLLHAARPQAYLQQSGAELVRSGASVKMSCKASGYTFTSYNLH<br>WVKQTPGQGLEWIGYIYPGNGGTNYNQKFKGKATLTADTSSSTAYMQISSLTSED<br>SAVYFCARGGIYYYGSSLDYWGQTTLTVSSGGGGSGGGGSGGGGSNIVLTQSP<br>ASLAVSLGQRATISCRASESVDNYGTTFMYWYQQKPGQPPKLLIYLASNLESGVPA<br>RFSGSGSGTDFTLTIDPVEADDAATYYCQQNKEDPWTFGGGTKLEIKTTTPAPRPP<br>TPAPTIASQPLSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKFSRSADAPA<br>YQQGQNQLYNELNLGRREEYDVLDKRRGRDPEMGGKPRRKNPQEGLYNELQKD<br>KMAEAYSEIGMKGERRRGKHDGLYQGLSTATKDTYDALHMQALPPR |
| 16135-V3 CAR | 90 | MALPVTALLLPLALLLHAARPQAYLQQSGAELVRSGASVKMSCKASGYTFTSYNLH<br>WVKQTPGQGLEWIGYIYPGNGGTNYNQKFKGKATLTADTSSSTAYMQISSLTSED<br>SAVYFCARGGIYYYGSSLDYWGQTTLTVSSGGGGSGGGGSGGGGSNIVLTQSP<br>ASLAVSLGQRATISCRASESVDNYGTTFMYWYQQKPGQPPKLLIYLASNLESGVPA<br>RFSGSGSGTDFTLTIDPVEADDAATYYCQQNKEDPWTFGGGTKLEIKEPKSPDKT<br>HTCPPCPAPPVAGPSVFLFPPKPKDTLMIARTPEVTCVVVDVSHEDPEVKFNWYV<br>DGVEVHNAKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQKSLSLSP<br>GKIYIWAPLAGTCGVLLLSLVITLYCKRGRKKLLYIFKQPFMRPVQTTQEEDGCSCR<br>FPEEEEGGCELRVKFSRSADAPAYQQGQNQLYNELNLGRREEYDVLDKRRGRDPE<br>MGGKPRRKNPQEGLYNELQKDKMAEAYSEIGMKGERRRGKHDGLYQGLSTAT<br>KDTYDALHMQALPPR |
| 10F7-V1 CAR | 91 | MALPVTALLLPLALLLHAARPQAYLQQSGAELVRSGASVKMSCKASGYTFTSYNM<br>HWVKQTPGQGLEWIGYIYPGNGGTNYNQKFKDKATLTADTSSSTAYMQISSLTSE<br>DSAVYFCARGGQLGRPWFAYWGQGTLVTVSAGGGGSGGGGSGGGGSNIVLTQ<br>SPASLAASPGQRATISCRASESVDSYGNTFMYWYQQKPGQPPKLLIYLASNLESGV<br>PVRFSGSGSRTDFTLTIDPVEADDAATYYCQQNNEDPWTFGGGTKVEIKGLAVSTI<br>SSFFPPGYQIYIWAPLAGTCGVLLLSLVITLYCKRGRKKLLYIFKQPFMRPVQTTQEE<br>DGCSCRFPEEEEGGCELRVKFSRSADAPAYQQGQNQLYNELNLGRREEYDVLDKR<br>RGRDPEMGGKPRRKNPQEGLYNELQKDKMAEAYSEIGMKGERRRGKHDGLY<br>QGLSTATKDTYDALHMQALPPR |
| 10F7-V2 CAR | 92 | MALPVTALLLPLALLLHAARPQAYLQQSGAELVRSGASVKMSCKASGYTFTSYNM<br>HWVKQTPGQGLEWIGYIYPGNGGTNYNQKFKDKATLTADTSSSTAYMQISSLTSE<br>DSAVYFCARGGQLGRPWFAYWGQGTLVTVSAGGGGSGGGGSGGGGSNIVLTQ<br>SPASLAASPGQRATISCRASESVDSYGNTFMYWYQQKPGQPPKLLIYLASNLESGV<br>PVRFSGSGSRTDFTLTIDPVEADDAATYYCQQNNEDPWTFGGGTKVEIKTTTPAP<br>RPPTPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSRSAD<br>APAYQQGQNQLYNELNLGRREEYDVLDKRRGRDPEMGGKPRRKNPQEGLYNEL<br>QKDKMAEAYSEIGMKGERRRGKHDGLYQGLSTATKDTYDALHMQALPPR |
| 10F7-V3 CAR | 93 | MALPVTALLLPLALLLHAARPQAYLQQSGAELVRSGASVKMSCKASGYTFTSYNM<br>HWVKQTPGQGLEWIGYIYPGNGGTNYNQKFKDKATLTADTSSSTAYMQISSLTSE<br>DSAVYFCARGGQLGRPWFAYWGQGTLVTVSAGGGGSGGGGSGGGGSNIVLTQ<br>SPASLAASPGQRATISCRASESVDSYGNTFMYWYQQKPGQPPKLLIYLASNLESGV<br>PVRFSGSGSRTDFTLTIDPVEADDAATYYCQQNNEDPWTFGGGTKVEIKEPKSPD<br>KTHTCPPCPAPPVAGPSVFLFPPKPKDTLMIARTPEVTCVVVDVSHEDPEVKFNW<br>YVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQKSLSL<br>SPGKIYIWAPLAGTCGVLLLSLVITLYCKRGRKKLLYIFKQPFMRPVQTTQEEDGCSC<br>RFPEEEEGGCELRVKFSRSADAPAYQQGQNQLYNELNLGRREEYDVLDKRRGRDP<br>EMGGKPRRKNPQEGLYNELQKDKMAEAYSEIGMKGERRRGKHDGLYQGLSTA<br>TKDTYDALHMQALPPR |
| 27136-V1 CAR | 94 | MALPVTALLLPLALLLHAARPQVQLKQSGPGLVQPSQSLSITCTVSGFSLTSYNIDW<br>VRQSPGKGLEWLGVIWSGGSTDYNAAFISRLKISKDDSKSQVFFKMNSLQSDDTA<br>IYYCARHSPLVSTPDWYFDVWGAGTTVTVSSGGGGSGGGGSGGGGSQIVLTQSP |

TABLE 1-continued

Polypeptide sequences of anti-CD38 CARs based on the V1, V2 and V3 versions
in FIG. 8, and of their corresponding components used to make them

| Name of CAR | SEQ ID # | Polypeptide sequence |
|---|---|---|
| | | AIMSASPGEKVTMTCSTSSSVSYMHWYQQKSGTSPKRWIYDTSKLASGVPARFS<br>GSGSGTSYSLTINNMEAEDAATYSCQQWSSYPPTFGGGTKLEIKGLAVSTISSFFPP<br>GYQIYIWAPLAGTCGVLLLSLVITLYCKRGRKKLLYIFKQPFMRPVQTTQEEDGCSC<br>RFPEEEEGGCELRVKFSRSADAPAYQQGQNQLYNELNLGRREEYDVLDKRRGRDP<br>EMGGKPRRKNPQEGLYNELQKDKMAEAYSEIGMKGERRRGKGHDGLYQGLSTA<br>TKDTYDALHMQALPPR |
| 2766-V2 CAR | 95 | MALPVTALLLPLALLLHAARPQVQLKQSGPGLVQPSQSLSITCTVSGFSLTSYNIDW<br>VRQSPGKGLEWLGVIWSGGSTDYNAAFISRLKISKDDSKSQVFFKMNSLQSDDTA<br>IYYCARHSPLVSTPDWYFDVWGAGTTVTVSSGGGGSGGGGSGGGGSQIVLTQSP<br>AIMSASPGEKVTMTCSTSSSVSYMHWYQQKSGTSPKRWIYDTSKLASGVPARFS<br>GSGSGTSYSLTINNMEAEDAATYSCQQWSSYPPTFGGGTKLEIKTTTPAPRPPTPA<br>PTIASQPLSLRPEACRPAAGGAVHTRGLDFACDIYIWAPLAGTCGVLLLSLVITLYCK<br>RGRKKLLYIFKQPFMRPVQTTQEEDGCSCRFPEEEEGGCELRVKFSRSADAPAYQ<br>QGQNQLYNELNLGRREEYDVLDKRRGRDPEMGGKPRRKNPQEGLYNELQKDK<br>MAEAYSEIGMKGERRRGKGHDGLYQGLSTATKDTYDALHMQALPPR |
| 2786-V3 CAR | 96 | MALPVTALLLPLALLLHAARPQVQLKQSGPGLVQPSQSLSITCTVSGFSLTSYNIDW<br>VRQSPGKGLEWLGVIWSGGSTDYNAAFISRLKISKDDSKSQVFFKMNSLQSDDTA<br>IYYCARHSPLVSTPDWYFDVWGAGTTVTVSSGGGGSGGGGSGGGGSQIVLTQSP<br>AIMSASPGEKVTMTCSTSSSVSYMHWYQQKSGTSPKRWIYDTSKLASGVPARFS<br>GSGSGTSYSLTINNMEAEDAATYSCQQWSSYPPTFGGGTKLEIKEPKSPDKTHTCP<br>PCPAPPVAGPSVFLFPPKPKDTLMIARTPEVTCVVVDVSHEDPEVKFNWYVDGVE<br>VHNAKTKPREEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQPENNYKTT<br>PPVLDSDGSFFLYSKLTVDKSRWQQGNVFSCSVMHEALHNHYTQKSLSLSPGKIYI<br>WAPLAGTCGVLLLSLVITLYCKRGRKKLLYIFKQPFMRPVQTTQEEDGCSCRFPEEE<br>EGGCELRVKFSRSADAPAYQQGQNQLYNELNLGRREEYDVLDKRRGRDPEMGG<br>KPRRKNPQEGLYNELQKDKMAEAYSEIGMKGERRRGKGHDGLYQGLSTATKDTY<br>DALHMQALPPR |
| 13F11-V1 CAR | 97 | MALPVTALLLPLALLLHAARPQIQLVQSGPELKKPGETVKISCKASGYTFKKYGMN<br>WVKQAPGKGLKWMGWINTNTGEPTYAEEFKGRFAFSLETSASTAYLQINNLKNE<br>DTATYFCARWYYGSTPSSYTMDYWGQGTSVTVSSGGGGSGGGGSGGGGSETTV<br>TQSPASLSVATGEKVTIRCITSTDIDDDMNWYQQKPGEPPKVLISEGNTLRPGVPS<br>RFSSSGYGTDFVFTIENTLSEDVADYYCLQSNNMPYTFGGGTKLEIKGLAVSTISSFF<br>PPGYQIYIWAPLAGTCGVLLLSLVITLYCKRGRKKLLYIFKQPFMRPVQTTQEEDGC<br>SCRFPEEEEGGCELRVKFSRSADAPAYQQGQNQLYNELNLGRREEYDVLDKRRGR<br>DPEMGGKPRRKNPQEGLYNELQKDKMAEAYSEIGMKGERRRGKGHDGLYQGLS<br>TATKDTYDALHMQALPPR |
| 13F11-V2 CAR | 98 | MALPVTALLLPLALLLHAARPQIQLVQSGPELKKPGETVKISCKASGYTFKKYGMN<br>WVKQAPGKGLKWMGWINTNTGEPTYAEEFKGRFAFSLETSASTAYLQINNLKNE<br>DTATYFCARWYYGSTPSSYTMDYWGQGTSVTVSSGGGGSGGGGSGGGGSETTV<br>TQSPASLSVATGEKVTIRCITSTDIDDDMNWYQQKPGEPPKVLISEGNTLRPGVPS<br>RFSSSGYGTDFVFTIENTLSEDVADYYCLQSNNMPYTFGGGTKLEIKTTTPAPRPPT<br>PAPTIASQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSADAPAY<br>QQGQNQLYNELNLGRREEYDVLDKRRGRDPEMGGKPRRKNPQEGLYNELQKDK<br>MAEAYSEIGMKGERRRGKGHDGLYQGLSTATKDTYDALHMQALPPR |
| 13F11-V3 CAR | 99 | MALPVTALLLPLALLLHAARPQIQLVQSGPELKKPGETVKISCKASGYTFKKYGMN<br>WVKQAPGKGLKWMGWINTNTGEPTYAEEFKGRFAFSLETSASTAYLQINNLKNE<br>DTATYFCARWYYGSTPSSYTMDYWGQGTSVTVSSGGGGSGGGGSGGGGSETTV<br>TQSPASLSVATGEKVTIRCITSTDIDDDMNWYQQKPGEPPKVLISEGNTLRPGVPS<br>RFSSSGYGTDFVFTIENTLSEDVADYYCLQSNNMPYTFGGGTKLEIKEPKSPDKTHT<br>CPPCPAPPVAGPSVFLFPPKPKDTLMIARTPEVTCVVVDVSHEDPEVKFNWYVDG<br>VEVHNAKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK<br>IYIWAPLAGTCGVLLLSLVITLYCKRGRKKLLYIFKQPFMRPVQTTQEEDGCSCRFPE<br>EEEGGCELRVKFSRSADAPAYQQGQNQLYNELNLGRREEYDVLDKRRGRDPEMG<br>GKPRRKNPQEGLYNELQKDKMAEAYSEIGMKGERRRGKGHDGLYQGLSTATKDT<br>YDALHMQALPPR |
| 28F5-V1 CAR | 100 | MALPVTALLLPLALLLHAARPQIQLVQSGPELKKPGETVKISCKASGYTFTKYGMN<br>WVKQTPGKGLKWMGWINTNSGEPTYAEEFKGRFAFSLETSASTAYLQINNLKNE<br>DTATYFCARGAYYRYDGEVSYYAMDYWGQGTSVTVSSGGGGSGGGGSGGGGS<br>QIILTQSPAIMSASLGERVTMTCTATSSLSSSYLHWYQQKPGSSPKLWIYSTSHLAS<br>GVPARFSGGGSGTSYSLTISSSMEAEDAATYYCHQYHLSPYTFGGGTKLEIKGLAVST<br>ISSFFPPGYQIYIWAPLAGTCGVLLLSLVITLYCKRGRKKLLYIFKQPFMRPVQTTQEE<br>DGCSCRFPEEEEGGCELRVKFSRSADAPAYQQGQNQLYNELNLGRREEYDVLDKR<br>RGRDPEMGGKPRRKNPQEGLYNELQKDKMAEAYSEIGMKGERRRGKGHDGLY<br>QGLSTATKDTYDALHMQALPPR |

TABLE 1-continued

Polypeptide sequences of anti-CD38 CARs based on the V1, V2 and V3 versions in FIG. 8, and of their corresponding components used to make them

| Name of CAR | SEQ ID # | Polypeptide sequence |
| --- | --- | --- |
| 28F5-V2 CAR | 101 | MALPVTALLLPLALLLHAARPQIQLVQSGPELKKPGETVKISCKASGYTFTKYGMN WVKQTPGKGLKWMGWINTNSGEPTYAEEFKGRFAFSLETSASTAYLQINNLKNE DTATYFCARGAYYRYDGEVSYYAMDYWGQGTSVTVSSGGGGSGGGGSGGGGS QIILTQSPAIMSASLGERVTMTCTATSSLSSSYLHWYQQKPGSSPKLWIYSTSHLAS GVPARFSGGGSGTSYSLTISSMEAEDAATYYCHQYHLSPYTFGGGTKLEIKTTTPAP RPPTPAPTIASQPLSLRPEACRPAAGGAVHTRGLDFACDIYIWAPLAGTCGVLLLSL VITLYCKRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR |
| 28F5-V3 CAR | 102 | MALPVTALLLPLALLLHAARPQIQLVQSGPELKKPGETVKISCKASGYTFTKYGMN WVKQTPGKGLKWMGWINTNSGEPTYAEEFKGRFAFSLETSASTAYLQINNLKNE DTATYFCARGAYYRYDGEVSYYAMDYWGQGTSVTVSSGGGGSGGGGSGGGGS QIILTQSPAIMSASLGERVTMTCTATSSLSSSYLHWYQQKPGSSPKLWIYSTSHLAS GVPARFSGGGSGTSYSLTISSMEAEDAATYYCHQYHLSPYTFGGGTKLEIKEPKSPD KTHTCPPCPAPPVAGPSVFLFPPKPKDTLMIARTPEVTCVVVDVSHEDPEVKFNW YVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSL SPGKIYIWAPLAGTCGVLLLSLVITLYCKRGRKKLLYIFKQPFMRPVQTTQEEDGCSC RFPEEEEGGCELRVKFSRSADAPAYQQGQNQLYNELNLGRREEYDVLDKRRGRDP EMGGKPRRKNPQEGLYNELQKDKMAEAYSEIGMKGERRRGKGHDGLYQGLSTA TKDTYDALHMQALPPR |
| GMB005-V1 CAR | 103 | MALPVTALLLPLALLLHAARPEVQLLESGGGLVQPGGSLRLSCAVSGFTFNSFAMS WVRQAPGKGLEWVSAISGSGGGTYYADSVKGRFTISRDNSKNTLYLQMNSLRAE DTAVYFCAKDKILWFGEPVFDYWGQGTLVTVSSASGGGGSGGGGSGGGGSEIVL TQSPATLSLSPGERATLSCRASQSVSSYLAWYQQKPGQAPRLLIYDASNRATGIPA RFSGSGSGTDFTLTISSLEPEDFAVYYCQQRSNWPPTFGQGTKVEIKGLAVSTISSF FPPGYQIYIWAPLAGTCGVLLLSLVITLYCKRGRKKLLYIFKQPFMRPVQTTQEEDG CSCRFPEEEEGGCELRVKFSRSADAPAYQQGQNQLYNELNLGRREEYDVLDKRRG RDPEMGGKPRRKNPQEGLYNELQKDKMAEAYSEIGMKGERRRGKGHDGLYQGL STATKDTYDALHMQALPPR |
| GMB005-V2 CAR | 104 | MALPVTALLLPLALLLHAARPEVQLLESGGGLVQPGGSLRLSCAVSGFTFNSFAMS WVRQAPGKGLEWVSAISGSGGGTYYADSVKGRFTISRDNSKNTLYLQMNSLRAE DTAVYFCAKDKILWFGEPVFDYWGQGTLVTVSSASGGGGSGGGGSGGGGSEIVL TQSPATLSLSPGERATLSCRASQSVSSYLAWYQQKPGQAPRLLIYDASNRATGIPA RFSGSGSGTDFTLTISSLEPEDFAVYYCQQRSNWPPTFGQGTKVEIKTTTPAPRPPT PAPTIASQPLSLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFSRSADAPAY QQGQNQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| GMB005-V3 CAR | 105 | MALPVTALLLPLALLLHAARPEVQLLESGGGLVQPGGSLRLSCAVSGFTFNSFAMS WVRQAPGKGLEWVSAISGSGGGTYYADSVKGRFTISRDNSKNTLYLQMNSLRAE DTAVYFCAKDKILWFGEPVFDYWGQGTLVTVSSASGGGGSGGGGSGGGGSEIVL TQSPATLSLSPGERATLSCRASQSVSSYLAWYQQKPGQAPRLLIYDASNRATGIPA RFSGSGSGTDFTLTISSLEPEDFAVYYCQQRSNWPPTFGQGTKVEIKEPKSPDKTH TCPPCPAPPVAGPSVFLFPPKPKDTLMIARTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPG KIYIWAPLAGTCGVLLLSLVITLYCKRGRKKLLYIFKQPFMRPVQTTQEEDGCSCRFP EEEEGGCELRVKFSRSADAPAYQQGQNQLYNELNLGRREEYDVLDKRRGRDPEM GGKPRRKNPQEGLYNELQKDKMAEAYSEIGMKGERRRGKGHDGLYQGLSTATK DTYDALHMQALPPR |

According to a preferred embodiment, the anti-CD38 specific chimeric antigen receptor (anti-CD38 CAR) of the invention comprises a polypeptide sequence displaying at least 90%, at least 95%, at least 98% or at least 99% identity to one selected from SEQ ID NO. 82-84 (25A10), SEQ ID NO. 100-102 (28F5), SEQ ID NO. 97-99 (13F11) and SEQ ID NO. 88-90 (16B5).

According to a more preferred embodiment, the anti-CD38 specific chimeric antigen receptor (anti-CD38 CAR) of the invention comprises a polypeptide sequence displaying at least 90%, at least 95%, at least 98% or at least 99% identity to one selected from SEQ ID NO. 82-84 (25A10) and SEQ ID NO. 100-102 (28F5).

According to a more preferred embodiment, the anti-CD38 specific chimeric antigen receptor (anti-CD38 CAR) of the invention comprises a polypeptide sequence displaying at least 90%, at least 95%, at least 98% or at least 99% identity to SEQ ID NO. 82-84 (25A10).

According to a even more preferred embodiment, the anti-CD38 specific chimeric antigen receptor (anti-CD38 CAR) of the invention comprises a polypeptide sequence displaying at least 90%, at least 95%, at least 98% or at least 99% identity to SEQ ID NO. 82 (25A10-v1).

According to a more preferred embodiment, the anti-CD38 specific chimeric antigen receptor (anti-CD38 CAR) of the invention comprises a polypeptide sequence displaying at least 90%, at least 95%, at least 98% or at least 99% identity to NO. 100-102 (28F5).

According to a more preferred embodiment, the anti-CD38 specific chimeric antigen receptor (anti-CD38 CAR) of the invention comprises a polypeptide sequence displaying at least 90%, at least 95%, at least 98% or at least 99% identity to one selected from SEQ ID NO. 97-99 (13F11).

The present invention is more particularly drawn to immune cells that are endowed with a CAR presenting some identity with those described in the present application and that would bear rare-cutting endonuclease induced mutations in a gene encoding the cell marker targeted by said CAR (i.e. the CAR displays affinity with the product of said inactivated gene). By identity is meant at least 70%, preferably 80%, more preferably 90% and even more preferably 95% polynucleotide or polypeptide identity as determined by the software such as FASTA, or BLAST which are available as a part of the GCG sequence analysis package (University of Wisconsin, Madison, Wis.). BLASTP "Identities" shows the number and fraction of total residues in the high scoring sequence pairs which are identical. Amino acid sequences having these degrees of identity or similarity or any intermediate degree of identity of similarity to the amino acid sequences disclosed herein are contemplated and encompassed by this disclosure. The same applies with respect to polynucleotide sequences using BLASTN.

The present invention relates also to an engineered immune cell (preferably T cell) which expresses an anti-CD38 specific chimeric antigen receptor (anti-CD38 CAR) such as described previously, said immune cell having its endogenous CD38 gene genetically inactivated or mutated, said CD38 antigen being present both on the surface of said immune cell and the pathological cell.

In a preferred embodiment, said engineered immune cell expresses an anti-CD38 specific chimeric antigen receptor (anti-CD38 CAR), said immune cell having its endogenous CD38 and TCR genes genetically inactivated or mutated.

In an embodiment, said engineered immune cell expresses an anti-CD38 specific chimeric antigen receptor (anti-CD38 CAR), said immune cell having its endogenous CD38, TCR and dCK genes genetically inactivated or mutated.

In a preferred embodiment, said engineered immune cell expresses an anti-CD38 specific chimeric antigen receptor (anti-CD38 CAR) which has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), said immune cell (preferably T cell) having its endogenous CD38 gene genetically inactivated or mutated, said CD38 antigen being present both on the surface of said immune cell and the pathological cell.

In a more preferred embodiment, said engineered immune cell expresses an anti-CD38 specific chimeric antigen receptor (anti-CD38 CAR) which has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), said immune cell (preferably T cell) having its endogenous CD38 and TCR genes genetically inactivated or mutated, said CD38 antigen being present both on the surface of said immune cell and the pathological cell.

In the above embodiments, said genetic inactivation or mutation is performed preferably by the use of specific rare-cutting endonuclease such as described in the present invention.

The present invention relates also to a population comprising at least two an engineered immune cells (preferably T cells) which expresses an anti-CD38 specific chimeric antigen receptor (anti-CD38 CAR) such as described previously, said immune cell having its endogenous CD38 gene genetically inactivated or mutated, said CD38 antigen being present both on the surface of said immune cell and the pathological cell.

In a preferred embodiment, said population comprises at two engineered immune cells expressing an anti-CD38 specific chimeric antigen receptor (anti-CD38 CAR) which has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), said immune cells (preferably T cells) having its endogenous CD38 gene genetically inactivated or mutated, said CD38 antigen being present both on the surface of said immune cell and the pathological cell.

Extracellular Domain

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

Single-Chain Variable Antibodies (scFvs)

The antigen binding domain of the anti-CD38 CARs of the invention can be any domain that binds to the off-tissue antigen including but not limited to a monoclonal antibody, a recombinant antibody, a human antibody, a humanized antibody, and a functional fragment thereof.

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system, and more especially by a T cell transduced with a viral vector comprising a nucleic acid sequence encoding CDR regions of an antibody. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.).

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind GD3 using the functional assays described herein.

According to one embodiment, the anti-CD38 specific chimeric antigen receptor (anti-CD38 CAR) of the invention comprise $V_H$ and $V_L$ variable chain which polypeptide sequence display at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4).

Said above sequences of anti-CD38VH and VL chains and their respective corresponding CDRs are presented in the following Table 2.

TABLE 2

Sequences of VH and VL chains of the 8 couple of scFy anti-CD38 antibodies and their respective CDR.

| Name | VH or VL chain | SEQ ID # | Polypeptide or nucleic acid sequence |
|---|---|---|---|
| 25A10 | VL | 10 | DIVMTQSPSSLTVTAGEKVTMSCKSSQSLLHSGNQRNYLT WYQQKPGQPPKLLIYWASTRESGVPDRFTGSGSGTDFTL TISSVQAEDLAVYYCQNDYDYPYTFGGGTKLEIK |
| | CDR1 | 11 | QSLLHSGNQRNY |
| | CDR2 | 12 | WAS |
| | CDR3 | 13 | QNDYDYPYT |
| | VH | 14 | EVQLQQSGAELVRPGASVKLSCTASGFNIKDSLIHWVKQR PEQGLEWIGWIDPEDDKTKYAPKFQDKATLTADTSSNTA YLQLSTLTSEDTAIYYCVSRYINYYFAYWGQGTTLTVSS |
| | CDR1 | 15 | GFNIKDSL |
| | CDR2 | 16 | IDPEDDKT |
| | CDR3 | 17 | VSRYINYYFAY |
| 29B4 | VL | 18 | DIVMTQSHKFMSTSVGDRVNITCKASQDVNTAVAWYQ QKPGQSPKLLIYWASTRHAGVPDRFTGSGSGTDYALTISS VQAEDLALYYCQQHYSTPRTFGGGTKLEIK |
| | CDR1 | 19 | QDVNTA |
| | CDR2 | 20 | WAS |
| | CDR3 | 21 | QQHYSTPRT |
| | VH | 22 | EVQLVESGGGLVKPGGSLKLSCAASGFTFSDYFMYWVRQ TPEKRLEWVAIISDGGIYTYYPDSVKGRFTISRDNAKNNLYL QMSSLKSEDTAMYYCARDGRDDYDGWYFDVWGAGTTV TVSS |
| | CDR1 | 23 | GFTFSDYF |

TABLE 2-continued

Sequences of VH and VL chains of the 8 couple of scFv anti-CD38 antibodies and their respective CDR.

| Name | VH or VL chain | SEQ ID # | Polypeptide or nucleic acid sequence |
|---|---|---|---|
| | CDR2 | 24 | ISDGGIYT |
| | CDR3 | 25 | ARDGRDDYDGWYFDV |
| 16B5 | VL | 26 | NIVLTQSPASLAVSLGQRATISCRASESVDNYGTTFMYWYQQKPGQPPKLLIYLASNLESGVPARFSGSGSGTDFTLTIDPVEADDAATYYCQQNKEDPWTFGGGTKLEIK |
| | CDR1 | 27 | ESVDNYGTTF |
| | CDR2 | 28 | LAS |
| | CDR3 | 29 | QQNKEDPWT |
| | VH | 30 | QAYLQQSGAELVRSGASVKMSCKASGYTFTSYNLHWVKQTPGQGLEWIGYIYPGNGGTNYNQKFKGKATLTADTSSSTAYMQISSLTSEDSAVYFCARGGIYYYGSSLDYWGQGTTLTVSS |
| | CDR1 | 31 | GYTFTSYN |
| | CDR2 | 32 | IYPGNGGT |
| | CDR3 | 33 | ARGGIYYYGSSLDY |
| 10F7 | VL | 34 | NIVLTQSPASLAASPGQRATISCRASESVDSYGNTFMYWYQQKPGQPPKLLIYLASNLESGVPVRFSGSGSRTDFTLTIDPVEADDAATYYCQQNNEDPWTFGGGTKVEIK |
| | CDR1 | 35 | ESVDSYGNTF |
| | CDR2 | 36 | LAS |
| | CDR3 | 37 | QQNNEDPWT |
| | VH | 38 | QAYLQQSGAELVRSGASVKMSCKASGYTFTSYNMHWVKQTPGQGLEWIGYIYPGNGGTNYNQKFKDKATLTADTSSSTAYMQISSLTSEDSAVYFCARGGQLGRPWFAYWGQGTLVTVSA |
| | CDR1 | 39 | GYTFTSYN |
| | CDR2 | 40 | IYPGNGGT |
| | CDR3 | 41 | ARGGQLGRPWFAY |
| 27B6 | VL | 42 | QIVLTQSPAIMSASPGEKVTMTCSTSSSVSYMHWYQQKSGTSPKRWIYDTSKLASGVPARFSGSGSGTSYSLTINNMEAEDAATYSCQQWSSYPPTFGGGTKLEIK |
| | CDR1 | 43 | SSVSY |
| | CDR2 | 44 | DTS |
| | CDR3 | 45 | QQWSSYPPT |
| | VH | 46 | QVQLKQSGPGLVQPSQSLSITCTVSGFSLTSYNIDWVRQSPGKGLEWLGVIWSGGSTDYNAAFISRLKISKDDSKSQVFFKMNSLQSDDTAIYYCARHSPLVSTPDWYFDVWGAGTTVTVSS |
| | CDR1 | 47 | GFSLTSYN |
| | CDR2 | 48 | IWSGGST |
| | CDR3 | 49 | ARHSPLVSTPDWYFDV |
| 13F11 | VL | 50 | ETTVTQSPASLSVATGEKVTIRCITSTDIDDDMNWYQQKPGEPPKVLISEGNTLRPGVPSRFSSSGYGTDFVFTIENTLSEDVADYYCLQSNNMPYTFGGGTKLEIK |
| | CDR1 | 51 | TDIDDD |
| | CDR2 | 52 | EGN |
| | CDR3 | 53 | LQSNNMPYT |
| | VH | 54 | QIQLVQSGPELKKPGETVKISCKASGYTFKKYGMNWVKQAPGKGLKWMGWINTNTGEPTYAEEFKGRFAFSLETSASTAYLQINNLKNEDTATYFCARWYYGSTPSSYTMDYWGQGTSVTVSS |
| | CDR1 | 55 | GYTFKKYG |
| | CDR2 | 56 | INTNTGEP |
| | CDR3 | 57 | ARWYYGSTPSSYTMDY |
| 28F5 | VL | 58 | QIILTQSPAIMSASLGERVTMTCTATSSLSSSYLHWYQQKPGSSPKLWIYSTSHLASGVPARFSGGGSGTSYSLTISSMEAEDAATYYCHQYHLSPYTFGGGTKLEIK |
| | CDR1 | 59 | SSLSSSY |
| | CDR2 | 60 | STS |
| | CDR3 | 61 | HQYHLSPYT |
| | VH | 62 | QIQLVQSGPELKKPGETVKISCKASGYTFTKYGMNWVKQTPGKGLKWMGWINTNSGEPTYAEEFKGRFAFSLETSASTAYLQINNLKNEDTATYFCARGAYYRYDGEVSYYAMDYWGQGTSVTVSS |
| | CDR1 | 63 | GYTFTKYG |
| | CDR2 | 64 | INTNSGEP |
| | CDR3 | 65 | ARGAYYRYDGEVSYYAMDY |

TABLE 2-continued

Sequences of VH and VL chains of the 8 couple of scFv anti-CD38 antibodies and their respective CDR.

| Name | VH or VL chain | SEQ ID # | Polypeptide or nucleic acid sequence |
|---|---|---|---|
| GMB005 | VL | 66 | EIVLTQSPATLSLSPGERATLSCRASQSVSSYLAWYQQKPG<br>QAPRLLIYDASNRATGIPARFSGSGSGTDFTLTISSLEPEDF<br>AVYYCQQRSNWPPTFGQGTKVEIK |
|  | CDR1 | 67 | QSVSSY |
|  | CDR2 | 68 | DAS |
|  | CDR3 | 69 | QQRSNWPPT |
|  | VH | 70 | EVQLLESGGGLVQPGGSLRLSCAVSGFTFNSFAMSWVRQ<br>APGKGLEWVSAISGSGGGTYYADSVKGRFTISRDNSKNTL<br>YLQMNSLRAEDTAVYFCAKDKILWFGEPVFDYWGQGTL<br>VTVSSAS |
|  | CDR1 | 71 | GFTFNSFA |
|  | CDR2 | 72 | ISGSGGGT |
|  | CDR3 | 73 | AKDKILWFGEPVFDY |

According to a preferred embodiment, the anti-CD38 specific chimeric antigen receptor (anti-CD38 CAR) of the invention comprise $V_H$ and $V_L$ variable chain which polypeptide sequence display at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11) or SEQ ID NO. 30 and 26 (16B5).

According to a more preferred embodiment, the anti-CD38 specific chimeric antigen receptor (anti-CD38 CAR) of the invention comprise $V_H$ and $V_L$ variable chain which polypeptide sequence display at least 90%, at least 95%, at least 98% or at least 99% identity to respectively SEQ ID NO. 14 and 10 (25A10) or SEQ ID NO. 62 and 58 (28F5).

According to one embodiment, the anti-CD38 specific chimeric antigen receptor (anti-CD38 CAR) of the invention comprises $V_H$ and $V_L$ variable regions containing the CDRs sequences of respectively SEQ ID NO.15-17 and SEQ ID NO.11-13; respectively SEQ ID NO.63-65 and SEQ ID NO.59-61; respectively SEQ ID NO.55-57 and SEQ ID NO.51-53; respectively SEQ ID NO.31-33 and SEQ ID NO.27-29; respectively SEQ ID NO.39-41 and SEQ ID NO.35-37; respectively SEQ ID NO.47-49 and SEQ ID NO.43-45 or respectively SEQ ID NO.23-25 and SEQ ID NO.19-21.

In a preferred embodiment, the anti-CD38 specific chimeric antigen receptor (anti-CD38 CAR) of the invention comprises $V_H$ and $V_L$ variable regions containing the CDRs sequences of respectively SEQ ID NO.15-17 and SEQ ID NO.11-13; respectively SEQ ID NO.63-65 and SEQ ID NO.59-61; respectively SEQ ID NO.55-57 and SEQ ID NO.51-53 or respectively SEQ ID NO.31-33.

In a more preferred embodiment, the anti-CD38 specific chimeric antigen receptor (anti-CD38 CAR) of the invention comprises $V_H$ and $V_L$ variable regions containing the CDRs sequences of respectively SEQ ID NO.15-17 and SEQ ID NO.11-13 or respectively SEQ ID NO.63-65 and SEQ ID NO.59-61.

In addition to the CAR targeting the antigen marker, which is common to the pathological cells and the T-cells, such as CD38, it is envisioned to express further CARs directed towards other antigen markers not necessarily expressed by the T-cells, so as to enhancing T-cells specificity.

In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains.

Examples of chimeric antigen receptor that can be further expressed by the T-cells to create multi-specific cells, are antigen receptors directed against multiple myeloma or lymphoblastic leukemia antigen markers, such as TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708), and FCRL5 (UNIPROT Q68SN8).

As further examples for conferring another specificity alongside CD38, the antigen of the target can be from any cluster of differentiation molecules (e.g. CD16, CD64, CD78, CD96, CLL1, CD116, CD117, CD71, CD45, CD71, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C(TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. Antigens are not necessarily surface marker antigens but can be also endogenous small antigens presented by HLA class I at the surface of the cells.

Downregulation or mutation of target antigens is commonly observed in cancer cells, creating antigen-loss escape variants. Thus, to offset tumor escape and render immune cell more specific to target, the CD38 specific CAR according to the invention can comprise another extracellular ligand-binding domains, to simultaneously bind different elements in target thereby augmenting immune cell activation and function.

In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR.

CARs with a Lower Affinity for CD38

According to another embodiment, anti-CD38 of the invention comprises scFvs with a lower affinity for CD38 antigen.

Such CARs are designed to prevent a possible risk of toxicity linked to the use in vivo of such engineered immune cells.

By "affinity" is meant a measure of the binding strength between antibody and a simple hapten or antigen determinant. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. In the case of an antibody (Ab) binding to an antigen (Ag), the affinity constant is used (expressed as inverted dissociation constant). Ab Ag=AbAg Ka= [AbAca=1 [Ab)] [Ag] K, The chemical equilibrium of antibody binding is also the ratio of the on-rate (k forward) and off-rate (kback) constants. Two antibodies can have the same affinity, but one may have both a high on- and off-rate constant, while the other may have both a low on- and off-rate constant.=kforward=on-rate kback off-rate Antibody activity in functional assays (e.g., cell lysis assay) is also reflective of antibody affinity. In various embodiments of the invention, the antigen recognizing receptor has low affinity. Low affinity includes micromolar and nanomolar affinities (e.g. $10^{-5}$, $5\times10^{-6}$, $10^{-6}$, $5\times10^{-7}$, $10^{-7}$, $5\times10^{-8}$, $10^{-8}$, $5\times10^{-9}$, $10^{-9}$ M). Antibody and affinities can be phenotypically characterized and compared using functional assay (e.g., cell lysis assay).

The present invention encompasses also anti-CD38 CARs with a low affinity for CD38 antigen, such as those comprising VH and VL chains in their scFvs corresponding to the monoclonal 2C2, 5G9, 9E2, 28B9, 26D8, 15D1, and 23F2 antibodies.

According to one preferred embodiment, said anti-CD38 CARs with a low affinity for CD38 antigen comprise VH and VL chains in their scFvs corresponding to the monoclonal 2C2 or 5G9 antibodies (called also m2C2 and m5G9).

According to an embodiment, $V_H$ and $V_L$ of said scFvs displaying a lower affinity for CD38 antigen comprise a polypeptide sequence displaying at least 90%, at least 95%, at least 98% or at least 99% identity to respectively VH and VL chains of m2C2 antibody of SEQ ID NO. 132 (EVKLVESGGGLVQPGGSLKLSCATSGFTFSDYYMF-WVRQTPEKRLEWVAYISNGDGNTYYPDTLKGR-FTISRDNA NNTLYLQMSRLKSEDTAMYYCARSIS-RYFDVWGAGTTVTVSS) and SEQ ID NO. 133 (DIVMTQSPATLSVTPGDRVSLSCRASQSISDFLHWY-QQKSHESPRLLIKYVSQSISGIPSRFSGSGSGSD-FTLSINSVE PEDVGVYYCQNAHSFPSTFGGGT-KLEIK); or to respectively VH and VL chains of m5G9 antibody of SEQ ID NO.134 (EIHLQQSGPELVKPGAS-VKISCKASGYSFTDYNIYWVKQSHGESLEWVGYID-PYNGGAYYNQKFKAMATLTVDKS SSTAFMHLNSLT-SEDSAVYYCARKGVYGLAYWGQGTLVTVSS) and SEQ ID NO.135 (DIQMTQSPASLSVSVGETVTITCRAS-ESIYSN LAWYQQKQGKSPQLLVYASTH-LADGVPSRFSGSGSGAQYSLKI NS LQSEDFGSYYC-QHFWGTPYTFGGGTKLEIK);

or to respectively VH and VL chains of m9E2 antibody of SEQ ID NO.142 (EVQLQQSGPELEKPGASVKISCKAS-GYSFTDYNMNWVKQSNGKSLEWIGNIDPDYGGT-TYNQKFKGKATLTVDK SSSTAYMQLRSLTSED-SAVYYCARSGYRYGFVYWGQGTLVTVSA) and SEQ ID NO.143 (DIVMTQAAFSNPVTLGTSASISCRSSK-SLLHSNGITYLYWYLQKPGQSPQLLIYQMSNLAS-GVPDRFSSSGSGTDFT LRISRVEAEDVGVYYCAQN-LELPWTFGGGTKLEIK), or to respectively VH and VL chains of m28B9 antibody of SEQ ID NO.144 (EVQLQQSGAELVRPGAS-VKLSCTASGFNIKDDYLHWMKQRPEQGLEWIGRID-PANGNTKSDPKFQDKATIDADT SSNTAYLQLNSLT-SEDTAVYYCAKGPWFPYWGQGTLVTVSA) and SEQ ID NO.145 (DIQMTQSPASQSASLGESVTIT-CLASQTIGTWLAWYQQKPGKSPQLLIYAAT-SLADGVPSRFSGSGSGTKFSFKISS LQAEDFVSYHC-QQLYRTPLTFGGGTKLEIK);

or to respectively VH and VL chains of m26D8 antibody of SEQ ID NO.146 (QVQLQQPGAEMVRPGAS-VKLSCKASGYTFTDYWMHWVKQRPGQGLEWIG-KIDPSDSETHYHQKFKDKATLTV DKSSSTAYLQFK-SLTSEDSAVHYCAREGIWLRYAMDYWGQGTSVTVSS) and SEQ ID NO.147 (DIVMTQSQKFMSTSVGDRVS-VTCKASQNVGTNVAWYQQKPGQSPKALI-YSASYRYSGVPDRFTGSGSGTDFTLT VSSVQSED-LAEYFCQQYNSYPYTFGGGTKLEIK).

or to respectively VH and VL chains of m15D1 antibody of SEQ ID NO.148 (EVQLQQSGPELVKPGASVKM-SCRASGYSITDYNMHWVKQSHGKSLEWIGYIDPDN-GATNNNQKFKGKATLTVD KSSSTAYMQLSSLTSED-SAVYYCARSEGYQYYYAMDYWGQGTSVTVSS) and SEQ ID NO.149 (DIVMTQAAFSNPVALGTSASISC-SSSKSLLHSNGITYLHWYLQRPGQSPQLLIYRMSN-LASGVPDRFSGSGSGTDFT LRISRVEAEDVGVYY-CAQMVERPWTFGGGTKLEIK), or to respectively VH and VL chains of m23F2 antibody of SEQ ID NO.150 (QVQVQQPGAELVKPGASVKLSCK-ASGYTFTSYWINWVKQRPGQGLEWIGNIYPGSSST-NHNEKFKSKATLTVDT SSSTAYMQLSS-LTSDDSAVYYCARRGSSPSYTMDYWGQGTSVTVSS) and SEQ ID NO.151 (DIVLTQSPASLAVAL-GQRATISCRASKSVSTFGYSYMHWYQQKPGQAP-KLLIYLASNLESGVPARFSGSGSGTDFTL KIH-PVEEEDAATYYCLHSRELPWTFGGGTKLEIK).

According to a preferred embodiment, $V_H$ and $V_L$ of said scFvs displaying a lower affinity for CD38 antigen comprise a polypeptide sequence displaying at least 90%, at least 95%, at least 98% or at least 99% identity to respectively VH and VL chains of m2C2 antibody of SEQ ID NO. 132 (EVKLVESGGGLVQPGGSLKLSCATSGFTFSDYYMF- WVRQTPEKRLEWVAYISNGDGNTYYPDTLKGR-
FTISRDNA NNTLYLQMSRLKSEDTAMYYCARSIS-
RYFDVWGAGTTVTVSS) and SEQ ID NO. 133
(DIVMTQSPATLSVTPGDRVSLSCRASQSISDFLHWY-
QQKSHESPRLLIKYVSQSISGIPSRFSGSGSGSD-
FTLSINSVE PEDVGVYYCQNAHSFPSTFGGGT-
KLEIK); and to respectively VH and VL chains of m5G9
antibody of SEQ ID NO.134 (EIHLQQSGPELVKPGAS-
VKISCKASGYSFTDYNIYWVKQSHGESLEWVGYID-
PYNGGAYYNQKFKAMATLTVDKS SSTAFMHLNSLT-
SEDSAVYYCARKGVYGLAYWGQGTLVTVSS) and
SEQ ID NO.135 (DIQMTQSPASLSVSVGETVTITCRAS-
ESIYSN LAWYQQKQGKSPQLLVYASTH-
LADGVPSRFSGSGSGAQYSLKI NS LQSEDFGSYYC-
QHFWGTPYTFGGGTKLEIK).

According to one embodiment, the anti-CD38 CARs with a low affinity for CD38 antigen of the present invention comprise an extra cellular ligand binding-domain comprising VH and VL from a monoclonal anti-CD38 antibody, a hinge, a transmembrane domain, a cytoplasmic domain including a signaling domain—preferably CD3 zeta signaling domain, and a co-stimulatory domain—preferably from 4-1BB-, wherein said V$_H$ and V$_L$ comprise a polypeptide sequence displaying at least 90%, at least 95%, at least 98% or at least 99% identity to respectively VH and VL chains of m2C2 antibody of SEQ ID NO. 132 (EVKLVESGGGLVQPGG-
SLKLSCATSGFTFSDYYMFWVRQTPEKRLEWVAYIS-
NGDGNTYYPDTLKGRFTISRDNA NNTLYLQMSR-
LKSEDTAMYYCARSISRYFDVWGAGTTVTVSS) and
SEQ ID NO. 133 (DIVMTQSPATLSVT-
PGDRVSLSCRASQSISDFLHWYQQKSHESPRL-
LIKYVSQSISGIPSRFSGSGSGSDFTLSINSVE PED-
VGVYYCQNAHSFPSTFGGGTKLEIK); and to respectively VH and VL chains of m5G9 antibody of SEQ ID NO.134 (EIHLQQSGPELVKPGASVKISCKASGYS-
FTDYNIYWVKQSHGESLEWVGYIDPYNGGAYYN-
QKFKAMATLTVDKS SSTAFMHLNSLTSEDSAVYY-
CARKGVYGLAYWGQGTLVTVSS) and SEQ ID NO.135
(DIQMTQSPASLSVSVGETVTITCRASESIYSNLAWY-
QQKQGKSPQLLVYASTHLADGVPSRFSGSGSGAQYS-
LKINS LQSEDFGSYYCQHFWGTPYTFGGGTKLEIK).

According to a particular embodiment, an anti-CD38 specific chimeric antigen receptor (anti-CD38 CAR) having one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said V$_H$ and V$_L$ comprise a polypeptide sequence displaying at least 90%, at least 95%, at least 98% or at least 99% identity to respectively VH and VL chains of m2C2 antibody of SEQ ID NO. 132 (EVKLVESGGGLVQPGG-
SLKLSCATSGFTFSDYYMFWVRQTPEKRLEWVAYIS-
NGDGNTYYPDTLKGRFTISRDNA NNTLYLQMSR-
LKSEDTAMYYCARSISRYFDVWGAGTTVTVSS) and
SEQ ID NO. 133 (DIVMTQSPATLSVT-
PGDRVSLSCRASQSISDFLHWYQQKSHESPRL-
LIKYVSQSISGIPSRFSGSGSGSDFTLSINSVE PED-
VGVYYCQNAHSFPSTFGGGTKLEIK); and to respectively VH and VL chains of m5G9 antibody of SEQ ID NO.134 (EIHLQQSGPELVKPGASVKISCKASGYS-
FTDYNIYWVKQSHGESLEWVGYIDPYNGGAYYN-
QKFKAMATLTVDKS SSTAFMHLNSLTSEDSAVYY-
CARKGVYGLAYWGQGTLVTVSS) and SEQ ID NO.135
(DIQMTQSPASLSVSVGETVTITCRASESIYSN LAWY-
QQKQGKSPQLLVYASTHLADGVPSRFSGSGSGAQYS-
LKI NS LQSEDFGSYYCQHFWGTPYTFGGGTKLEIK).

According to a more particular embodiment, the anti-CD38 specific chimeric antigen receptor (anti-CD38 CAR) of the invention comprises a polypeptide sequence displaying at least 90%, at least 95%, at least 98% or at least 99% identity to SEQ ID NO.136-138 (corresponding respectively to m5G9 versions V1, V2 and V3).

According to another more particular embodiment, the anti-CD38 specific chimeric antigen receptor (anti-CD38 CAR) of the invention comprises a polypeptide sequence displaying at least 90%, at least 95%, at least 98% or at least 99% identity to SEQ ID NO.139-141 (corresponding respectively to m2C2 versions V1, V2 and V3).

According to another embodiment, the immune cell of the present invention is engineered to express anti-CD38 CAR having a low affinity for CD38 antigen.

According to another embodiment, the immune cell which is engineered to express anti-CD38 CAR having a low affinity for CD38 antigen, is further engineered to have its endogenous CD38 gene inactivated by knock-out, preferably by using a rare cutting endonuclease.

Transmembrane Domain

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or ε, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1)

A CAR according to the invention generally further comprises a transmembrane domain (TM) such as CD8α and 4-1BB and more particularly CD8α, showing at least 90%, at least 95%, at least 98% or at least 99% identity to SEQ ID NO.79.

The transmembrane domain can further comprise a hinge region between said extracellular ligand-binding domain and said transmembrane domain.

Hinge

The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 77, SEQ ID NO. 76 and SEQ ID NO.78, or hinge polypeptides which display preferably at least 80%, more preferably at least 90%, 95% 97% or 99% sequence identity with these polypeptides.

Intracellular Domain

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence of SEQ ID NO: 81.

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 80.

Multi-Subunit CAR

Chimeric antigen receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI (FIG. 18) to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions. The multi-chain CAR (mcCAR) construct may have a polycistronic structure such as depicted in FIG. 19.

Accordingly, the CAR expressed by the engineered T-cell according to the invention can be a multi-chain chimeric antigen receptor (CAR) particularly adapted to the production and expansion of engineered T-cells of the present invention. Such multi-chain CARs comprise at least two of the following components:

a) one polypeptide comprising the transmembrane domain of FcεRI alpha chain and an extracellular ligand-binding domain, b) one polypeptide comprising a part of N- and C-terminal cytoplasmic tail and the transmembrane domain of FcεRI beta chain and/or c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005 (WO2014/039523).

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand binding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies. Bispecific or multi-specific CARs as described in WO 2014/4011988 are incorporated by reference.

Similarly as described before with respect to single-chain CARs, the present invention encompasses immune cells endowed with multi-chain CARs which target specifically the CD38 cell surface marker. According to a preferred embodiment of the invention the CARs described above are expressed in immune cells, whereas inactivation of the endogenous genes encoding said surface marker is induced by expression of a rare-cutting endonuclease.

According to a preferred embodiment, the multi-chain CAR (mcCAR) of the invention comprises at a transmembrane polypeptide from the alpha chain of high-affinity IgE receptor (FcεRI) fused to an extracellular CD38 ligand binding domain.

According to a more preferred embodiment, said anti-CD38 multi-chain CAR comprises further a second transmembrane polypeptide from the gamma or beta chain of FcεRI fused to a signal transducing domain.

According to an even more preferred embodiment, said anti-CD38 multi-chain CAR comprises a third transmembrane polypeptide from the gamma or beta chain of FcεRI comprising a co-stimulatory domain.

According to a preferred embodiment, wherein said CD38 ligand binding domain of above anti-CD38 mcCAR, which is fused to said alpha chain of FcεRI, is a single-chain variable fragment (scFv) comprising heavy ($V_H$) and light ($V_L$) chains conferring specificity to CD38.

In a more preferred embodiment, said $V_H$ of above anti-CD38 mcCAR comprises a polypeptide sequence displaying at least 90% identity to one selected from SEQ ID NO. 14, 62, 54 and 30.

In another more preferred embodiment, said $V_L$ of above anti-CD38 mcCAR comprises a polypeptide displaying at least 90% identity to one selected from SEQ ID NO. 10, 58, 50 and 26.

In an embodiment, said alpha chain of FcεRI of above anti-CD38 mcCAR is fused to said extracellular ligand-binding domain by a hinge from CD8α, IgG1 or FcRIIIα proteins.

In an embodiment, said signal transducing domain of above anti-CD38 mcCAR is fused to the gamma or beta chain of FcεRI is from the TCR zeta chain, the FCεRβ chain, the FcεRIγ chain, or includes an immunoreceptor tyrosine-based activation motif (ITAM).

In a preferred embodiment, said signal transducing domain of above anti-CD38 mcCAR is from CD3zeta, and preferably comprising a polypeptide sequence displaying at least 90% identity to SEQ ID NO.81.

In an embodiment, said second or third polypeptide of above anti-CD38 mcCAR comprises a co-stimulatory domain from the cytoplasmic domain of a costimulatory molecule selected from CD27, CD28, 4-1BB, OX40, CD30, CD40, PD-1, ICOS, lymphocyte function-associated antigen-1 (LFA-1), CD2, CD7, CD8, LIGHT, NKG2C, B7-H3, a ligand that specifically binds with CD83, and any combination thereof.

In a preferred embodiment, said above co-stimulatory domain is from 4-1BB and comprises a polypeptide sequence displaying at least 90% identity to SEQ ID NO.80.

Figure 20:
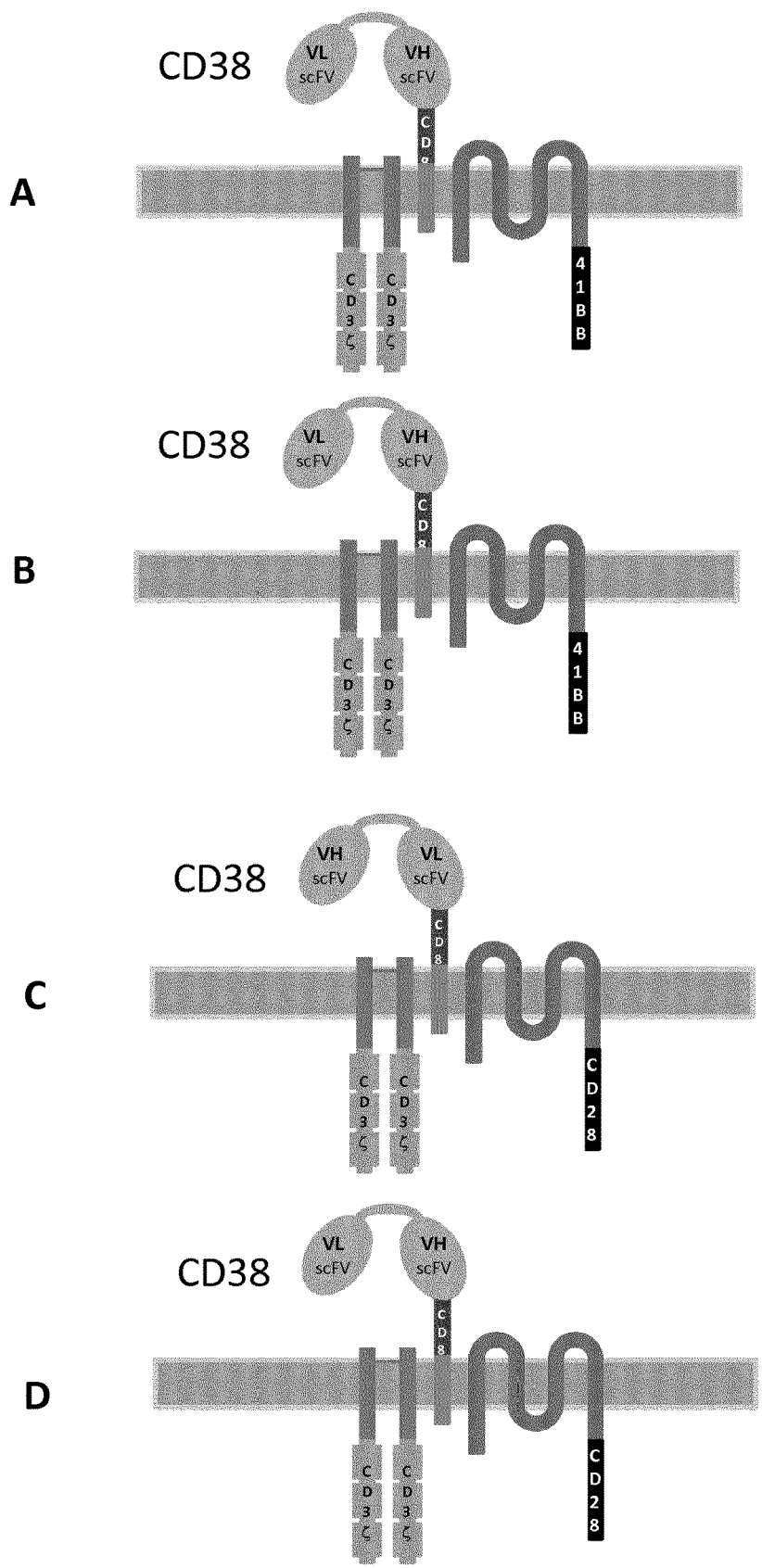

Examples of different architectures of the CD38 specific multi-chain CAR according to the invention are presented in FIG. 20.

Constructions of exemplary anti-CD38 mcCAR comprising the three polypeptide gamma, alpha and beta are presented in the following Table 3.

TABLE 3

Exemplary polypeptides forming anti-CD38 multi-chain CARs

| | Precursor BCMA muti-chain CAR polypeptide structure | | | | | | |
|---|---|---|---|---|---|---|---|
| Multi chain | Gamma polypeptide | | | | Alpha polypeptide | | |
| CAR Designation | FcεRI γ-SP | FcεRI γ -ΔITAM | CD3ζ-IC | P2A | FcεRI α-SP | CD8α hinge | VH |
| 25A10 anti-CD38mcCAR (4-1BB costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 14 |
| 28F5 anti-CD38 mcCAR (4-1BB costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 62 |
| 13F11 anti-CD38 mcCAR (4-1BB costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 54 |
| 16B6 anti-CD38 mcCAR (4-1BB costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 30 |
| 25A10 anti-CD38mcCAR (CD28 costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 14 |
| 28F5 anti-CD38 mcCAR (CD28 costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 62 |
| 13F11 anti-CD38 mcCAR (CD28 costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 54 |

TABLE 3-continued

Exemplary polypeptides forming anti-CD38 multi-chain CARs

| | | | | | | | |
|---|---|---|---|---|---|---|---|
| 16B6 anti-CD38 mcCAR (CD28 costimul. domain) | SEQ ID NO. 106 | SEQ ID NO. 107 | SEQ ID NO. 10 | SEQ ID NO. 108 | SEQ ID NO. 110 | SEQ ID NO. 77 | SEQ ID NO. 30 |

Precursor BCMA muti-chain CAR polypeptide structure

| Multi chain CAR Designation | Alpha polypeptide | | | | Beta polypeptide | |
|---|---|---|---|---|---|---|
| | G4SX3 Linker | VL | FcεRI α-TM-IC | T2A | FcεR1γΔI TAM | co-stimulalion. domain |
| 25A10 anti-CD38mcCAR (4-1BB costimul. domain) | SEQ ID NO. 75 | SEQ ID NO. 10 | SEQ ID NO. 111 | SEQ ID NO. 109 | SEQ ID NO. 112 | SEQ ID NO. 80 |
| 28F5 anti-CD38 mcCAR (4-1BB costimul. domain) | SEQ ID NO. 75 | SEQ ID NO. 58 | SEQ ID NO. 111 | SEQ ID NO. 109 | SEQ ID NO. 112 | SEQ ID NO. 80 |
| 13F11 anti-CD38 mcCAR (4-1BB costimul. domain) | SEQ ID NO. 75 | SEQ ID NO. 50 | SEQ ID NO. 111 | SEQ ID NO. 109 | SEQ ID NO. 112 | SEQ ID NO. 80 |
| 16B6 anti-CD38 mcCAR (4-1BB costimul. domain) | SEQ ID NO. 75 | SEQ ID NO. 26 | SEQ ID NO. 111 | SEQ ID NO. 109 | SEQ ID NO. 112 | SEQ ID NO. 80 |
| 25A10 anti-CD38mcCAR (CD28 costimul. domain) | SEQ ID NO. 75 | SEQ ID NO. 10 | SEQ ID NO. 111 | SEQ ID NO. 109 | SEQ ID NO. 112 | SEQ ID NO. 113 |
| 28F5 anti-CD38 mcCAR (CD28 costimul. domain) | SEQ ID NO. 75 | SEQ ID NO. 58 | SEQ ID NO. 111 | SEQ ID NO. 109 | SEQ ID NO. 112 | SEQ ID NO. 113 |
| 13F11 anti-CD38 mcCAR (CD28 costimul. domain) | SEQ ID NO. 75 | SEQ ID NO. 50 | SEQ ID NO. 111 | SEQ ID NO. 109 | SEQ ID NO. 112 | SEQ ID NO. 113 |
| 16B6 anti-CD38 mcCAR (CD28 costimul. domain) | SEQ ID NO. 75 | SEQ ID NO. 26 | SEQ ID NO. 111 | SEQ ID NO. 109 | SEQ ID NO. 112 | SEQ ID NO. 113 |

Activation and Expansion of T Cells

The method according to the invention generally includes a further step of activating and/or expanding the T-cells. This can be done prior to or after genetic modification of the T cells, using the methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. According to these methods, the T cells of the invention can be expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T-cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

On one embodiment, said T cells of the invention can undergo robust in vivo T cell expansion and can persist for an extended amount of time.

According to one embodiment, said T cells of the invention can undergo robust in vivo T cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

Gene Inactivation of CD38 Antigen

The antigen marker CD38 has been used as specific markers in diagnostic methods for a while, especially with respect to Leukemia pathological cells, but not in therapy. Indeed, although this marker was identified in the art as quite specific marker, it could not be used as target for immunotherapy because antibodies directed against this marker would have destroyed or interfered with patients' T-cells.

In a first embodiment, the method of the invention concerns a method of preparing appropriate immune cells, preferably T-cells for immunotherapy comprising the step of:

(a) Genetically inactivating or mutating a gene encoding the CD38 gene in an immune cell, which is involved in the expression or presentation of the CD38 antigen marker, said CD38 antigen marker being present both on the surface of said immune cell and the pathological cell;

(b) Expressing into said immune cell a transgene encoding a chimeric antigen receptor directed against said CD38 antigen marker such as presented in the previous sections, said antigen marker being present at the surface of said pathological cell.

In another embodiment, said method for engineered CD38 antigen-inactivated and CD38 CAR expressing appropriate immune cells, preferably T-cells for immunotherapy comprises the step of:

(a) Genetically inactivating or mutating a gene encoding the CD38 gene in an immune cell as described in the present invention, combined with the inactivation or mutation of another gene or other genes; said gene(s) being selected in the group consisting of gene(s) involved in engraftment of allogeneic immune cells, as immune checkpoints, in conferring drug resistance or in conferring resistance to immunosuppressive agent;

(b) Expressing into said immune cell a transgene encoding a chimeric antigen receptor directed against said CD38 antigen marker such as described in other sections and in claim 1.

In a particular embodiment, said method to engineer cells comprises at least one of the following steps:

(a) providing an immune cell, preferably T-cell, from a blood sample;

(b) introducing into said immune cell a rare-cutting endonuclease able to selectively inactivate by DNA cleavage, preferably by double-strand break respectively:

said gene encoding CD38 antigen, and at least one gene encoding a component involved in engraftment of allogeneic immune cells, as immune checkpoints, in conferring drug resistance or in conferring resistance to immunosuppressive agent).

(c) expanding said cells.

In a preferred embodiment, said additional gene(s) to be inactivated or mutated during step a) is or are selected in the group consisting of TCR, beta2M, PD-1, CTLA-4, dCK, DHFR, MGMT, IMPDH2, MDR1, CD52, GR.

In another embodiment, said rare-cutting endonuclease can be a meganuclease, a Zinc finger nuclease, a TALE-nuclease, a Casp9 nuclease or a Cpf1 nuclease. In a preferred embodiment, said rare-cutting endonuclease is a TALE-nuclease.

In a particular embodiment, inactivation of CD38 antigen and of gene(s) involved in engraftment of allogeneic immune cells, as immune checkpoints, in conferring drug resistance or in conferring resistance to immunosuppressive agent can be done at a precise genomic location targeted by a specific rare-cutting endonuclease such as TALE-nuclease, wherein said specific endonuclease catalyzes a cleavage and wherein an exogenous nucleic acid successively comprising at least a region of homology and a sequence to inactivate CD38 targeted gene and said above other gene(s) which is integrated by homologous recombination. In another embodiment, several genes can be, successively or at the same time, inactivated by using several specific rare-cutting endonucleases respectively and specifically targeting one defined gene and several specific polynucleotides for specific gene inactivation.

In a preferred embodiment, said method for engineered KO CD38 and anti-CD38 CAR expressing immune cells comprises the step of:

(a) Genetically inactivating the CD38 gene in an immune cell, said target CD38 being selected in the group consisting of SEQ ID 1, 4 and 7, by using respectively the left and right TALE nuclease of SEQ 2-3, SEQ 5-6, and SEQ 8-9;

(b) Expressing into said immune cell a transgene encoding a chimeric antigen receptor directed against CD38 antigen, said specific anti-CD38 CAR having one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4).

In another preferred embodiment, said method for engineered KO CD38 and CD38+ expressing immune cells comprises the step of:

(a) Genetically inactivating the CD38 gene in an immune cell, said target CD38 being selected in the group consisting of SEQ ID 1, 4 and 7, by using respectively the left and right TALE nuclease of SEQ 2-3, SEQ 5-6, and SEQ 8-9;

(b) Expressing into said immune cell a transgene encoding an anti-CD38 specific chimeric antigen receptor (anti-CD38 CAR), wherein said $V_H$ and $V_L$ comprise the CDRs sequences of respectively SEQ ID NO.15-17 and SEQ ID NO.11-13; respectively SEQ ID NO.63-65 and SEQ ID NO.59-61; respectively SEQ ID NO.55-57 and SEQ ID NO.51-53; respectively SEQ ID NO.31-33 and SEQ ID NO.27-29, respectively SEQ ID NO.39-41 and SEQ ID NO.35-37, respectively SEQ ID NO.47-49 and SEQ ID NO.45-43, respectively SEQ ID NO.55-57 and SEQ ID NO.51-53, respectively SEQ ID NO.63-65 and SEQ ID NO.59-61, respectively SEQ ID NO.71-73 and SEQ ID NO.67-69.

In more preferred embodiment, said method for engineered KO CD38 and anti-CD38 CAR expressing immune cells comprises the step of:

(a) Genetically inactivating the CD38 gene in an immune cell, said target CD38 of SEQ ID 4, by using respectively the left and right TALE nuclease of SEQ 5-6;

(b) Expressing into said immune cell a transgene encoding an anti-CD38 specific chimeric antigen receptor (anti-CD38 CAR) comprising a polypeptide sequence displaying at least 90%, at least 95%, at least 98% or at least 99% identity to one selected from SEQ ID NO. 82-84 (25A10), SEQ ID NO. 100-102 (28F5), SEQ ID NO. 97-99 (13F11) and SEQ ID NO. 88-90 (16B5).

In even more preferred embodiment, said method for engineered KO CD38 and anti-CD38 CAR expressing immune cells comprises the step of:

(a) Genetically inactivating the CD38 gene in an immune cell, said target CD38 of SEQ ID 4, by using respectively the left and right TALE nuclease of SEQ 5-6;

(b) Expressing into said immune cell a transgene encoding an anti-CD38 specific chimeric antigen receptor (anti-CD38 CAR) comprising a polypeptide sequence displaying at least 90%, at least 95%, at least 98% or at least 99% identity to one selected from SEQ ID NO. 82-84 (25A10) and SEQ ID NO. 100-102 (28F5).

In still even more preferred embodiment, said method for engineered KO CD38 and anti-CD38 CAR expressing immune cells comprises the step of:

(a) Genetically inactivating the CD38 gene in an immune cell, said target CD38 of SEQ ID 4, by using respectively the left and right TALE nuclease of SEQ 5-6;

(b) Expressing into said immune cell a transgene encoding an anti-CD38 specific chimeric antigen receptor (anti-CD38 CAR) comprising a polypeptide sequence displaying at least 90%, at least 95%, at least 98% or at least 99% identity to SEQ ID NO. 82 (25A10-v1 CAR).

The immune cells according to the invention are endowed with a anti-CD38 chimeric antigen receptor directed to the CD38 antigen marker that is commonly expressed by the pathological cells and immune cells, or known to be present on the surface of said T Cells. The expression "known to be present" means that the antigen marker is reported to be found on the surface of the immune cells grown in natural conditions in-vivo, especially in the blood, but not necessarily when they are cultured in-vitro. In any event, the method of the invention results into the absence of the CD38 antigen marker on the surface of the immune cell, thereby preventing the chimeric antigen receptor from reacting with the engineered T-cell surface. In this respect, the method may include a further step of purifying the resulting T-cells by excluding the cells presenting said marker antigen on their surface.

By inactivating a gene it is intended that the gene of interest is not expressed in a functional protein form. In particular embodiments, the genetic modification of the method relies on the expression, in provided cells to engineer, of a rare-cutting endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

According to a preferred embodiment of the invention, the gene mutation or inactivation of step a) of the above method is performed using a rare-cutting endonuclease.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In a particular embodiment, said rare-cutting endonuclease according to the present invention 5 is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; *Mali*, Yang et al. 2013).

TAL-Nucleases

In a preferred embodiment, the inactivation of the CD38 gene in step a) of the previously presented method is performed by the use of TAL-nuclease.

In a more preferred embodiment, said TAL-nuclease targets a CD38 gene sequence of SEQ ID NO.1, 4 or 7.

According a still more preferred embodiment, said inactivation of CD38 antigen is performed by using the TALE-nucleases of SEQ ID NO.2-3, 5-6 or 8-9.

Said above sequences for CD38 targets and their corresponding left and right TALE nuclease are presented in the following Table 4.

TABLE 4

Sequences of two other CD38 targets and the corresponding TALENs for their inactivation

| Name | SEQ ID # | Nucleic acid sequence and repeats sequence |
|---|---|---|
| CD38ex1-T2 target | 1 | TGAGGTGGGTTGGCGACtaaggcgcaccggTGGGCACTGCGGGGACA |
| CD38ex1-T2 Left TALEN | 2 | MGDPKKKRKVIDYPYDVPDYAIDIADLRTLGYSQQQQEKIKPKVRSTVAQHHEALV GHGFTHAHIVALSQHPAALGTVAVKYQDMIAALPEATHEAIVGVGKQWSGARAL EALLTVAGELRGPPLQLDTGQLLKIAKRGGVTAVEAVHAWRNALTGAPLNLTPQQ VVAIASNNGGKQALETVQRLLPVLCQAHGLTPEQVVAIASNIGGKQALETVQALLP VLCQAHGLTPQQVVAIASNNGGKQALETVQRLLPVLCQAHGLTPQQVVAIASNN GGKQALETVQRLLPVLCQAHGLTPQQVVAIASNGGGKQALETVQRLLPVLCQAH GLTPQQVVAIASNNGGKQALETVQRLLPVLCQAHGLTPQQVVAIASNNGGKQAL ETVQRLLPVLCQAHGLTPQQVVAIASNNGGKQALETVQRLLPVLCQAHGLTPQQ VVAIASNGGGKQALETVQRLLPVLCQAHGLTPQQVVAIASNGGGKQALETVQRLL PVLCQAHGLTPQQVVAIASNNGGKQALETVQRLLPVLCQAHGLTPQQVVAIASN NGGKQALETVQRLLPVLCQAHGLTPEQVVAIASHDGGKQALETVQRLLPVLCQA HGLTPQQVVAIASNNGGKQALETVQRLLPVLCQAHGLTPEQVVAIASNIGGKQAL ETVQALLPVLCQAHGLTPQQVVAIASNGGGRPALESIVAQLSRPDPALAALTNDH LVALACLGGRPALDAVKKGLGDPISRSQLVKSELEEKKSELRHKLKYVPHEYIELIEIA RNSTQDRILEMKVMEFFMKVYGYRGKHLGGSRKPDGAIYTVGSPIDYGVIVDTKA YSGGYNLPIGQADEMQRYVEENQTRNKHINPNEWWKVYPSSVTEFKFLFVSGHF KGNYKAQLTRLNHITNCNGAVLSVEELLIGGEMIKAGTLTLEEVRRKFNNGEINFAA D Repeat sequence TALEN: NN-NI-NN-NN-NG-NN-NN-NN-NG-NG-NN-NN-HD-NN-NI-NG |
| CD38ex1-T2 Right TALEN | 3 | MGDPKKKRKVIDKETAAAKFERQHMDSIDIADLRTLGYSQQQQEKIKPKVRSTVA QHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGA PLNLTPQQVVAIASNNGGKQALETVQRLLPVLCQAHGLTPQQVVAIASNGGGKQ ALETVQRLLPVLCQAHGLTPEQVVAIASHDGGKQALETVQRLLPVLCQAHGLTPE QVVAIASHDGGKQALETVQRLLPVLCQAHGLTPEQVVAIASHDGGKQALETVQRL LPVLCQAHGLTPEQVVAIASHDGGKQALETVQRLLPVLCQAHGLTPQQVVAIASN NGGKQALETVQRLLPVLCQAHGLTPEQVVAIASHDGGKQALETVQRLLPVLCQA HGLTPEQVVAIASNIGGKQALETVQALLPVLCQAHGLTPQQVVAIASNNGGKQAL ETVQRLLPVLCQAHGLTPQQVVAIASNGGGKQALETVQRLLPVLCQAHGLTPQQ VVAIASNNGGKQALETVQRLLPVLCQAHGLTPEQVVAIASHDGGKQALETVQRLL PVLCQAHGLTPEQVVAIASHDGGKQALETVQRLLPVLCQAHGLTPEQVVAIASHD GGKQALETVQRLLPVLCQAHGLTPQQVVAIASNGGGRPALESIVAQLSRPDPALA ALTNDHLVALACLGGRPALDAVKKGLGDPISRSQLVKSELEEKKSELRHKLKYVPHE YIELIEIARNSTQDRILEMKVMEFFMKVYGYRGKHLGGSRKPDGAIYTVGSPIDYGV IVDTKAYSGGYNLPIGQADEMQRYVEENQTRNKHINPNEWWKVYPSSVTEFKFLF VSGHFKGNYKAQLTRLNHITNCNGAVLSVEELLIGGEMIKAGTLTLEEVRRKFNNG EINFAAD Repeat sequence TALEN: NN-NG-HD-HD-HD-HD-NN-HD-NI-NN-NG-NN-HD-HD-HD-NG |
| CD38-1 target | 4 | TGCGAGTTCAGCCCGGTgtccggggacaaacccTGCTGCCGGCTCTCTA |
| CD38-1 Left TALEN | 5 | MGDPKKKRKVIDYPYDVPDYAIDIADLRTLGYSQQQQEKIKPKVRSTVAQHHEALV GHGFTHAHIVALSQHPAALGTVAVKYQDMIAALPEATHEAIVGVGKQWSGARAL EALLTVAGELRGPPLQLDTGQLLKIAKRGGVTAVEAVHAWRNALTGAPLNLTPQQ VVAIASNGGGKQALETVQRLLPVLCQAHGLTPEQVVAIASNNGGKQALETVQALL PVLCQAHGLTPQQVVAIASHDGGKQALETVQRLLPVLCQAHGLTPQQVVAIASN NGGKQALETVQRLLPVLCQAHGLTPQQVVAIASNIGGKQALETVQRLLPVLCQAH GLTPQQVVAIASNNGGKQALETVQRLLPVLCQAHGLTPQQVVAIASNGGGKQAL ETVQRLLPVLCQAHGLTPQQVVAIASNGGGKQALETVQRLLPVLCQAHGLTPQQ VVAIASHDGGKQALETVQRLLPVLCQAHGLTPQQVVAIASNIGGKQALETVQRLL |

TABLE 4-continued

Sequences of two other CD38 targets and the corresponding TALENs for their inactivation

| Name | SEQ ID # | Nucleic acid sequence and repeats sequence |
|---|---|---|
| | | PVLCQAHGLTPQQVVAIASNNGGKQALETVQRLLPVLCQAHGLTPQQVVAIASH DGGKQALETVQRLLPVLCQAHGLTPEQVVAIASHDGGKQALETVQRLLPVLCQA HGLTPQQVVAIASHDGGKQALETVQRLLPVLCQAHGLTPEQVVAIASNNGGKQA LETVQALLPVLCQAHGLTPQQVVAIASNNGGKQALETVQRLLPVLCQAHGLTPEQ VVAIASNGGGRPALESIVAQLSRPDPALAALTNDHLVALACLGGRPALDAVKKGLG DPISRSQLVKSELEEKKSELRHKLKYVPHEYIELIEIARNSTQDRILEMKVMEFFMKV YGYRGKHLGGSRKPDGAIYTVGSPIDYGVIVDTKAYSGGYNLPIGQADEMQRYVE ENQTRNKHINPNEWWKVYPSSVTEFKFLFVSGHFKGNYKAQLTRLNHITNCNGA VLSVEELLIGGEMIKAGTLTLEEVRRKFNNGEINFAAD<br>Repeat sequence TALEN: NG-NN-HD-NN-NI-NN-NG-NG-HD-NI-NN-HD-HD-HD-NN-NN-NG |
| CD38-1_Right TALEN | 6 | MGDPKKKRKVIDKETAAAKFERQHMDSIDIADLRTLGYSQQQQEKIKPKVRSTVA QHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGA PLN LTPQQVVAIASNNGGKQALETVQRLLPVLCQAHGLTPQQVVAIASNNGGKQ ALETVQRLLPVLCQAHGLTPEQVVAIASHDGGKQALETVQRLLPVLCQAHGLTPE QVVAIASNGGGKQALETVQRLLPVLCQAHGLTPEQVVAIASNNGGKQALETVQR LLPVLCQAHGLTPEQVVAIASHDGGKQALETVQRLLPVLCQAHGLTPQQVVAIAS HDGGKQALETVQRLLPVLCQAHGLTPEQVVAIASNNGGKQALETVQRLLPVLCQ AHGLTPEQVVAIASNNGGKQALETVQALLPVLCQAHGLTPQQVVAIASHDGGKQ ALETVQRLLPVLCQAHGLTPQQVVAIASNGGGKQALETVQRLLPVLCQAHGLTPQ QVVAIASHDGGKQALETVQRLLPVLCQAHGLTPEQVVAIASNGGGKQALETVQR LLPVLCQAHGLTPEQVVAIASHDGGKQALETVQRLLPVLCQAHGLTPEQVVAIAS NGGGKQALETVQRLLPVLCQAHGLTPQQVVAIASNIGGRPALESIVAQLSRPDPAL AALTNDHLVALACLGGRPALDAVKKGLGDPISRSQLVKSELEEKKSELRHKLKYVPH EYIELIEIARNSTQDRILEMKVMEFFMKVYGYRGKHLGGSRKPDGAIYTVGSPIDYG VIVDTKAYSGGYNLPIGQADEMQRYVEENQTRNKHINPNEWWKVYPSSVTEFKF LFVSGHFKGNYKAQLTRLNHITNCNGAVLSVEELLIGGEMIKAGTLTLEEVRRKFNN GEINFAAD<br>Repeat sequence TALEN: NG-NN-HD-NG-NN-HD-HD-NN-NN-HD-NG-HD-NG-HD-NG-NI |
| CD38-2_target | 7 | TGATCCTCGTCGTGGTgctcgcggtggtcgtccCGAGGTGGCGCCAGCA |
| CD38-2 Left TALEN | 8 | MGDPKKKRKVIDYPYDVPDYAIDIADLRTLGYSQQQQEKIKPKVRSTVAQHHEALV GHGFTHAHIVALSQHPAALGTVAVKYQDMIAALPEATHEAIVGVGKQWSGARAL EALLTVAGELRGPPLQLDTGQLLKIAKRGGVTAVEAVHAWRNALTGAPLNLTPQQ VVAIASNGGGKQALETVQRLLPVLCQAHGLTPEQVVAIASNNGGKQALETVQALL PVLCQAHGLTPQQVVAIASNIGGKQALETVQRLLPVLCQAHGLTPQQVVAIASNG GGKQALETVQRLLPVLCQAHGLTPQQVVAIASHDGGKQALETVQRLLPVLCQAH GLTPQQVVAIASHDGGKQALETVQRLLPVLCQAHGLTPQQVVAIASNGGGKQAL ETVQRLLPVLCQAHGLTPQQVVAIASHDGGKQALETVQRLLPVLCQAHGLTPQQ VVAIASNNGGKQALETVQRLLPVLCQAHGLTPQQVVAIASNGGGKQALETVQRL LPVLCQAHGLTPQQVVAIASHDGGKQALETVQRLLPVLCQAHGLTPQQVVAIASN NGGKQALETVQRLLPVLCQAHGLTPEQVVAIASNGGGKQALETVQRLLPVLCQA HGLTPQQVVAIASNNGGKQALETVQRLLPVLCQAHGLTPEQVVAIASNNGGKQA LETVQALLPVLCQAHGLTPQQVVAIASNGGGRPALESIVAQLSRPDPALAALTND HLVALACLGGRPALDAVKKGLGDPISRSQLVKSELEEKKSELRHKLKYVPHEYIELIEI ARNSTQDRILEMKVMEFFMKVYGYRGKHLGGSRKPDGAIYTVGSPIDYGVIVDTK AYSGGYNLPIGQADEMQRYVEENQTRNKHINPNEWWKVYPSSVTEFKFLFVSGH FKGNYKAQLTRLNHITNCNGAVLSVEELLIGGEMIKAGTLTLEEVRRKFNNGEINFA AD<br>Repeat sequence TALEN: NG-NN-NI-NG-HD-HD-NG-HD-NN-NG-HD-NN-NG-NN-NN-NG |
| CD38-2 Right TALEN | 9 | MGDPKKKRKVIDKETAAAKFERQHMDSIDIADLRTLGYSQQQQEKIKPKVRSTVA QHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGA PLNLTPQQVVAIASHDGGKQALETVQRLLPVLCQAHGLTPQQVVAIASNNGGKQ ALETVQRLLPVLCQAHGLTPEQVVAIASNIGGKQALETVQRLLPVLCQAHGLTPEQ VVAIASNNGGKQALETVQRLLPVLCQAHGLTPEQVVAIASNNGGKQALETVQRLL PVLCQAHGLTPEQVVAIASNGGGKQALETVQRLLPVLCQAHGLTPQQVVAIASN NGGKQALETVQRLLPVLCQAHGLTPEQVVAIASNNGGKQALETVQRLLPVLCQA HGLTPEQVVAIASHDGGKQALETVQALLPVLCQAHGLTPQQVVAIASNNGGKQA LETVQRLLPVLCQAHGLTPQQVVAIASHDGGKQALETVQRLLPVLCQAHGLTPQQ VVAIASHDGGKQALETVQRLLPVLCQAHGLTPEQVVAIASNIGGKQALETVQRLLP VLCQAHGLTPEQVVAIASNNGGKQALETVQRLLPVLCQAHGLTPEQVVAIASHDG GKQALETVQRLLPVLCQAHGLTPQQVVAIASNIGGRPALESIVAQLSRPDPALAAL TNDHLVALACLGGRPALDAVKKGLGDPISRSQLVKSELEEKKSELRHKLKYVPHEYI ELIEIARNSTQDRILEMKVMEFFMKVYGYRGKHLGGSRKPDGAIYTVGSPIDYGVI VDTKAYSGGYNLPIGQADEMQRYVEENQTRNKHINPNEWWKVYPSSVTEFKFLF VSGHFKGNYKAQLTRLNHITNCNGAVLSVEELLIGGEMIKAGTLTLEEVRRKFNNG EINFAAD |

TABLE 4-continued

Sequences of two other CD38 targets and the corresponding TALENs for their inactivation

| Name | SEQ ID # | Nucleic acid sequence and repeats sequence |
|---|---|---|
| | | Repeat sequence TALEN: HD-NN-NI-NN-NN-NG-NN-NN-HD-NN-HD-HD-NI-NN-HD-NI |

"TALE-nuclease" or "MBBBD-nuclease" refers to engineered proteins resulting from the fusion of a DNA binding domain typically derived from Transcription Activator Like Effector proteins (TALE) or Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France).

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins AvrBs3, PthXo1, AvrHah1, PthA, Tal1c as non-limiting examples.

These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

Other engineered DNA binding domains can be used as alternative sequences to form so-called modular base-per-base specific nucleic acid binding domains (MBBBD) as described in WO 2014/018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). These nucleic acid binding polypeptides comprise modules of about 31 to 33 amino acids that are base specific. These modules display less than 40% sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins.

The present invention encompasses a method for engineered T-cells in order to inactivate the expression of the genes encoding CD38 antigen marker by using specific TALE-nucleases.

Particularly suitable for the realization of the invention, TALE-nucleases such as the ones in SEQ ID NO: 2-3; 5-6; 8-9 for the CD38 gene. These specific TALE-nucleases, their sequence target and the protocol used are presented more thoroughly in the following Example 1.

Cas 9

In another embodiment, the gene inactivation of CD38 in step a) of the previously presented method is performed using the Cas 9 RNA-guided endonuclease.

In another embodiment, said RNA-guided endonuclease is split into at least 2 polypeptides, one comprising RuvC and another comprising HNH.

Cas9, also named Csn1 (COG3513) is a large protein that participates in both crRNA biogenesis and in the destruction of invading DNA. Cas9 has been described in different bacterial species such as *S. thermophiles, Listeria innocua* (Gasiunas, Barrangou et al. 2012; Jinek, Chylinski et al. 2012) and *S. Pyogenes* (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold) (Makarova, Grishin et al. (2006).

By "Cas9" is meant an engineered endonuclease or a homologue of Cas9 which is capable of processing target nucleic acid sequence. In particular embodiment, Cas9 can induce a cleavage in the nucleic acid target sequence which can correspond to either a double-stranded break or a single-stranded break. Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a *S. pyogenes* Cas9 endonuclease (COG3513). In the frame aspects of the present invention, such Cas9 variants remain functional, i.e. they retain the capacity of processing a target nucleic acid sequence. Cas9 variant can also be homologues of *S. pyogenes* Cas9 which can comprise deletions from, or insertions or substitutions of, at least one residue within the amino acid sequence of *S. pyogenes* Cas9. Any combination of deletion, insertion, and substitution may also be made to arrive at the final construct, provided that the final construct possesses the desired activity, in particular the capacity of binding a guide RNA or nucleic acid target sequence.

RuvC/RNaseH motif includes proteins that show wide spectra of nucleolytic functions, acting both on RNA and DNA (RNaseH, RuvC, DNA transposases and retroviral integrases and PIWI domain of Argonaut proteins). In the present invention the RuvC catalytic domain of the Cas9 protein can be characterized by the sequence motif: D-[I/L]-G-X-X-S-X-G-W-A (SEQ ID NO: 152), wherein X represents any one of the natural 20 amino acids and [I/L] represents isoleucine or leucine. In other terms, the present invention relates to Cas9 variant which comprises at least D-[I/L]-G-X-X-S-X-G-W-A sequence (SEQ ID NO: 152), wherein X represents any one of the natural 20 amino acids and [I/L] represents isoleucine or leucine.

HNH motif is characteristic of many nucleases that act on double-stranded DNA including colicins, restriction enzymes and homing endonucleases. The domain HNH (SMART ID: SM00507, SCOP nomenclature:HNH family) is associated with a range of DNA binding proteins, performing a variety of binding and cutting functions. The ones with known function are involved in a range of cellular processes including bacterial toxicity, homing functions in groups I and II introns and inteins, recombination, developmentally controlled DNA rearrangement, phage packaging, and restriction endonuclease activity (Dalgaard, Klar et al. 1997). These proteins are found in viruses, archaebacteria, eubacteria, and eukaryotes. Interestingly, as with the LAGLI-DADG (SEQ ID NO: 153) and the GIY-YIG motifs, the HNH motif is often associated with endonuclease domains of self-propagating elements like inteins, Group I, and Group II introns (Dalgaard, Klar et al. 1997). The HNH domain can be characterized by the presence of a conserved Asp/His residue flanked by conserved His (amino-terminal) and His/Asp/Glu (carboxy-terminal) residues at some distance. A substantial number of these proteins can also have a CX2C motif on either side of the central Asp/His residue. Structurally, the HNH motif appears as a central hairpin of twisted β-strands, which are flanked on each side by an a helix (Kleanthous, Kuhlmann et al. 1999). The large HNH domain of Cas9 is represented by SEQ ID NO.5. In the present invention, the HNH motif can be characterized by the sequence motif: Y-X-X-D-H-X-X-P-X-S-X-X-X-D-X-S (SEQ ID NO: 154), wherein X represents any one of the natural 20 amino acids. The present invention relates to a Cas9 variant which comprises at least Y-X-X-D-H-X-X-P-X-S-X-X-X-D-X-S sequence (SEQ ID NO: 154) wherein X represents any one of the natural 20 amino acids.

This invention can be of particular interest to easily do targeted multiplex gene modifications and to create an inducible nuclease system by introduction of the guide RNA to the Cas9 cells. For the purpose of the present invention, the inventors have established that Cas9 protein can be divided into two separate split Cas9 RuvC and HNH domains which can process target nucleic acid sequence together or separately with the guide RNA.

Also the RuvC and HNH domains from different RNA guided endonucleases or Cas homologues may be assembled to improve nuclease efficiency or specificity. The domains from different species can be either split into two proteins or fused to each other to form a variant Cas protein. The Cas9 split system is deemed particularly suitable for an inducible method of genome targeting and to avoid the potential toxic effect of the Cas9 overexpression within the cell. Indeed, a first split Cas9 domain can be introduced into the cell, preferably by stably transforming said cell with a transgene encoding said split domain. Then, the complementary split part of Cas9 can be introduced into the cell, such that the two split parts reassemble into the cell to reconstitute a functional Cas9 protein at the desired time.

The reduction of the size of the split Cas9 compared to wild type Cas9 ease the vectorization and the delivery into the cell, for example, by using cell penetrating peptides. Re-arranging domains from different Cas proteins, allows to modulate the specificity and nuclease activity, for instance, by targeting PAM motifs that are slightly different from *S. pyogenes* Cas9

Split Cas9 System

The previous characterization of the RuvC and HNH domains has prompted the inventors to engineer Cas9 protein to create split Cas9 protein. Surprisingly, the inventors showed that these two split Cas9 could process together or separately the nucleic acid target. This observation allows developing a new Cas9 system using split Cas9 protein. Each split Cas9 domains can be prepared and used separately. Thus, this split system displays several advantages for vectorization and delivery of the RNA guided endonuclease in T-cells, allowing delivering a shorter and/or inactive protein, and is particularly suitable to induce genome engineering in T-cells at the desired time and thus limiting the potential toxicity of an integrated Cas9 nuclease.

By "Split Cas9" is meant here a reduced or truncated form of a Cas9 protein or Cas9 variant, which comprises either a RuvC or HNH domain, but not both of these domains. Such "Split Cas9" can be used independently with guide RNA or in a complementary fashion, like for instance, one Split Cas9 providing a RuvC domain and another providing the HNH domain. Different split RNA guided endonucleases may be used together having either RuvC and/or NHN domains.

Each Cas9 split domain can be derived from the same or from different Cas9 homologues. Many homologues of Cas9 have been identified in genome databases.

Said Cas9 split domains (RuvC and HNH domains) can be simultaneously or sequentially introduced into the cell such that said split Cas9 domain(s) process the target nucleic acid sequence in the cell. Said Cas9 split domains and guide RNA can be introduced into the cell by using cell penetrating peptides or other transfection methods as described elsewhere.

In another aspect of the invention, only one split Cas9 domain, referred to as compact Cas9 is introduced into said cell. Indeed, surprisingly the inventors showed that the split Cas9 domain comprising the RuvC motif as described above is capable of cleaving a target nucleic acid sequence independently of split domain comprising the HNH motif. Thus, they could establish that the guide RNA does not need the presence of the HNH domain to bind to the target nucleic acid sequence and is sufficiently stable to be bound by the RuvC split domain. In a preferred embodiment, said split Cas9 domain alone is capable of nicking said target nucleic acid sequence.

Each split domain can be fused to at least one active domain in the N-terminal and/or C-terminal end, said active domain can be selected from the group consisting of: nuclease (e.g. endonuclease or exonuclease), polymerase, kinase, phosphatase, methylase, demethylase, acetylase, desacetylase, topoisomerase, integrase, transposase, ligase, helicase, recombinase, transcriptional activator (e.g. VP64, VP16), transcriptional inhibitor (e.g; KRAB), DNA end processing enzyme (e.g. Trex2, Tdt), reporter molecule (e.g. fluorescent proteins, lacZ, luciferase).

HNH domain is responsible for nicking of one strand of the target double-stranded DNA and the RuvC-like RNaseH fold domain is involved in nicking of the other strand (comprising the PAM motif) of the double-stranded nucleic acid target (Jinek, Chylinski et al. 2012). However, in wild-type Cas9, these two domains result in blunt cleavage of the invasive DNA within the same target sequence (proto-spacer) in the immediate vicinity of the PAM (Jinek, Chylinski et al. 2012). Cas 9 can be a nickase and induces a nick event within different target sequences.

As non-limiting example, Cas9 or split Cas9 can comprise mutation(s) in the catalytic residues of either the HNH or RuvC-like domains, to induce a nick event within different target sequences. As non-limiting example, the catalytic residues of the Cas9 protein are those corresponding to amino acids D10, D31, H840, H868, N882 and N891 or aligned positions using CLUSTALW method on homologues of Cas Family members. Any of these residues can be replaced by any other amino acids, preferably by alanine residue. Mutation in the catalytic residues means either substitution by another amino acids, or deletion or addition of amino acids that induce the inactivation of at least one of the catalytic domain of cas9. (cf. In a particular embodiment, Cas9 or split Cas9 may comprise one or several of the above mutations. In another particular embodiment, split Cas9 comprises only one of the two RuvC and HNH catalytic domains. In the present invention, Cas9 from different species, Cas9 homologues, Cas9 engineered and functional variant thereof can be used. The invention envisions the use of any RNA guided endonuclease or split RNA guided endonucleases variants to perform nucleic acid cleavage in a genetic sequence of interest.

Meganucleases

Rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease ("LAGLIDADG" disclosed as SEQ ID NO: 153), to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease. By modular DNA binding nuclease is meant any fusion proteins comprising at least one catalytic domain of an endonuclease and at least one DNA binding domain or protein specifying a nucleic acid target sequence. The DNA binding domain is generally a RNA or DNA-binding domain formed by an independently folded polypeptide or protein domain that contains at least one motif that recognizes double- or single-stranded polynucleotides. Many such polypeptides have been described in the art having the ability to bind specific nucleic acid sequences. Such binding domains often comprise, as non-limiting examples, helix-turn helix domains, leucine zipper domains, winged helix domains, helix-loop-helix domains, HMG-box domains, Immunoglobin domains, B3 domain or engineered zinc finger domain.

Zinc-Finger Nucleases

Initially developed to cleave DNA in vitro, "Zinc Finger Nucleases" (ZFNs) are a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (Genome editing with engineered zinc finger nucleases (2010) *Nature reviews Genetics* 11:636-646).

Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp.

The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

Delivery Methods

The inventors have considered any means known in the art to allow delivery inside cells or subcellular compartments of said cells the polynucleotides expressing the endonucleases, their possible co-effectors (e.g. guide RNA or DNA associated with Cas9 or Argonaute nucleases) as well as the chimeric antigen receptors. These means include viral transduction, electroporation and also liposomal delivery means, polymeric carriers, chemical carriers, lipoplexes, polyplexes, dendrimers, nanoparticles, emulsion, natural endocytosis or phagocytose pathway as non-limiting examples.

As a preferred embodiment of the invention, polynucleotides encoding the endonucleases of the present invention are transfected under mRNA form in order to obtain transient expression and avoid chromosomal integration of foreign DNA, for example by electroporation. The inventors have determined different optimal conditions for mRNA electroporation in T-cell displayed in Table 5. The inventor used the cytoPulse technology which allows, by the use of pulsed electric fields, to transiently permeabilize living cells for delivery of material into the cells (U.S. Pat. No. 6,010,613 and WO 2004/083379). Pulse duration, intensity as well as the interval between pulses can be modified in order to reach the best conditions for high transfection efficiency with minimal mortality. Basically, the first high electric field pulses allow pore formation, while subsequent lower electric field pulses allow to moving the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

According to another embodiment, said CD38 CARs selected are cloned in a lentiviral vector encoding for the suicide gene RQR8 which is be under the control of promotor such as EF1a.

According to a preferred embodiment, the CD38 CARs are transduced on T cells on CD38 deficient T cells. The expression of the CAR is usually assessed by flow cytometry and the anti-CD38 CAR T cells phenotype and function are tested. This is described in more details thereafter.

Non Alloreactive T Cells

Although the method of the invention could be carried out in-vivo as part of a gene therapy, for instance, by using viral vectors targeting T-cells in blood circulation, which would include genetic sequences expressing a specific rare-cutting endonuclease along with other genetic sequences expressing a CAR, the method of the invention is more generally intended to be practiced ex-vivo on cultured T-cells obtainable from patients or donors.

According to one embodiment, the immune cell to be engineered such as presented in the present invention is derived from a primary stem cell, iPS or hES cell.

In another embodiment, said immune cell is derived from a patient affected by the development of pathological cells.

The engineered T-cells engineered ex-vivo can be either re-implanted into a patient from where they originate, as part of an autologous treatment, or to be used as part of an allogeneic treatment. In this later case, it is preferable to further engineer the cells to make them non-alloreactive to ensure their proper engraftment. Accordingly, the method of the invention may include additional steps of procuring the T-cells from a donor and to inactivate genes thereof involved in MHC recognition and or being targets of immunosuppressive drugs such as described for instance in WO 2013/176915.

T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant

TABLE 5

Different cytopulse programs used to determine the minimal voltage required for electroporation in PBMC derived T-cells.

| | Group 1 | | | | Group 2 | | | | Group 3 | | | |
|---|---|---|---|---|---|---|---|---|---|---|---|---|
| Cyto-pulse program | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

Viral Transduction

According to the present invention, the use of retroviral vectors and more preferably of lentiviral vectors is particularly suited for expressing the chimeric antigen receptors into the T-cells. Methods for viral transduction are well known in the art (Walther et al. (2000) Viral Vectors for Gene Transfer. Drugs. 60(2):249-271). Integrative viral vectors allow the stable integration of the polynucleotides in the T-cells genome and to expressing the chimeric antigen receptors over a longer period of time.

(C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD.

Thus, still according to the invention, engraftment of the T-cells may be improved by inactivating at least one gene encoding a TCR component. TCR is rendered not functional in the cells by inactivating TCR alpha gene and/or TCR beta gene(s).

With respect to the use of Cas9/CRISPR system, the inventors have determined appropriate target sequences within the 3 exons encoding TCR, allowing a significant reduction of toxicity in living cells, while retaining cleavage efficiency. The preferred target sequences are presented in Table 2 in the application WO2014/191128.

MHC antigens are also proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called HLA antigens (for human leukocyte antigens) in human cells. Like TCR, the MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

Thus, in order to provide less alloreactive T-cells, the method of the invention can further comprise the step of inactivating or mutating one HLA gene.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The TapI and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (Fehling et al. (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (Grandea et al. (2000) *Immunity* 13:213-222 and Garbi et al. (2000) *Nat. Immunol.* 1:234-238). Any of the above genes may be inactivated as part of the present invention as disclosed, for instance in WO 2012/012667.

In another embodiment, the method of preparing immune cells includes a further step of inactivating a gene encoding 132m. Beta-2 microglobulin, also known as B2M, is the light chain of MHC class I molecules, and as such an integral part of the major histocompatibility complex In human, B2M is encoded by the b2m gene which is located on chromosome 15, opposed to the other MHC genes which are located as gene cluster on chromosome 6. The human protein is composed of 119 amino acids (SEQ ID NO: 1) and has a molecular weight of 11.800 Daltons. Mice models deficient for beta-2 microglobulin have shown that B2M is necessary for cell surface expression of MHC class I and stability of the peptide binding groove. It was further shown that haemopoietic transplants from mice that are deficient for normal cell-surface MHC I expression are rejected by NK1.1+ cells in normal mice because of a targeted mutation in the beta-2 microglobulin gene, suggesting that deficient expression of MHC I molecules renders marrow cells susceptible to rejection by the host immune system (Bix et al. 1991).

Insertion of at Least One Epitope in the Extracellular Domain of the Anti-CD38-Single Chain CAR An anti-CD38 CAR of the invention may include at least the insertion of at least one epitope in the extracellular domain of said CAR. This is intended to temptatively deplete the immune cells endowed with the CAR in the event of in vivo adverse effects such as a cytokine storm. Moreover, such insertion of epitope or "epitope-tagging" may be useful to sort or purify the engineered immune cells in-vitro during their manufacturing process. Said at least one epitope may be any antigenic peptide which is enough immunogenic to be bound by a specific antibody recognizing such peptide. For instance, this can be obtained, for instance, by inserting at least one, and preferably two copies of a CD20 mimotope, preferably of sequence CPYS-NPSLCS (SEQ ID NO.114), into the CAR polypeptide sequence. For purpose of simplication hereafter, the order of the scFvs from the N terminal end to the C terminal end is presented as follows: the VH chain and then the VL chain. However, it can be envisioned in the scope of the present invention that this order is inversed: VL chain and then the VL chain.

Different positions of the at least one CD20 mimotope within the anti-CD38 CAR of the invention are schematized in FIG. 21A and FIG. 21B. Said two copies of a CD20 mimotope can be linked to each other and also to the $V_L$ by a linker. They can also be inserted between the anti-CD38 scFv and the hinge (such as CD8alpha), by using an optional linker. The CD20 mimotopes can be bound by anti-CD20 antibodies, such as Rituximab (McLaughlin P, et al. 1998).

Accordingly, the anti-CD38 CAR of the present invention may comprise VH and a VL chains which are able to bind to CD38 cell surface antigen, optionally humanized, a linker L, a suicide domain, a hinge or part of it, a transmembrane domain, a co-stimulatory domain and a stimulatory domain.

More specifically, the epitopes can be included into the CAR of the present invention such as follows:

In some embodiments, the extracellular binding domain comprises at least 1, 2, 3, 4, 5, 6, 7, 8, 9 or 10 mAb-specific epitopes.

In some embodiments, the extracellular binding domain comprises at least 1, 2 or 3 mAb-specific epitopes.

In some embodiments, when the extracellular binding domain comprises several mAb-specific epitopes, all the mAb-specific epitopes are identical.

In some embodiments, when the extracellular binding domain comprises several mAb-specific epitopes, the mAb-specific epitopes are not identical. For example, the extracellular binding domain can comprises three mAb-specific epitopes, two of them being identical and the third one being different.

In some embodiments, the extracellular binding domain comprises a VH, a VL, one or more mAb-specific epitopes, preferably 1, 2 or 3, more preferably 2 or 3 mAb-specific epitopes.

In some embodiments, the extracellular binding domain comprises the following sequence (Nterm is located on the left hand side):

$V_1$-$L_1$-$V_2$-$(L)_x$-Epitope1-$(L)_x$;
$V_1$-L1-$V_2$-$(L)_x$-Epitope1-$(L)_x$-Epitope2-$(L)_x$;
$V_1$-L1-$V_2$-$(L)_x$-Epitope1-$(L)_x$-Epitope2-$(L)_x$-Epitope3-$(L)_x$;
$(L)_x$-Epitope1-$(L)_x$-$V_1$-$L_1$-$V_2$;
$(L)_x$-Epitope1-$(L)_x$-Epitope2-$(L)_x$-$V_1$-L1-$V_2$;
Epitope1-$(L)_x$-Epitope2-$(L)_x$-Epitope3-$(L)_x$-$V_1$-L1-$V_2$;
$(L)_x$-Epitope1-$(L)_x$-$V_1$-L1-$V_2$-$(L)_x$-Epitope2-$(L)_x$;
$(L)_x$-Epitope1-$(L)_x$-$V_1$-L1-$V_2$-$(L)_x$-Epitope2-$(L)_x$-Epitope3-$(L)_x$;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$;
$(L)_x$-Epitope1-$(L)_x$-Epitope2-$(L)_x$-V-L1-$V_2$-$(L)_x$-Epitope3-$(L)_x$;
$(L)_x$-Epitope1-$(L)_x$-Epitope2-$(L)_x$-V-L1-$V_2$-$(L)_x$-Epitope3-$(L)_x$-Epitope4-$(L)_x$;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$;
$(L)_x$-Epitope1-$(L)_x$-$V_1$-$(L)_x$-Epitope2-$(L)_x$-$V_2$-$(L)_x$-Epitope3-$(L)_x$;
$V_1$-$L_1$-$V_2$-L-Epitope1;
$V_1$-$L_1$-$V_2$-L-Epitope1-L;
$V_1$-$L_1$-$V_2$-L-Epitope1-L-Epitope2;
$V_1$-$L_1$-$V_2$-L-Epitope1-L-Epitope2-L;
$V_1$-$L_1$-$V_2$-L-Epitope1-L-Epitope2-L-Epitope3;
$V_1$-$L_1$-$V_2$-L-Epitope1-L-Epitope2-L-Epitope3-L;
$V_1$-$L_1$-$V_2$-Epitope1;
$V_1$-$L_1$-$V_2$-Epitope1-L;
$V_1$-$L_1$-$V_2$-Epitope1-L-Epitope2;
$V_1$-$L_1$-$V_2$-Epitope1-L-Epitope2-L;
$V_1$-$L_1$-$V_2$-Epitope1-L-Epitope2-L-Epitope3;
$V_1$-$L_1$-$V_2$-Epitope1-L-Epitope2-L-Epitope3-L;
Epitope1-V-$L_1$-$V_2$;
Epitope1-L-V-$L_1$-$V_2$;
L-Epitope1-V-$L_1$-$V_2$;
L-Epitope1-L-V-$L_1$-$V_2$;
Epitope1-L-Epitope2-V-$L_1$-$V_2$;
Epitope1-L-Epitope2-L-V-L-$V_2$;
L-Epitope1-L-Epitope2-V-L-$V_2$;
L-Epitope1-L-Epitope2-L-V-$L_1$-$V_2$;
Epitope1-L-Epitope2-L-Epitope3-V-L-$V_2$;
Epitope1-L-Epitope2-L-Epitope3-L-$V_1$-$L_1$-$V_2$;
L-Epitope1-L-Epitope2-L-Epitope3-$V_1$-$L_1$-$V_2$;
L-Epitope1-L-Epitope2-L-Epitope3-L-$V_1$-$L_1$-$V_2$;
$V_1$-L-Epitope1-L-$V_2$;
L-Epitope1-L-$V_1$-L-Epitope2-L-$V_2$;
$V_1$-L-Epitope1-L-$V_2$-L-Epitope2-L;
$V_1$-L-Epitope1-L-$V_2$-L-Epitope2-L-Epitope3;
$V_1$-L-Epitope1-L-$V_2$-L-Epitope2-Epitope3;
$V_1$-L-Epitope1-L-$V_2$-L-Epitope2-L-Epitope3-Epitope4;
L-Epitope1-L-$V_1$-L-Epitope2-L-$V_2$-L-Epitope3-L;

Epitope1-L-$V_1$-L-Epitope2-L-$V_2$-L-Epitope3-L;
L-Epitope1-L-$V_1$-L-Epitope2-L-$V_2$-L-Epitope3;
L-Epitope1-L-$V_1$-$L_1$-$V_2$-L-Epitope2-L;
L-Epitope1-L-$V_1$-$L_1$-$V_2$-L-Epitope2-L-Epitope3;
L-Epitope1-L-$V_1$-$L_1$-$V_2$-L-Epitope2-Epitope3, or,
Epitope1-L-$V_1$-$L_1$-$V_2$-L-Epitope2-L-Epitope3-Epitope 4.
wherein, $V_1$ and $V_2$ are $V_H$ and $V_L$ of an ScFv (i.e, $V_1$ is $V_L$ and $V_2$ is $V_H$ or $V_1$ is $V_H$ and $V_2$ is $V_L$);

$L_1$ is any linker suitable to link the VH chain to the VL chain in an ScFv;

L is a linker, preferably comprising glycine and serine residues, and each occurrence of L in the extracellular binding domain can be identical or different to other occurrence of L in the same extracellular binding domain, and, x is 0 or 1 and each occurrence of x is independently from the others; and, epitope 1, epitope 2 and epitope 3 are mAb-specific epitopes and can be identical or different.

In some embodiments, the extracellular binding domain comprises the following sequence (Nterm is located on the left hand side):

$V_H$-L-$V_L$-L-Epitope1-L-Epitope2-L;
L-Epitope1-L-$V_H$-L-Epitope2-L-$V_L$-L-Epitope3-L;
$V_L$-L1-$V_H$-L-Epitope1-L-Epitope2-L; or,
L-Epitope1-L-$V_L$-L-Epitope2-L-$V_H$-L-Epitope3-L.
wherein L, L1, epitope 1, epitope 2 and epitope 3 are as defined above.

In some embodiments, $L_1$ is a linker comprising Glycine and/or Serine. In some embodiment, $L_1$ is a linker comprising the amino acid sequence (Gly-Gly-Gly-Ser)$_n$ (SEQ ID NO: 155) or (Gly-Gly-Gly-Gly-Ser)$_n$ (SEQ ID NO: 156), where n is 1, 2, 3, 4 or 5. In some embodiments $L_1$ is (Gly$_4$Ser)$_4$ (SEQ ID NO: 157) or (Gly$_4$Ser)$_3$ (SEQ ID NO: 75).

In some embodiment, L is a flexible linker, preferably comprising Glycine and/or Serine. In some embodiments, L has an amino acid sequence selected from SGG, GGS, SGGS (SEQ ID NO: 158), SSGGS (SEQ ID NO: 159), GGGG (SEQ ID NO: 160), SGGGG (SEQ ID NO: 161), GGGGS (SEQ ID NO: 162), SGGGGS (SEQ ID NO: 163), GGGGGS (SEQ ID NO: 164), SGGGGGS (SEQ ID NO: 165), SGGGGG (SEQ ID NO: 166), GSGGGGS (SEQ ID NO: 167), GGGGGGGS (SEQ ID NO: 168), SGGGGGGG (SEQ ID NO: 169), SGGGGGGGS (SEQ ID NO: 170), or SGGGGSGGGS (SEQ ID NO: 171) preferably SGG, SGGS (SEQ ID NO: 158), SSGGS (SEQ ID NO: 159), GGGG (SEQ ID NO: 160), SGGGGS (SEQ ID NO: 163), SGGGGGS (SEQ ID NO: 165), SGGGGG (SEQ ID NO: 166), GSGGGGS (SEQ ID NO: 167) or SGGGGSGGGGS (SEQ ID NO: 171). In some embodiment, when the extracellular binding domain comprises several occurrences of L, all the Ls are identical. In some embodiments, when the extracellular binding domain comprises several occurrences of L, the Ls are not all identical. In some embodiments, L is SGGGGS (SEQ ID NO: 163). In some embodiments, the extracellular binding domain comprises several occurrences of L and all the Ls are SGGGGS (SEQ ID NO: 163).

In some embodiments, Epitope 1, Epitope 2 and Epitope 3 are identical or different and are selected from mAb-specific epitopes having an amino acid sequence of anyone of SEQ ID NO 114 to SEQ ID NO 121 such as presented in the following Table 6.

TABLE 6

Mimotopes and epitopes with their corresponding sequences

Rituximab

| Mimotope | SEQ ID NO 114 | CPYSNPSLCS |
|---|---|---|

Palivizumab

| Epitope | SEQ ID NO 115 | NSELLSLINDMPITNDQKKLMSNN |
|---|---|---|

Cetuximab

| Mimotope 1 | SEQ ID NO 116 | CQFDLSTRRLKC |
|---|---|---|
| Mimotope 2 | SEQ ID NO 117 | CQYNLSSRALKC |
| Mimotope 3 | SEQ ID NO 118 | CVWQRWQKSYVC |
| Mimotope 4 | SEQ ID NO 119 | CMWDRFSRWYKC |

Nivolumab

| Epitope A | SEQ ID NO 120 | SFVLNWYRMSPSNQTDKLAAFPEDR |
|---|---|---|
| Epitope B | SEQ ID NO 121 | SGTYLCGAISLAPKAQIKE |

In some embodiments, Epitope 1, Epitope 2 and Epitope 3 are identical or different and are selected from mAb-specific epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, alemtuzumab or ustekinumab.

According to another embodiment, the epitope is a mimotope. As a macromolecule, often a peptide, which mimics the structure of an epitope, the mimotope has the advantage to be smaller than conventional epitope, and therefore may be beneficial for a non-conformational sequence and easier to reproduce in a long polypeptide such a CAR. Mimotopes are known for several pharmaceutically-approved mAb such as two 10 amino acid peptides for cetuximab (Riemer et al., 2005), or a 24 AA for palivizumab (Arbiza et al, 1992). As these mimotopes can be identified by phage display, it is possible to try several of them in order to obtain a sequence which does not perturb the scFv for the same mAb. Furthermore, their use can enhance a complement-dependent cytotoxicity (CDC).

In a preferred embodiment, the epitope introduced within the chimeric scFv is the CD20 mimotope (SEQ ID NO.114) and the infused mAb presenting an affinity to this mimotope—for sorting and/or depletion purpose(s)—is rituximab.

In one embodiment, said at least one epitope is inserted between the VH and VL chains of the anti-CD38 CAR, optionally linked to said VH and VL chains by one linker.

In some embodiments, the term "linker" as used in the context of a scFv refers to a peptide linker that consists of amino acids such as glycine and/or serine residues used alone or in combination, to link variable heavy and variable light chain regions together. In one embodiment, the flexible polypeptide linker is a Glycine/Serine linker and comprises the amino acid sequence (Gly-Gly-Gly-Ser)$_n$ (SEQ ID NO: 172) or (Gly-Gly-Gly-Gly-Ser)$_n$ (SEQ ID NO: 162), where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, (Gly$_4$Ser)$_4$ (SEQ ID NO: 157) or (Gly$_4$Ser)$_3$ (SEQ ID NO: 75). In another embodiment, the linkers include multiple repeats of (Gly$_x$Ser)$_n$, where x=1, 2, 3, 4 or 5 and n is 1, 2, 3, 4, 5, 6, 7, 8, 9 or 10 (SEQ ID NO: 173), such as multiple repeat of (GlySer), (Gly$_2$Ser) or (Gly$_5$Ser) (SEQ ID NO: 164). Also included within the scope of the invention are linkers described in WO2012/138475, incorporated herein by reference.

In an embodiment, said CD38 specific chimeric antigen receptor (anti-CD38 CAR) has one of the polypeptide structure selected from V1, V2 or V3, as illustrated in FIG. 8, wherein one CD20 mimotope is inserted between the VH and VL chains of the anti-CD38 CAR, optionally linked to said VH and VL chains by one linker.

In a preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said V$_H$ and V$_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4) and wherein one CD20 mimotope is inserted between the VH and VL chains of the anti-CD38 CAR, optionally linked to said VH and VL chains by one linker.

In another embodiment, said at least one epitope is inserted at the N terminal end of the CAR—so upfront of the scFvs—, optionally linked to the VH chain and to the N terminal end of the CAR by one linker.

In another embodiment, said at least one epitope is inserted between the scFvs and the hinge of the CAR, optionally linked to the VL chain and to the hinge by one linker.

In a preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said V$_H$ and V$_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein one epitope is inserted between the scFvs and the hinge of the CAR, optionally linked to the VL chain and to the hinge by one linker.

In a more preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4) and wherein one epitope is inserted between the scFvs and the hinge of the CAR, optionally linked to the VL chain and to the hinge by one linker.

In a preferred embodiment, at least two epitopes are inserted in the extracellular domain of the anti-CD38 CAR of the present invention.

In an embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), said extra-binding domain comprising VH and VL chains directed against CD38 and a FcγRIIIα or CD8α or IgG1 hinge;

wherein said 2 epitopes being inserted in tandem between the scFvs and said hinge, and optionally a linker being interspaced between the 2 epitopes and/or between the VH and the 2 epitopes.

In an embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and two CD20 mimotopes, said extra-binding domain comprising VH and VL chains directed against CD38 and a FcγRIIIα or CD8α or IgG1 hinge;

wherein said 2 epitopes being inserted in tandem upfront the scFvs i.e. at the N terminal end of the CAR— and optionally, a linker being interspaced between the 2 epitopes and/or at the N terminal end of the CAR.

According to one embodiment, at least two epitopes are inserted in the extracellular domain in such a way that the VH is located between them, all these components being optionally interspaced by at least one linker.

According to another embodiment, two epitopes are inserted in the extracellular domain in such a way that the VL is located between them, all these components being optionally interspaced by at least one linker.

In a preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein two epitopes are inserted in the extracellular domain in such a way that the VL is located between them, all these components being optionally interspaced by at least one linker.

In a more preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein two epitopes are inserted in the extracellular domain in such a way that the VL is located between them, all these components being optionally interspaced by at least one linker.

According to another embodiment, said CD38 specific chimeric antigen receptor (anti-CD38 CAR) comprises an extracellular binding domain wherein at least two epitopes are inserted in the extracellular domain in such a way that the VH and VL chains ar located between them, all these components being optionally interspaced by at least one linker.

In a preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein two epitopes are inserted in the extracellular domain in such a way that the VH and VL chains ar located between them, all these components being optionally interspaced by at least one linker.

In a more preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein two epitopes are inserted in the extracellular domain in such a way that the VH and VL chains ar located between them, all these components being optionally interspaced by at least one linker.

In another embodiment, three epitopes are inserted in the extracellular domain of the anti-CD38 CAR of the present invention.

According to a particular embodiment, said CD38 specific CAR of the invention contains an extracellular binding domain wherein three epitopes are inserted in the extracellular domain in such a way that the VH and VL chains ar located between them, all these components being optionally interspaced by at least one linker.

In a preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and wherein three epitopes are inserted in the extracellular domain in such a way that the VH and VL chains ar located between them, all these components being optionally interspaced by at least one linker.

In a more preferred embodiment, said CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), all these components being optionally interspaced by at least one linker.

In another embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), and three CD20 epitopes, said extra-binding domain comprising VH and VL chains directed against CD38 and a FcγRIIIα or CD8α or IgG1 hinge;

wherein said 3 epitopes being inserted in tandem between the scFvs and said hinge, and optionally a linker being interspaced between the 3 epitopes and/or between the VH and the 3 epitopes.

In another embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), two CD20 epitopes, and one CD34 epitope;

said extra-binding domain comprising VH and VL chains directed against CD38 and a FcγRIIIα or CD8α or IgG1 hinge;

said 2 epitopes being inserted in tandem between the scFvs and said hinge, and said CD34 epitope being inserted between the said 2 CD20 epitopes, all components being optionally interspaced between them by a linker.

In some embodiment, Epitope 1 is an mAb-specific epitope having an amino acid sequence of SEQ ID NO 114 or 116-119.

In some embodiment, Epitope 2 is an mAb-specific epitope having an amino acid sequence of SEQ ID NO 114 or 116-119.

In some embodiment, Epitope 3 and Epitope 4 are mAbs-specific epitope having an amino acid sequence of SEQ ID NO 114 or 116-119.

In some embodiment, one of Epitope 1, Epitope 2, Epitope 3 and Epitope 4 is a CD34 epitope, preferably an epitope of SEQ ID NO 122 or 123. In some embodiment, one of Epitope1, Epitope 2, Epitope 3 and Epitope 4 is a CD34 epitope, preferably an epitope of SEQ ID NO 122 or 123 and the other mAb specific epitopes are CD20 mimotopes, preferably mimotope of SEQ ID NO 114.

In a preferred embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), two CD20 epitopes having an amino acid sequence selected in the group consisting of SEQ ID NO 114 or 116-119, said CD20 epitopes being identical or different.

In a preferred embodiment, CD38 specific chimeric antigen receptor (anti-CD38 CAR) has one of the polypeptide structure selected from V2 as illustrated in FIG. 8, said structure comprising an extra cellular ligand binding-domain comprising VH and VL from a monoclonal anti-CD38 antibody, a CD8α hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising two CD20 epitopes having an amino acid sequence selected in the group consisting of SEQ ID NO 114 or 116-119, said CD20 epitopes being identical or different.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.124.

In a preferred embodiment, CD38 specific chimeric antigen receptor (anti-CD38 CAR) has one of the polypeptide structure selected from V1 as illustrated in FIG. 8, said structure comprising an extra cellular ligand binding-domain comprising VH and VL from a monoclonal anti-CD38 antibody, a FcRIIIα hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 62 and 58 (28F5), said anti-CD38 CAR comprising two CD20 epitopes having an amino acid sequence selected in the group consisting of SEQ ID NO 114 or 116-119, said CD20 epitopes being identical or different.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.126.

In a preferred embodiment, CD38 specific chimeric antigen receptor (anti-CD38 CAR) has one of the polypeptide structure selected from V2 as illustrated in FIG. 8, said structure comprising an extra cellular ligand binding-domain comprising VH and VL from a monoclonal anti-CD38 antibody, a CD8α hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising two CD20 epitopes having an amino acid sequence selected in the group consisting of SEQ ID NO 114 or 116-119, said CD20 epitopes being identical or different.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.126.

In a preferred embodiment, CD38 specific chimeric antigen receptor (anti-CD38 CAR) has one of the polypeptide structure selected from V2 as illustrated in FIG. 8, said structure comprising an extra cellular ligand binding-domain comprising VH and VL from a monoclonal anti-CD38 antibody, a FcRIIIα hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising two CD20 epitopes having an amino acid sequence selected in the group consisting of SEQ ID NO 114 or 116-119, said CD20 epitopes being identical or different.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.128.

In one embodiment, CD38 specific chimeric antigen receptor (anti-CD38 CAR) has one of the polypeptide structure selected from V1, V2 and V3, as illustrated in FIG. 8, said structure comprising an extra cellular ligand binding-domain comprising VH and VL from a monoclonal anti-CD38 antibody, a hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), SEQ ID NO. 62 and 58 (28F5), SEQ ID NO. 54 and 50 (13F11), SEQ ID NO. 30 and 26 (16B5), SEQ ID NO. 38 and 34 (10F7), SEQ ID NO.46 and 42 (27B6) or SEQ ID NO. 22 and 18 (29B4), three CD20 epitopes having an amino acid sequence selected in the group consisting of SEQ ID NO 114 or 116-119, said CD20 epitopes being identical or different, and one CD34 epitope having an amino acid sequence of SEQ ID NO.122 or 123.

In a preferred embodiment, CD38 specific chimeric antigen receptor (anti-CD38 CAR) has one of the polypeptide structure selected from V2 as illustrated in FIG. 8, said structure comprising an extra cellular ligand binding-domain comprising VH and VL from a monoclonal anti-CD38 antibody, a CD8α hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 62 and 58 (28F5), said anti-CD38 CAR comprising three CD20 epitopes having an amino acid sequence selected in the group consisting of SEQ ID NO 114 or 116-119, said CD20 epitopes being identical or different, and one CD34 epitope having an amino acid sequence of SEQ ID NO.122 or 123.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.125.

In a preferred embodiment, CD38 specific chimeric antigen receptor (anti-CD38 CAR) has one of the polypeptide structure selected from V1 as illustrated in FIG. 8, said structure comprising an extra cellular ligand binding-domain comprising VH and VL from a monoclonal anti-CD38 antibody, a FcRIIIα hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 62 and 58 (28F5), said anti-CD38 CAR comprising three CD20 epitopes having an amino acid sequence selected in the group consisting of SEQ ID NO 114 or 116-119; said CD20 epitopes being identical or different, and one CD34 epitope having an amino acid sequence of SEQ ID NO.122 or 123.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.127.

In a preferred embodiment, CD38 specific chimeric antigen receptor (anti-CD38 CAR) has one of the polypeptide structure selected from V2 as illustrated in FIG. 8, said structure comprising an extra cellular ligand binding-domain comprising VH and VL from a monoclonal anti-CD38 antibody, a CD8α hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising three CD20 epitopes having an amino acid sequence selected in the group consisting of SEQ ID NO 114 or 116-119; said CD20 epitopes being identical or different, and one CD34 epitope having an amino acid sequence of SEQ ID NO.122 or 123.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.129.

In a preferred embodiment, CD38 specific chimeric antigen receptor (anti-CD38 CAR) has one of the polypeptide structure selected from $V_1$ as illustrated in FIG. 8, said structure comprising an extra cellular ligand binding-domain comprising VH and VL from a monoclonal anti-CD38 antibody, a CD8α hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising two CD20 epitopes having an amino acid sequence selected in the group consisting of SEQ ID NO 114 or 116-119; said CD20 epitopes being identical or different.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.130.

In a preferred embodiment, CD38 specific chimeric antigen receptor (anti-CD38 CAR) has one of the polypeptide structure selected from $V_1$ as illustrated in FIG. 8, said structure comprising an extra cellular ligand binding-domain comprising VH and VL from a monoclonal anti-CD38 antibody, a FcRIIIα hinge, a transmembrane domain, a cytoplasmic domain including a CD3 zeta signaling domain and a co-stimulatory domain from 4-1BB, wherein said $V_H$ and $V_L$ comprise a polypeptide sequence displaying at least 90%, at least 95%, at least 98% or at least 99% identity to respectively SEQ ID NO. 14 and 10 (25A10), said anti-CD38 CAR comprising three CD20 epitopes having an amino acid sequence selected in the group consisting of SEQ ID NO 114 or 116-119, said CD20 epitopes being identical or different, and one CD34 epitope having an amino acid sequence of SEQ ID NO.122 or 123.

In more preferred embodiment, CD38 specific chimeric antigen receptor (anti-CD38 CAR) comprises a polypeptide sequence displaying at least 90%, at least 95%, at least 98% or at least 99% identity to respectively SEQ ID NO.131.

Method of Engineering Drug-Resistant T-Cells

To improve cancer therapy and selective engraftment of allogeneic T-cells, drug resistance can be conferred to the engineered T-cells to protect them from the toxic side effects of chemotherapy or immunosuppressive agents. Indeed, the inventors have observed that most patients were treated with chemotherapy and immune depleting agents as a standard of care, prior to receiving T-cell immunotherapy. Also they found that they could take advantage of these treatments to help the selection of the engineered T-cells, either by adding chemotherapy drugs in culture media for expansion of the cells ex-vivo prior to treatment, or by obtaining a selective expansion of the engineered T-cells in-vivo in patients under chemotherapy or immunosuppressive treatments.

Also the drug resistance of T-cells also permits their enrichment in or ex vivo, as T-cells which express the drug resistance gene, will survive and multiply relative to drug sensitive cells. In particular, the present invention relates to a method of engineering allogeneic and drug resistance T-cells resistant for immunotherapy comprising:

(a) Providing a T-cell;
(b) Selecting at least one drug;
(c) Modifying T-cell to confer drug resistance to said T-cell;
(d) Expanding said engineered T-cell in the presence of said drug, and optionally the preceding steps may be combined with the steps of the methods as previously described.

Drug resistance can be conferred to a T-cell by inactivating one or more gene(s) responsible for the cell's sensitivity to the drug (drug sensitizing gene(s)), such as the hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Another example if the inactivation of the CD3 normally expressed at the surface of the T-cell can confer resistance to anti-CD3 antibodies such as teplizumab.

In an embodiment, the resistance gene to be inactivated is the one which encodes the deoxycytidine kinase (dCk). Deoxycytidine kinase (DCK) is required for the phosphorylation of several deoxyribonucleosides and their nucleoside analogs. Deficiency of DCK is associated with resistance to antiviral and anticancer chemotherapeutic agents. Conversely, increased deoxycytidine kinase activity is associated with increased activation of these compounds to cytotoxic nucleoside triphosphate derivatives. DCK is clinically important because of its relationship to drug resistance and sensitivity (Hazra S, Szewczak A, Ort S, Konrad M, Lavie A (2011) "Post-translational phosphorylation of serine 74 of human deoxycytidine kinase favors the enzyme adopting the open conformation making it competent for nucleoside binding and release". Biochemistry 50 (14): 2870-8).

Drug resistance can also be conferred to a T-cell by expressing a drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to a greater extent than the proliferation of a corresponding cell without the drug resistance gene. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell. Said drug resistance gene can be expressed in the cell either by introducing a transgene encoding said gene into the cell or by integrating said drug resistance gene into the genome of the cell by homologous recombination. Several other drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 ((Schweitzer, Dicker et al. 1990); International application WO 94/24277; U.S. Pat. No. 6,642,043).

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or S351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue.

Another drug resistance gene is the mutant form of calcineurin. Calcineurin (PP2B) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. Correspondence of amino acid positions described herein is frequently expressed in terms of the positions of the amino acids of the form of wild-type human calcineurin heterodimer (GenBank: ACX34092.1).

In another particular embodiment, said mutant form can comprise at least one mutated amino acid of the wild type calcineurin heterodimer b at positions: V120, N123, L124 or K125, preferably double mutations at positions L124 and K125. Correspondence of amino acid positions described herein is frequently expressed in terms of the positions of the amino acids of the form of wild-type human calcineurin heterodimer b polypeptide (GenBank: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140 (UniProtKB: P16455).

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (NP_000918).

Drug resistance gene can also be cytotoxic antibiotics, such as ble gene or mcrA gene. Ectopic expression of ble gene or mcrA in an immune cell gives a selective advantage when exposed to the chemotherapeutic agent, respectively the bleomycine or the mitomycin C.

The T-cells can also be made resistant to immunosuppressive agents. An immunosuppressive agent is an agent that suppresses immune function by one of several mechanisms of action. In other words, an immunosuppressive agent is a role played by a compound which is exhibited by a capability to diminish the extent and/or voracity of an immune response. As non-limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non-limiting examples, targets for immunosuppressive agent can be a receptor for an immunosuppressive agent such as: CD52, glucocorticoid receptor (GR), a FKBP family gene member and a cyclophilin family gene member.

In immunocompetent hosts, allogeneic cells are normally rapidly rejected by the host immune system. It has been demonstrated that, allogeneic leukocytes present in non-irradiated blood products will persist for no more than 5 to 6 days. Thus, to prevent rejection of allogeneic cells, the host's immune system must be effectively suppressed. Glucocorticoidsteroids are widely used therapeutically for immunosuppression. This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol-(GPI) linked glycoprotein (Waldmann and Hale, 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

As a preferred embodiment of the above steps, said gene of step (b), specific for an immunosuppressive treatment, is CD52, and the immunosuppressive treatment of step (d) comprises a humanized antibody targeting CD52 antigen. As another embodiment, said gene of step (b), specific for an immunosuppressive treatment, is a glucocorticoid receptor (GR) and the immunosuppressive treatment of step d) comprises a corticosteroid such as dexamethasone. As another embodiment, said target gene of step (b), specific for an immunosuppressive treatment, is a FKBP family gene member or a variant thereof and the immunosuppressive treatment of step (d) comprises FK506 also known as Tacrolimus or fujimycin. As another embodiment, said FKBP family gene member is FKBP12 or a variant thereof. As another embodiment, said gene of step (b), specific for an immunosuppressive treatment, is a cyclophilin family gene member or a variant thereof and the immunosuppressive treatment of step (d) comprises cyclosporine.

In a particular embodiment of the invention, the genetic modification step of the method relies on the inactivation of two genes selected from the group consisting of CD52 and GR, CD52 and TCR alpha, CDR52 and TCR beta, GR and TCR alpha, GR and TCR beta, TCR alpha and TCR beta. In another embodiment, the genetic modification step of the method relies on the inactivation of more than two genes. The genetic modification is preferably operated ex-vivo using at least two RNA guides targeting the different genes.

By inactivating a gene it is intended that the gene of interest is not expressed in a functional protein form.

Engineering Highly Active T Cells for Immunotherapy

According to the present invention, the T-cells can be selected from the group consisting of inflammatory T-lymphocytes, cytotoxic T-lymphocytes, regulatory T-lymphocytes or helper T-lymphocytes. In another embodiment, said cell can be derived from the group consisting of CD4+T-lymphocytes and CD8+T-lymphocytes. They can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Prior to expansion and genetic modification of the cells of the invention, a source of cells can be obtained from a subject through a variety of non-limiting methods. T-cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described.

As a further aspect of the invention, the T-cells according to the invention may be further engineered, preferably genetically engineered, to enhance their activity and/or activation, especially by modulating the expression of proteins involved in overall T-cell regulation, referred to as "immune-checkpoints".

Immune Check Points

It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1, {Meyaard, 1997 #122}), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 {Nicoll, 1999 #123}, SIGLEC9 {Zhang, 2000 #124; Ikehara, 2004 #125}, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF {Quigley, 2010 #121}, GUCY1A2, GUCY1A3, GUCY1B2, GUCY1B3 which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune check-point, in particular PD1 and/or CTLA-4 or any immune-checkpoint proteins referred to in Table 7.

TABLE 7

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC3 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Arginine/ tryptophan starvation | | EIF2AK4 |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

Therapeutic Applications

In a general aspect, the present invention relates to methods for new adoptive immunotherapy strategies in treating diseases linked with the development of pathological cells, such as cancer, infections and auto-immune diseases.

As a main objective of the invention is the possibility to target pathological cells that bear specific antigen markers in common with T-cells. By pathological cell is meant any types of cells present in a patient, which are deemed causing health deterioration.

In general, pathological cells are malignant or infected cells that need to be reduced or eliminated to obtain remission of a patient.

These anti-CD38 CARs immune cells, particularly when they have undergone a CD38 gene inactivation, are useful as medicament can for treating a CD38-expressing cell-mediated pathological condition or a condition characterized by the direct or indirect activity of a CD38-expressing cell, such as MM, MM, RRMM, ALL, NHL lymphoma (as referred above), their related complication, and their related conditions.

In an embodiment, said anti-CD38 CAR in immune cells CD8 gene-inactivated are used as medicament and they comprise a polypeptide sequence displaying at least 90%, at least 95%, at least 98% or at least 99% identity to one selected from SEQ ID NO. 82-84 (25A10), SEQ ID NO. 100-102 (28F5), SEQ ID NO. 97-99 (13F11), SEQ ID NO. 88-90 (16B5), SEQ ID NO. 91-93 (10F7), SEQ ID NO.94-96 (27B6) and SEQ ID NO. 85-87(29B4), more preferably from SEQ ID NO. 82-84 (25A10), SEQ ID NO. 100-102 (28F5), SEQ ID NO. 97-99 (13F11) and SEQ ID NO. 88-90 (16B5), and more preferably from SEQ ID NO. 82-84 (25A10) and SEQ ID NO. 100-102 (28F5).

In a preferred embodiment, said anti-CD38 CAR in immune cells CD8 gene-inactivated are used as medicament and they comprise a polypeptide sequence displaying at least 90%, at least 95%, at least 98% or at least 99% identity to one selected from SEQ ID NO. 82-84 (25A10) and SEQ ID NO. 100-102 (28F5).

In a more preferred embodiment, said anti-CD38 CAR in immune cells CD8 gene-inactivated are used as medicament and they comprise a polypeptide sequence displaying at least 90%, at least 95%, at least 98% or at least 99% identity to one selected from SEQ ID NO. 82 (25A10-$V_1$ CAR).

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The immune cells, such as T-cells, engineered according to one of the previous methods may be pooled, frozen, and administrated to one or several patients. Accordingly the present invention encompass a method for treating an immune disease by directing engineered T-cells as previously described against patient's own T-cells. When they are made non-alloreactive, they are available as an "off the shelf" therapeutic product, which means that they can be universally infused to patients in need thereof.

In one embodiment, isolated cell obtained by the different methods or cell line derived from said isolated cell as previously described can be used as a medicament.

In a preferred embodiment, said isolated cell according to the invention or cell line derived from said isolated cell can be used in the manufacture of a medicament for treatment of a cancer in a patient in need thereof.

In a preferred embodiment, the cancer that may be treated using the anti-CD38 CAR-expressing cells of the present invention is leukemia or lymphoma, a disease associated to leukemia or lymphoma or a complication thereof.

In a particular embodiment, an anti-CD38 CAR expressing T cell is provided as a medicament for the treatment of CD38+ hematological malignancies and in particular to those which have progressed on or after standard therapy or for whom there is no effective standard therapy (refractory/relapsed patients).

By "Relapsed": it is referred to a subject in whom the hematological malignancy has been treated and improved but in whom the hematological malignancy recurred.

By "Refracted": it is referred to a subject in whom the hematological malignancy has been treated without any improvement and the hematological malignancy thus progressed.

In the context of the disclosure the CD38+ hematological malignancy is in particular selected from the group consisting of non-Hodgkin's lymphoma (NHL) (including, e.g. Burkitt's lymphoma (BL) and T cell lymphoma (TCL)), multiple myeloma (MM), chronic lymphocytic leukemia (CLL) (such as e.g. B chronic lymphocytic leukemia (B-CLL) or hairy cell leukemia (HCL)), B and T acute lymphocytic leukemia (ALL), acute myeloid leukemia (AML), Hodgkin's Lymphoma (HL), and chronic myeloid leukemia (CML), wherein the cancerous cells are or comprise CD38+ cells.

In particular, CD38+ hematological malignancies are B-cell non-Hodgkins Lymphoma (NHL), multiple myeloma (MM), acute myeloid leukaemia (AML), acute lymphoblastic leukaemia (B-cell ALL) and/or chronic lymphocytic leukaemia (CLL), more particularly multiple myeloma (MM), most particularly relapsed and/or refractory multiple Myeloma.

Methods to identify a hematological malignancy are known to the skilled in the art and include as a first step a complete blood count (CBC) and a test of the peripheral blood smear. Definitive diagnosis usually requires an adequate bone marrow aspiration and/or biopsy for morphology studies eventually complemented by flow cytometry analysis, cytogenetics and further molecular techniques. Techniques to confirm that the cells derived from this hematological malignancy are CD38$^+$ are known to the skilled in the art and include standard molecular biology techniques such as, for example, polymerase chain reaction (PCR) and/or immunochemical methods such as Western Blot analysis.

In a preferred embodiment, the invention provides a treatment for CD38+ hematological malignancies such as presented above in patients over 60 years or in patients of less than 20 years.

In a preferred embodiment, said medicament can be used for the treatment of multiple myeloma (MM) of an MM subtype such as refractory/relapsed multiple myeloma (RRMM).

In another embodiment, said medicament can be used for the treatment of the acute lymphoblastic leukemia (ALL).

Multiple Myeloma

Multiple myeloma may be detected by the presence of monoclonal proteins (M proteins). "M-Protein" refers to a paraprotein (a monoclonal protein, or M protein). This paraprotein is an immunoglobulin or immunoglobulin light-chain that is produced in excess by the clonal proliferation of plasma cells. Amounts higher than a certain threshold indicate multiple Myeloma. The M-protein is usually quantified in the serum as well as in the urine. The M-protein level in the serum is measured by typically serum electrophoresis or by for example specific immunoglobulin assays; however, specific immunoglobulin quantification always overestimates the M-protein because normal immunoglobulins are included in the result. For this reason, baseline and follow-up measurements of the M-protein should be done by the same method (Riches P G et al., 1991).

Dosages/Group of Patients with MM to be Treated

In one embodiment, M-protein in serum of higher than 0.5 g/dL indicates multiple myeloma.

In one embodiment, M-protein in urine of higher than 200 mg in a 24-hr urine indicate multiple Myeloma (MM).

In another embodiment, elevated serum free light chains (FLC) with FLC greater than about 10 mg/dL and with abnormal FLC ratio indicates multiple Myeloma. MM might be further identified by immunoglobulin light chain found in the urine, this paraprotein is called Bence Jones protein and is a urinary paraprotein composed of free light chains, wherein the light chains are lambda (λ) and/or kappa (κ) free light chains. These free light chains (FLC) may be measured by commercial tests. The free light chain measurement refers to the measurement of the FLC kappa and FLC lambda free light chains giving a free light chain ratio (FLC) of FLC kappa to FLC lambda (FLC K/λ ratio), wherein a normal FLC K/λ ratio ranges from 0.26 to 1.65.

In patients with multiple myeloma, either of the light chains, kappa or lambda, may be dominantly produced which results in changes of the FLC K/λ ratio. Abnormal FLC K/λ ratios indicating multiple myeloma are thus FLC K/λ ratios lower than 0.26 or higher than 1.65

Therefore, in one embodiment, the subject having multiple myeloma has a) measurable serum M-protein of greater than about 0.5 g/dL, and/or b) urine M-protein of greater than about 200 mg (24-hr urine), and/or c) elevated serum free light chains (FLC) with FLC greater than about 10 mg/dL with abnormal FLC ratio.

In one embodiment, subjects to be treated by the engineered immune cells of the invention have multiple myeloma and certain genetic features, such as a translocation between chromosomes 9 and 22, known as the Philadelphia chromosome; or a translocation between chromosomes 4 and 11 [t(4;11)(q21;q23)]; a hyperdiploidy such as trisomy 4, 10, 17), or chromosome 9p deletion.

Therefore in one embodiment, the subject to be treated by the isolated cells of the invention has a 17p deletion, t (4, 14), t (14, 16), t (14, 20) and/or more than 3 copies of 1q21. It is known in the art, that subjects having multiple myeloma and certain genetic features, such as the chromosomal deletion 17p, the translocations t (4, 14), t (14, 16), t (14, 20) or amplifications such as more than 3 copies of 1q21 are associated with a worse outcome (Avet-Loiseau H et al., 2011). Researchers such as Van Laar et al. (2014) have developed a genomic profiling test for subjects with multiple Myeloma. This type of test allows doctors to classify subjects with multiple myeloma based on its genomic expression profile and not just a few chromosomal abnormalities.

In one embodiment, the subject may have a high-risk gene expression profiling (GEP) signature. For instance, this topic is described in more details in Shaughnessy et al (2007).

The subject may have any combination of the above mentioned features.

Acute Lymphoblastic Leukemia (ALL)

In one embodiment, the leukemia which can be treated by the medicament of the present invention is acute lymphoblastic leukemia (ALL).

In another embodiment of any of the above, the leukemia is pediatric (childhood) ALL.

In another embodiment of any of the above, the leukemia is relapsed ALL.

In another embodiment of any of the above, the leukemia is refractory ALL.

In another embodiment of any of the above, the leukemia is drug-resistant ALL.

In a further embodiment, the leukemia is glucocorticoid-resistant ALL.

In still another embodiment, said medicament can be used for the treatment of a B-cell non-Hodgkin's lymphoma (NHL) patients such as mantle cell leukemia (MCL).

Other CD38-Mediated Pathological Conditions

According to another embodiment, the engineered immune cells of the invention ar used to treat CD38+ cell-mediated solid tumors such as prostate, seminal vesicle, appendix or to a pathology such as diabetes (Antonelli et al; 2004).

Associated Treatments

In some embodiments, the subject has been previously treated with an anti-cancer therapy. In particular said, said previous anti-cancer therapy may be selected from the group constituted of chemotherapy, targeted cancer therapies, radiotherapy, bone marrow and/or stem cell transplantation and immunotherapy. In a more preferred embodiment, the present invention provides a pediatric treatment, in particular a pediatric treatment against MM, RRMM or-related diseases or complications.

In one embodiment, the subject has been previously treated with bortezomib and/or lenalidomide.

"Radiation therapy" or "radiation" uses high-energy radiation to remove cancer cells. Radiation therapy might be used before a bone marrow or peripheral blood stem cell transplant.

"Bone marrow and/or stem cell transplantation" refers to a cell transplantation aimed to restore stem cells that were destroyed by high doses of chemotherapy and/or radiation therapy. Sources of stem cells include bone marrow, peripheral blood or umbilical cord blood. Depending on the source of stem cells that are transplanted, the procedure might be distinguished into bone marrow transplant (BMT) or peripheral blood stem cell transplant (PBSCT) or umbilical cord blood transplantation (UCBT). Furthermore bone marrow and/or stem cell transplantation might refer to an autologous stem cell transplantation and/or an allogeneic transplantation.

Resistance to Drug or Immunosuppressive Agent

The engineered immune cells, as previously described, when they are made resistant to chemotherapy drugs and immunosuppressive drugs that are used as standards of care, especially methotrexate and the combination of fludarabine and Cyclophosphamide, are particularly suited for treating various forms of cancer. Indeed, the present invention preferably relies on cells or population of cells, In this aspect, it is expected that the chemotherapy and/or immunosuppressive treatment should help the selection and expansion of the engineered T-cells in-vivo.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Administration

In another aspect, the present invention relies on methods for treating patients in need thereof, said method comprising at least one of the following steps:

(a) providing an immune-cell obtainable by any one of the methods previously described;

(b) Administrating said transformed immune cells to said patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

An embodiment of the present invention is related to a method for treating a patient comprising:

(a) Diagnosing said patient for the presence of pathological cells presenting CD38-specific antigen markers in common with immune cells;

(b) Preparing a population of engineered immune cells according to the method presented in details previously, (c) Administrating said engineered immune cells to said patient diagnosed for said pathological cells.

The step of diagnostic of well-known for the skill man in the art, for instance reference can be made to Dürig J, Naschar M, Schmücker U, Renzing-Köhler K, Hölter T, Hüttmann A, Dührsen U, (2002) "CD38 expression is an important prognostic marker in chronic lymphocytic leukaemia" Leukemia. 16(1):30-5.

Example of Steps to Engineer T-Cells According to the Invention for Immunotherapy For a better understanding of the invention, it is provided below an example of the steps to follow to produce T-cells directed against leukemia CD38 positive cells:

1. Providing T-cells from a cell culture or from a blood sample from one individual patient or from blood bank and activating said T cells using anti-CD3/C28 activator beads (Dynabeads®). The beads provide both the primary and co-stimulatory signals that are required for activation and expansion of T cells.

2. Transducing said cells with a retroviral vector comprising a transgene encoding a Chimeric antigen receptor consisting of the fusion of CD3zeta activation domain, 4-1BB co-stimulation domain, a transmembrane domain and a hinge from CD28α,FcεIIIγ or IgG1 fused to a sequence encoding the variable chain of an anti-CD38 antibody. For security improvement of the transformed T-cell, a suicide gene sensitive to rituximab may further be introduced as described in WO 2013/153391 into the lentiviral vector separated by T2A splitting sequences.

3. (optionally) Engineering non alloreactive and/or resistant T cells:

a) It is possible to Inactivate TCR alpha in said cells to eliminate the TCR from the surface of the cell and prevent recognition of host tissue as foreign by TCR of allogenic and thus to avoid GvHD by following the protocols set forth in WO 2013/176915.

b) It is also possible to inactive one gene encoding target for an immunosuppressive agent or a chemotherapy drug to render said cells resistant to immunosuppressive or chemotherapy treatment to prevent graft rejection without affecting transplanted T cells. In this example, target of immunosuppressive agents is CD52 and immunosuppressive agent is a humanized monoclonal anti-CD52 antibody (ex: Alemtuzumab) as described in WO 2013/176915.

4. Gene Inactivation is performed by electoporating T-cells with mRNA encoding specific TAL-endonuclease (TALEN™—Cellectis, 8 rue de la Croix Jarry, France). Inactivated T cells are sorted using magnetic beads. For example, T cells still expressing the CD38 targeted gene (can be removed by fixation on a solid surface, and inactivated cells are not exposed of the stress of being passed through a column. This gentle method increases the concentration of properly engineered T-cells.

5. Expansion in vitro of engineered T-cells prior to administration to a patient or in vivo following administration to a patient through stimulation of CD3 complex. Before administration step, patients can be subjected to an immunosuppressive treatment such as CAMPATH1-H, a humanized monoclonal anti-CD52 antibody.

6. Optionally exposed said cells with bispecific antibodies ex vivo prior to administration to a patient or in vivo following administration to a patient to bring the engineered cells into proximity to a target antigen.

General Methods

Primary T-Cell Cultures

T cells were purified from Buffy coat samples provided by EFS (Etablissement Français du Sang, Paris, France) using EasySep™ Direct Human T Cell Isolation Kit (Stem cells). Purified T cells were activated in X-Vivo™-15 medium (Lonza) supplemented with 20 ng/mL Human IL-2, 5% Human serum, and Dynabeads Human T activator CD3/CD28 at a bead:cell ratio 1:1 (Life Technologies).

CD38 TALEN Transfection

A schematic representation is shown in FIG. 8.

Heterodimeric TALE-nuclease targeting two 17-bp long sequences (called half targets) separated by an 15-bp spacer within CD38 gene were designed and produced. Each half target is recognized by repeats of the half TALE-nucleases listed in Table 3. The sequences of the CD38 targets are provided in FIG. 5. Each TALE-nuclease construct was subcloned using restriction enzyme digestion (insert:SfaNI-Bbvl and vector:BsmBI) in a mammalian expression vector (pCSL10794) under the control of the T7 promoter. mRNA encoding TALE-nuclease cleaving CD38 genomic sequence were produced using the mMESSAGE mMACHINE T7 Kit (Life Technologies) and purified using RNeasy Mini Spin Columns (Qiagen). Transfections were done using Cytopulse technology, by applying two 0.1 mS pulses at 3000V/cm followed by four 0.2 mS pulses at 325V/cm in 0.4 cm gap cuvettes in a final volume of 200 µl of "Cytoporation buffer T" (BTX Harvard Apparatus). Cells were immediately diluted in X-Vivo™-15 media (Lonza) and incubated at 30° C. with 5% $CO_2$. IL-2 (from Miltenyi Biotec was added 2h after electroporation at 20 ng/mL. 18 hours later, cells were transferred at 37° C. with 5% $CO_2$.

CD38 Negative T Cells Purification

Six days after CD38 TALEN transfection, CD38 negative cells were purified by magnetic separation using CD38 microbeads kit according to the manufacturer's specifications (Miltenyi).

CAR mRNA Transfection

Transfections were done at Day 4 or Day 11 after T-cell purification and activation. 5 millions of cells were transfected with 15 µg of mRNA encoding the different CAR constructs. CAR mRNAs were produced using the mMESSAGE mMACHINE T7 Kit (Life Technologies) and purified using RNeasy Mini Spin Columns (Qiagen). Transfections were done using Cytopulse technology, by applying two 0.1 mS pulses at 3000V/cm followed by four 0.2 mS pulses at 325V/cm in 0.4 cm gap cuvettes in a final volume of 200 µl of "Cytoporation buffer T" (BTX Harvard Apparatus). Cells were immediately diluted in X-Vivo™-15 media (Lonza) and incubated at 37° C. with 5% $CO_2$. IL-2 (from Miltenyi Biotec was added 2h after electroporation at 20 ng/mL.

Degranulation Assay (CD107a Mobilization)

T-cells were incubated in 96-well plates (40,000 cells/well), together with an equal amount of cells expressing various levels of the CD38 protein. Co-cultures were maintained in a final volume of 100 µl of X-Vivo™-15 medium (Lonza) for 6 hours at 37° C. with 5% $CO_2$. CD107a staining was done during cell stimulation, by the addition of a fluorescent anti-CD107a antibody at the beginning of the co-culture, together with 1 µg/ml of anti-CD49d, 1 µg/ml of anti-CD28, and 1× Monensin solution. After the 5h incubation period, cells were stained with a fixable viability dye and fluorochrome-conjugated anti-CD8 and anti-CD3 and analyzed by flow cytometry. The degranulation activity was determined as the % of viable/CD3+/CD8+/CD107a+ cells, and by determining the mean fluorescence intensity signal (MFI) for CD107a staining among CD8+ cells. Degranulation assays were carried out 24h after mRNA transfection.

Cytotoxicity Assay

T-cells were incubated in 96-well plates (100,000 cells/well), together with 10,000 target cells (expressing CD38) and 10,000 control (CD38neg) cells in the same well. Target and control cells were labelled with fluorescent intracellular dyes (CFSE or Cell Trace Violet) before co-culturing them with CAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or CD38neg control cells) was determined and the % of specific cell lysis was calculated. Cytotoxicity assays were carried out 48h after mRNA transfection.

Figure 3:
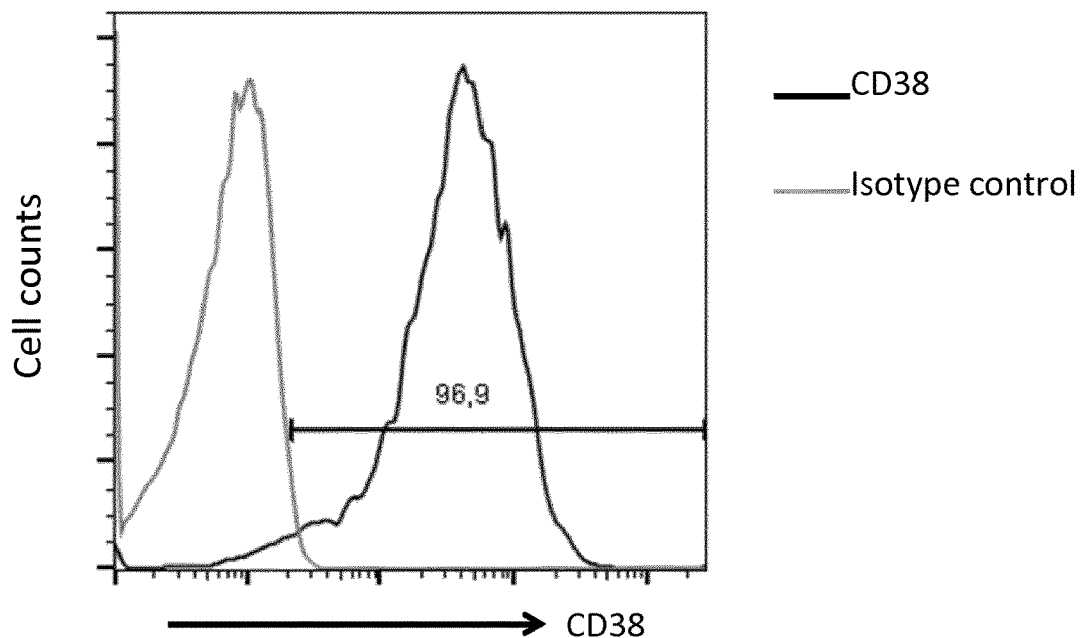
FIG. 3A-B: Expression of CD38 in T cells: Fresly isolated T cells were cultured with anti-CD3-CD28 coated microbeads (Dynabeads, life technologies)+20 ng/ml human IL2 (Miltenyi). A: CD38 expression by T cells at Day 6 after activation. B: CD38 expression by T cells over 3 weeks after activation.
Figure 3:
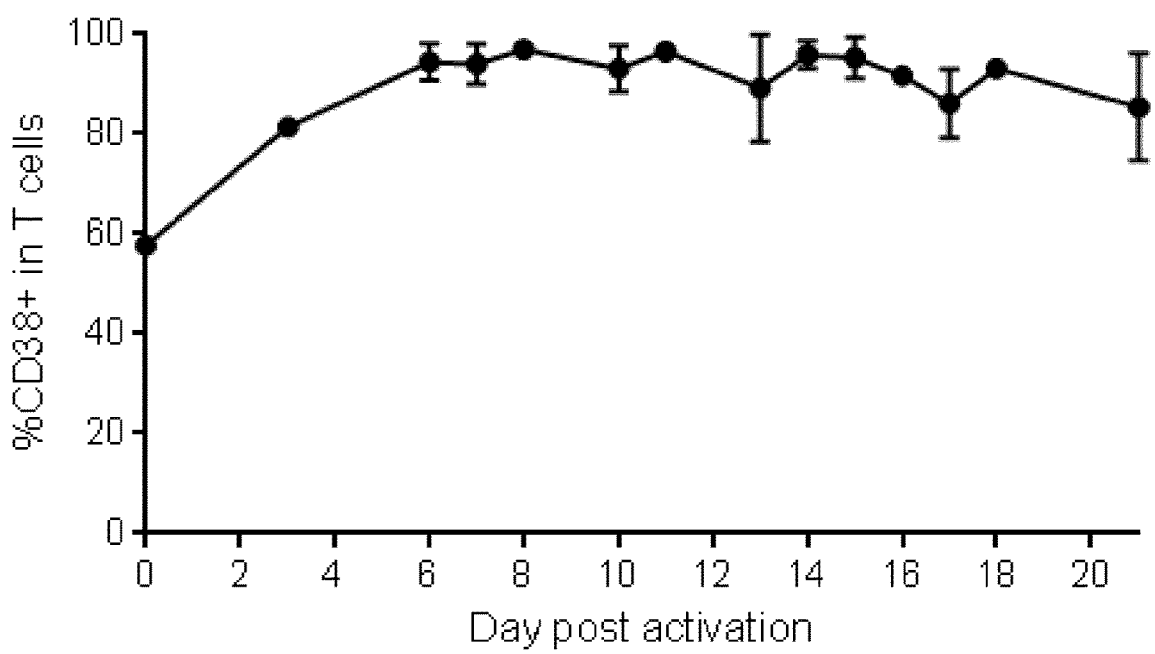

Example 1: Inactivation of CD38 Antigen in T Cells by Knock-Out (KO) Using TALE Nuclease CD38 is also highly expressed by activated T cells. CD38 expression by T cells after activation with CD3/CD28 beads and IL-2 was analyzed by FACS every 3-4 days for 17 days (FIG. 3A). It was observed that more than 90% of T cells express CD38 between day 6 and day 17 after activation (FIG. 3B).

Figure 4:
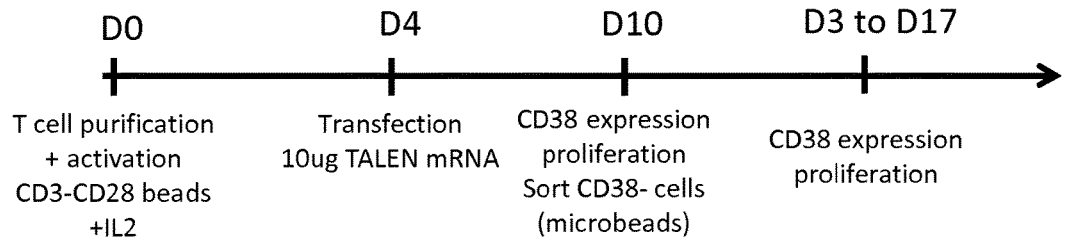
FIG. 4A-C: Time scales for 3 experiments performed in the present invention: A: Talen-inactivation of the endogenous CD38 in T cells; B: transfection of mRNA encoding CAR in WT T cells; C: transfection of mRNA encoding CAR after T cell activation in purified CD38 deficient T cells
Figure 4:
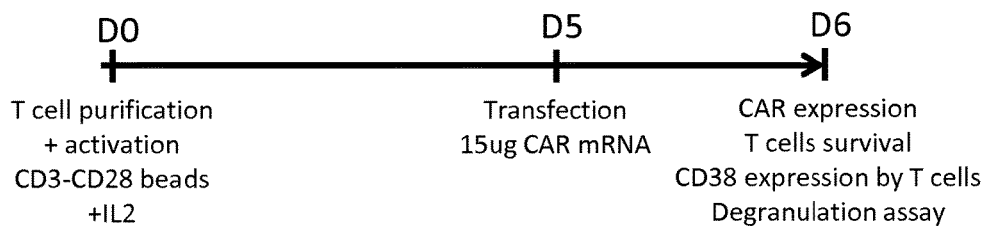
Figure 4:
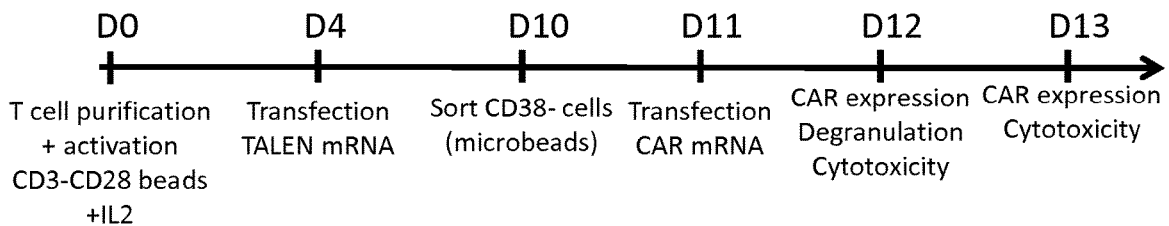

Thus in order to avoid killing of activated T cells by anti-CD38 CAR+ T cells, CD38 surface expression in T cells needs to be prevented. This may be accomplished by the inactivation of the CD38 gene using TALE-nucleases. The experiment was performed as presented in FIG. 4A.

Heterodimeric TALE-nucleases targeting two 17-pb long sequences separated by a 13-pb spacer within the CD38 gene were designed and produced. Each half target is recognized by repeats of the half TALE-nucleases listed in the Table 4 and FIG. 5.

Each TALE-nuclease construct was subcloned using restriction enzyme digestion in a mammalian expression vector under the control of the T7 promoter. mRNA encoding TALE-nuclease cleaving CD38 were synthesized from plasmids carrying the coding sequence downstream from the T7 promoter.

Figure 6:
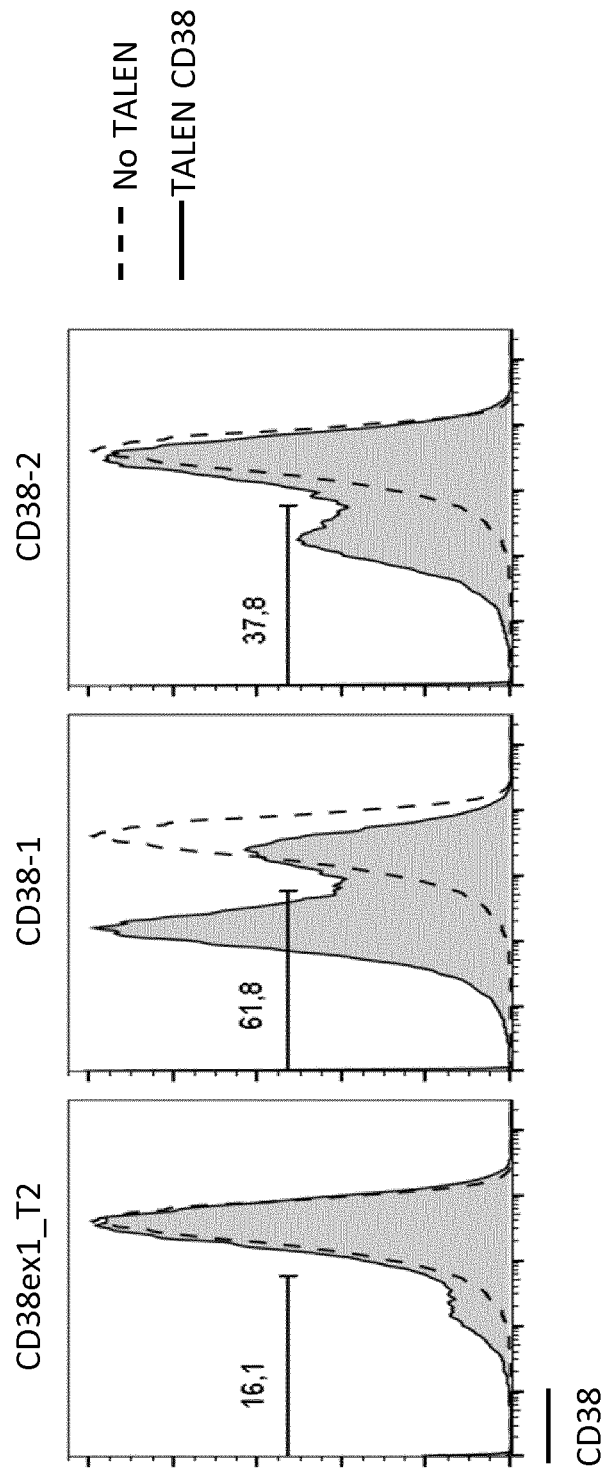
FIG. 6: Percentage of CD38 negative T cells 7 days after TALEN mRNA transfection; the 3 pairs of TALEN CD38ex1-T2, CD38-1

Purified T cells activated during 4 days with anti CD3/CD28 coated beads and recombinant IL-2 were transfected by electroporation (Cytopulse) with each of the 2 mRNAs (10 ug each) encoding both half TALE-nucleases. To investigate, the CD38 KO, the percentage of CD38 negative T cells was assessed by flow cytometry at day 7 (FIG. 6). The three TALENs were able to induce CD38 KO but the CD38-1 was the most efficient (60.95%+/−7.6 $CD38^{neg}$ T cells).

Figure 7:
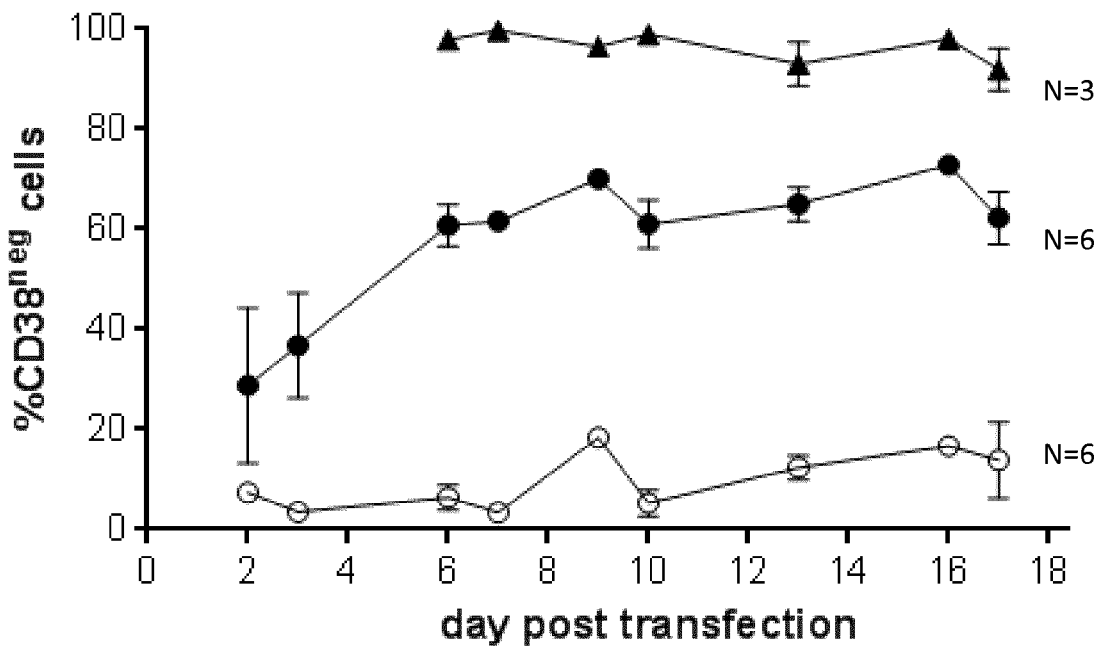
FIG. 7A-B: A: Percentage of CD38 negative T cells over the 17 days of culture with IL-2 after TALEN mRNA transfection. B: T cell growth (i.e. factor of proliferation) over the 11 days of culture in presence of IL-2 after CD38 negative T cells purification –Day 6 after T cells electroporation and Day 10 after T cells activation—[legend: empty circle: No TALEN; full circle: TALEN CD38-1 and triangle: purified negative CD38 (TALEN CD38-1); N represents the number of tests performed for each case]
Figure 7:
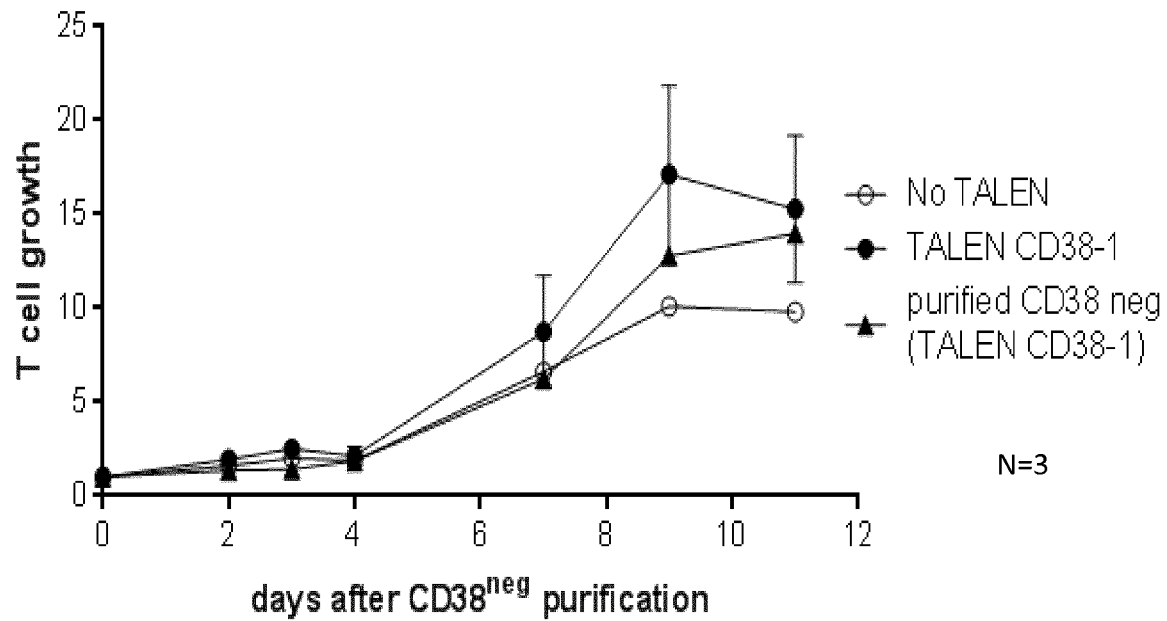

The CD38 inactivation induced by the CD38-1 TALEN was stable in culture for 3 weeks (FIG. 7A). CD38 deficient T cells could be easily sorted using the anti-CD38 microbeads (Miltenyi) (FIG. 7A). The proliferation rate of purified CD38 deficient T cells was comparable with non-transfected or non-purified T cells (FIG. 7B).

In two independent experiments, CD38 TALEN transfection were performed by using 2 μg of RNA per $10^6$ of T cells and using electroporation, it is shown in FIG. 23 that such transfection induce CD38 KO with high frequency. In another experiment, a comparison of 2 μg and 1 μg or 0.5 μg per million cells was tested. The amount of mRNA TALEN didn't modify the proliferation rate of T cells (FIG. 24B) but decrease in the % of CD38 negative cells (FIG. 24A).

Example 2: Study of Anti-CD38 CARs Activity after mRNA Transfection in WT T Cells CAR Structure Eight pairs of scFvs have been tested, their sequences SEQ ID NO: 10 to 73 including their corresponding CDRs are presented in Table 2.

For each pair of scFvs, 3 different CARs constructs have been designed with the 41BB costimulatory domain, the CD3 activation domain, the CD8α transmembrane domain and 3 different hinges of sequences SEQ ID NO: 76, 77 and 78) respectively:

$V_1$: FcεRIIIα hinge
$V_2$: CD8α hinge
$V_3$: IgG1 hinge.

Figure 1:
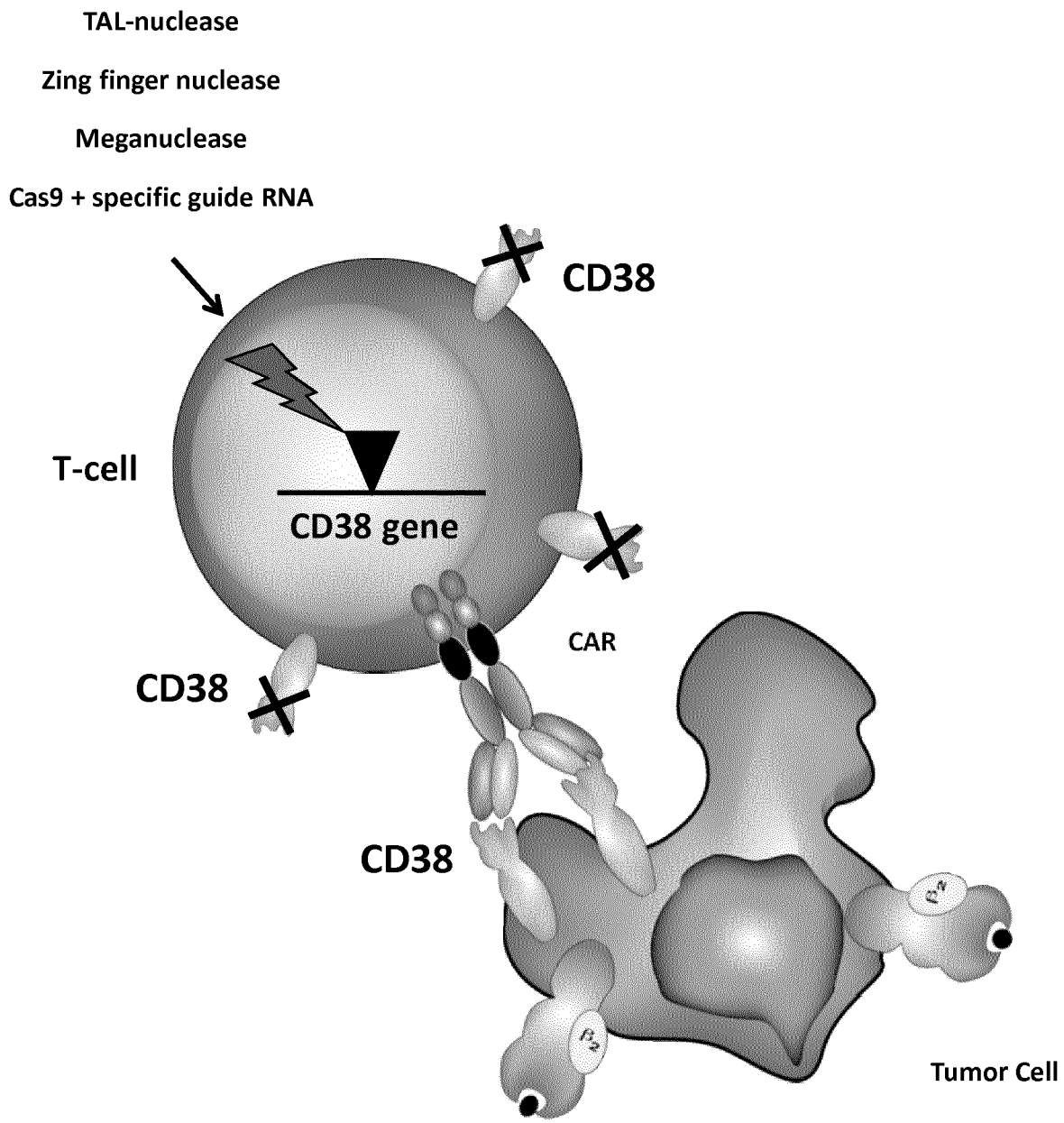
FIG. 1: Schematic representation of an engineered T-cell according to the present invention disrupted for CD38 and endowed with a chimeric antigen receptor (represented as a single-chain CAR) targeting a malignant cell bearing the antigen marker CD38.
Figure 2:
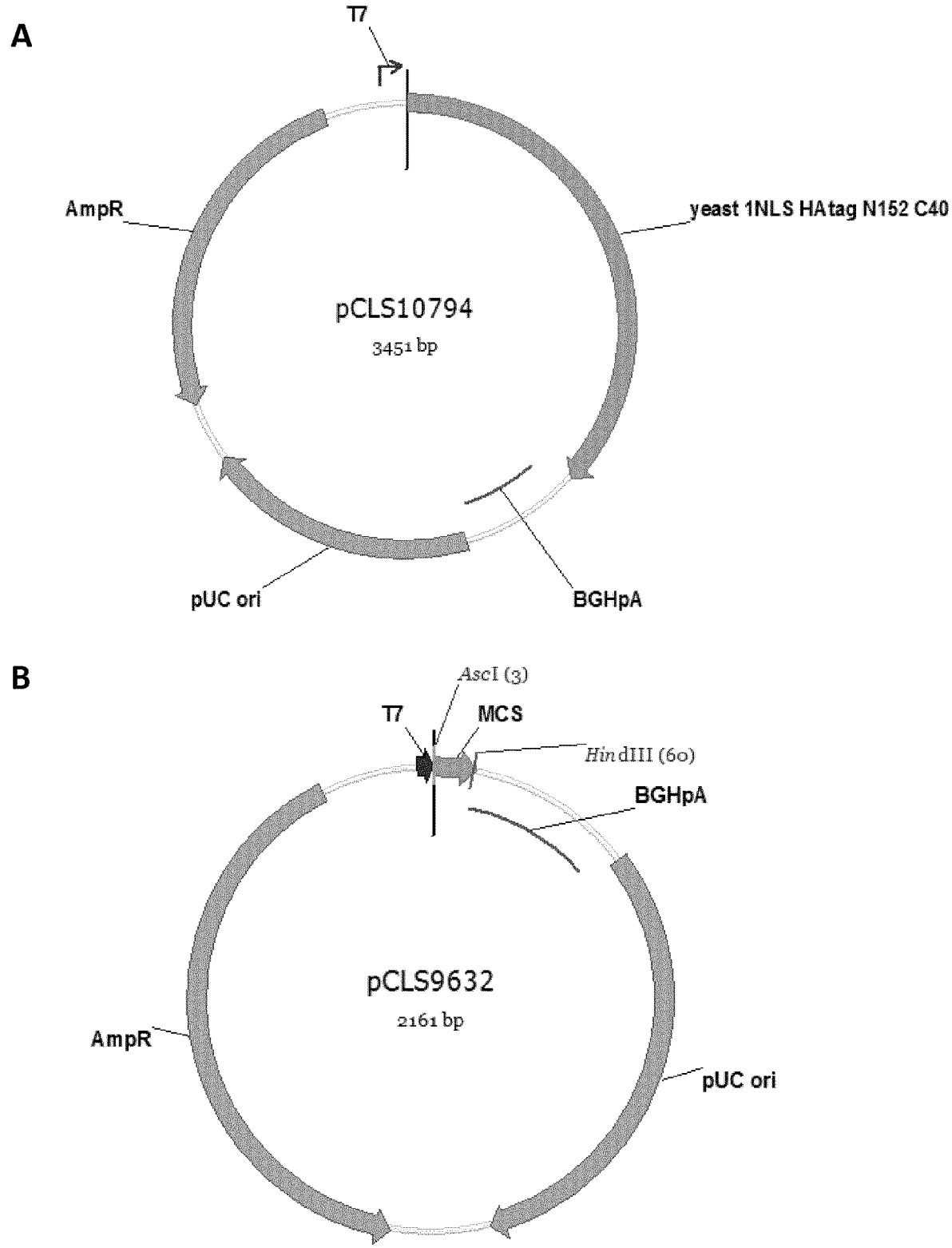
FIG. 2A-B: A: Schematic representation of in a mammalian expression vector (pCSL10794) under the control of the T7 promoter, which is used for the subcloning of each TALE-nuclease construct using restriction enzyme digestion (insert: SfaNI-Bbvl and vector: BsmBI). B: Schematic representation of in a mammalian expression vector (pCLS9632) under the control of the T7 promoter, which is used for the subcloning of each CAR constructs using restriction enzyme digestion (Ascl et HindIII).

The FIG. 9 and FIG. 2A shows respectively the name of plasmids of the different versions of the CAR created for the subcloning and the one used as backbone. Also the value of Kd for their respective scFvs are provided.

The Table 1 shows the sequences SEQ ID NO: 82 to 105 for all the 24 different anti-CD38 CARs (8 pairs of scFvx3 versions V1, V2& V3) and of their constituents (except scFvs presented in Table 2).

Selection of Target Cells

The CAR molecules generated were screened for degranulation and cytotoxic activity toward target cell lines expressing CD38 following transient transfection of T cells with CAR mRNA. Target cell lines expressing different expression levels of CD38 (FIG. 3B) were used for activity testing (FIG. 10A and FIG. 10B).

The number of CD38 molecules per cell was evaluated by Qifikit assay (DAKO Company) for the following cell lines:

U266 CD38+B-cell myeloma (48216 molecules/cell) and U266 CD38− (230 molecules/cell) obtained from U266B1 cell line (#ATCC® TIB-196™) by magnetic separation using anti-CD38 microbeads;

MOLP8, a multiple myeloma cell line (#DSMZ ACC 569) expressing high levels of CD38 (259889 molecules/cell);

Daudi (#ATCC® CCL-213™), a cell line derived from Burkitt lymphoma expressing high levels of CD38;

K562 (#ATCC® CCL-243), a cell line CD38 negative cell line derived from chronic myelogenous leukemia.

CAR mRNA Transfection in WT T Cells at Day 5 after T Cell Activation

T cells were purified from buffy coat samples and activated using anti-CD3/CD28 coated beads. Cells were transfected 5 days after activation with 15 μg of mRNA encoding anti-CD38 CAR (time scale of the experiment is presented in FIG. 4C). The CAR expression and the degranulation capacity of CART cells were assessed 24 hours after the transfection.

Despite CD38 expression on T cells, significant T cell mortality after CAR mRNA transfection at Day 5 was not observed.

Expression

Three detection methods were assessed on cells transfected 5 days after activation: an anti-Fab antibody, the L-protein staining and a CD38-Fc protein (produced by LakePharma) staining (FIG. 11). The anti-CD38 CARs 13F11-V2, 16B5-V2&V3, 25A10-V1&V2, 28F5-V1&V2, GMB005-V1&V2&V3 were detectable by at least one method. Some CARs were undetectable by any of these methods but were able to degranulate in a CD38 dependent manner (see next section).

Degranulation Capacity

The CAR T cell degranulation was evaluated by flow cytometry. The read-out is the CD107a expression at the T cell plasma membrane after 5 hours incubation with target cells (FIG. 12). Most of the scFv's induce T cell degranulation in a CD38 dependent manner except 10F7, 27B6 and 29B4

The 3 versions (V1, V2 and V3) of the scFv's 13F11, 16B5, 25A10, 28F5 and the tool CAR GMB005-V$_1$ were selected for screening at day 12.

Example 3: Evaluation of the Effect of CD38 KO and Purification of CD38 Negative T Cells on the Activity of a Serial Anti-CD38 CARs Obtained by mRNA Transfection i. Comparison CAR mRNA Screening in WT/CD38-Deficient/Purified CD38 Deficient T Cells T cells were purified from buffy coat samples and activated using anti-CD3/CD28 coated beads (time scale of the experiment is presented in FIG. 4B). Cells were transfected 12 days after activation with 15 µg of mRNA encoding anti-CD38 CAR and 24h after CAR mRNA transfection, a significant mortality of T cells was observed.

The CD38 KO and CD38 negative purification has been tested and evaluated. CD38-1 TALEN mRNA was transfected (or not) in T cells at day 4 after activation with anti-CD3/CD28 coated beads. 6 days after CD38 negative cells were purified (or not) by using magnetic separation (Miltenyi's protocol). The day after, CAR mRNAs were transfected. The CAR expression and degranulation capacity of CART cells were assessed 24 hours after the transfection. CAR expression and cytotoxic capacity of CART cells were assessed 48 hours after the transfection. The anti-CD38 CARs, 13F11-V2 and -V3 were used for the analysis. After 24 hours of CAR mRNAs transfection, T cell viability was increased in CD38 KO T cells with purified CD38 KO T cells displaying the best viability (FIG. 13A).

Expression

CAR expression was analyzed by flow cytometry using CD38-Fc protein. CAR expression was detectable at higher levels at day 1 and day 2 in CD38-deficient T cells. No significant difference was observed between the purified or non-purified CD38 KO T cells (FIG. 13B).

Degranulation Capacity

The percentage of T cells that have degranulated after incubation with target cell lines is CD38-independent in wt CAR T cells but is CD38-dependent when CAR T cells are CD38-deficient (FIG. 14A). The purification step has no effect on CAR T cell degranulation in the tested conditions.

Cytotoxic Activity

Forty-eight hours after CAR mRNAs transfection, there was no cytotoxic activity of CAR T cells against target cell lines. This cytotoxic activity was restored in CD38 deficient CAR T cells. This cytotoxic activity was CD38-dependent but no difference was observed between purified and non-purified CD38-deficient T cells (FIG. 14B).

Altogether, these results indicate the improved effect of CD38 inactivation (induced by CD38-1 TALEN) on the cytotoxic activity before anti-CD38 CAR mRNA transfection in T cells. Next experiments were performed by using purified CD38-deficient T cells.

ii. CAR mRNA Transfection at Day 12 after T Cell Activation in Purified CD38 Deficient T Cells T cells were purified from buffy coat samples and activated using anti-CD3/CD28 coated beads and IL-2. CD38-1 TALEN mRNA was transfected in T cells at day 4 after activation, 6 days later CD38 negative cells were purified by using magnetic separation (Miltenyi). The day after, CAR mRNAs were transfected. The CAR expression and degranulation capacity of CART cells were assessed 24 hours after the transfection. CAR expression and cytotoxic capacity of CART cells were assessed 48 hours after the transfection.

Expression

All CARs were detected 24h after transfection except the 25A10-V3 However, the latter expressed anti-CD38 CAR above the background. The 13F11-V2, 25A10-V1, 25A10-V2 and 28F5-V2 were highly expressed (more than 80%). The CAR-V2 and -V3 expression were more stable at 48h than -V1 (FIG. 15).

Degranulation Capacity

Most of the CART cells were able to degranulate against CD38 expressing cell lines. Only the 16B5-V3, 28F5-V3, 25A10-V3 show low degranulation capacity. The CART cells that present the best ratios (>2) of degranulation against U266 CD38+ and U266 CD38− were 13F11-V1, -V3, 16B5-V1, -2 25A10-V1, 28F5-V1, -V2 and GMB005-V1 (FIG. 16). The CAR-V1 and -V3 were able to degranulate at lower level against autologous T cells CD38+ than CAR-V2.

Cytotoxic Activity

Most of the CAR T cells were able to kill efficiently (more than 20% in 4 hours) CD38+ target cells lines FIG. 17). The 16B5-V2, 25A10-V2 and 28F5-V2 that are highly cytotoxic against CD38+ target cells lines are also highly cytotoxic against autologous activated T cells. Interestingly, the -V1 version of the 25A10 and 28F5 were cytotoxic against CD38$^{hi}$ cells lines but presented a lower cytotoxic activity for the autologous T cells.

From all these results et from all the CARs tested, it appears that the CARs 25A10-V1, 25A10-V2, 28F5-V1 and 28F5-V2—particularly when they have their CD38 gene inactivated—show a higher potential in terms of cytotoxicity towards cancerous CD38-expressing cells, while showing a reduced effect in the interaction with the T cells (i.e. other activated CD38 T cells from the same donor).

Figure 22A:
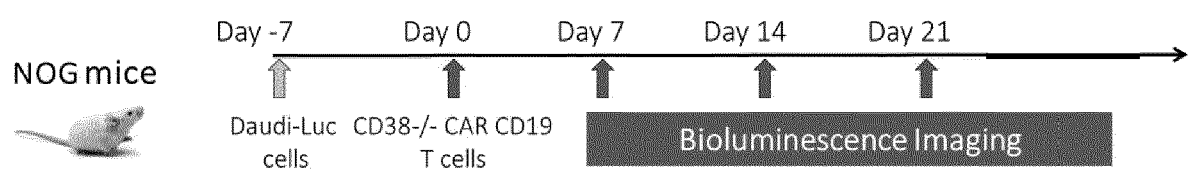
Figure 22B:
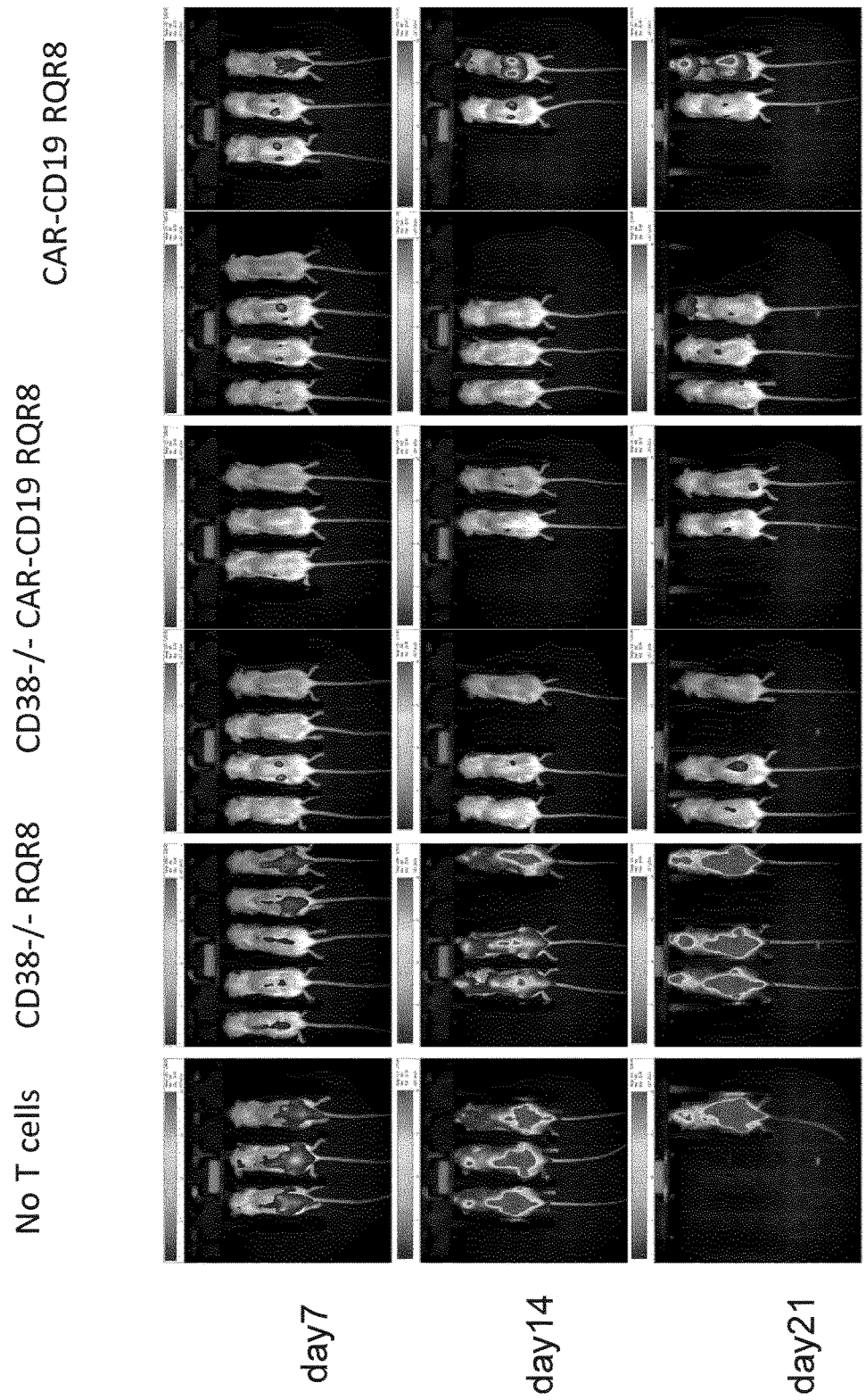
Figure 22C:
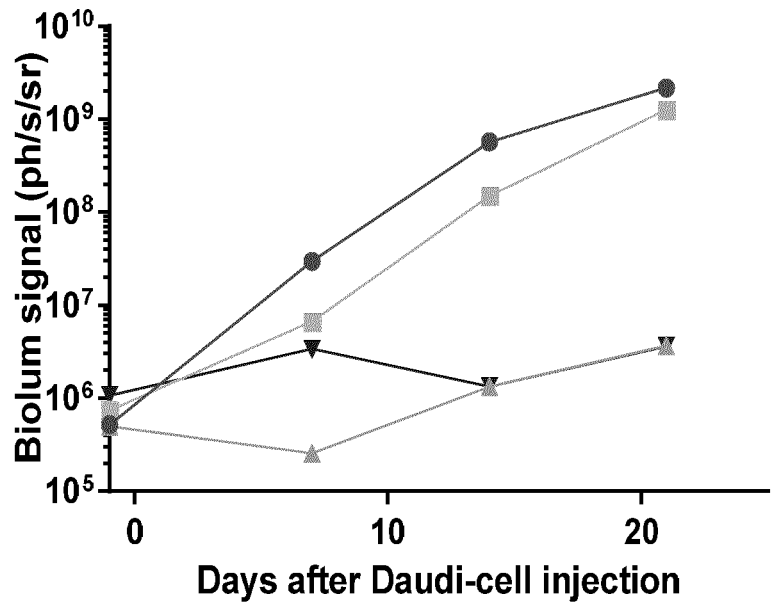
Figure 22D:
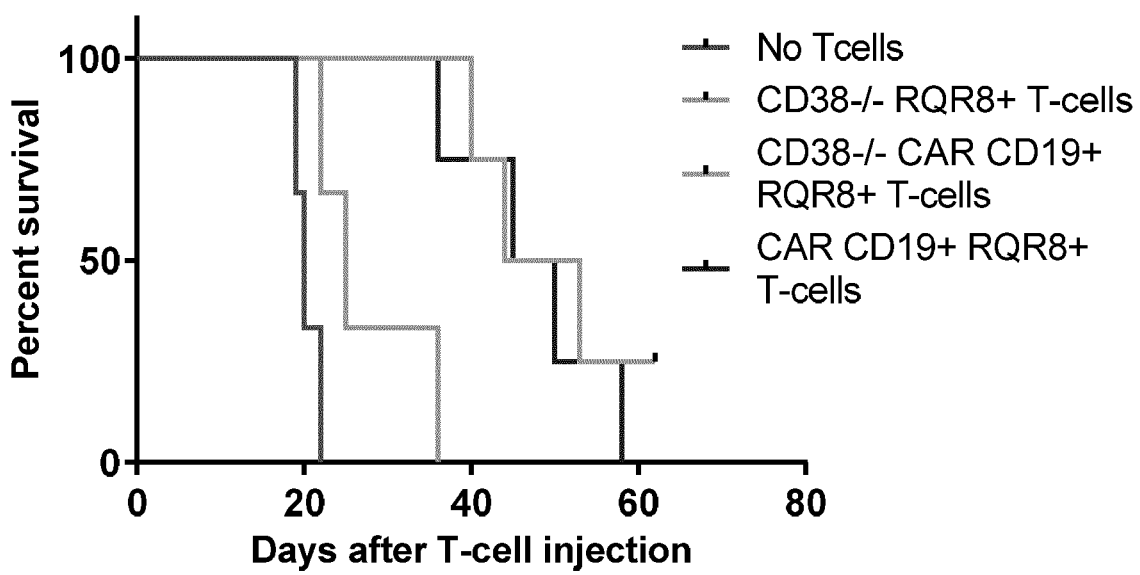

Example 4: Evaluation of the Impact of CD38-KO for Anti-CD19 CAR Activity In Vivo To evaluate the impact of CD38-KO for CAR activity, NOG mice were sublethally irradiated 8 days before injection of T-cells. At Day (−7) 5×10$^5$-Daudi Luciferase cells/mice were iv injected. Mice were then infused with wt or CD38−/− CAR-CD19 RQR8 T-cells. The tool CD19 CAR comprising FMC63 scfv correspond to the polynucleotide having the sequence SEQ ID NO.16 disclosed in WO2014/184143. CAR-CD19 RQR8 T-cells were obtained by co-expression of both anti-CD19 and RQR8 accordingly to methods disclosed in prior art such as Donnelly M L et al, (2001) *J Gen Virol.*; 82(Pt 5):1027-1041. Bioluminescent signal was assessed at D(−1), D7, D14, D21 and D28 post injection of T-cells (FIG. 22A and FIG. 22B). When the tumor progression and the survival rate are assessed, it is shown that the CD38−/− CAR-CD19 RQR8 cells presented the same anti-tumor activity in vivo than CAR-CD19 RQR8 T cells (FIG. 22C) and T cells endowing CD19 CAR and KO CD38 deficient survived longer (FIG. 22D). Thus, CD38-KO doesn't affect the anti-tumor activity of CAR T-cells in vivo.

Example 5: Evaluation of Activity of Anti-CD38 CAR Obtained by Lentiviral Transduction in Double KO TRAC/CD38 T Cells CAR Cloning in Expression Plasmid The 4 anti-CD38 CARs 25A10-v1, 25A10-v2, 28F5-v1 and 28F5-v2 were cloned using the restriction enzyme XmaI into the final rLV backbone containing RQR8 (pCCL-RQR8-T2A-CAR) under the control of the EF1a promoter. The sequences of these plasmids have been analyzed and the plasmids have been sent to Vectalys (France) for rLV production.

rLV CD38 CAR Transduction in Function of rLV MOI

The CAR CD38 rLV dose needed to transduce primary T cells was assessed at day 7 after T cell activation.

T cells were transfected with CD38 TALEN mRNA at day 3 after activation and transduced 4 days later with the 4 CAR candidate rLVs (25A10-v1, -v2, 28F5-v1 and -v2) at MOI 5, 10 and 15.

The transduction efficiency was assessed 3 days after transduction by detection of the percentages of positive CAR or positive RQR8 cells. No significant difference of transduction efficiency between the 3 MOIs was observed (FIG. 25A and FIG. 25B respectively). The following rLV screening will be perform with a transduction at MOI 5.

Screening with CD38-KO and TCR-KO Attributes

The outline of the process is shown in FIG. 26. The parameters are the following: T cells were activated by using Dynabeads CD3-CD28, the culture were made by using medium Xvivo+5% human serum heat inactivated+IL-2 20 ng/ml, a double KO (DKO) CD38-TRAC was performed by using a ratio of 2 µg TALEN mRNA per million of cells (5 million cells/cuvette); the transduction was performed by using rLV from Vectalys (France) at a MOI of 5.

To assess the cytotoxic capacities of the CARs, the MOLP8, Daudi, U266 CD38+ and U266 CD38− were used as target cells previously used during the mRNA screen. These cell lines are mostly multiple myeloma cell lines (except Daudi) expressing different levels of CD38.

The rLV CAR screen has been done in 3 different experiments, using 3 different PBMC donors. The CAR expression, enrichment of CD38 negative cells after CAR transduction and the cytotoxic capacity of the 4 CARs 25A10-v1, -v2, 28F5-v1 and -v2 were analysed.

Evaluation of Anti-CD38 CAR Expression and CART Phenotyping

The screening of the 4 CARs 25A10-v1, -v2, 28F5-v1 and -v2 after rLV transduction in DKO T cells has shown that all the CARs were expressed at the T cell surface with a high efficiency (>40%) and 3 of them above 80% (FIG. 27C). RQR8 expression was correlated with CAR expression (FIG. 27A). Most of the T cells were CD38 negative when T cells have been transduced by CD38 CARs (FIG. 27A). It is shown also that 60-85% of T cells endowed with the above 4 CARs were DKO TRAC/CD38 (FIG. 27B).

The DKO CD38 CART cells were mainly CD8+(FIG. 28A) and presented an effector/effector memory phenotype. There was no difference between CAR constructs (FIG. 28B).

Evaluation of CAR Activity In Vitro

Figure 29A:
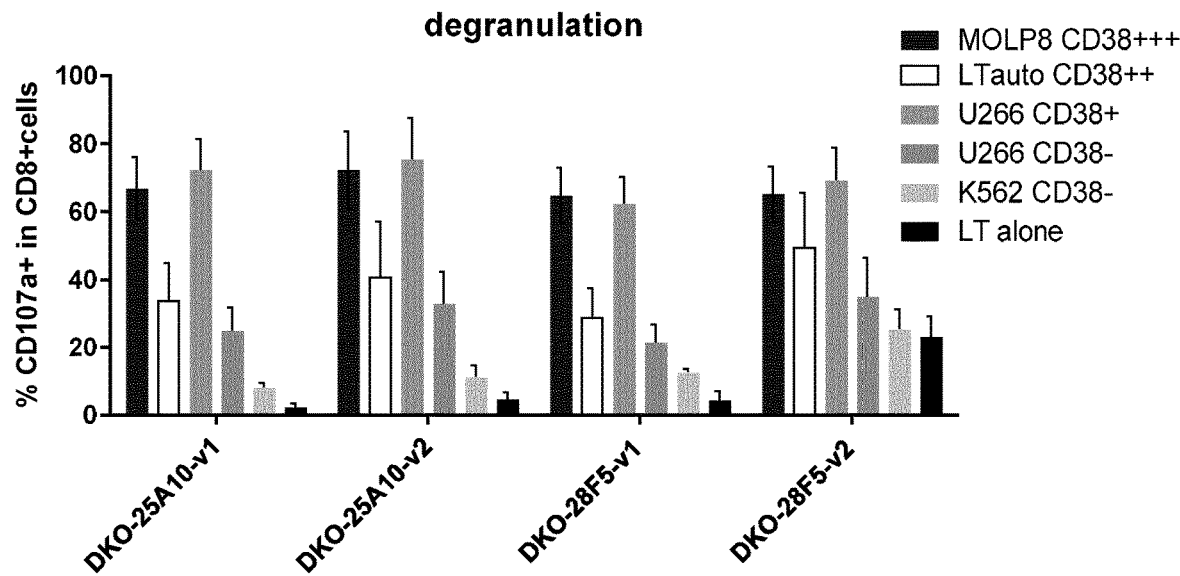
Figure 29B:
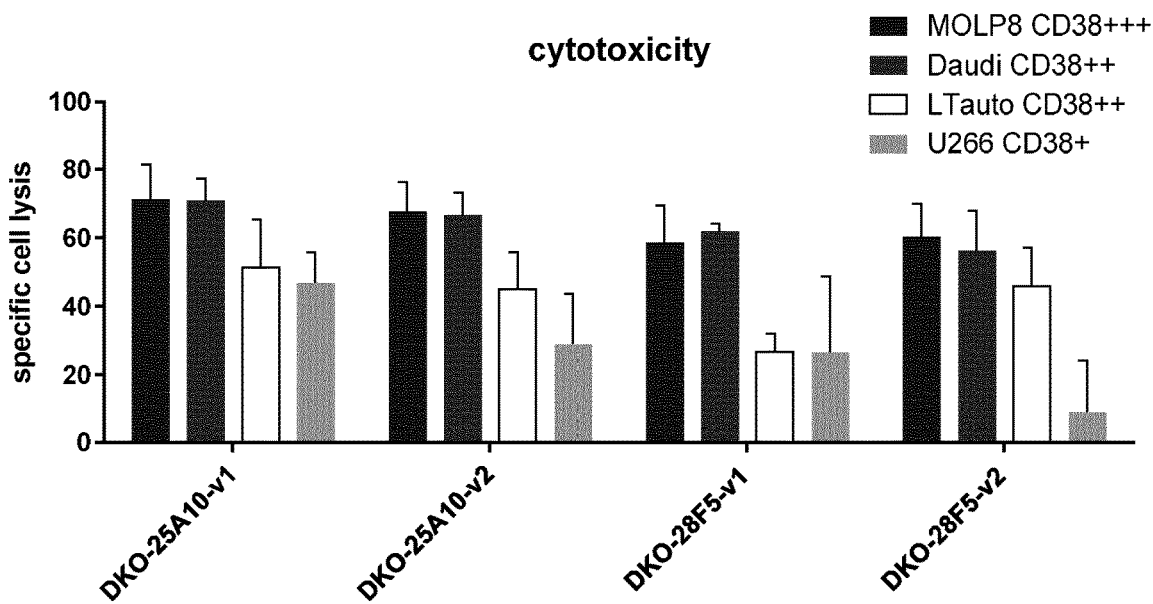

The CART degranulation was evaluated by flow cytometry. The read-out is the CD107a expression at the T cell plasma membrane after 5 hours of incubation with target cells These CARs were able to degranulate with a high efficiency against CD38+ multiple myeloma cell lines as well as against CD38+ T cells (FIG. 29A). The 4 CD38 CAR candidates were able to induce lysis of CD38+ multiple myeloma cell lines in a CD38 dose dependent manner (FIG. 29B).

Example 6: Evaluation of Anti-CD38 CAR T Cells Against T Cells Acute Lymphoblastic Leukemia (T-ALL)

As shown in FIG. 30, T-ALL cells expressed a high expression level of CD38. This pathology could be another application for the treatment based on the administration of anti-CD38 T cells in patient.

Development of a New T-ALL Cell Line with CD38-KO

All T-ALL cells lines tested were CD38+. To evaluate the CAR activity against T-ALL a negative cell line was needed as control. The CD38-KO CCRF-CEM cell lines has been generated by transfection of the CCRF-CEM cells with CD38 TALEN mRNA. CD38 negative cells were purified by magnetic separation (anti-CD38 microbeads, Miltenyi—FIG. 31). The new cell line has been used as negative control for the cytotoxicity assay.

Evaluation of Anti-CD38 CAR T Cell Activity Against T-ALL Cell Lines

Anti-CD38 CAR T cell activity against T-ALL cell lines was assessed by analysis of their degranulation after coculture with several T-ALL cell lines expressing CD38. The high majority (>70%) of UCART38 were able to degranulate in presence of T-ALL CD38+ cells (FIG. 32A). The cytotoxicity of UCART38 against T-ALL cells in vitro has been evaluated by coculture of UCART38 with T-ALL cells during 4h. UCART38 cells were able to induce lysis of CD38+T-ALL cells (FIG. 32B).

REFERENCES

Antonelli A, Ferrannini E. (2004) "CD38 autoimmunity: recent advances and relevance to human diabetes." *J Endocrinol Invest.* 27(7):695-707.

Avet-Loiseau H, Malard F, Campion L, Magrangeas F, Sebban C, Lioure B, Decaux O, Lamy T, Legros L, Fuzibet J G, Michallet M, Corront B, Lenain P, Hulin C, Mathiot C, Attal M, Facon T, Harousseau J L, Minvielle S, Moreau P; Intergroupe Francophone du Myélome. (2011) "Translocation t(14;16) and multiple myeloma: is it really an independent prognostic factor?" *Blood.* 2011 Feb. 10; 117(6):2009-11.

Bardenheuer, W., K. Lehmberg, et al. (2005). "Resistance to cytarabine and gemcitabine and in vitro selection of transduced cells after retroviral expression of cytidine deaminase in human hematopoietic progenitor cells." *Leukemia* 19(12): 2281-8.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Brewin, J., C. Mancao, et al. (2009). "Generation of EBV-specific cytotoxic T cells that are resistant to calcineurin inhibitors for the treatment of posttransplantation lymphoproliferative disease." *Blood* 114(23): 4792-803.

Cambier, J. C. (1995) "Antigen and Fc Receptor Signaling: The Awesome Power of the Immunoreceptor Tyrosine-I Based Activation Motif (ITAM)" *The Journal of Immunology* 155 (7) 3281-3285.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Dalgaard, J. Z., A. J. Klar, et al. (1997). "Statistical modeling and analysis of the LAGLIDADG family of site-specific endonucleases ("LAGLIDADG" disclosed as SEQ ID NO: 153) and identification of an intein that encodes a site-specific endonuclease of the HNH family." *Nucleic Acids Res* 25(22): 4626-38.

Deltcheva, E., K. Chylinski, et al. (2011). "CRISPR RNA maturation by trans-encoded small RNA and host factor RNase Ill." *Nature* 471(7340): 602-7.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Hacke, K., J. A. Treger, et al. (2013). "Genetic modification of mouse bone marrow by lentiviral vector-mediated delivery of hypoxanthine-Guanine phosphoribosyltransferase short hairpin RNA confers chemoprotection against 6-thioguanine cytotoxicity." *Transplant Proc* 45(5): 2040-4.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Jonnalagadda, M., C. E. Brown, et al. (2013). "Engineering human T cells for resistance to methotrexate and mycophenolate mofetil as an in vivo cell selection strategy." *PLoS One* 8(6): e65519.

Kushman, M. E., S. L. Kabler, et al. (2007). "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected $V_{79}MZ$ cells co-expressing hCYP1A1." *Carcinogenesis* 28(1): 207-14.

Lackner, G., N. Moebius, et al. (2011). "Complete genome sequence of *Burkholderia rhizoxinica*, an Endosymbiont of *Rhizopus microsporus*." *J Bacteriol* 193(3): 783-4.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mak, A. N., P. Bradley, et al. (2012). "The crystal structure of TAL effector PthXo1 bound to its DNA target." *Science* 335(6069): 716-9.

Mali, P., L. Yang, et al. (2013). "RNA-guided human genome engineering via Cas9." *Science* 339(6121): 823-6.

Metzger, H. et al. (1986) "The Receptor with High Affinity for Immunoglobulin E" *Annual Review of Immunology.* 4: 419-470

Mihara, K., Yanagihara K., Takigahira, M., Imai, C., Kitanaka, A., Takihara, Y., Kimura A (2009) "Activated T-cell-mediated immunotherapy with a chimeric receptor against CD38 in B-cell non-Hodgkin lymphoma". *J Immunother.* 32(7):737-43

Moscou, M. J. and A. J. Bogdanove (2009). "A simple cipher governs DNA recognition by TAL effectors." *Science* 326(5959): 1501.

Nivens, M. C., T. Felder, et al. (2004). "Engineered resistance to camptothecin and antifolates by retroviral coexpression of tyrosyl DNA phosphodiesterase-I and thymidylate synthase." *Cancer Chemother Pharmacol* 53(2): 107-15.

Park, T. S., S. A. Rosenberg, et al. (2011). "Treating cancer with genetically engineered T cells." *Trends Biotechnol* 29(11): 550-7.

Sangiolo, D., M. Lesnikova, et al. (2007). "Lentiviral vector conferring resistance to mycophenolate mofetil and sensitivity to ganciclovir for in vivo T-cell selection." *Gene Ther* 14(21): 1549-54.

Schweitzer, B. I., A. P. Dicker, et al. (1990). "Dihydrofolate reductase as a therapeutic target." *Faseb J* 4(8): 2441-52.

Shaughnessy J D Jr, Zhan F, Burington B E, Huang Y, Colla S, Hanamura I, Stewart J P, Kordsmeier B, Randolph C, Williams D R, Xiao Y, Xu H, Epstein J, Anaissie E, Krishna S G, Cottler-Fox M, Hollmig K, Mohiuddin A, Pineda-Roman M, Tricot G, van Rhee F, Sawyer J, Alsayed Y, Walker R, Zangari M, Crowley J, Barlogie B., (2007) "A validated gene expression model of high-risk multiple myeloma is defined by deregulated expression of genes mapping to chromosome 1.", *Blood.* 2007 Mar. 15; 109(6):2276-84

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." *J Gene Med* 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." *Mol Ther* 3(1): 88-96.

Van Laar, R., Flinchum, R, Brown, N., Ramsey, J., Riccitelli, S., Heuck, C., Barlogie, B. and Shaughnessy J D., (2014) "Translating a gene expression signature for multiple myeloma prognosis into a robust high-throughput assay for clinical use" *BMC Medical Genomics,* 7:25

Waldmann H. and Hale G. (2005) "CAMPATH: from concept to clinic". *Phil. Trans. R. Soc. B* 360: 1707-1711.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." *Mol Ther* 14(2): 236-44.

Zielske, S. P., J. S. Reese, et al. (2003). "In vivo selection of MGMT(P140K) lentivirus-transduced human NOD/SCID repopulating cells without pretransplant irradiation conditioning." *J Clin Invest* 112(10): 1561-70.

The invention claimed is:

1. An anti-CD38 specific chimeric antigen receptor (anti-CD38 CAR) comprising an extra cellular ligand binding-domain comprising VH and VL from a monoclonal anti-CD38 antibody, a hinge, a transmembrane domain, and a cytoplasmic domain comprising a CD3 zeta signaling domain and a co-stimulatory domain from 4-1BB,
wherein said VH and VL comprise the CDRs sequences of respectively SEQ ID NO.15-17 and SEQ ID NO.11-13; respectively SEQ ID NO.63-65 and SEQ ID NO.59-61; respectively SEQ ID NO.55-57 and SEQ ID NO.51-53; respectively SEQ ID NO.31-33 and SEQ ID NO.27-29; respectively SEQ ID NO.39-41 and SEQ ID NO.35-37; respectively SEQ ID NO.47-49 and SEQ ID NO.43-45; respectively SEQ ID NO.23-25 and SEQ ID NO.19-21.

2. The anti-CD38 CAR according to claim 1, wherein the transmembrane domain comprises a polypeptide sequence displaying at least 90% identity to SEQ ID NO.79.

3. The anti-CD38 CAR according to claim 1, wherein said VH and VL comprise a polypeptide sequence displaying at least 90% identity to respectively SEQ ID NO. 14 and 10, SEQ ID NO. 62 and 58, SEQ ID NO. 54 and 50, SEQ ID NO. 30 and 26, SEQ ID NO. 38 and 34, SEQ ID NO.46 and 42, or SEQ ID NO. 22 and 18.

4. The anti-CD38 CAR according to claim 1, wherein said VH and VL comprise a polypeptide sequence displaying at least 90% identity to respectively SEQ ID NO. 62 and 58.

5. The anti-CD38 CAR according to claim 1, wherein said VH and VL comprise the CDRs sequences of respectively SEQ ID NO.15-17 and SEQ ID NO.11-13.

6. The anti-CD38 CAR according to claim 1, comprising a polypeptide sequence displaying at least 90% identity to a polypeptide sequence selected from SEQ ID NO. 82-84, SEQ ID NO. 100-102, SEQ ID NO. 97-99, SEQ ID NO. 88-90, SEQ ID NO. 91-93, SEQ ID NO.94-96 and SEQ ID NO. 85-87.

7. The anti-CD38 CAR according to claim 6, comprising a polypeptide sequence displaying at least 90% identity to a polypeptide sequence selected from SEQ ID NO. 82-84.

8. The anti-CD38 CAR according to claim 6, comprising a polypeptide sequence displaying at least 90% identity to a polypeptide sequence selected from SEQ ID NO. 100-102.

9. The anti-CD38 CAR according to claim 6, comprising the polypeptide sequence of SEQ ID NO. 82.

10. The anti-CD38 CAR according to claim 1, comprising a hinge with at least 90% identity to one selected from SEQ ID NO. 76, SEQ ID NO. 77 and SEQ ID NO. 78.

11. The anti-CD38 CAR according to claim 1, comprising a hinge with at least 90% identity to SEQ ID NO. 77.

12. A method of cancer immunotherapy comprising administering an immune cell comprising the anti-CD38 CAR of claim 1 to a cancer patient.

13. A method of cancer immunotherapy comprising administering an immune cell comprising the anti-CD38 CAR of claim 6 to a cancer patient.

14. A method of cancer immunotherapy comprising administering an immune cell comprising the anti-CD38 CAR of claim 7 to a cancer patient.

15. A method of cancer immunotherapy comprising administering an immune cell comprising the anti-CD38 CAR of claim 9 to a cancer patient.

* * * * *

SEQUENCE LISTING

<160> NUMBER OF SEQ ID NOS: 174

<210> SEQ ID NO 1

```
<211> LENGTH: 47
<212> TYPE: DNA
<213> ORGANISM: Homo sapiens
<220> FEATURE:
<223> OTHER INFORMATION: CD38ex1-T2 TALEN target

<400> SEQUENCE: 1
tgaggtgggt tggcgactaa ggcgcaccgg tgggcactgc ggggaca            47

<210> SEQ ID NO 2
<211> LENGTH: 936
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38ex1-T2 Left TALEN

<400> SEQUENCE: 2
```

Met Gly Asp Pro Lys Lys Arg Lys Val Ile Asp Tyr Pro Tyr Asp
 1               5                  10                  15

Val Pro Asp Tyr Ala Ile Asp Ile Ala Asp Leu Arg Thr Leu Gly Tyr
                 20                  25                  30

Ser Gln Gln Gln Glu Lys Ile Lys Pro Lys Val Arg Ser Thr Val
             35                  40                  45

Ala Gln His His Glu Ala Leu Val Gly His Gly Phe Thr His Ala His
 50                  55                  60

Ile Val Ala Leu Ser Gln His Pro Ala Ala Leu Gly Thr Val Ala Val
 65                  70                  75                  80

Lys Tyr Gln Asp Met Ile Ala Ala Leu Pro Glu Ala Thr His Glu Ala
                 85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
        130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

```
Ile Ala Ser Asn Gly Gly Lys Gln Ala Leu Glu Thr Val Gln Arg
305                 310                 315                 320

Leu Leu Pro Val Leu Cys Gln Ala His Gly Leu Thr Pro Gln Gln Val
            325                 330                 335

Val Ala Ile Ala Ser Asn Asn Gly Gly Lys Gln Ala Leu Glu Thr Val
        340                 345                 350

Gln Arg Leu Leu Pro Val Leu Cys Gln Ala His Gly Leu Thr Pro Gln
    355                 360                 365

Gln Val Val Ala Ile Ala Ser Asn Asn Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Asn Gly Gly Lys Gln Ala
            405                 410                 415

Leu Glu Thr Val Gln Arg Leu Leu Pro Val Leu Cys Gln Ala His Gly
        420                 425                 430

Leu Thr Pro Gln Gln Val Val Ala Ile Ala Ser Asn Gly Gly Lys
    435                 440                 445

Gln Ala Leu Glu Thr Val Gln Arg Leu Leu Pro Val Leu Cys Gln Ala
450                 455                 460

His Gly Leu Thr Pro Gln Val Val Ala Ile Ala Ser Asn Gly Gly
465                 470                 475                 480

Gly Lys Gln Ala Leu Glu Thr Val Gln Arg Leu Leu Pro Val Leu Cys
            485                 490                 495

Gln Ala His Gly Leu Thr Pro Gln Gln Val Val Ala Ile Ala Ser Asn
        500                 505                 510

Asn Gly Gly Lys Gln Ala Leu Glu Thr Val Gln Arg Leu Leu Pro Val
    515                 520                 525

Leu Cys Gln Ala His Gly Leu Thr Pro Gln Gln Val Val Ala Ile Ala
530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
            565                 570                 575

Ile Ala Ser His Asp Gly Gly Lys Gln Ala Leu Glu Thr Val Gln Arg
        580                 585                 590

Leu Leu Pro Val Leu Cys Gln Ala His Gly Leu Thr Pro Gln Gln Val
    595                 600                 605

Val Ala Ile Ala Ser Asn Asn Gly Gly Lys Gln Ala Leu Glu Thr Val
610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
            645                 650                 655

Thr Val Gln Ala Leu Leu Pro Val Leu Cys Gln Ala His Gly Leu Thr
        660                 665                 670

Pro Gln Gln Val Val Ala Ile Ala Ser Asn Gly Gly Gly Arg Pro Ala
    675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720
```

```
Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
        770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
        850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
            915                 920                 925

Gly Glu Ile Asn Phe Ala Ala Asp
        930                 935

<210> SEQ ID NO 3
<211> LENGTH: 942
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38ex1-T2 Right TALEN

<400> SEQUENCE: 3

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125
```

```
Pro Pro Leu Gln Leu Asp Thr Gly Gln Leu Leu Lys Ile Ala Lys Arg
130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Asn Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
                195                 200                 205

Ile Ala Ser Asn Gly Gly Gly Lys Gln Ala Leu Glu Thr Val Gln Arg
210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Glu
            260                 265                 270

Gln Val Val Ala Ile Ala Ser His Asp Gly Gly Lys Gln Ala Leu Glu
        275                 280                 285

Thr Val Gln Arg Leu Leu Pro Val Leu Cys Gln Ala His Gly Leu Thr
290                 295                 300

Pro Glu Gln Val Val Ala Ile Ala Ser His Asp Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser His Asp Gly Gly Lys
            340                 345                 350

Gln Ala Leu Glu Thr Val Gln Arg Leu Leu Pro Val Leu Cys Gln Ala
        355                 360                 365

His Gly Leu Thr Pro Gln Gln Val Val Ala Ile Ala Ser Asn Asn Gly
370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser His
                405                 410                 415

Asp Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
        435                 440                 445

Ser Asn Ile Gly Gly Lys Gln Ala Leu Glu Thr Val Gln Ala Leu Leu
450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser Asn Gly Gly Gly Lys Gln Ala Leu Glu Thr Val
        515                 520                 525

Gln Arg Leu Leu Pro Val Leu Cys Gln Ala His Gly Leu Thr Pro Gln
530                 535                 540

Gln Val Val Ala Ile Ala Ser Asn Asn Gly Gly Lys Gln Ala Leu Glu
```

```
545                 550                 555                 560
Thr Val Gln Arg Leu Leu Pro Val Leu Cys Gln Ala His Gly Leu Thr
                565                 570                 575
Pro Glu Gln Val Val Ala Ile Ala Ser His Asp Gly Gly Lys Gln Ala
                580                 585                 590
Leu Glu Thr Val Gln Arg Leu Leu Pro Val Leu Cys Gln Ala His Gly
                595                 600                 605
Leu Thr Pro Glu Gln Val Val Ala Ile Ala Ser His Asp Gly Gly Lys
            610                 615                 620
Gln Ala Leu Glu Thr Val Gln Arg Leu Leu Pro Val Leu Cys Gln Ala
625                 630                 635                 640
His Gly Leu Thr Pro Glu Gln Val Val Ala Ile Ala Ser His Asp Gly
                645                 650                 655
Gly Lys Gln Ala Leu Glu Thr Val Gln Arg Leu Leu Pro Val Leu Cys
                660                 665                 670
Gln Ala His Gly Leu Thr Pro Gln Gln Val Val Ala Ile Ala Ser Asn
                675                 680                 685
Gly Gly Gly Arg Pro Ala Leu Glu Ser Ile Val Ala Gln Leu Ser Arg
            690                 695                 700
Pro Asp Pro Ala Leu Ala Ala Leu Thr Asn Asp His Leu Val Ala Leu
705                 710                 715                 720
Ala Cys Leu Gly Gly Arg Pro Ala Leu Asp Ala Val Lys Lys Gly Leu
                725                 730                 735
Gly Asp Pro Ile Ser Arg Ser Gln Leu Val Lys Ser Glu Leu Glu Glu
                740                 745                 750
Lys Lys Ser Glu Leu Arg His Lys Leu Lys Tyr Val Pro His Glu Tyr
            755                 760                 765
Ile Glu Leu Ile Glu Ile Ala Arg Asn Ser Thr Gln Asp Arg Ile Leu
            770                 775                 780
Glu Met Lys Val Met Glu Phe Phe Met Lys Val Tyr Gly Tyr Arg Gly
785                 790                 795                 800
Lys His Leu Gly Gly Ser Arg Lys Pro Asp Gly Ala Ile Tyr Thr Val
                805                 810                 815
Gly Ser Pro Ile Asp Tyr Gly Val Ile Val Asp Thr Lys Ala Tyr Ser
                820                 825                 830
Gly Gly Tyr Asn Leu Pro Ile Gly Gln Ala Asp Glu Met Gln Arg Tyr
                835                 840                 845
Val Glu Glu Asn Gln Thr Arg Asn Lys His Ile Asn Pro Asn Glu Trp
850                 855                 860
Trp Lys Val Tyr Pro Ser Ser Val Thr Glu Phe Lys Phe Leu Phe Val
865                 870                 875                 880
Ser Gly His Phe Lys Gly Asn Tyr Lys Ala Gln Leu Thr Arg Leu Asn
                885                 890                 895
His Ile Thr Asn Cys Asn Gly Ala Val Leu Ser Val Glu Glu Leu Leu
            900                 905                 910
Ile Gly Gly Glu Met Ile Lys Ala Gly Thr Leu Thr Leu Glu Glu Val
            915                 920                 925
Arg Arg Lys Phe Asn Asn Gly Glu Ile Asn Phe Ala Ala Asp
930                 935                 940

<210> SEQ ID NO 4
<211> LENGTH: 49
<212> TYPE: DNA
<213> ORGANISM: Homo sapiens
```

```
<220> FEATURE:
<223> OTHER INFORMATION: CD38-1 TALEN target

<400> SEQUENCE: 4
tgcgagttca gcccggtgtc cggggacaaa ccctgctgcc ggctctcta         49

<210> SEQ ID NO 5
<211> LENGTH: 970
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38-1 Left TALEN

<400> SEQUENCE: 5
```

| | | | | | | | | | | | | | | |
|---|---|---|---|---|---|---|---|---|---|---|---|---|---|---|
| Met | Gly | Asp | Pro | Lys | Lys | Lys | Arg | Lys | Val | Ile | Asp | Tyr | Pro | Tyr |
| 1 | | | | 5 | | | | | 10 | | | | | 15 |
| Asp | Val | Pro | Asp | Tyr | Ala | Ile | Asp | Ile | Ala | Asp | Leu | Arg | Thr | Leu | Gly | Tyr |

Met Gly Asp Pro Lys Lys Lys Arg Lys Val Ile Asp Tyr Pro Tyr
1               5                   10                  15

Asp Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Asn Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Ile Gly Gly Lys Gln Ala Leu Glu Thr Val Gln Arg
305                 310                 315                 320

```
Leu Leu Pro Val Leu Cys Gln Ala His Gly Leu Thr Pro Gln Gln Val
                325                 330                 335
Val Ala Ile Ala Ser Asn Asn Gly Gly Lys Gln Ala Leu Glu Thr Val
            340                 345                 350
Gln Arg Leu Leu Pro Val Leu Cys Gln Ala His Gly Leu Thr Pro Gln
        355                 360                 365
Gln Val Val Ala Ile Ala Ser Asn Gly Gly Lys Gln Ala Leu Glu
    370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser His Asp Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Ile Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Gln Gln Val Val Ala Ile Ala Ser Asn
            500                 505                 510
Asn Gly Gly Lys Gln Ala Leu Glu Thr Val Gln Arg Leu Leu Pro Val
        515                 520                 525
Leu Cys Gln Ala His Gly Leu Thr Pro Gln Gln Val Val Ala Ile Ala
    530                 535                 540
Ser His Asp Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser His Asp Gly Gly Lys Gln Ala Leu Glu Thr Val
    610                 615                 620
Gln Arg Leu Leu Pro Val Leu Cys Gln Ala His Gly Leu Thr Pro Glu
625                 630                 635                 640
Gln Val Val Ala Ile Ala Ser Asn Asn Gly Gly Lys Gln Ala Leu Glu
                645                 650                 655
Thr Val Gln Ala Leu Leu Pro Val Leu Cys Gln Ala His Gly Leu Thr
            660                 665                 670
Pro Gln Gln Val Val Ala Ile Ala Ser Asn Asn Gly Gly Lys Gln Ala
        675                 680                 685
Leu Glu Thr Val Gln Arg Leu Leu Pro Val Leu Cys Gln Ala His Gly
    690                 695                 700
Leu Thr Pro Glu Gln Val Val Ala Ile Ala Ser Asn Gly Gly Gly Arg
705                 710                 715                 720
Pro Ala Leu Glu Ser Ile Val Ala Gln Leu Ser Arg Pro Asp Pro Ala
                725                 730                 735
```

```
Leu Ala Ala Leu Thr Asn Asp His Leu Val Ala Leu Ala Cys Leu Gly
                740                 745                 750

Gly Arg Pro Ala Leu Asp Ala Val Lys Lys Gly Leu Gly Asp Pro Ile
        755                 760                 765

Ser Arg Ser Gln Leu Val Lys Ser Glu Leu Glu Glu Lys Lys Ser Glu
    770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
        820                 825                 830

Gly Ser Arg Lys Pro Asp Gly Ala Ile Tyr Thr Val Gly Ser Pro Ile
    835                 840                 845

Asp Tyr Gly Val Ile Val Asp Thr Lys Ala Tyr Ser Gly Gly Tyr Asn
850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
        900                 905                 910

Lys Gly Asn Tyr Lys Ala Gln Leu Thr Arg Leu Asn His Ile Thr Asn
    915                 920                 925

Cys Asn Gly Ala Val Leu Ser Val Glu Glu Leu Leu Ile Gly Gly Glu
930                 935                 940

Met Ile Lys Ala Gly Thr Leu Thr Leu Glu Glu Val Arg Arg Lys Phe
945                 950                 955                 960

Asn Asn Gly Glu Ile Asn Phe Ala Ala Asp
                965                 970

<210> SEQ ID NO 6
<211> LENGTH: 942
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38-1_Right  TALEN

<400> SEQUENCE: 6

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
                20                  25                  30

Leu Arg Thr Leu Gly Tyr Ser Gln Gln Gln Glu Lys Ile Lys Pro
            35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110
```

```
Ala Arg Ala Leu Glu Ala Leu Leu Thr Val Ala Gly Glu Leu Arg Gly
            115                 120                 125

Pro Pro Leu Gln Leu Asp Thr Gly Gln Leu Leu Lys Ile Ala Lys Arg
130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Gly Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
            195                 200                 205

Ile Ala Ser Asn Asn Gly Gly Lys Gln Ala Leu Glu Thr Val Gln Arg
            210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Glu
            260                 265                 270

Gln Val Val Ala Ile Ala Ser Asn Gly Gly Gly Lys Gln Ala Leu Glu
            275                 280                 285

Thr Val Gln Arg Leu Leu Pro Val Leu Cys Gln Ala His Gly Leu Thr
            290                 295                 300

Pro Glu Gln Val Val Ala Ile Ala Ser Asn Asn Gly Gly Lys Gln Ala
305                 310                 315                 320

Leu Glu Thr Val Gln Arg Leu Leu Pro Val Leu Cys Gln Ala His Gly
            325                 330                 335

Leu Thr Pro Glu Gln Val Val Ala Ile Ala Ser His Asp Gly Gly Lys
            340                 345                 350

Gln Ala Leu Glu Thr Val Gln Arg Leu Leu Pro Val Leu Cys Gln Ala
            355                 360                 365

His Gly Leu Thr Pro Gln Gln Val Val Ala Ile Ala Ser His Asp Gly
            370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
                405                 410                 415

Asn Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
            435                 440                 445

Ser Asn Asn Gly Gly Lys Gln Ala Leu Glu Thr Val Gln Ala Leu Leu
450                 455                 460

Pro Val Leu Cys Gln Ala His Gly Leu Thr Pro Gln Gln Val Val Ala
465                 470                 475                 480

Ile Ala Ser His Asp Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser Asn Gly Gly Gly Lys Gln Ala Leu Glu Thr Val
            515                 520                 525

Gln Arg Leu Leu Pro Val Leu Cys Gln Ala His Gly Leu Thr Pro Gln
```

```
            530                 535                 540
Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Glu Gln Val Val Ala Ile Ala Ser Asn Gly Gly Lys Gln Ala
                580                 585                 590

Leu Glu Thr Val Gln Arg Leu Leu Pro Val Leu Cys Gln Ala His Gly
            595                 600                 605

Leu Thr Pro Glu Gln Val Val Ala Ile Ala Ser His Asp Gly Gly Lys
        610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser Asn Gly Gly
                645                 650                 655

Gly Lys Gln Ala Leu Glu Thr Val Gln Arg Leu Leu Pro Val Leu Cys
                660                 665                 670

Gln Ala His Gly Leu Thr Pro Gln Gln Val Val Ala Ile Ala Ser Asn
                675                 680                 685

Ile Gly Gly Arg Pro Ala Leu Glu Ser Ile Val Ala Gln Leu Ser Arg
        690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
                740                 745                 750

Lys Lys Ser Glu Leu Arg His Lys Leu Lys Tyr Val Pro His Glu Tyr
                755                 760                 765

Ile Glu Leu Ile Glu Ile Ala Arg Asn Ser Thr Gln Asp Arg Ile Leu
        770                 775                 780

Glu Met Lys Val Met Glu Phe Phe Met Lys Val Tyr Gly Tyr Arg Gly
785                 790                 795                 800

Lys His Leu Gly Gly Ser Arg Lys Pro Asp Gly Ala Ile Tyr Thr Val
                805                 810                 815

Gly Ser Pro Ile Asp Tyr Gly Val Ile Val Asp Thr Lys Ala Tyr Ser
                820                 825                 830

Gly Gly Tyr Asn Leu Pro Ile Gly Gln Ala Asp Glu Met Gln Arg Tyr
            835                 840                 845

Val Glu Glu Asn Gln Thr Arg Asn Lys His Ile Asn Pro Asn Glu Trp
850                 855                 860

Trp Lys Val Tyr Pro Ser Ser Val Thr Glu Phe Lys Phe Leu Phe Val
865                 870                 875                 880

Ser Gly His Phe Lys Gly Asn Tyr Lys Ala Gln Leu Thr Arg Leu Asn
                885                 890                 895

His Ile Thr Asn Cys Asn Gly Ala Val Leu Ser Val Glu Glu Leu Leu
                900                 905                 910

Ile Gly Gly Glu Met Ile Lys Ala Gly Thr Leu Thr Leu Glu Glu Val
            915                 920                 925

Arg Arg Lys Phe Asn Asn Gly Glu Ile Asn Phe Ala Ala Asp
930                 935                 940

<210> SEQ ID NO 7
```

```
<211> LENGTH: 49
<212> TYPE: DNA
<213> ORGANISM: Homo sapiens
<220> FEATURE:
<223> OTHER INFORMATION: CD38-2_TALEN target

<400> SEQUENCE: 7
tgatcctcgt cgtggtgctc gcggtggtcg tcccgaggtg gcgccagca            49

<210> SEQ ID NO 8
<211> LENGTH: 936
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38-2 Left TALEN

<400> SEQUENCE: 8
```

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Asn Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

Ile Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Gly Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

-continued

```
Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
            325                 330                 335

Val Ala Ile Ala Ser His Asp Gly Gly Lys Gln Ala Leu Glu Thr Val
        340                 345                 350

Gln Arg Leu Leu Pro Val Leu Cys Gln Ala His Gly Leu Thr Pro Gln
    355                 360                 365

Gln Val Val Ala Ile Ala Ser Asn Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Gln Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Gly Gly Lys
        435                 440                 445

Gln Ala Leu Glu Thr Val Gln Arg Leu Leu Pro Val Leu Cys Gln Ala
    450                 455                 460

His Gly Leu Thr Pro Gln Val Val Ala Ile Ala Ser Asn Gly Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Gln Gln Val Val Ala Ile Ala Ser His
            500                 505                 510

Asp Gly Gly Lys Gln Ala Leu Glu Thr Val Gln Arg Leu Leu Pro Val
        515                 520                 525

Leu Cys Gln Ala His Gly Leu Thr Pro Gln Gln Val Val Ala Ile Ala
    530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser Asn Gly Gly Gly Lys Gln Ala Leu Glu Thr Val Gln Arg
            580                 585                 590

Leu Leu Pro Val Leu Cys Gln Ala His Gly Leu Thr Pro Gln Gln Val
        595                 600                 605

Val Ala Ile Ala Ser Asn Asn Gly Gly Lys Gln Ala Leu Glu Thr Val
    610                 615                 620

Gln Arg Leu Leu Pro Val Leu Cys Gln Ala His Gly Leu Thr Pro Glu
625                 630                 635                 640

Gln Val Val Ala Ile Ala Ser Asn Asn Gly Gly Lys Gln Ala Leu Glu
                645                 650                 655

Thr Val Gln Ala Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720
```

-continued

```
Pro Ala Leu Asp Ala Val Lys Lys Gly Leu Gly Asp Pro Ile Ser Arg
            725                 730                 735
Ser Gln Leu Val Lys Ser Glu Leu Glu Glu Lys Lys Ser Glu Leu Arg
        740                 745                 750
His Lys Leu Lys Tyr Val Pro His Glu Tyr Ile Glu Leu Ile Glu Ile
        755                 760                 765
Ala Arg Asn Ser Thr Gln Asp Arg Ile Leu Glu Met Lys Val Met Glu
    770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
Gly Val Ile Val Asp Thr Lys Ala Tyr Ser Gly Gly Tyr Asn Leu Pro
            820                 825                 830
Ile Gly Gln Ala Asp Glu Met Gln Arg Tyr Val Glu Glu Asn Gln Thr
        835                 840                 845
Arg Asn Lys His Ile Asn Pro Asn Glu Trp Trp Lys Val Tyr Pro Ser
    850                 855                 860
Ser Val Thr Glu Phe Lys Phe Leu Phe Val Ser Gly His Phe Lys Gly
865                 870                 875                 880
Asn Tyr Lys Ala Gln Leu Thr Arg Leu Asn His Ile Thr Asn Cys Asn
                885                 890                 895
Gly Ala Val Leu Ser Val Glu Glu Leu Leu Ile Gly Gly Glu Met Ile
            900                 905                 910
Lys Ala Gly Thr Leu Thr Leu Glu Glu Val Arg Arg Lys Phe Asn Asn
        915                 920                 925
Gly Glu Ile Asn Phe Ala Ala Asp
    930                 935

<210> SEQ ID NO 9
<211> LENGTH: 942
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD38-2 Right TALEN

<400> SEQUENCE: 9

Met Gly Asp Pro Lys Lys Lys Arg Lys Val Ile Asp Lys Glu Thr Ala
1               5                   10                  15
Ala Ala Lys Phe Glu Arg Gln His Met Asp Ser Ile Asp Ile Ala Asp
            20                  25                  30
Leu Arg Thr Leu Gly Tyr Ser Gln Gln Gln Gln Glu Lys Ile Lys Pro
        35                  40                  45
Lys Val Arg Ser Thr Val Ala Gln His His Glu Ala Leu Val Gly His
    50                  55                  60
Gly Phe Thr His Ala His Ile Val Ala Leu Ser Gln His Pro Ala Ala
65                  70                  75                  80
Leu Gly Thr Val Ala Val Lys Tyr Gln Asp Met Ile Ala Ala Leu Pro
                85                  90                  95
Glu Ala Thr His Glu Ala Ile Val Gly Val Gly Lys Gln Trp Ser Gly
            100                 105                 110
Ala Arg Ala Leu Glu Ala Leu Leu Thr Val Ala Gly Glu Leu Arg Gly
        115                 120                 125
```

```
Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser His Asp Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
        195                 200                 205

Ile Ala Ser Asn Asn Gly Gly Lys Gln Ala Leu Glu Thr Val Gln Arg
210                 215                 220

Leu Leu Pro Val Leu Cys Gln Ala His Gly Leu Thr Pro Glu Gln Val
225                 230                 235                 240

Val Ala Ile Ala Ser Asn Ile Gly Gly Lys Gln Ala Leu Glu Thr Val
                245                 250                 255

Gln Arg Leu Leu Pro Val Leu Cys Gln Ala His Gly Leu Thr Pro Glu
            260                 265                 270

Gln Val Val Ala Ile Ala Ser Asn Asn Gly Gly Lys Gln Ala Leu Glu
        275                 280                 285

Thr Val Gln Arg Leu Leu Pro Val Leu Cys Gln Ala His Gly Leu Thr
290                 295                 300

Pro Glu Gln Val Val Ala Ile Ala Ser Asn Asn Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser Asn Gly Gly Gly Lys
            340                 345                 350

Gln Ala Leu Glu Thr Val Gln Arg Leu Leu Pro Val Leu Cys Gln Ala
        355                 360                 365

His Gly Leu Thr Pro Gln Gln Val Val Ala Ile Ala Ser Asn Asn Gly
370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
                405                 410                 415

Asn Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
        435                 440                 445

Ser His Asp Gly Gly Lys Gln Ala Leu Glu Thr Val Gln Ala Leu Leu
450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser His Asp Gly Gly Lys Gln Ala Leu Glu Thr Val
        515                 520                 525

Gln Arg Leu Leu Pro Val Leu Cys Gln Ala His Gly Leu Thr Pro Gln
530                 535                 540

Gln Val Val Ala Ile Ala Ser His Asp Gly Gly Lys Gln Ala Leu Glu
```

Thr Val Gln Arg Leu Leu Pro Val Leu Cys Gln Ala His Gly Leu Thr
545                 550                 555                 560

Pro Glu Gln Val Val Ala Ile Ala Ser Asn Ile Gly Gly Lys Gln Ala
            565                 570                 575

Leu Glu Thr Val Gln Arg Leu Leu Pro Val Leu Cys Gln Ala His Gly
                580                 585                 590

Leu Thr Pro Glu Gln Val Val Ala Ile Ala Ser Asn Asn Gly Gly Lys
        595                 600                 605

Gln Ala Leu Glu Thr Val Gln Arg Leu Leu Pro Val Leu Cys Gln Ala
610                 615                 620

His Gly Leu Thr Pro Glu Gln Val Val Ala Ile Ala Ser His Asp Gly
    625                 630                 635                 640

Gly Lys Gln Ala Leu Glu Thr Val Gln Arg Leu Leu Pro Val Leu Cys
                645                 650                 655

Gln Ala His Gly Leu Thr Pro Gln Gln Val Val Ala Ile Ala Ser Asn
            660                 665                 670

Ile Gly Gly Arg Pro Ala Leu Glu Ser Ile Val Ala Gln Leu Ser Arg
        675                 680                 685

Pro Asp Pro Ala Leu Ala Ala Leu Thr Asn Asp His Leu Val Ala Leu
690                 695                 700

Ala Cys Leu Gly Gly Arg Pro Ala Leu Asp Ala Val Lys Lys Gly Leu
    705                 710                 715                 720

Gly Asp Pro Ile Ser Arg Ser Gln Leu Val Lys Ser Glu Leu Glu Glu
                725                 730                 735

Lys Lys Ser Glu Leu Arg His Lys Leu Lys Tyr Val Pro His Glu Tyr
            740                 745                 750

Ile Glu Leu Ile Glu Ile Ala Arg Asn Ser Thr Gln Asp Arg Ile Leu
        755                 760                 765

Glu Met Lys Val Met Glu Phe Phe Met Lys Val Tyr Gly Tyr Arg Gly
770                 775                 780

Lys His Leu Gly Gly Ser Arg Lys Pro Asp Gly Ala Ile Tyr Thr Val
    785                 790                 795                 800

Gly Ser Pro Ile Asp Tyr Gly Val Ile Val Asp Thr Lys Ala Tyr Ser
                805                 810                 815

Gly Gly Tyr Asn Leu Pro Ile Gly Gln Ala Asp Glu Met Gln Arg Tyr
            820                 825                 830

Val Glu Glu Asn Gln Thr Arg Asn Lys His Ile Asn Pro Asn Glu Trp
        835                 840                 845

Trp Lys Val Tyr Pro Ser Ser Val Thr Glu Phe Lys Phe Leu Phe Val
850                 855                 860

Ser Gly His Phe Lys Gly Asn Tyr Lys Ala Gln Leu Thr Arg Leu Asn
    865                 870                 875                 880

His Ile Thr Asn Cys Asn Gly Ala Val Leu Ser Val Glu Glu Leu Leu
                885                 890                 895

Ile Gly Gly Glu Met Ile Lys Ala Gly Thr Leu Thr Leu Glu Glu Val
            900                 905                 910

Arg Arg Lys Phe Asn Asn Gly Glu Ile Asn Phe Ala Ala Asp
        915                 920                 925

<210> SEQ ID NO 10
<211> LENGTH: 113
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: VL chain for 25A10

<400> SEQUENCE: 10

Asp Ile Val Met Thr Gln Ser Pro Ser Ser Leu Thr Val Thr Ala Gly
1               5                  10                  15

Glu Lys Val Thr Met Ser Cys Lys Ser Ser Gln Ser Leu Leu His Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Asp Tyr Pro Tyr Thr Phe Gly Gly Gly Thr Lys Leu Glu Ile
            100                 105                 110

Lys

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 25A10

<400> SEQUENCE: 11

Gln Ser Leu Leu His Ser Gly Asn Gln Arg Asn Tyr
1               5                  10

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 25A10

<400> SEQUENCE: 12

Trp Ala Ser
1

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 25A10

<400> SEQUENCE: 13

Gln Asn Asp Tyr Asp Tyr Pro Tyr Thr
1               5
```

```
<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 25A10

<400> SEQUENCE: 14

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Ser
            20                  25                  30

Leu Ile His Trp Val Lys Gln Arg Pro Glu Gln Gly Leu Glu Trp Ile
        35                  40                  45

Gly Trp Ile Asp Pro Glu Asp Asp Lys Thr Lys Tyr Ala Pro Lys Phe
    50                  55                  60

Gln Asp Lys Ala Thr Leu Thr Ala Asp Thr Ser Ser Asn Thr Ala Tyr
65                  70                  75                  80

Leu Gln Leu Ser Thr Leu Thr Ser Glu Asp Thr Ala Ile Tyr Tyr Cys
                85                  90                  95

Val Ser Arg Tyr Ile Asn Tyr Tyr Phe Ala Tyr Trp Gly Gln Gly Thr
            100                 105                 110

Thr Leu Thr Val Ser Ser
        115

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 25A10

<400> SEQUENCE: 15

Gly Phe Asn Ile Lys Asp Ser Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 25A10

<400> SEQUENCE: 16

Ile Asp Pro Glu Asp Asp Lys Thr
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 25A10
```

<400> SEQUENCE: 17

Val Ser Arg Tyr Ile Asn Tyr Tyr Phe Ala Tyr
1               5                   10

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 29B4

<400> SEQUENCE: 18

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Ala Gly Val Pro Asp Arg Phe Thr Gly
    50                  55                  60

Ser Gly Ser Gly Thr Asp Tyr Ala Leu Thr Ile Ser Ser Val Gln Ala
65                  70                  75                  80

Glu Asp Leu Ala Leu Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 29B4

<400> SEQUENCE: 19

Gln Asp Val Asn Thr Ala
1               5

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 29B4

<400> SEQUENCE: 20

Trp Ala Ser
1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: CDR3 of VL chain for 29B4

<400> SEQUENCE: 21

Gln Gln His Tyr Ser Thr Pro Arg Thr
1               5

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 29B4

<400> SEQUENCE: 22

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Phe Met Tyr Trp Val Arg Gln Thr Pro Glu Lys Arg Leu Glu Trp Val
        35                  40                  45

Ala Ile Ile Ser Asp Gly Gly Ile Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Gly Arg Asp Asp Tyr Asp Gly Trp Tyr Phe Asp Val Trp
            100                 105                 110

Gly Ala Gly Thr Thr Val Thr Val Ser Ser
        115                 120

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 29B4

<400> SEQUENCE: 23

Gly Phe Thr Phe Ser Asp Tyr Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 29B4

<400> SEQUENCE: 24

Ile Ser Asp Gly Gly Ile Tyr Thr
1               5

```
<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 29B4

<400> SEQUENCE: 25

Ala Arg Asp Gly Arg Asp Asp Tyr Asp Gly Trp Tyr Phe Asp Val
1               5                   10                  15

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 16B5

<400> SEQUENCE: 26

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Thr Thr Phe Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 16B5

<400> SEQUENCE: 27

Glu Ser Val Asp Asn Tyr Gly Thr Thr Phe
1               5                   10

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 16B5

<400> SEQUENCE: 28

Leu Ala Ser
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 16B5

<400> SEQUENCE: 29

Gln Gln Asn Lys Glu Asp Pro Trp Thr
1               5

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 16B5

<400> SEQUENCE: 30

Gln Ala Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Tyr
            20                  25                  30

Asn Leu His Trp Val Lys Gln Thr Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Lys Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Gly Ile Tyr Tyr Tyr Gly Ser Ser Leu Asp Tyr Trp Gly
            100                 105                 110

Gln Gly Thr Thr Leu Thr Val Ser Ser
        115                 120

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 16B5

<400> SEQUENCE: 31

Gly Tyr Thr Phe Thr Ser Tyr Asn
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: CDR2 of VH chain for 16B5

<400> SEQUENCE: 32

Ile Tyr Pro Gly Asn Gly Gly Thr
1               5

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 16B5

<400> SEQUENCE: 33

Ala Arg Gly Gly Ile Tyr Tyr Tyr Gly Ser Ser Leu Asp Tyr
1               5                   10

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 10F7

<400> SEQUENCE: 34

Asn Ile Val Leu Thr Gln Ser Pro Ala Ser Leu Ala Ala Ser Pro Gly
1               5                   10                  15

Gln Arg Ala Thr Ile Ser Cys Arg Ala Ser Glu Ser Val Asp Ser Tyr
            20                  25                  30

Gly Asn Thr Phe Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Val
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Val Glu Ile Lys
            100                 105                 110

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 10F7

<400> SEQUENCE: 35

Glu Ser Val Asp Ser Tyr Gly Asn Thr Phe
1               5                   10

<210> SEQ ID NO 36
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: CDR2 of VL chain for 10F7

<400> SEQUENCE: 36

Leu Ala Ser
1

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 10F7

<400> SEQUENCE: 37

Gln Gln Asn Asn Glu Asp Pro Trp Thr
1               5

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 10F7

<400> SEQUENCE: 38

Gln Ala Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Tyr Ile Tyr Pro Gly Asn Gly Gly Thr Asn Tyr Asn Gln Lys Phe
        50                  55                  60

Lys Asp Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Gly Gln Leu Gly Arg Pro Trp Phe Ala Tyr Trp Gly Gln
            100                 105                 110

Gly Thr Leu Val Thr Val Ser Ala
        115                 120

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 10F7

<400> SEQUENCE: 39

Gly Tyr Thr Phe Thr Ser Tyr Asn
1               5
```

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 10F7

<400> SEQUENCE: 40

Ile Tyr Pro Gly Asn Gly Gly Thr
1               5

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 10F7

<400> SEQUENCE: 41

Ala Arg Gly Gly Gln Leu Gly Arg Pro Trp Phe Ala Tyr
1               5                   10

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 27B6

<400> SEQUENCE: 42

Gln Ile Val Leu Thr Gln Ser Pro Ala Ile Met Ser Ala Ser Pro Gly
1               5                   10                  15

Glu Lys Val Thr Met Thr Cys Ser Thr Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Asn Asn Met Glu Ala Glu
65                  70                  75                  80

Asp Ala Ala Thr Tyr Ser Cys Gln Gln Trp Ser Ser Tyr Pro Pro Thr
                85                  90                  95

Phe Gly Gly Gly Thr Lys Leu Glu Ile Lys
            100                 105

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 27B6

<400> SEQUENCE: 43

Ser Ser Val Ser Tyr
1               5

<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 27B6

<400> SEQUENCE: 44

Asp Thr Ser
1

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 27B6

<400> SEQUENCE: 45

Gln Gln Trp Ser Ser Tyr Pro Pro Thr
1               5

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 27B6

<400> SEQUENCE: 46

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Asn Ile Asp Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
    50                  55                  60

Ser Arg Leu Lys Ile Ser Lys Asp Asp Ser Lys Ser Gln Val Phe Phe
65                  70                  75                  80

Lys Met Asn Ser Leu Gln Ser Asp Asp Thr Ala Ile Tyr Tyr Cys Ala
                85                  90                  95

Arg His Ser Pro Leu Val Ser Thr Pro Asp Trp Tyr Phe Asp Val Trp
            100                 105                 110

Gly Ala Gly Thr Thr Val Thr Val Ser Ser
        115                 120

<210> SEQ ID NO 47
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: CDR1 of VH chain for 27B6

<400> SEQUENCE: 47

Gly Phe Ser Leu Thr Ser Tyr Asn
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 27B6

<400> SEQUENCE: 48

Ile Trp Ser Gly Gly Ser Thr
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 27B6

<400> SEQUENCE: 49

Ala Arg His Ser Pro Leu Val Ser Thr Pro Asp Trp Tyr Phe Asp Val
1               5                   10                  15

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 13F11

<400> SEQUENCE: 50

Glu Thr Thr Val Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Val Leu Ile
            35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asn Asn Met Pro Tyr
                85                  90                  95

Thr Phe Gly Gly Gly Thr Lys Leu Glu Ile Lys
            100                 105

<210> SEQ ID NO 51
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 13F11

<400> SEQUENCE: 51

Thr Asp Ile Asp Asp Asp
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 13F11

<400> SEQUENCE: 52

Glu Gly Asn
1

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 13F11

<400> SEQUENCE: 53

Leu Gln Ser Asn Asn Met Pro Tyr Thr
1               5

<210> SEQ ID NO 54
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 13F11

<400> SEQUENCE: 54

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Lys Lys Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Tyr Tyr Gly Ser Thr Pro Ser Ser Tyr Thr Met Asp Tyr
            100                 105                 110
```

```
Trp Gly Gln Gly Thr Ser Val Thr Val Ser Ser
        115                 120
```

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 13F11

<400> SEQUENCE: 55

```
Gly Tyr Thr Phe Lys Lys Tyr Gly
1               5
```

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 13F11

<400> SEQUENCE: 56

```
Ile Asn Thr Asn Thr Gly Glu Pro
1               5
```

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 13F11

<400> SEQUENCE: 57

```
Ala Arg Trp Tyr Tyr Gly Ser Thr Pro Ser Ser Tyr Thr Met Asp Tyr
1               5                   10                  15
```

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for 28F5

<400> SEQUENCE: 58

```
Gln Ile Ile Leu Thr Gln Ser Pro Ala Ile Met Ser Ala Ser Leu Gly
1               5                   10                  15

Glu Arg Val Thr Met Thr Cys Thr Ala Thr Ser Ser Leu Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser His Leu Ala Ser Gly Val Pro Ala Arg Phe Ser
        50                  55                  60

Gly Gly Gly Ser Gly Thr Ser Tyr Ser Leu Thr Ile Ser Ser Met Glu
65                  70                  75                  80
```

```
Ala Glu Asp Ala Ala Thr Tyr Tyr Cys His Gln Tyr His Leu Ser Pro
                85                  90                  95
Tyr Thr Phe Gly Gly Gly Thr Lys Leu Glu Ile Lys
            100                 105
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for 28F5

<400> SEQUENCE: 59

```
Ser Ser Leu Ser Ser Ser Tyr
1               5
```

<210> SEQ ID NO 60
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for 28F5

<400> SEQUENCE: 60

```
Ser Thr Ser
1
```

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for 28F5

<400> SEQUENCE: 61

```
His Gln Tyr His Leu Ser Pro Tyr Thr
1               5
```

<210> SEQ ID NO 62
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for 28F5

<400> SEQUENCE: 62

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Lys Tyr
            20                  25                  30
Gly Met Asn Trp Val Lys Gln Thr Pro Gly Lys Gly Leu Lys Trp Met
        35                  40                  45
Gly Trp Ile Asn Thr Asn Ser Gly Glu Pro Thr Tyr Ala Glu Glu Phe
    50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Gly Ala Tyr Tyr Arg Tyr Asp Gly Glu Val Ser Tyr Tyr Ala
            100                 105                 110

Met Asp Tyr Trp Gly Gln Gly Thr Ser Val Thr Val Ser Ser
        115                 120                 125

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for 28F5

<400> SEQUENCE: 63

Gly Tyr Thr Phe Thr Lys Tyr Gly
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for 28F5

<400> SEQUENCE: 64

Ile Asn Thr Asn Ser Gly Glu Pro
1               5

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for 28F5

<400> SEQUENCE: 65

Ala Arg Gly Ala Tyr Tyr Arg Tyr Asp Gly Glu Val Ser Tyr Tyr Ala
1               5                   10                  15

Met Asp Tyr

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain for GMB005

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                    20                  25                  30
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VL chain for GMB005

<400> SEQUENCE: 67

```
Gln Ser Val Ser Ser Tyr
1               5
```

<210> SEQ ID NO 68
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VL chain for GMB005

<400> SEQUENCE: 68

```
Asp Ala Ser
1
```

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VL chain for GMB005

<400> SEQUENCE: 69

```
Gln Gln Arg Ser Asn Trp Pro Pro Thr
1               5
```

<210> SEQ ID NO 70
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain for GMB005

<400> SEQUENCE: 70

```
Glu Val Gln Leu Leu Glu Ser Gly Gly Gly Leu Val Gln Pro Gly Gly
```

```
                1               5                   10                  15
Ser Leu Arg Leu Ser Cys Ala Val Ser Gly Phe Thr Phe Asn Ser Phe
                    20                  25                  30

Ala Met Ser Trp Val Arg Gln Ala Pro Gly Lys Gly Leu Glu Trp Val
                    35                  40                  45

Ser Ala Ile Ser Gly Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Phe Cys
                    85                  90                  95

Ala Lys Asp Lys Ile Leu Trp Phe Gly Glu Pro Val Phe Asp Tyr Trp
                    100                 105                 110

Gly Gln Gly Thr Leu Val Thr Val Ser Ser Ala Ser
            115                 120

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR1 of VH chain for GMB005

<400> SEQUENCE: 71

Gly Phe Thr Phe Asn Ser Phe Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR2 of VH chain for GMB005

<400> SEQUENCE: 72

Ile Ser Gly Ser Gly Gly Gly Thr
1               5

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR3 of VH chain for GMB005

<400> SEQUENCE: 73

Ala Lys Asp Lys Ile Leu Trp Phe Gly Glu Pro Val Phe Asp Tyr
1               5                   10                  15

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: CD8a;-Signal peptide (SP)

<400> SEQUENCE: 74

Met Ala Leu Pro Val Thr Ala Leu Leu Leu Pro Leu Ala Leu Leu Leu
1               5                   10                  15

His Ala Ala Arg Pro
            20

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 75

Gly Gly Gly Gly Ser Gly Gly Gly Gly Ser Gly Gly Gly Gly Ser
1               5                   10                  15

<210> SEQ ID NO 76
<211> LENGTH: 16
<212> TYPE: PRT
<213> ORGANISM: Homo sapiens
<220> FEATURE:
<223> OTHER INFORMATION: FCRIIIa; hinge

<400> SEQUENCE: 76

Gly Leu Ala Val Ser Thr Ile Ser Ser Phe Phe Pro Pro Gly Tyr Gln
1               5                   10                  15

<210> SEQ ID NO 77
<211> LENGTH: 45
<212> TYPE: PRT
<213> ORGANISM: Homo sapiens
<220> FEATURE:
<223> OTHER INFORMATION: CD8a; hinge

<400> SEQUENCE: 77

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 78
<211> LENGTH: 231
<212> TYPE: PRT
<213> ORGANISM: Homo sapiens
<220> FEATURE:
<223> OTHER INFORMATION: IgG1 hinge

<400> SEQUENCE: 78

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
```

```
                    50                  55                  60
Gly Val Glu Val His Asn Ala Lys Thr Lys Pro Arg Glu Gln Tyr
 65                  70                  75                  80

Asn Ser Thr Tyr Arg Val Val Ser Val Leu Thr Val Leu His Gln Asp
                     85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 79
<211> LENGTH: 24
<212> TYPE: PRT
<213> ORGANISM: Homo sapiens
<220> FEATURE:
<223> OTHER INFORMATION: CD8a; TM domain

<400> SEQUENCE: 79

Ile Tyr Ile Trp Ala Pro Leu Ala Gly Thr Cys Gly Val Leu Leu Leu
 1               5                  10                  15

Ser Leu Val Ile Thr Leu Tyr Cys
                20

<210> SEQ ID NO 80
<211> LENGTH: 42
<212> TYPE: PRT
<213> ORGANISM: Homo sapiens
<220> FEATURE:
<223> OTHER INFORMATION: 4-1 BB co-stimulatory domain

<400> SEQUENCE: 80

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 81
<211> LENGTH: 112
<212> TYPE: PRT
<213> ORGANISM: Homo sapiens
<220> FEATURE:
<223> OTHER INFORMATION: CD3ζ activation domain

<400> SEQUENCE: 81
```

```
Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 82
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10-V1 CAR

<400> SEQUENCE: 82

```
Met Ala Leu Pro Val Thr Ala Leu Leu Leu Pro Leu Ala Leu Leu Leu
1               5                  10                  15

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
        35                  40                  45

Asn Ile Lys Asp Ser Leu Ile His Trp Val Lys Gln Arg Pro Glu Gln
    50                  55                  60

Gly Leu Glu Trp Ile Gly Trp Ile Asp Pro Glu Asp Asp Lys Thr Lys
65                  70                  75                  80

Tyr Ala Pro Lys Phe Gln Asp Lys Ala Thr Leu Thr Ala Asp Thr Ser
                85                  90                  95

Ser Asn Thr Ala Tyr Leu Gln Leu Ser Thr Leu Thr Ser Glu Asp Thr
            100                 105                 110

Ala Ile Tyr Tyr Cys Val Ser Arg Tyr Ile Asn Tyr Tyr Phe Ala Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Asp Ile Val Met Thr Gln
145                 150                 155                 160

Ser Pro Ser Ser Leu Thr Val Thr Ala Gly Glu Lys Val Thr Met Ser
                165                 170                 175

Cys Lys Ser Ser Gln Ser Leu Leu His Ser Gly Asn Gln Arg Asn Tyr
            180                 185                 190

Leu Thr Trp Tyr Gln Gln Lys Pro Gly Gln Pro Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240
```

```
Glu Asp Leu Ala Val Tyr Tyr Cys Gln Asn Asp Tyr Asp Tyr Pro Tyr
                245                 250                 255

Thr Phe Gly Gly Gly Thr Lys Leu Glu Ile Lys Gly Leu Ala Val Ser
        260                 265                 270

Thr Ile Ser Ser Phe Phe Pro Pro Gly Tyr Gln Ile Tyr Ile Trp Ala
            275                 280                 285

Pro Leu Ala Gly Thr Cys Gly Val Leu Leu Leu Ser Leu Val Ile Thr
        290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Gly Gly Cys Glu Leu Arg Val Lys
                340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
        370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
    450                 455                 460

<210> SEQ ID NO 83
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10-V2 CAR

<400> SEQUENCE: 83

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
        35                  40                  45

Asn Ile Lys Asp Ser Leu Ile His Trp Val Lys Gln Arg Pro Glu Gln
    50                  55                  60

Gly Leu Glu Trp Ile Gly Trp Ile Asp Pro Glu Asp Asp Lys Thr Lys
65                  70                  75                  80

Tyr Ala Pro Lys Phe Gln Asp Lys Ala Thr Leu Thr Ala Asp Thr Ser
                85                  90                  95

Ser Asn Thr Ala Tyr Leu Gln Leu Ser Thr Leu Thr Ser Glu Asp Thr
            100                 105                 110

Ala Ile Tyr Tyr Cys Val Ser Arg Tyr Ile Asn Tyr Tyr Phe Ala Tyr
        115                 120                 125
```

Trp Gly Gln Gly Thr Thr Leu Thr Val Ser Ser Gly Gly Gly Ser
130                 135                 140

Gly Gly Gly Gly Ser Gly Gly Gly Ser Asp Ile Val Met Thr Gln
145                 150                 155                 160

Ser Pro Ser Ser Leu Thr Val Thr Ala Gly Glu Lys Val Thr Met Ser
                165                 170                 175

Cys Lys Ser Ser Gln Ser Leu Leu His Ser Gly Asn Gln Arg Asn Tyr
                180                 185                 190

Leu Thr Trp Tyr Gln Gln Lys Pro Gly Gln Pro Pro Lys Leu Leu Ile
                195                 200                 205

Tyr Trp Ala Ser Thr Arg Glu Ser Gly Val Pro Asp Arg Phe Thr Gly
210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Asp Tyr Pro Tyr
                245                 250                 255

Thr Phe Gly Gly Gly Thr Lys Leu Glu Ile Lys Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 84
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: 25A10-V3 CAR

<400> SEQUENCE: 84

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Ala Glu Leu
                20                  25                  30

Val Arg Pro Gly Ala Ser Val Lys Leu Ser Cys Thr Ala Ser Gly Phe
            35                  40                  45

Asn Ile Lys Asp Ser Leu Ile His Trp Val Lys Gln Arg Pro Glu Gln
        50                  55                  60

Gly Leu Glu Trp Ile Gly Trp Ile Asp Pro Glu Asp Asp Lys Thr Lys
65                  70                  75                  80

Tyr Ala Pro Lys Phe Gln Asp Lys Ala Thr Leu Thr Ala Asp Thr Ser
                85                  90                  95

Ser Asn Thr Ala Tyr Leu Gln Leu Ser Thr Leu Thr Ser Glu Asp Thr
            100                 105                 110

Ala Ile Tyr Tyr Cys Val Ser Arg Tyr Ile Asn Tyr Tyr Phe Ala Tyr
        115                 120                 125

Trp Gly Gln Gly Thr Thr Leu Thr Val Ser Ser Gly Gly Gly Gly Ser
130                 135                 140

Gly Gly Gly Gly Ser Gly Gly Gly Ser Asp Ile Val Met Thr Gln
145                 150                 155                 160

Ser Pro Ser Ser Leu Thr Val Thr Ala Gly Glu Lys Val Thr Met Ser
                165                 170                 175

Cys Lys Ser Ser Gln Ser Leu Leu His Ser Gly Asn Gln Arg Asn Tyr
            180                 185                 190

Leu Thr Trp Tyr Gln Gln Lys Pro Gly Gln Pro Pro Lys Leu Leu Ile
        195                 200                 205

Tyr Trp Ala Ser Thr Arg Glu Ser Gly Val Pro Asp Arg Phe Thr Gly
210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Asp Tyr Pro Tyr
                245                 250                 255

Thr Phe Gly Gly Gly Thr Lys Leu Glu Ile Lys Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
370                 375                 380

Lys Thr Ile Ser Lys Ala Lys Gly Gln Pro Arg Glu Pro Gln Val Tyr
385                 390                 395                 400
```

Thr Leu Pro Pro Ser Arg Asp Glu Leu Thr Lys Asn Gln Val Ser Leu
            405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
            450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Ile Tyr Ile Trp Ala Pro Leu Ala Gly Thr Cys Gly Val Leu
            500                 505                 510

Leu Leu Ser Leu Val Ile Thr Leu Tyr Cys Lys Arg Gly Arg Lys Lys
            515                 520                 525

Leu Leu Tyr Ile Phe Lys Gln Pro Phe Met Arg Pro Val Gln Thr Thr
            530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
            595                 600                 605

Met Gly Gly Lys Pro Arg Arg Lys Asn Pro Gln Glu Gly Leu Tyr Asn
            610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 85
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 29B4-V1 CAR

<400> SEQUENCE: 85

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Lys Leu Ser Cys Ala Ala Ser Gly Phe
            35                  40                  45

Thr Phe Ser Asp Tyr Phe Met Tyr Trp Val Arg Gln Thr Pro Glu Lys
        50                  55                  60

Arg Leu Glu Trp Val Ala Ile Ile Ser Asp Gly Gly Ile Tyr Thr Tyr
65                  70                  75                  80

Tyr Pro Asp Ser Val Lys Gly Arg Phe Thr Ile Ser Arg Asp Asn Ala
                85                  90                  95

Lys Asn Asn Leu Tyr Leu Gln Met Ser Ser Leu Lys Ser Glu Asp Thr
            100                 105                 110

Ala Met Tyr Tyr Cys Ala Arg Asp Gly Arg Asp Asp Tyr Asp Gly Trp
        115                 120                 125

Tyr Phe Asp Val Trp Gly Ala Gly Thr Thr Val Thr Val Ser Ser Gly
    130                 135                 140

Gly Gly Gly Ser Gly Gly Gly Gly Ser Gly Gly Gly Ser Asp Ile
145                 150                 155                 160

Val Met Thr Gln Ser His Lys Phe Met Ser Thr Ser Val Gly Asp Arg
                165                 170                 175

Val Asn Ile Thr Cys Lys Ala Ser Gln Asp Val Asn Thr Ala Val Ala
            180                 185                 190

Trp Tyr Gln Gln Lys Pro Gly Gln Ser Pro Lys Leu Leu Ile Tyr Trp
        195                 200                 205

Ala Ser Thr Arg His Ala Gly Val Pro Asp Arg Phe Thr Gly Ser Gly
    210                 215                 220

Ser Gly Thr Asp Tyr Ala Leu Thr Ile Ser Ser Val Gln Ala Glu Asp
225                 230                 235                 240

Leu Ala Leu Tyr Tyr Cys Gln Gln His Tyr Ser Thr Pro Arg Thr Phe
                245                 250                 255

Gly Gly Gly Thr Lys Leu Glu Ile Lys Gly Leu Ala Val Ser Thr Ile
            260                 265                 270

Ser Ser Phe Phe Pro Pro Gly Tyr Gln Ile Tyr Ile Trp Ala Pro Leu
        275                 280                 285

Ala Gly Thr Cys Gly Val Leu Leu Leu Ser Leu Val Ile Thr Leu Tyr
    290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
                325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
        355                 360                 365

Asn Glu Leu Asn Leu Gly Arg Arg Glu Glu Tyr Asp Val Leu Asp Lys
    370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445

Asp Ala Leu His Met Gln Ala Leu Pro Pro Arg
    450                 455

<210> SEQ ID NO 86
<211> LENGTH: 488
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 29B4-V2 CAR

<400> SEQUENCE: 86

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Lys Pro Gly Gly Ser Leu Lys Leu Ser Cys Ala Ala Ser Gly Phe
        35                  40                  45

Thr Phe Ser Asp Tyr Phe Met Tyr Trp Val Arg Gln Thr Pro Glu Lys
    50                  55                  60

Arg Leu Glu Trp Val Ala Ile Ile Ser Asp Gly Gly Ile Tyr Thr Tyr
65                  70                  75                  80

Tyr Pro Asp Ser Val Lys Gly Arg Phe Thr Ile Ser Arg Asp Asn Ala
                85                  90                  95

Lys Asn Asn Leu Tyr Leu Gln Met Ser Ser Leu Lys Ser Glu Asp Thr
            100                 105                 110

Ala Met Tyr Tyr Cys Ala Arg Asp Gly Arg Asp Asp Tyr Asp Gly Trp
        115                 120                 125

Tyr Phe Asp Val Trp Gly Ala Gly Thr Thr Val Thr Val Ser Ser Gly
    130                 135                 140

Gly Gly Gly Ser Gly Gly Gly Ser Gly Gly Gly Ser Asp Ile
145                 150                 155                 160

Val Met Thr Gln Ser His Lys Phe Met Ser Thr Ser Val Gly Asp Arg
                165                 170                 175

Val Asn Ile Thr Cys Lys Ala Ser Gln Asp Val Asn Thr Ala Val Ala
            180                 185                 190

Trp Tyr Gln Gln Lys Pro Gly Gln Ser Pro Lys Leu Leu Ile Tyr Trp
        195                 200                 205

Ala Ser Thr Arg His Ala Gly Val Pro Asp Arg Phe Thr Gly Ser Gly
    210                 215                 220

Ser Gly Thr Asp Tyr Ala Leu Thr Ile Ser Ser Val Gln Ala Glu Asp
225                 230                 235                 240

Leu Ala Leu Tyr Tyr Cys Gln Gln His Tyr Ser Thr Pro Arg Thr Phe
                245                 250                 255

Gly Gly Gly Thr Lys Leu Glu Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
```

```
                    370                 375                 380
Asp Ala Pro Ala Tyr Gln Gln Gly Gln Asn Gln Leu Tyr Asn Glu Leu
385                 390                 395                 400

Asn Leu Gly Arg Arg Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 87
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 29B4-V3 CAR

<400> SEQUENCE: 87

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Lys Pro Gly Gly Ser Leu Lys Leu Ser Cys Ala Ala Ser Gly Phe
            35                  40                  45

Thr Phe Ser Asp Tyr Phe Met Tyr Trp Val Arg Gln Thr Pro Glu Lys
        50                  55                  60

Arg Leu Glu Trp Val Ala Ile Ile Ser Asp Gly Gly Ile Tyr Thr Tyr
65                  70                  75                  80

Tyr Pro Asp Ser Val Lys Gly Arg Phe Thr Ile Ser Arg Asp Asn Ala
                85                  90                  95

Lys Asn Asn Leu Tyr Leu Gln Met Ser Ser Leu Lys Ser Glu Asp Thr
                100                 105                 110

Ala Met Tyr Tyr Cys Ala Arg Asp Gly Arg Asp Asp Tyr Asp Gly Trp
            115                 120                 125

Tyr Phe Asp Val Trp Gly Ala Gly Thr Thr Val Thr Val Ser Ser Gly
        130                 135                 140

Gly Gly Gly Ser Gly Gly Gly Gly Ser Gly Gly Gly Gly Ser Asp Ile
145                 150                 155                 160

Val Met Thr Gln Ser His Lys Phe Met Ser Thr Ser Val Gly Asp Arg
                165                 170                 175

Val Asn Ile Thr Cys Lys Ala Ser Gln Asp Val Asn Thr Ala Val Ala
                180                 185                 190

Trp Tyr Gln Gln Lys Pro Gly Gln Ser Pro Lys Leu Leu Ile Tyr Trp
            195                 200                 205

Ala Ser Thr Arg His Ala Gly Val Pro Asp Arg Phe Thr Gly Ser Gly
        210                 215                 220

Ser Gly Thr Asp Tyr Ala Leu Thr Ile Ser Ser Val Gln Ala Glu Asp
```

-continued

```
                225                 230                 235                 240
Leu Ala Leu Tyr Tyr Cys Gln Gln His Tyr Ser Thr Pro Arg Thr Phe
                    245                 250                 255
Gly Gly Gly Thr Lys Leu Glu Ile Lys Glu Pro Lys Ser Pro Asp Lys
                    260                 265                 270
Thr His Thr Cys Pro Pro Cys Pro Ala Pro Val Ala Gly Pro Ser
                    275                 280                 285
Val Phe Leu Phe Pro Pro Lys Pro Lys Asp Thr Leu Met Ile Ala Arg
    290                 295                 300
Thr Pro Glu Val Thr Cys Val Val Asp Val Ser His Glu Asp Pro
305                 310                 315                 320
Glu Val Lys Phe Asn Trp Tyr Val Asp Gly Val Glu Val His Asn Ala
                    325                 330                 335
Lys Thr Lys Pro Arg Glu Glu Gln Tyr Asn Ser Thr Tyr Arg Val Val
                    340                 345                 350
Ser Val Leu Thr Val Leu His Gln Asp Trp Leu Asn Gly Lys Glu Tyr
                    355                 360                 365
Lys Cys Lys Val Ser Asn Lys Ala Leu Pro Ala Pro Ile Glu Lys Thr
            370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                    405                 410                 415
Leu Val Lys Gly Phe Tyr Pro Ser Asp Ile Ala Val Glu Trp Glu Ser
                    420                 425                 430
Asn Gly Gln Pro Glu Asn Asn Tyr Lys Thr Thr Pro Pro Val Leu Asp
            435                 440                 445
Ser Asp Gly Ser Phe Phe Leu Tyr Ser Lys Leu Thr Val Asp Lys Ser
        450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                    485                 490                 495
Ile Tyr Ile Trp Ala Pro Leu Ala Gly Thr Cys Gly Val Leu Leu Leu
                    500                 505                 510
Ser Leu Val Ile Thr Leu Tyr Cys Lys Arg Gly Arg Lys Lys Leu Leu
            515                 520                 525
Tyr Ile Phe Lys Gln Pro Phe Met Arg Pro Val Gln Thr Thr Gln Glu
        530                 535                 540
Glu Asp Gly Cys Ser Cys Arg Phe Pro Glu Glu Glu Glu Gly Gly Cys
545                 550                 555                 560
Glu Leu Arg Val Lys Phe Ser Arg Ser Ala Asp Ala Pro Ala Tyr Gln
                    565                 570                 575
Gln Gly Gln Asn Gln Leu Tyr Asn Glu Leu Asn Leu Gly Arg Arg Glu
                580                 585                 590
Glu Tyr Asp Val Leu Asp Lys Arg Arg Gly Arg Asp Pro Glu Met Gly
                595                 600                 605
Gly Lys Pro Arg Arg Lys Asn Pro Gln Glu Gly Leu Tyr Asn Glu Leu
        610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                    645                 650                 655
```

```
Thr Ala Thr Lys Asp Thr Tyr Asp Ala Leu His Met Gln Ala Leu Pro
            660                 665                 670

Pro Arg

<210> SEQ ID NO 88
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 16B5-V1 CAR

<400> SEQUENCE: 88

Met Ala Leu Pro Val Thr Ala Leu Leu Leu Pro Leu Ala Leu Leu Leu
1               5                   10                  15

His Ala Ala Arg Pro Gln Ala Tyr Leu Gln Gln Ser Gly Ala Glu Leu
            20                  25                  30

Val Arg Ser Gly Ala Ser Val Lys Met Ser Cys Lys Ala Ser Gly Tyr
        35                  40                  45

Thr Phe Thr Ser Tyr Asn Leu His Trp Val Lys Gln Thr Pro Gly Gln
    50                  55                  60

Gly Leu Glu Trp Ile Gly Tyr Ile Tyr Pro Gly Asn Gly Gly Thr Asn
65                  70                  75                  80

Tyr Asn Gln Lys Phe Lys Gly Lys Ala Thr Leu Thr Ala Asp Thr Ser
                85                  90                  95

Ser Ser Thr Ala Tyr Met Gln Ile Ser Ser Leu Thr Ser Glu Asp Ser
            100                 105                 110

Ala Val Tyr Phe Cys Ala Arg Gly Gly Ile Tyr Tyr Gly Ser Ser
        115                 120                 125

Leu Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asn Ile Val
145                 150                 155                 160

Leu Thr Gln Ser Pro Ala Ser Leu Ala Val Ser Leu Gly Gln Arg Ala
                165                 170                 175

Thr Ile Ser Cys Arg Ala Ser Glu Ser Val Asp Asn Tyr Gly Thr Thr
            180                 185                 190

Phe Met Tyr Trp Tyr Gln Gln Lys Pro Gly Gln Pro Pro Lys Leu Leu
        195                 200                 205

Ile Tyr Leu Ala Ser Asn Leu Glu Ser Gly Val Pro Ala Arg Phe Ser
    210                 215                 220

Gly Ser Gly Ser Gly Thr Asp Phe Thr Leu Thr Ile Asp Pro Val Glu
225                 230                 235                 240

Ala Asp Asp Ala Ala Thr Tyr Tyr Cys Gln Gln Asn Lys Glu Asp Pro
                245                 250                 255

Trp Thr Phe Gly Gly Gly Thr Lys Leu Glu Ile Lys Gly Leu Ala Val
            260                 265                 270

Ser Thr Ile Ser Ser Phe Phe Pro Pro Gly Tyr Gln Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320
```

```
Gln Pro Phe Met Arg Pro Val Gln Thr Thr Gln Glu Glu Asp Gly Cys
                325                 330                 335

Ser Cys Arg Phe Pro Glu Glu Glu Gly Gly Cys Glu Leu Arg Val
        340                 345                 350

Lys Phe Ser Arg Ser Ala Asp Ala Pro Ala Tyr Gln Gln Gly Gln Asn
            355                 360                 365

Gln Leu Tyr Asn Glu Leu Asn Leu Gly Arg Arg Glu Glu Tyr Asp Val
        370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 89
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 16B5-V2 CAR

<400> SEQUENCE: 89

Met Ala Leu Pro Val Thr Ala Leu Leu Leu Pro Leu Ala Leu Leu Leu
1               5                   10                  15

His Ala Ala Arg Pro Gln Ala Tyr Leu Gln Gln Ser Gly Ala Glu Leu
                20                  25                  30

Val Arg Ser Gly Ala Ser Val Lys Met Ser Cys Lys Ala Ser Gly Tyr
            35                  40                  45

Thr Phe Thr Ser Tyr Asn Leu His Trp Val Lys Gln Thr Pro Gly Gln
        50                  55                  60

Gly Leu Glu Trp Ile Gly Tyr Ile Tyr Pro Gly Asn Gly Gly Thr Asn
65              70                  75                  80

Tyr Asn Gln Lys Phe Lys Gly Lys Ala Thr Leu Thr Ala Asp Thr Ser
                85                  90                  95

Ser Ser Thr Ala Tyr Met Gln Ile Ser Ser Leu Thr Ser Glu Asp Ser
            100                 105                 110

Ala Val Tyr Phe Cys Ala Arg Gly Gly Ile Tyr Tyr Gly Ser Ser
        115                 120                 125

Leu Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asn Ile Val
145                 150                 155                 160

Leu Thr Gln Ser Pro Ala Ser Leu Ala Val Ser Leu Gly Gln Arg Ala
                165                 170                 175

Thr Ile Ser Cys Arg Ala Ser Glu Ser Val Asp Asn Tyr Gly Thr Thr
            180                 185                 190

Phe Met Tyr Trp Tyr Gln Gln Lys Pro Gly Gln Pro Pro Lys Leu Leu
        195                 200                 205
```

```
Ile Tyr Leu Ala Ser Asn Leu Glu Ser Gly Val Pro Ala Arg Phe Ser
            210                 215                 220

Gly Ser Gly Ser Gly Thr Asp Phe Thr Leu Thr Ile Asp Pro Val Glu
225                 230                 235                 240

Ala Asp Asp Ala Ala Thr Tyr Tyr Cys Gln Gln Asn Lys Glu Asp Pro
                245                 250                 255

Trp Thr Phe Gly Gly Gly Thr Lys Leu Glu Ile Lys Thr Thr Thr Pro
                260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 90
<211> LENGTH: 677
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 16B5-V3 CAR

<400> SEQUENCE: 90

Met Ala Leu Pro Val Thr Ala Leu Leu Leu Pro Leu Ala Leu Leu Leu
1               5                   10                  15

His Ala Ala Arg Pro Gln Ala Tyr Leu Gln Gln Ser Gly Ala Glu Leu
            20                  25                  30

Val Arg Ser Gly Ala Ser Val Lys Met Ser Cys Lys Ala Ser Gly Tyr
        35                  40                  45

Thr Phe Thr Ser Tyr Asn Leu His Trp Val Lys Gln Thr Pro Gly Gln
    50                  55                  60
```

Gly Leu Glu Trp Ile Gly Tyr Ile Tyr Pro Gly Asn Gly Thr Asn
65                  70                  75                  80

Tyr Asn Gln Lys Phe Lys Gly Lys Ala Thr Leu Thr Ala Asp Thr Ser
                85                  90                  95

Ser Ser Thr Ala Tyr Met Gln Ile Ser Ser Leu Thr Ser Glu Asp Ser
            100                 105                 110

Ala Val Tyr Phe Cys Ala Arg Gly Gly Ile Tyr Tyr Gly Ser Ser
        115                 120                 125

Leu Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asn Ile Val
145                 150                 155                 160

Leu Thr Gln Ser Pro Ala Ser Leu Ala Val Ser Leu Gly Gln Arg Ala
                165                 170                 175

Thr Ile Ser Cys Arg Ala Ser Glu Ser Val Asp Asn Tyr Gly Thr Thr
            180                 185                 190

Phe Met Tyr Trp Tyr Gln Gln Lys Pro Gly Gln Pro Pro Lys Leu Leu
        195                 200                 205

Ile Tyr Leu Ala Ser Asn Leu Glu Ser Gly Val Pro Ala Arg Phe Ser
    210                 215                 220

Gly Ser Gly Ser Gly Thr Asp Phe Thr Leu Thr Ile Asp Pro Val Glu
225                 230                 235                 240

Ala Asp Asp Ala Ala Thr Tyr Tyr Cys Gln Gln Asn Lys Glu Asp Pro
                245                 250                 255

Trp Thr Phe Gly Gly Gly Thr Lys Leu Glu Ile Lys Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser

```
            485                 490                 495
Pro Gly Lys Ile Tyr Ile Trp Ala Pro Leu Ala Gly Thr Cys Gly Val
            500                 505                 510

Leu Leu Leu Ser Leu Val Ile Thr Leu Tyr Cys Lys Arg Gly Arg Lys
            515                 520                 525

Lys Leu Leu Tyr Ile Phe Lys Gln Pro Phe Met Arg Pro Val Gln Thr
            530                 535                 540

Thr Gln Glu Glu Asp Gly Cys Ser Cys Arg Phe Pro Glu Glu Glu
545                 550                 555                 560

Gly Gly Cys Glu Leu Arg Val Lys Phe Ser Arg Ser Ala Asp Ala Pro
                565                 570                 575

Ala Tyr Gln Gln Gly Gln Asn Gln Leu Tyr Asn Glu Leu Asn Leu Gly
            580                 585                 590

Arg Arg Glu Glu Tyr Asp Val Leu Asp Lys Arg Arg Gly Arg Asp Pro
            595                 600                 605

Glu Met Gly Gly Lys Pro Arg Arg Lys Asn Pro Gln Glu Gly Leu Tyr
            610                 615                 620

Asn Glu Leu Gln Lys Asp Lys Met Ala Glu Ala Tyr Ser Glu Ile Gly
625                 630                 635                 640

Met Lys Gly Glu Arg Arg Arg Gly Lys Gly His Asp Gly Leu Tyr Gln
                645                 650                 655

Gly Leu Ser Thr Ala Thr Lys Asp Thr Tyr Asp Ala Leu His Met Gln
            660                 665                 670

Ala Leu Pro Pro Arg
            675

<210> SEQ ID NO 91
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10F7-V1 CAR

<400> SEQUENCE: 91

Met Ala Leu Pro Val Thr Ala Leu Leu Leu Pro Leu Ala Leu Leu Leu
1               5                   10                  15

His Ala Ala Arg Pro Gln Ala Tyr Leu Gln Gln Ser Gly Ala Glu Leu
                20                  25                  30

Val Arg Ser Gly Ala Ser Val Lys Met Ser Cys Lys Ala Ser Gly Tyr
            35                  40                  45

Thr Phe Thr Ser Tyr Asn Met His Trp Val Lys Gln Thr Pro Gly Gln
        50                  55                  60

Gly Leu Glu Trp Ile Gly Tyr Ile Tyr Pro Gly Asn Gly Thr Asn
65                  70                  75                  80

Tyr Asn Gln Lys Phe Lys Asp Lys Ala Thr Leu Thr Ala Asp Thr Ser
                85                  90                  95

Ser Ser Thr Ala Tyr Met Gln Ile Ser Ser Leu Thr Ser Glu Asp Ser
            100                 105                 110

Ala Val Tyr Phe Cys Ala Arg Gly Gly Gln Leu Gly Arg Pro Trp Phe
        115                 120                 125

Ala Tyr Trp Gly Gln Gly Thr Leu Val Thr Val Ser Ala Gly Gly Gly
    130                 135                 140

Gly Ser Gly Gly Gly Gly Ser Gly Gly Gly Gly Ser Asn Ile Val Leu
```

| | | 145 | | | 150 | | | 155 | | | 160 |

Thr Gln Ser Pro Ala Ser Leu Ala Ala Ser Pro Gly Gln Arg Ala Thr
                165                170                175

Ile Ser Cys Arg Ala Ser Glu Ser Val Asp Ser Tyr Gly Asn Thr Phe
                180                185                190

Met Tyr Trp Tyr Gln Gln Lys Pro Gly Gln Pro Pro Lys Leu Leu Ile
            195                200                205

Tyr Leu Ala Ser Asn Leu Glu Ser Gly Val Pro Val Arg Phe Ser Gly
        210                215                220

Ser Gly Ser Arg Thr Asp Phe Thr Leu Thr Ile Asp Pro Val Glu Ala
225                230                235                240

Asp Asp Ala Ala Thr Tyr Tyr Cys Gln Gln Asn Asn Glu Asp Pro Trp
                245                250                255

Thr Phe Gly Gly Gly Thr Lys Val Glu Ile Lys Gly Leu Ala Val Ser
            260                265                270

Thr Ile Ser Ser Phe Phe Pro Pro Gly Tyr Gln Ile Tyr Ile Trp Ala
        275                280                285

Pro Leu Ala Gly Thr Cys Gly Val Leu Leu Leu Ser Leu Val Ile Thr
        290                295                300

Leu Tyr Cys Lys Arg Gly Arg Lys Lys Leu Leu Tyr Ile Phe Lys Gln
305                310                315                320

Pro Phe Met Arg Pro Val Gln Thr Thr Gln Glu Glu Asp Gly Cys Ser
            325                330                335

Cys Arg Phe Pro Glu Glu Glu Gly Gly Cys Glu Leu Arg Val Lys
            340                345                350

Phe Ser Arg Ser Ala Asp Ala Pro Ala Tyr Gln Gln Gly Gln Asn Gln
        355                360                365

Leu Tyr Asn Glu Leu Asn Leu Gly Arg Arg Glu Glu Tyr Asp Val Leu
        370                375                380

Asp Lys Arg Arg Gly Arg Asp Pro Glu Met Gly Gly Lys Pro Arg Arg
385                390                395                400

Lys Asn Pro Gln Glu Gly Leu Tyr Asn Glu Leu Gln Lys Asp Lys Met
            405                410                415

Ala Glu Ala Tyr Ser Glu Ile Gly Met Lys Gly Glu Arg Arg Arg Gly
            420                425                430

Lys Gly His Asp Gly Leu Tyr Gln Gly Leu Ser Thr Ala Thr Lys Asp
        435                440                445

Thr Tyr Asp Ala Leu His Met Gln Ala Leu Pro Pro Arg
    450                455                460

<210> SEQ ID NO 92
<211> LENGTH: 490
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: 10F7-V2 CAR

<400> SEQUENCE: 92

Met Ala Leu Pro Val Thr Ala Leu Leu Leu Pro Leu Ala Leu Leu Leu
1                  5                    10                  15

His Ala Ala Arg Pro Gln Ala Tyr Leu Gln Gln Ser Gly Ala Glu Leu
            20                25                30

Val Arg Ser Gly Ala Ser Val Lys Met Ser Cys Lys Ala Ser Gly Tyr

```
            35                  40                  45
Thr Phe Thr Ser Tyr Asn Met His Trp Val Lys Gln Thr Pro Gly Gln
 50                  55                  60

Gly Leu Glu Trp Ile Gly Tyr Ile Tyr Pro Gly Asn Gly Gly Thr Asn
 65                  70                  75                  80

Tyr Asn Gln Lys Phe Lys Asp Lys Ala Thr Leu Thr Ala Asp Thr Ser
                 85                  90                  95

Ser Ser Thr Ala Tyr Met Gln Ile Ser Ser Leu Thr Ser Glu Asp Ser
                100                 105                 110

Ala Val Tyr Phe Cys Ala Arg Gly Gly Gln Leu Gly Arg Pro Trp Phe
            115                 120                 125

Ala Tyr Trp Gly Gln Gly Thr Leu Val Thr Val Ser Ala Gly Gly Gly
            130                 135                 140

Gly Ser Gly Gly Gly Gly Ser Gly Gly Gly Gly Ser Asn Ile Val Leu
145                 150                 155                 160

Thr Gln Ser Pro Ala Ser Leu Ala Ala Ser Pro Gly Gln Arg Ala Thr
                165                 170                 175

Ile Ser Cys Arg Ala Ser Glu Ser Val Asp Ser Tyr Gly Asn Thr Phe
                180                 185                 190

Met Tyr Trp Tyr Gln Gln Lys Pro Gly Gln Pro Pro Lys Leu Leu Ile
            195                 200                 205

Tyr Leu Ala Ser Asn Leu Glu Ser Gly Val Pro Val Arg Phe Ser Gly
            210                 215                 220

Ser Gly Ser Arg Thr Asp Phe Thr Leu Thr Ile Asp Pro Val Glu Ala
225                 230                 235                 240

Asp Asp Ala Ala Thr Tyr Tyr Cys Gln Gln Asn Asn Glu Asp Pro Trp
                245                 250                 255

Thr Phe Gly Gly Gly Thr Lys Val Glu Ile Lys Thr Thr Thr Pro Ala
                260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
            290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
            355                 360                 365

Pro Glu Glu Glu Glu Gly Gly Cys Glu Leu Arg Val Lys Phe Ser Arg
            370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Arg Gly Lys Gly His
            450                 455                 460
```

```
Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 93
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10F7-V3 CAR

<400> SEQUENCE: 93

Met Ala Leu Pro Val Thr Ala Leu Leu Leu Pro Leu Ala Leu Leu Leu
1               5                   10                  15

His Ala Ala Arg Pro Gln Ala Tyr Leu Gln Gln Ser Gly Ala Glu Leu
                20                  25                  30

Val Arg Ser Gly Ala Ser Val Lys Met Ser Cys Lys Ala Ser Gly Tyr
            35                  40                  45

Thr Phe Thr Ser Tyr Asn Met His Trp Val Lys Gln Thr Pro Gly Gln
        50                  55                  60

Gly Leu Glu Trp Ile Gly Tyr Ile Tyr Pro Gly Asn Gly Gly Thr Asn
65                  70                  75                  80

Tyr Asn Gln Lys Phe Lys Asp Lys Ala Thr Leu Thr Ala Asp Thr Ser
                85                  90                  95

Ser Ser Thr Ala Tyr Met Gln Ile Ser Ser Leu Thr Ser Glu Asp Ser
            100                 105                 110

Ala Val Tyr Phe Cys Ala Arg Gly Gly Gln Leu Gly Arg Pro Trp Phe
        115                 120                 125

Ala Tyr Trp Gly Gln Gly Thr Leu Val Thr Val Ser Ala Gly Gly Gly
    130                 135                 140

Gly Ser Gly Gly Gly Gly Ser Gly Gly Gly Gly Ser Asn Ile Val Leu
145                 150                 155                 160

Thr Gln Ser Pro Ala Ser Leu Ala Ala Ser Pro Gly Gln Arg Ala Thr
                165                 170                 175

Ile Ser Cys Arg Ala Ser Glu Ser Val Asp Ser Tyr Gly Asn Thr Phe
            180                 185                 190

Met Tyr Trp Tyr Gln Gln Lys Pro Gly Gln Pro Pro Lys Leu Leu Ile
        195                 200                 205

Tyr Leu Ala Ser Asn Leu Glu Ser Gly Val Pro Val Arg Phe Ser Gly
    210                 215                 220

Ser Gly Ser Arg Thr Asp Phe Thr Leu Thr Ile Asp Pro Val Glu Ala
225                 230                 235                 240

Asp Asp Ala Ala Thr Tyr Tyr Cys Gln Gln Asn Asn Glu Asp Pro Trp
                245                 250                 255

Thr Phe Gly Gly Gly Thr Lys Val Glu Ile Lys Glu Pro Lys Ser Pro
            260                 265                 270

Asp Lys Thr His Thr Cys Pro Pro Cys Pro Ala Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320
```

Asp Pro Glu Val Lys Phe Asn Trp Tyr Val Asp Gly Val Glu Val His
            325                 330                 335

Asn Ala Lys Thr Lys Pro Arg Glu Glu Gln Tyr Asn Ser Thr Tyr Arg
        340                 345                 350

Val Val Ser Val Leu Thr Val Leu His Gln Asp Trp Leu Asn Gly Lys
    355                 360                 365

Glu Tyr Lys Cys Lys Val Ser Asn Lys Ala Leu Pro Ala Pro Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
            405                 410                 415

Thr Cys Leu Val Lys Gly Phe Tyr Pro Ser Asp Ile Ala Val Glu Trp
        420                 425                 430

Glu Ser Asn Gly Gln Pro Glu Asn Asn Tyr Lys Thr Thr Pro Pro Val
    435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
            485                 490                 495

Gly Lys Ile Tyr Ile Trp Ala Pro Leu Ala Gly Thr Cys Gly Val Leu
        500                 505                 510

Leu Leu Ser Leu Val Ile Thr Leu Tyr Cys Lys Arg Gly Arg Lys Lys
    515                 520                 525

Leu Leu Tyr Ile Phe Lys Gln Pro Phe Met Arg Pro Val Gln Thr Thr
530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
            565                 570                 575

Tyr Gln Gln Gly Gln Asn Gln Leu Tyr Asn Glu Leu Asn Leu Gly Arg
        580                 585                 590

Arg Glu Glu Tyr Asp Val Leu Asp Lys Arg Arg Gly Arg Asp Pro Glu
    595                 600                 605

Met Gly Gly Lys Pro Arg Arg Lys Asn Pro Gln Glu Gly Leu Tyr Asn
610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
            645                 650                 655

Leu Ser Thr Ala Thr Lys Asp Thr Tyr Asp Ala Leu His Met Gln Ala
        660                 665                 670

Leu Pro Pro Arg
        675

<210> SEQ ID NO 94
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

-continued

<223> OTHER INFORMATION: 27B6-V1 CAR

<400> SEQUENCE: 94

```
Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Pro Gly Leu
            20                  25                  30

Val Gln Pro Ser Gln Ser Leu Ser Ile Thr Cys Thr Val Ser Gly Phe
        35                  40                  45

Ser Leu Thr Ser Tyr Asn Ile Asp Trp Val Arg Gln Ser Pro Gly Lys
    50                  55                  60

Gly Leu Glu Trp Leu Gly Val Ile Trp Ser Gly Gly Ser Thr Asp Tyr
65                  70                  75                  80

Asn Ala Ala Phe Ile Ser Arg Leu Lys Ile Ser Lys Asp Asp Ser Lys
                85                  90                  95

Ser Gln Val Phe Phe Lys Met Asn Ser Leu Gln Ser Asp Asp Thr Ala
            100                 105                 110

Ile Tyr Tyr Cys Ala Arg His Ser Pro Leu Val Ser Thr Pro Asp Trp
        115                 120                 125

Tyr Phe Asp Val Trp Gly Ala Gly Thr Thr Val Thr Val Ser Ser Gly
    130                 135                 140

Gly Gly Gly Ser Gly Gly Gly Ser Gly Gly Gly Ser Gln Ile
145                 150                 155                 160

Val Leu Thr Gln Ser Pro Ala Ile Met Ser Ala Ser Pro Gly Glu Lys
                165                 170                 175

Val Thr Met Thr Cys Ser Thr Ser Ser Val Ser Tyr Met His Trp
            180                 185                 190

Tyr Gln Gln Lys Ser Gly Thr Ser Pro Lys Arg Trp Ile Tyr Asp Thr
        195                 200                 205

Ser Lys Leu Ala Ser Gly Val Pro Ala Arg Phe Ser Gly Ser Gly Ser
    210                 215                 220

Gly Thr Ser Tyr Ser Leu Thr Ile Asn Asn Met Glu Ala Glu Asp Ala
225                 230                 235                 240

Ala Thr Tyr Ser Cys Gln Gln Trp Ser Ser Tyr Pro Pro Thr Phe Gly
                245                 250                 255

Gly Gly Thr Lys Leu Glu Ile Lys Gly Leu Ala Val Ser Thr Ile Ser
            260                 265                 270

Ser Phe Phe Pro Pro Gly Tyr Gln Ile Tyr Ile Trp Ala Pro Leu Ala
        275                 280                 285

Gly Thr Cys Gly Val Leu Leu Leu Ser Leu Val Ile Thr Leu Tyr Cys
    290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400
```

Gln Glu Gly Leu Tyr Asn Glu Leu Gln Lys Asp Lys Met Ala Glu Ala
            405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
450                 455

<210> SEQ ID NO 95
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 27B6-V2 CAR

<400> SEQUENCE: 95

Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Pro Gly Leu
            20                  25                  30

Val Gln Pro Ser Gln Ser Leu Ser Ile Thr Cys Thr Val Ser Gly Phe
        35                  40                  45

Ser Leu Thr Ser Tyr Asn Ile Asp Trp Val Arg Gln Ser Pro Gly Lys
    50                  55                  60

Gly Leu Glu Trp Leu Gly Val Ile Trp Ser Gly Ser Thr Asp Tyr
65                  70                  75                  80

Asn Ala Ala Phe Ile Ser Arg Leu Lys Ile Ser Lys Asp Asp Ser Lys
                85                  90                  95

Ser Gln Val Phe Phe Lys Met Asn Ser Leu Gln Ser Asp Asp Thr Ala
            100                 105                 110

Ile Tyr Tyr Cys Ala Arg His Ser Pro Leu Val Ser Thr Pro Asp Trp
        115                 120                 125

Tyr Phe Asp Val Trp Gly Ala Gly Thr Thr Val Thr Val Ser Ser Gly
    130                 135                 140

Gly Gly Gly Ser Gly Gly Gly Gly Ser Gly Gly Gly Gly Ser Gln Ile
145                 150                 155                 160

Val Leu Thr Gln Ser Pro Ala Ile Met Ser Ala Ser Pro Gly Glu Lys
                165                 170                 175

Val Thr Met Thr Cys Ser Thr Ser Ser Val Ser Tyr Met His Trp
            180                 185                 190

Tyr Gln Gln Lys Ser Gly Thr Ser Pro Lys Arg Trp Ile Tyr Asp Thr
        195                 200                 205

Ser Lys Leu Ala Ser Gly Val Pro Ala Arg Phe Ser Gly Ser Gly Ser
    210                 215                 220

Gly Thr Ser Tyr Ser Leu Thr Ile Asn Asn Met Glu Ala Glu Asp Ala
225                 230                 235                 240

Ala Thr Tyr Ser Cys Gln Gln Trp Ser Ser Tyr Pro Pro Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

```
Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 96
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 27B6-V3 CAR

<400> SEQUENCE: 96

Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Pro Gly Leu
                20                  25                  30

Val Gln Pro Ser Gln Ser Leu Ser Ile Thr Cys Thr Val Ser Gly Phe
            35                  40                  45

Ser Leu Thr Ser Tyr Asn Ile Asp Trp Val Arg Gln Ser Pro Gly Lys
    50                  55                  60

Gly Leu Glu Trp Leu Gly Val Ile Trp Ser Gly Gly Ser Thr Asp Tyr
65                  70                  75                  80

Asn Ala Ala Phe Ile Ser Arg Leu Lys Ile Ser Lys Asp Asp Ser Lys
                85                  90                  95

Ser Gln Val Phe Phe Lys Met Asn Ser Leu Gln Ser Asp Asp Thr Ala
                100                 105                 110

Ile Tyr Tyr Cys Ala Arg His Ser Pro Leu Val Ser Thr Pro Asp Trp
            115                 120                 125

Tyr Phe Asp Val Trp Gly Ala Gly Thr Thr Val Thr Val Ser Ser Gly
    130                 135                 140
```

```
Gly Gly Gly Ser Gly Gly Gly Ser Gly Gly Gly Ser Gln Ile
145             150             155             160

Val Leu Thr Gln Ser Pro Ala Ile Met Ser Ala Ser Pro Gly Glu Lys
                165             170             175

Val Thr Met Thr Cys Ser Thr Ser Ser Val Ser Tyr Met His Trp
            180             185             190

Tyr Gln Gln Lys Ser Gly Thr Ser Pro Lys Arg Trp Ile Tyr Asp Thr
        195             200             205

Ser Lys Leu Ala Ser Gly Val Pro Ala Arg Phe Ser Gly Ser Gly Ser
    210             215             220

Gly Thr Ser Tyr Ser Leu Thr Ile Asn Asn Met Glu Ala Glu Asp Ala
225             230             235             240

Ala Thr Tyr Ser Cys Gln Gln Trp Ser Ser Tyr Pro Pro Thr Phe Gly
            245             250             255

Gly Gly Thr Lys Leu Glu Ile Lys Glu Pro Lys Ser Pro Asp Lys Thr
            260             265             270

His Thr Cys Pro Pro Cys Pro Ala Pro Pro Val Ala Gly Pro Ser Val
        275             280             285

Phe Leu Phe Pro Pro Lys Pro Lys Asp Thr Leu Met Ile Ala Arg Thr
    290             295             300

Pro Glu Val Thr Cys Val Val Val Asp Val Ser His Glu Asp Pro Glu
305             310             315             320

Val Lys Phe Asn Trp Tyr Val Asp Gly Val Glu Val His Asn Ala Lys
            325             330             335

Thr Lys Pro Arg Glu Glu Gln Tyr Asn Ser Thr Tyr Arg Val Val Ser
        340             345             350

Val Leu Thr Val Leu His Gln Asp Trp Leu Asn Gly Lys Glu Tyr Lys
    355             360             365

Cys Lys Val Ser Asn Lys Ala Leu Pro Ala Pro Ile Glu Lys Thr Ile
    370             375             380

Ser Lys Ala Lys Gly Gln Pro Arg Glu Pro Gln Val Tyr Thr Leu Pro
385             390             395             400

Pro Ser Arg Asp Glu Leu Thr Lys Asn Gln Val Ser Leu Thr Cys Leu
            405             410             415

Val Lys Gly Phe Tyr Pro Ser Asp Ile Ala Val Glu Trp Glu Ser Asn
            420             425             430

Gly Gln Pro Glu Asn Asn Tyr Lys Thr Thr Pro Pro Val Leu Asp Ser
        435             440             445

Asp Gly Ser Phe Phe Leu Tyr Ser Lys Leu Thr Val Asp Lys Ser Arg
    450             455             460

Trp Gln Gln Gly Asn Val Phe Ser Cys Ser Val Met His Glu Ala Leu
465             470             475             480

His Asn His Tyr Thr Gln Lys Ser Leu Ser Leu Ser Pro Gly Lys Ile
            485             490             495

Tyr Ile Trp Ala Pro Leu Ala Gly Thr Cys Gly Val Leu Leu Leu Ser
            500             505             510

Leu Val Ile Thr Leu Tyr Cys Lys Arg Gly Arg Lys Lys Leu Leu Tyr
    515             520             525

Ile Phe Lys Gln Pro Phe Met Arg Pro Val Gln Thr Thr Gln Glu Glu
    530             535             540

Asp Gly Cys Ser Cys Arg Phe Pro Glu Glu Glu Glu Gly Gly Cys Glu
545             550             555             560

Leu Arg Val Lys Phe Ser Arg Ser Ala Asp Ala Pro Ala Tyr Gln Gln
```

```
                          565                 570                 575
Gly Gln Asn Gln Leu Tyr Asn Glu Leu Asn Leu Gly Arg Arg Glu Glu
                580                 585                 590

Tyr Asp Val Leu Asp Lys Arg Arg Gly Arg Asp Pro Glu Met Gly Gly
            595                 600                 605

Lys Pro Arg Arg Lys Asn Pro Gln Glu Gly Leu Tyr Asn Glu Leu Gln
        610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
                660                 665                 670

Arg

<210> SEQ ID NO 97
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 13F11-V1 CAR

<400> SEQUENCE: 97

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
                20                  25                  30

Lys Lys Pro Gly Glu Thr Val Lys Ile Ser Cys Lys Ala Ser Gly Tyr
            35                  40                  45

Thr Phe Lys Lys Tyr Gly Met Asn Trp Val Lys Gln Ala Pro Gly Lys
        50                  55                  60

Gly Leu Lys Trp Met Gly Trp Ile Asn Thr Asn Thr Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
                100                 105                 110

Ala Thr Tyr Phe Cys Ala Arg Trp Tyr Tyr Gly Ser Thr Pro Ser Ser
            115                 120                 125

Tyr Thr Met Asp Tyr Trp Gly Gln Gly Thr Ser Val Thr Val Ser Ser
        130                 135                 140

Gly Gly Gly Gly Ser Gly Gly Gly Ser Gly Gly Gly Gly Ser Glu
145                 150                 155                 160

Thr Thr Val Thr Gln Ser Pro Ala Ser Leu Ser Val Ala Thr Gly Glu
                165                 170                 175

Lys Val Thr Ile Arg Cys Ile Thr Ser Thr Asp Ile Asp Asp Asp Met
                180                 185                 190

Asn Trp Tyr Gln Gln Lys Pro Gly Glu Pro Lys Val Leu Ile Ser
            195                 200                 205

Glu Gly Asn Thr Leu Arg Pro Gly Val Pro Ser Arg Phe Ser Ser Ser
        210                 215                 220

Gly Tyr Gly Thr Asp Phe Val Phe Thr Ile Glu Asn Thr Leu Ser Glu
225                 230                 235                 240
```

Asp Val Ala Asp Tyr Tyr Cys Leu Gln Ser Asn Asn Met Pro Tyr Thr
            245                 250                 255

Phe Gly Gly Gly Thr Lys Leu Glu Ile Lys Gly Leu Ala Val Ser Thr
        260                 265                 270

Ile Ser Ser Phe Phe Pro Pro Gly Tyr Gln Ile Tyr Ile Trp Ala Pro
        275                 280                 285

Leu Ala Gly Thr Cys Gly Val Leu Leu Leu Ser Leu Val Ile Thr Leu
        290                 295                 300

Tyr Cys Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
                340                 345                 350

Ser Arg Ser Ala Asp Ala Pro Ala Tyr Gln Gln Gly Gln Asn Gln Leu
                355                 360                 365

Tyr Asn Glu Leu Asn Leu Gly Arg Arg Glu Glu Tyr Asp Val Leu Asp
        370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
                420                 425                 430

Gly His Asp Gly Leu Tyr Gln Gly Leu Ser Thr Ala Thr Lys Asp Thr
                435                 440                 445

Tyr Asp Ala Leu His Met Gln Ala Leu Pro Pro Arg
        450                 455                 460

<210> SEQ ID NO 98
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 13F11-V2 CAR

<400> SEQUENCE: 98

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
                20                  25                  30

Lys Lys Pro Gly Glu Thr Val Lys Ile Ser Cys Lys Ala Ser Gly Tyr
            35                  40                  45

Thr Phe Lys Lys Tyr Gly Met Asn Trp Val Lys Gln Ala Pro Gly Lys
        50                  55                  60

Gly Leu Lys Trp Met Gly Trp Ile Asn Thr Asn Thr Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Trp Tyr Tyr Gly Ser Thr Pro Ser Ser
        115                 120                 125

Tyr Thr Met Asp Tyr Trp Gly Gln Gly Thr Ser Val Thr Val Ser Ser
            130                 135                 140

Gly Gly Gly Gly Ser Gly Gly Gly Ser Gly Gly Gly Gly Ser Glu
145                 150                 155                 160

Thr Thr Val Thr Gln Ser Pro Ala Ser Leu Ser Val Ala Thr Gly Glu
                165                 170                 175

Lys Val Thr Ile Arg Cys Ile Thr Ser Thr Asp Ile Asp Asp Asp Met
            180                 185                 190

Asn Trp Tyr Gln Gln Lys Pro Gly Glu Pro Pro Lys Val Leu Ile Ser
            195                 200                 205

Glu Gly Asn Thr Leu Arg Pro Gly Val Pro Ser Arg Phe Ser Ser
210                 215                 220

Gly Tyr Gly Thr Asp Phe Val Phe Thr Ile Glu Asn Thr Leu Ser Glu
225                 230                 235                 240

Asp Val Ala Asp Tyr Tyr Cys Leu Gln Ser Asn Asn Met Pro Tyr Thr
                245                 250                 255

Phe Gly Gly Gly Thr Lys Leu Glu Ile Lys Thr Thr Thr Pro Ala Pro
            260                 265                 270

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
            485

<210> SEQ ID NO 99
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: 13F11-V3 CAR

<400> SEQUENCE: 99

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Lys Lys Tyr Gly Met Asn Trp Val Lys Gln Ala Pro Gly Lys
    50                  55                  60

Gly Leu Lys Trp Met Gly Trp Ile Asn Thr Asn Thr Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Trp Tyr Gly Ser Thr Pro Ser Ser
        115                 120                 125

Tyr Thr Met Asp Tyr Trp Gly Gln Gly Thr Ser Val Thr Val Ser Ser
    130                 135                 140

Gly Gly Gly Gly Ser Gly Gly Gly Ser Gly Gly Gly Gly Ser Glu
145                 150                 155                 160

Thr Thr Val Thr Gln Ser Pro Ala Ser Leu Ser Val Ala Thr Gly Glu
                165                 170                 175

Lys Val Thr Ile Arg Cys Ile Thr Ser Thr Asp Ile Asp Asp Asp Met
            180                 185                 190

Asn Trp Tyr Gln Gln Lys Pro Gly Glu Pro Pro Lys Val Leu Ile Ser
        195                 200                 205

Glu Gly Asn Thr Leu Arg Pro Gly Val Pro Ser Arg Phe Ser Ser Ser
    210                 215                 220

Gly Tyr Gly Thr Asp Phe Val Phe Thr Ile Glu Asn Thr Leu Ser Glu
225                 230                 235                 240

Asp Val Ala Asp Tyr Tyr Cys Leu Gln Ser Asn Asn Met Pro Tyr Thr
                245                 250                 255

Phe Gly Gly Gly Thr Lys Leu Glu Ile Lys Glu Pro Lys Ser Pro Asp
            260                 265                 270

Lys Thr His Thr Cys Pro Pro Cys Pro Ala Pro Val Ala Gly Pro
        275                 280                 285

Ser Val Phe Leu Phe Pro Pro Lys Pro Lys Asp Thr Leu Met Ile Ala
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400
```

```
Leu Pro Pro Ser Arg Asp Glu Leu Thr Lys Asn Gln Val Ser Leu Thr
            405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
            435                 440                 445
Asp Ser Asp Gly Ser Phe Phe Leu Tyr Ser Lys Leu Thr Val Asp Lys
            450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
            485                 490                 495
Lys Ile Tyr Ile Trp Ala Pro Leu Ala Gly Thr Cys Gly Val Leu Leu
            500                 505                 510
Leu Ser Leu Val Ile Thr Leu Tyr Cys Lys Arg Gly Arg Lys Lys Leu
            515                 520                 525
Leu Tyr Ile Phe Lys Gln Pro Phe Met Arg Pro Val Gln Thr Thr Gln
            530                 535                 540
Glu Glu Asp Gly Cys Ser Cys Arg Phe Pro Glu Glu Glu Glu Gly Gly
545                 550                 555                 560
Cys Glu Leu Arg Val Lys Phe Ser Arg Ser Ala Asp Ala Pro Ala Tyr
            565                 570                 575
Gln Gln Gly Gln Asn Gln Leu Tyr Asn Glu Leu Asn Leu Gly Arg Arg
            580                 585                 590
Glu Glu Tyr Asp Val Leu Asp Lys Arg Arg Gly Arg Asp Pro Glu Met
            595                 600                 605
Gly Gly Lys Pro Arg Arg Lys Asn Pro Gln Glu Gly Leu Tyr Asn Glu
610                 615                 620
Leu Gln Lys Asp Lys Met Ala Glu Ala Tyr Ser Glu Ile Gly Met Lys
625                 630                 635                 640
Gly Glu Arg Arg Arg Gly Lys Gly His Asp Gly Leu Tyr Gln Gly Leu
            645                 650                 655
Ser Thr Ala Thr Lys Asp Thr Tyr Asp Ala Leu His Met Gln Ala Leu
            660                 665                 670
Pro Pro Arg
    675

<210> SEQ ID NO 100
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F5-V1 CAR

<400> SEQUENCE: 100

Met Ala Leu Pro Val Thr Ala Leu Leu Leu Pro Leu Ala Leu Leu Leu
1               5                   10                  15
His Ala Ala Arg Pro Gln Ile Gln Leu Val Gln Ser Gly Pro Glu Leu
            20                  25                  30
Lys Lys Pro Gly Glu Thr Val Lys Ile Ser Cys Lys Ala Ser Gly Tyr
            35                  40                  45
Thr Phe Thr Lys Tyr Gly Met Asn Trp Val Lys Gln Thr Pro Gly Lys
        50                  55                  60
```

Gly Leu Lys Trp Met Gly Trp Ile Asn Thr Asn Ser Gly Glu Pro Thr
 65                  70                  75                  80

Tyr Ala Glu Glu Phe Lys Gly Arg Phe Ala Phe Ser Leu Glu Thr Ser
                 85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Gly Ala Tyr Arg Tyr Asp Gly Glu
        115                 120                 125

Val Ser Tyr Tyr Ala Met Asp Tyr Trp Gly Gln Gly Thr Ser Val Thr
    130                 135                 140

Val Ser Ser Gly Gly Gly Gly Ser Gly Gly Gly Gly Ser Gly Gly Gly
145                 150                 155                 160

Gly Ser Gln Ile Ile Leu Thr Gln Ser Pro Ala Ile Met Ser Ala Ser
                165                 170                 175

Leu Gly Glu Arg Val Thr Met Thr Cys Thr Ala Thr Ser Ser Leu Ser
            180                 185                 190

Ser Ser Tyr Leu His Trp Tyr Gln Gln Lys Pro Gly Ser Ser Pro Lys
        195                 200                 205

Leu Trp Ile Tyr Ser Thr Ser His Leu Ala Ser Gly Val Pro Ala Arg
    210                 215                 220

Phe Ser Gly Gly Ser Gly Thr Ser Tyr Ser Leu Thr Ile Ser Ser
225                 230                 235                 240

Met Glu Ala Glu Asp Ala Ala Thr Tyr Tyr Cys His Gln Tyr His Leu
                245                 250                 255

Ser Pro Tyr Thr Phe Gly Gly Gly Thr Lys Leu Glu Ile Lys Gly Leu
            260                 265                 270

Ala Val Ser Thr Ile Ser Ser Phe Phe Pro Pro Gly Tyr Gln Ile Tyr
        275                 280                 285

Ile Trp Ala Pro Leu Ala Gly Thr Cys Gly Val Leu Leu Leu Ser Leu
    290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

<210> SEQ ID NO 101
<211> LENGTH: 493
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F5-V2 CAR

<400> SEQUENCE: 101

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
    35                  40                  45

Thr Phe Thr Lys Tyr Gly Met Asn Trp Val Lys Gln Thr Pro Gly Lys
50                  55                  60

Gly Leu Lys Trp Met Gly Trp Ile Asn Thr Asn Ser Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Gly Ala Tyr Tyr Arg Tyr Asp Gly Glu
        115                 120                 125

Val Ser Tyr Tyr Ala Met Asp Tyr Trp Gly Gln Gly Thr Ser Val Thr
    130                 135                 140

Val Ser Ser Gly Gly Gly Ser Gly Gly Gly Ser Gly Gly Gly
145                 150                 155                 160

Gly Ser Gln Ile Ile Leu Thr Gln Ser Pro Ala Ile Met Ser Ala Ser
                165                 170                 175

Leu Gly Glu Arg Val Thr Met Thr Cys Thr Ala Thr Ser Ser Leu Ser
            180                 185                 190

Ser Ser Tyr Leu His Trp Tyr Gln Gln Lys Pro Gly Ser Ser Pro Lys
        195                 200                 205

Leu Trp Ile Tyr Ser Thr Ser His Leu Ala Ser Gly Val Pro Ala Arg
    210                 215                 220

Phe Ser Gly Gly Gly Ser Gly Thr Ser Tyr Ser Leu Thr Ile Ser Ser
225                 230                 235                 240

Met Glu Ala Glu Asp Ala Ala Thr Tyr Tyr Cys His Gln Tyr His Leu
                245                 250                 255

Ser Pro Tyr Thr Phe Gly Gly Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys

```
                    370                 375                 380
Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
        450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 102
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F5-V3 CAR

<400> SEQUENCE: 102

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Lys Tyr Gly Met Asn Trp Val Lys Gln Thr Pro Gly Lys
    50                  55                  60

Gly Leu Lys Trp Met Gly Trp Ile Asn Thr Asn Ser Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Gly Ala Tyr Tyr Arg Tyr Asp Gly Glu
        115                 120                 125

Val Ser Tyr Tyr Ala Met Asp Tyr Trp Gly Gln Gly Thr Ser Val Thr
    130                 135                 140

Val Ser Ser Gly Gly Gly Gly Ser Gly Gly Gly Ser Gly Gly Gly
145                 150                 155                 160

Gly Ser Gln Ile Ile Leu Thr Gln Ser Pro Ala Ile Met Ser Ala Ser
                165                 170                 175

Leu Gly Glu Arg Val Thr Met Thr Cys Thr Ala Thr Ser Ser Leu Ser
            180                 185                 190

Ser Ser Tyr Leu His Trp Tyr Gln Gln Lys Pro Gly Ser Ser Pro Lys
        195                 200                 205

Leu Trp Ile Tyr Ser Thr Ser His Leu Ala Ser Gly Val Pro Ala Arg
    210                 215                 220

Phe Ser Gly Gly Gly Ser Gly Thr Ser Tyr Ser Leu Thr Ile Ser Ser
```

-continued

```
                225                 230                 235                 240
        Met Glu Ala Glu Asp Ala Ala Thr Tyr Tyr Cys His Gln Tyr His Leu
                        245                 250                 255

Ser Pro Tyr Thr Phe Gly Gly Gly Thr Lys Leu Glu Ile Lys Glu Pro
                        260                 265                 270

Lys Ser Pro Asp Lys Thr His Thr Cys Pro Pro Cys Pro Ala Pro Pro
                        275                 280                 285

Val Ala Gly Pro Ser Val Phe Leu Phe Pro Pro Lys Pro Lys Asp Thr
                        290                 295                 300

Leu Met Ile Ala Arg Thr Pro Glu Val Thr Cys Val Val Val Asp Val
        305                 310                 315                 320

Ser His Glu Asp Pro Glu Val Lys Phe Asn Trp Tyr Val Asp Gly Val
                        325                 330                 335

Glu Val His Asn Ala Lys Thr Lys Pro Arg Glu Glu Gln Tyr Asn Ser
                        340                 345                 350

Thr Tyr Arg Val Val Ser Val Leu Thr Val Leu His Gln Asp Trp Leu
                        355                 360                 365

Asn Gly Lys Glu Tyr Lys Cys Lys Val Ser Asn Lys Ala Leu Pro Ala
                        370                 375                 380

Pro Ile Glu Lys Thr Ile Ser Lys Ala Lys Gly Gln Pro Arg Glu Pro
        385                 390                 395                 400

Gln Val Tyr Thr Leu Pro Pro Ser Arg Asp Glu Leu Thr Lys Asn Gln
                        405                 410                 415

Val Ser Leu Thr Cys Leu Val Lys Gly Phe Tyr Pro Ser Asp Ile Ala
                        420                 425                 430

Val Glu Trp Glu Ser Asn Gly Gln Pro Glu Asn Asn Tyr Lys Thr Thr
                        435                 440                 445

Pro Pro Val Leu Asp Ser Asp Gly Ser Phe Phe Leu Tyr Ser Lys Leu
                        450                 455                 460

Thr Val Asp Lys Ser Arg Trp Gln Gln Gly Asn Val Phe Ser Cys Ser
        465                 470                 475                 480

Val Met His Glu Ala Leu His Asn His Tyr Thr Gln Lys Ser Leu Ser
                        485                 490                 495

Leu Ser Pro Gly Lys Ile Tyr Ile Trp Ala Pro Leu Ala Gly Thr Cys
                        500                 505                 510

Gly Val Leu Leu Leu Ser Leu Val Ile Thr Leu Tyr Cys Lys Arg Gly
                        515                 520                 525

Arg Lys Lys Leu Leu Tyr Ile Phe Lys Gln Pro Phe Met Arg Pro Val
                        530                 535                 540

Gln Thr Thr Gln Glu Glu Asp Gly Cys Ser Cys Arg Phe Pro Glu Glu
        545                 550                 555                 560

Glu Glu Gly Gly Cys Glu Leu Arg Val Lys Phe Ser Arg Ser Ala Asp
                        565                 570                 575

Ala Pro Ala Tyr Gln Gln Gly Gln Asn Gln Leu Tyr Asn Glu Leu Asn
                        580                 585                 590

Leu Gly Arg Arg Glu Glu Tyr Asp Val Leu Asp Lys Arg Arg Gly Arg
                        595                 600                 605

Asp Pro Glu Met Gly Gly Lys Pro Arg Arg Lys Asn Pro Gln Glu Gly
                        610                 615                 620

Leu Tyr Asn Glu Leu Gln Lys Asp Lys Met Ala Glu Ala Tyr Ser Glu
        625                 630                 635                 640

Ile Gly Met Lys Gly Glu Arg Arg Arg Gly Lys Gly His Asp Gly Leu
                        645                 650                 655
```

Tyr Gln Gly Leu Ser Thr Ala Thr Lys Asp Thr Tyr Asp Ala Leu His
                660                 665                 670

Met Gln Ala Leu Pro Pro Arg
        675

<210> SEQ ID NO 103
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GMB005-V1 CAR

<400> SEQUENCE: 103

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Asn Ser Phe Ala Met Ser Trp Val Arg Gln Ala Pro Gly Lys
    50                  55                  60

Gly Leu Glu Trp Val Ser Ala Ile Ser Gly Ser Gly Gly Gly Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Phe Cys Ala Lys Asp Lys Ile Leu Trp Phe Gly Glu Pro
        115                 120                 125

Val Phe Asp Tyr Trp Gly Gln Gly Thr Leu Val Thr Val Ser Ser Ala
    130                 135                 140

Ser Gly Gly Gly Gly Ser Gly Gly Gly Ser Gly Gly Gly Gly Ser
145                 150                 155                 160

Glu Ile Val Leu Thr Gln Ser Pro Ala Thr Leu Ser Leu Ser Pro Gly
                165                 170                 175

Glu Arg Ala Thr Leu Ser Cys Arg Ala Ser Gln Ser Val Ser Ser Tyr
            180                 185                 190

Leu Ala Trp Tyr Gln Gln Lys Pro Gly Gln Ala Pro Arg Leu Leu Ile
        195                 200                 205

Tyr Asp Ala Ser Asn Arg Ala Thr Gly Ile Pro Ala Arg Phe Ser Gly
    210                 215                 220

Ser Gly Ser Gly Thr Asp Phe Thr Leu Thr Ile Ser Ser Leu Glu Pro
225                 230                 235                 240

Glu Asp Phe Ala Val Tyr Tyr Cys Gln Gln Arg Ser Asn Trp Pro Pro
                245                 250                 255

Thr Phe Gly Gln Gly Thr Lys Val Glu Ile Lys Gly Leu Ala Val Ser
            260                 265                 270

Thr Ile Ser Ser Phe Phe Pro Pro Gly Tyr Gln Ile Tyr Ile Trp Ala
        275                 280                 285

Pro Leu Ala Gly Thr Cys Gly Val Leu Leu Leu Ser Leu Val Ile Thr
    290                 295                 300

Leu Tyr Cys Lys Arg Gly Arg Lys Lys Leu Leu Tyr Ile Phe Lys Gln
305                 310                 315                 320

```
Pro Phe Met Arg Pro Val Gln Thr Thr Gln Glu Asp Gly Cys Ser
            325                 330                 335

Cys Arg Phe Pro Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 104
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GMB005-V2 CAR

<400> SEQUENCE: 104

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Asn Ser Phe Ala Met Ser Trp Val Arg Gln Ala Pro Gly Lys
    50                  55                  60

Gly Leu Glu Trp Val Ser Ala Ile Ser Gly Ser Gly Gly Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Phe Cys Ala Lys Asp Lys Ile Leu Trp Phe Gly Glu Pro
        115                 120                 125

Val Phe Asp Tyr Trp Gly Gln Gly Thr Leu Val Thr Val Ser Ser Ala
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Ala Thr Leu Ser Leu Ser Pro Gly
                165                 170                 175

Glu Arg Ala Thr Leu Ser Cys Arg Ala Ser Gln Ser Val Ser Ser Tyr
            180                 185                 190

Leu Ala Trp Tyr Gln Gln Lys Pro Gly Gln Ala Pro Arg Leu Leu Ile
        195                 200                 205
```

Tyr Asp Ala Ser Asn Arg Ala Thr Gly Ile Pro Ala Arg Phe Ser Gly
            210                 215                 220

Ser Gly Ser Gly Thr Asp Phe Thr Leu Thr Ile Ser Ser Leu Glu Pro
225                 230                 235                 240

Glu Asp Phe Ala Val Tyr Tyr Cys Gln Gln Arg Ser Asn Trp Pro Pro
                245                 250                 255

Thr Phe Gly Gln Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 105
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GMB005-V3 CAR

<400> SEQUENCE: 105

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Asn Ser Phe Ala Met Ser Trp Val Arg Gln Ala Pro Gly Lys
    50                  55                  60

```
Gly Leu Glu Trp Val Ser Ala Ile Ser Gly Ser Gly Gly Thr Tyr
 65                  70                  75                  80

Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Phe Cys Ala Lys Asp Lys Ile Leu Trp Phe Gly Glu Pro
        115                 120                 125

Val Phe Asp Tyr Trp Gly Gln Gly Thr Leu Val Thr Val Ser Ser Ala
130                 135                 140

Ser Gly Gly Gly Gly Ser Gly Gly Gly Ser Gly Gly Gly Gly Ser
145                 150                 155                 160

Glu Ile Val Leu Thr Gln Ser Pro Ala Thr Leu Ser Leu Ser Pro Gly
                165                 170                 175

Glu Arg Ala Thr Leu Ser Cys Arg Ala Ser Gln Ser Val Ser Ser Tyr
            180                 185                 190

Leu Ala Trp Tyr Gln Gln Lys Pro Gly Gln Ala Pro Arg Leu Leu Ile
        195                 200                 205

Tyr Asp Ala Ser Asn Arg Ala Thr Gly Ile Pro Ala Arg Phe Ser Gly
210                 215                 220

Ser Gly Ser Gly Thr Asp Phe Thr Leu Thr Ile Ser Ser Leu Glu Pro
225                 230                 235                 240

Glu Asp Phe Ala Val Tyr Tyr Cys Gln Gln Arg Ser Asn Trp Pro Pro
                245                 250                 255

Thr Phe Gly Gln Gly Thr Lys Val Glu Ile Lys Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Val Phe Ser Cys Ser Val Met His
465                 470                 475                 480
```

```
Glu Ala Leu His Asn His Tyr Thr Gln Lys Ser Leu Ser Leu Ser Pro
                485                 490                 495

Gly Lys Ile Tyr Ile Trp Ala Pro Leu Ala Gly Thr Cys Gly Val Leu
            500                 505                 510

Leu Leu Ser Leu Val Ile Thr Leu Tyr Cys Lys Arg Gly Arg Lys Lys
        515                 520                 525

Leu Leu Tyr Ile Phe Lys Gln Pro Phe Met Arg Pro Val Gln Thr Thr
    530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
                565                 570                 575

Tyr Gln Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
        595                 600                 605

Met Gly Gly Lys Pro Arg Arg Lys Asn Pro Gln Glu Gly Leu Tyr Asn
    610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
                645                 650                 655

Leu Ser Thr Ala Thr Lys Asp Thr Tyr Asp Ala Leu His Met Gln Ala
            660                 665                 670

Leu Pro Pro Arg
        675

<210> SEQ ID NO 106
<211> LENGTH: 18
<212> TYPE: PRT
<213> ORGANISM: Homo sapiens
<220> FEATURE:
<223> OTHER INFORMATION: FcεRI γ- signal peptide (SP)

<400> SEQUENCE: 106

Met Ile Pro Ala Val Val Leu Leu Leu Leu Leu Val Glu Gln Ala
1               5                   10                  15

Ala Ala

<210> SEQ ID NO 107
<211> LENGTH: 43
<212> TYPE: PRT
<213> ORGANISM: Homo sapiens
<220> FEATURE:
<223> OTHER INFORMATION: Fc Receptor for IgE, gamma chain, without ITAM)
      (FcεRI γ - DITAM)

<400> SEQUENCE: 107

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser
        35                  40

<210> SEQ ID NO 108
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: GSG-P2A ribosomal skip peptide (GSG-P2A)

<400> SEQUENCE: 108

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GSG-T2A ribosomal skip peptide (GSG-T2A)

<400> SEQUENCE: 109

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 110
<211> LENGTH: 25
<212> TYPE: PRT
<213> ORGANISM: Homo sapiens
<220> FEATURE:
<223> OTHER INFORMATION: FcεRI a- signal peptide (SP)

<400> SEQUENCE: 110

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 111
<211> LENGTH: 52
<212> TYPE: PRT
<213> ORGANISM: Homo sapiens
<220> FEATURE:
<223> OTHER INFORMATION: Fc Receptor for IgE, alpha chain, transmembrane
      and intracellular domain (FcεRI a-TM-IC)

<400> SEQUENCE: 111

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
            20                  25                  30

Arg Thr Arg Lys Gly Phe Arg Leu Leu Asn Pro His Pro Lys Pro Asn
        35                  40                  45

Pro Lys Asn Asn
    50

<210> SEQ ID NO 112
<211> LENGTH: 215
<212> TYPE: PRT
<213> ORGANISM: Homo sapiens
<220> FEATURE:
<223> OTHER INFORMATION: Receptor for IgE, beta chain, without ITAM
```

(FcεR1γ-δITAM)

<400> SEQUENCE: 112

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu
    210                 215

<210> SEQ ID NO 113
<211> LENGTH: 41
<212> TYPE: PRT
<213> ORGANISM: Homo sapiens
<220> FEATURE:
<223> OTHER INFORMATION: CD28 co-stimulatory domain (CD28-IC)

<400> SEQUENCE: 113

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CD20 mimotope

<400> SEQUENCE: 114

Cys Pro Tyr Ser Asn Pro Ser Leu Cys Ser

<210> SEQ ID NO 115
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope for palivizumab

<400> SEQUENCE: 115

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mimotope 1 for cetuximab

<400> SEQUENCE: 116

Cys Gln Phe Asp Leu Ser Thr Arg Arg Leu Lys Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mimotope 2 for cetuximab

<400> SEQUENCE: 117

Cys Gln Tyr Asn Leu Ser Ser Arg Ala Leu Lys Cys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mimotope 3 for cetuximab

<400> SEQUENCE: 118

Cys Val Trp Gln Arg Trp Gln Lys Ser Tyr Val Cys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Mimotope 4 for cetuximab

```
<400> SEQUENCE: 119

Cys Met Trp Asp Arg Phe Ser Arg Trp Tyr Lys Cys
1               5                   10

<210> SEQ ID NO 120
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope A for nivolumab

<400> SEQUENCE: 120

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope B for nivolumab

<400> SEQUENCE: 121

Ser Gly Thr Tyr Leu Cys Gly Ala Ile Ser Leu Ala Pro Lys Ala Gln
1               5                   10                  15

Ile Lys Glu

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope 1 for CD34

<400> SEQUENCE: 122

Thr Phe Ser Asn Val Ser Thr Asn Val Ser Tyr Gln Glu Thr
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope 2 for CD34

<400> SEQUENCE: 123

Asn Thr Asn Ser Ser Val Gln Ser Gln Thr Ser Val Ile Ser
1               5                   10

<210> SEQ ID NO 124
<211> LENGTH: 533
<212> TYPE: PRT
```

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: 28F5v2 CAR with 2 CD20 mimotopes

<400> SEQUENCE: 124

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Thr Phe Thr Lys Tyr Gly Met Asn Trp Val Lys Gln Thr Pro Gly Lys
    50                  55                  60

Gly Leu Lys Trp Met Gly Trp Ile Asn Thr Asn Ser Gly Glu Pro Thr
65                  70                  75                  80

Tyr Ala Glu Glu Phe Lys Gly Arg Phe Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Ala Arg Gly Ala Tyr Tyr Arg Tyr Asp Gly Glu
        115                 120                 125

Val Ser Tyr Tyr Ala Met Asp Tyr Trp Gly Gln Gly Thr Ser Val Thr
    130                 135                 140

Val Ser Ser Gly Gly Gly Gly Ser Gly Gly Gly Gly Ser Gly Gly Gly
145                 150                 155                 160

Gly Ser Gln Ile Ile Leu Thr Gln Ser Pro Ala Ile Met Ser Ala Ser
                165                 170                 175

Leu Gly Glu Arg Val Thr Met Thr Cys Thr Ala Thr Ser Ser Leu Ser
            180                 185                 190

Ser Ser Tyr Leu His Trp Tyr Gln Gln Lys Pro Gly Ser Ser Pro Lys
        195                 200                 205

Leu Trp Ile Tyr Ser Thr Ser His Leu Ala Ser Gly Val Pro Ala Arg
    210                 215                 220

Phe Ser Gly Gly Gly Ser Gly Thr Ser Tyr Ser Leu Thr Ile Ser Ser
225                 230                 235                 240

Met Glu Ala Glu Asp Ala Ala Thr Tyr Tyr Cys His Gln Tyr His Leu
                245                 250                 255

Ser Pro Tyr Thr Phe Gly Gly Gly Thr Lys Leu Glu Ile Lys Ser Asp
            260                 265                 270

Pro Gly Ser Gly Gly Gly Gly Ser Cys Pro Tyr Ser Asn Pro Ser Leu
        275                 280                 285

Cys Ser Gly Gly Gly Gly Ser Cys Pro Tyr Ser Asn Pro Ser Leu Cys
    290                 295                 300

Ser Gly Gly Gly Gly Ser Thr Thr Thr Pro Ala Pro Arg Pro Pro Thr
305                 310                 315                 320

Pro Ala Pro Thr Ile Ala Ser Gln Pro Leu Ser Leu Arg Pro Glu Ala
                325                 330                 335

Cys Arg Pro Ala Ala Gly Gly Ala Val His Thr Arg Gly Leu Asp Phe
            340                 345                 350

Ala Cys Asp Ile Tyr Ile Trp Ala Pro Leu Ala Gly Thr Cys Gly Val
        355                 360                 365

Leu Leu Leu Ser Leu Val Ile Thr Leu Tyr Cys Lys Arg Gly Arg Lys
```

```
                370                 375                 380
Lys Leu Leu Tyr Ile Phe Lys Gln Pro Phe Met Arg Pro Val Gln Thr
385                 390                 395                 400

Thr Gln Glu Glu Asp Gly Cys Ser Cys Arg Phe Pro Glu Glu Glu
                405                 410                 415

Gly Gly Cys Glu Leu Arg Val Lys Phe Ser Arg Ser Ala Asp Ala Pro
                420                 425                 430

Ala Tyr Gln Gln Gly Gln Asn Gln Leu Tyr Asn Glu Leu Asn Leu Gly
                435                 440                 445

Arg Arg Glu Glu Tyr Asp Val Leu Asp Lys Arg Arg Gly Arg Asp Pro
                450                 455                 460

Glu Met Gly Gly Lys Pro Arg Arg Lys Asn Pro Gln Glu Gly Leu Tyr
465                 470                 475                 480

Asn Glu Leu Gln Lys Asp Lys Met Ala Glu Ala Tyr Ser Glu Ile Gly
                485                 490                 495

Met Lys Gly Glu Arg Arg Arg Gly Lys Gly His Asp Gly Leu Tyr Gln
                500                 505                 510

Gly Leu Ser Thr Ala Thr Lys Asp Thr Tyr Asp Ala Leu His Met Gln
                515                 520                 525

Ala Leu Pro Pro Arg
    530

<210> SEQ ID NO 125
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F5v2 CAR with 2 CD20 mimotopes and 1 CD34
      epitope

<400> SEQUENCE: 125

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Ser Gly Gly Gly Gly Ser Gly Gly Gly Gly Ser Gln Ile
                35                  40                  45

Gln Leu Val Gln Ser Gly Pro Glu Leu Lys Lys Pro Gly Glu Thr Val
    50                  55                  60

Lys Ile Ser Cys Lys Ala Ser Gly Tyr Thr Phe Thr Lys Tyr Gly Met
65                  70                  75                  80

Asn Trp Val Lys Gln Thr Pro Gly Lys Gly Leu Lys Trp Met Gly Trp
                85                  90                  95

Ile Asn Thr Asn Ser Gly Glu Pro Thr Tyr Ala Glu Glu Phe Lys Gly
                100                 105                 110

Arg Phe Ala Phe Ser Leu Glu Thr Ser Ala Ser Thr Ala Tyr Leu Gln
                115                 120                 125

Ile Asn Asn Leu Lys Asn Glu Asp Thr Ala Thr Tyr Phe Cys Ala Arg
                130                 135                 140

Gly Ala Tyr Tyr Arg Tyr Asp Gly Glu Val Ser Tyr Tyr Ala Met Asp
145                 150                 155                 160

Tyr Trp Gly Gln Gly Thr Ser Val Thr Val Ser Ser Gly Gly Gly Gly
                165                 170                 175
```

```
Ser Gly Gly Gly Gly Ser Gly Gly Gly Ser Gln Ile Ile Leu Thr
            180                 185                 190

Gln Ser Pro Ala Ile Met Ser Ala Ser Leu Gly Glu Arg Val Thr Met
        195                 200                 205

Thr Cys Thr Ala Thr Ser Ser Leu Ser Ser Ser Tyr Leu His Trp Tyr
    210                 215                 220

Gln Gln Lys Pro Gly Ser Ser Pro Lys Leu Trp Ile Tyr Ser Thr Ser
225                 230                 235                 240

His Leu Ala Ser Gly Val Pro Ala Arg Phe Ser Gly Gly Ser Gly
                245                 250                 255

Thr Ser Tyr Ser Leu Thr Ile Ser Ser Met Glu Ala Glu Asp Ala Ala
            260                 265                 270

Thr Tyr Tyr Cys His Gln Tyr His Leu Ser Pro Tyr Thr Phe Gly Gly
        275                 280                 285

Gly Thr Lys Leu Glu Ile Lys Gly Ser Gly Gly Gly Ser Cys Pro
    290                 295                 300

Tyr Ser Asn Pro Ser Leu Cys Ser Gly Gly Gly Ser Glu Leu Pro
305                 310                 315                 320

Thr Gln Gly Thr Phe Ser Asn Val Ser Thr Asn Val Ser Pro Ala Lys
            325                 330                 335

Pro Thr Thr Thr Ala Cys Pro Tyr Ser Asn Pro Ser Leu Cys Thr Thr
        340                 345                 350

Thr Pro Ala Pro Arg Pro Pro Thr Pro Ala Pro Thr Ile Ala Ser Gln
    355                 360                 365

Pro Leu Ser Leu Arg Pro Glu Ala Cys Arg Pro Ala Ala Gly Gly Ala
370                 375                 380

Val His Thr Arg Gly Leu Asp Phe Ala Cys Asp Ile Tyr Ile Trp Ala
385                 390                 395                 400

Pro Leu Ala Gly Thr Cys Gly Val Leu Leu Leu Ser Leu Val Ile Thr
            405                 410                 415

Leu Tyr Cys Lys Arg Gly Arg Lys Lys Leu Leu Tyr Ile Phe Lys Gln
        420                 425                 430

Pro Phe Met Arg Pro Val Gln Thr Thr Gln Glu Glu Asp Gly Cys Ser
    435                 440                 445

Cys Arg Phe Pro Glu Glu Glu Gly Gly Cys Glu Leu Arg Val Lys
    450                 455                 460

Phe Ser Arg Ser Ala Asp Ala Pro Ala Tyr Gln Gln Gly Gln Asn Gln
465                 470                 475                 480

Leu Tyr Asn Glu Leu Asn Leu Gly Arg Arg Glu Glu Tyr Asp Val Leu
            485                 490                 495

Asp Lys Arg Arg Gly Arg Asp Pro Glu Met Gly Gly Lys Pro Arg Arg
        500                 505                 510

Lys Asn Pro Gln Glu Gly Leu Tyr Asn Glu Leu Gln Lys Asp Lys Met
    515                 520                 525

Ala Glu Ala Tyr Ser Glu Ile Gly Met Lys Gly Glu Arg Arg Arg Gly
    530                 535                 540

Lys Gly His Asp Gly Leu Tyr Gln Gly Leu Ser Thr Ala Thr Lys Asp
545                 550                 555                 560

Thr Tyr Asp Ala Leu His Met Gln Ala Leu Pro Arg
            565                 570

<210> SEQ ID NO 126
<211> LENGTH: 504
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 28F5v1 CAR with 2 CD20 mimotopes

<400> SEQUENCE: 126

```

```
                370                 375                 380
Glu Glu Glu Gly Gly Cys Glu Leu Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
                420                 425                 430

Arg Asp Pro Glu Met Gly Gly Lys Pro Arg Arg Lys Asn Pro Gln Glu
                435                 440                 445

Gly Leu Tyr Asn Glu Leu Gln Lys Asp Lys Met Ala Glu Ala Tyr Ser
450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
                500
```

<210> SEQ ID NO 127
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F5v1 CAR with 2 CD20 mimotopes and 1 CD34
      epitope

<400> SEQUENCE: 127

```
Met Ala Leu Pro Val Thr Ala Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Ser Gly Gly Gly Gly Ser Gly Gly Gly Gly Ser Gln Ile
                35                  40                  45

Gln Leu Val Gln Ser Gly Pro Glu Leu Lys Lys Pro Gly Glu Thr Val
    50                  55                  60

Lys Ile Ser Cys Lys Ala Ser Gly Tyr Thr Phe Thr Lys Tyr Gly Met
65                  70                  75                  80

Asn Trp Val Lys Gln Thr Pro Gly Lys Gly Leu Lys Trp Met Gly Trp
                85                  90                  95

Ile Asn Thr Asn Ser Gly Glu Pro Thr Tyr Ala Glu Glu Phe Lys Gly
                100                 105                 110

Arg Phe Ala Phe Ser Leu Glu Thr Ser Ala Ser Thr Ala Tyr Leu Gln
                115                 120                 125

Ile Asn Asn Leu Lys Asn Glu Asp Thr Ala Thr Tyr Phe Cys Ala Arg
                130                 135                 140

Gly Ala Tyr Tyr Arg Tyr Asp Gly Glu Val Ser Tyr Tyr Ala Met Asp
145                 150                 155                 160

Tyr Trp Gly Gln Gly Thr Ser Val Thr Val Ser Ser Gly Gly Gly Gly
                165                 170                 175

Ser Gly Gly Gly Gly Ser Gly Gly Gly Gly Ser Gln Ile Ile Leu Thr
                180                 185                 190

Gln Ser Pro Ala Ile Met Ser Ala Ser Leu Gly Glu Arg Val Thr Met
                195                 200                 205
```

```
Thr Cys Thr Ala Thr Ser Ser Leu Ser Ser Ser Tyr Leu His Trp Tyr
    210                 215                 220

Gln Gln Lys Pro Gly Ser Ser Pro Lys Leu Trp Ile Tyr Ser Thr Ser
225                 230                 235                 240

His Leu Ala Ser Gly Val Pro Ala Arg Phe Ser Gly Gly Ser Gly
                245                 250                 255

Thr Ser Tyr Ser Leu Thr Ile Ser Ser Met Glu Ala Glu Asp Ala Ala
                260                 265                 270

Thr Tyr Tyr Cys His Gln Tyr His Leu Ser Pro Tyr Thr Phe Gly Gly
                275                 280                 285

Gly Thr Lys Leu Glu Ile Lys Gly Ser Gly Gly Gly Ser Cys Pro
290                 295                 300

Tyr Ser Asn Pro Ser Leu Cys Ser Gly Gly Gly Ser Glu Leu Pro
305                 310                 315                 320

Thr Gln Gly Thr Phe Ser Asn Val Ser Thr Asn Val Ser Pro Ala Lys
                325                 330                 335

Pro Thr Thr Thr Ala Cys Pro Tyr Ser Asn Pro Ser Leu Cys Gly Leu
                340                 345                 350

Ala Val Ser Thr Ile Ser Ser Phe Phe Pro Pro Gly Tyr Gln Ile Tyr
                355                 360                 365

Ile Trp Ala Pro Leu Ala Gly Thr Cys Gly Val Leu Leu Leu Ser Leu
370                 375                 380

Val Ile Thr Leu Tyr Cys Lys Arg Gly Arg Lys Lys Leu Leu Tyr Ile
385                 390                 395                 400

Phe Lys Gln Pro Phe Met Arg Pro Val Gln Thr Thr Gln Glu Glu Asp
                405                 410                 415

Gly Cys Ser Cys Arg Phe Pro Glu Glu Glu Glu Gly Gly Cys Glu Leu
                420                 425                 430

Arg Val Lys Phe Ser Arg Ser Ala Asp Ala Pro Ala Tyr Gln Gln Gly
                435                 440                 445

Gln Asn Gln Leu Tyr Asn Glu Leu Asn Leu Gly Arg Arg Glu Glu Tyr
                450                 455                 460

Asp Val Leu Asp Lys Arg Arg Gly Arg Asp Pro Glu Met Gly Gly Lys
465                 470                 475                 480

Pro Arg Arg Lys Asn Pro Gln Glu Gly Leu Tyr Asn Glu Leu Gln Lys
                485                 490                 495

Asp Lys Met Ala Glu Ala Tyr Ser Glu Ile Gly Met Lys Gly Glu Arg
                500                 505                 510

Arg Arg Gly Lys Gly His Asp Gly Leu Tyr Gln Gly Leu Ser Thr Ala
                515                 520                 525

Thr Lys Asp Thr Tyr Asp Ala Leu His Met Gln Ala Leu Pro Pro Arg
530                 535                 540
```

<210> SEQ ID NO 128
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10v2 CAR with 2 CD20 mimotopes

<400> SEQUENCE: 128

```
Met Ala Leu Pro Val Thr Ala Leu Leu Leu Pro Leu Ala Leu Leu Leu
1               5                   10                  15
```

His Ala Ala Arg Pro Glu Val Gln Leu Gln Gln Ser Gly Ala Glu Leu
            20                  25                  30

Val Arg Pro Gly Ala Ser Val Lys Leu Ser Cys Thr Ala Ser Gly Phe
        35                  40                  45

Asn Ile Lys Asp Ser Leu Ile His Trp Val Lys Gln Arg Pro Glu Gln
    50                  55                  60

Gly Leu Glu Trp Ile Gly Trp Ile Asp Pro Glu Asp Asp Lys Thr Lys
65                  70                  75                  80

Tyr Ala Pro Lys Phe Gln Asp Lys Ala Thr Leu Thr Ala Asp Thr Ser
                85                  90                  95

Ser Asn Thr Ala Tyr Leu Gln Leu Ser Thr Leu Thr Ser Glu Asp Thr
            100                 105                 110

Ala Ile Tyr Tyr Cys Val Ser Arg Tyr Ile Asn Tyr Phe Ala Tyr
        115                 120                 125

Trp Gly Gln Gly Thr Thr Leu Thr Val Ser Ser Gly Gly Gly Ser
    130                 135                 140

Gly Gly Gly Gly Ser Gly Gly Gly Ser Asp Ile Val Met Thr Gln
145                 150                 155                 160

Ser Pro Ser Ser Leu Thr Val Thr Ala Gly Glu Lys Val Thr Met Ser
                165                 170                 175

Cys Lys Ser Ser Gln Ser Leu Leu His Ser Gly Asn Gln Arg Asn Tyr
            180                 185                 190

Leu Thr Trp Tyr Gln Gln Lys Pro Gly Gln Pro Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Asp Tyr Pro Tyr
                245                 250                 255

Thr Phe Gly Gly Gly Thr Lys Leu Glu Ile Lys Ser Asp Pro Gly Ser
            260                 265                 270

Gly Gly Gly Gly Ser Cys Pro Tyr Ser Asn Pro Ser Leu Cys Ser Gly
        275                 280                 285

Gly Gly Gly Ser Cys Pro Tyr Ser Asn Pro Ser Leu Cys Ser Gly Gly
    290                 295                 300

Gly Gly Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
            325                 330                 335

Ala Ala Gly Gly Ala Val His Thr Arg Gly Leu Asp Phe Ala Cys Asp
        340                 345                 350

Ile Tyr Ile Trp Ala Pro Leu Ala Gly Thr Cys Gly Val Leu Leu Leu
    355                 360                 365

Ser Leu Val Ile Thr Leu Tyr Cys Lys Arg Gly Arg Lys Lys Leu Leu
        370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Gly Gly Cys
            405                 410                 415

Glu Leu Arg Val Lys Phe Ser Arg Ser Ala Asp Ala Pro Ala Tyr Gln
        420                 425                 430

Gln Gly Gln Asn Gln Leu Tyr Asn Glu Leu Asn Leu Gly Arg Arg Glu

```
                        435                 440                 445
Glu Tyr Asp Val Leu Asp Lys Arg Arg Gly Arg Asp Pro Glu Met Gly
            450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
                515                 520                 525

Pro Arg
    530

<210> SEQ ID NO 129
<211> LENGTH: 569
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10v2 CAR with 2 CD20 mimotopes and 1 CD34
      epitope

<400> SEQUENCE: 129

Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
                20                  25                  30

Ser Leu Cys Ser Gly Gly Gly Gly Ser Gly Gly Gly Gly Ser Glu Val
            35                  40                  45

Gln Leu Gln Gln Ser Gly Ala Glu Leu Val Arg Pro Gly Ala Ser Val
        50                  55                  60

Lys Leu Ser Cys Thr Ala Ser Gly Phe Asn Ile Lys Asp Ser Leu Ile
65              70                  75                  80

His Trp Val Lys Gln Arg Pro Glu Gln Gly Leu Glu Trp Ile Gly Trp
                85                  90                  95

Ile Asp Pro Glu Asp Asp Lys Thr Lys Tyr Ala Pro Lys Phe Gln Asp
            100                 105                 110

Lys Ala Thr Leu Thr Ala Asp Thr Ser Ser Asn Thr Ala Tyr Leu Gln
        115                 120                 125

Leu Ser Thr Leu Thr Ser Glu Asp Thr Ala Ile Tyr Tyr Cys Val Ser
    130                 135                 140

Arg Tyr Ile Asn Tyr Tyr Phe Ala Tyr Trp Gly Gln Gly Thr Thr Leu
145                 150                 155                 160

Thr Val Ser Ser Gly Gly Gly Gly Ser Gly Gly Gly Gly Ser Gly Gly
                165                 170                 175

Gly Gly Asp Ile Val Met Thr Gln Ser Pro Ser Ser Leu Thr Val Thr
            180                 185                 190

Ala Gly Glu Lys Val Thr Met Ser Cys Lys Ser Ser Gln Ser Leu Leu
        195                 200                 205

His Ser Gly Asn Gln Arg Asn Tyr Leu Thr Trp Tyr Gln Gln Lys Pro
    210                 215                 220

Gly Gln Pro Pro Lys Leu Leu Ile Tyr Trp Ala Ser Thr Arg Glu Ser
225                 230                 235                 240
```

```
Gly Val Pro Asp Arg Phe Thr Gly Ser Gly Ser Gly Thr Asp Phe Thr
            245                 250                 255

Leu Thr Ile Ser Ser Val Gln Ala Glu Asp Leu Ala Val Tyr Tyr Cys
            260                 265                 270

Gln Asn Asp Tyr Asp Tyr Pro Tyr Thr Phe Gly Gly Gly Thr Lys Leu
            275                 280                 285

Glu Ile Lys Gly Ser Gly Gly Gly Gly Ser Cys Pro Tyr Ser Asn Pro
            290                 295                 300

Ser Leu Cys Ser Gly Gly Gly Gly Ser Glu Leu Pro Thr Gln Gly Thr
305                 310                 315                 320

Phe Ser Asn Val Ser Thr Asn Val Ser Pro Ala Lys Pro Thr Thr Thr
            325                 330                 335

Ala Cys Pro Tyr Ser Asn Pro Ser Leu Cys Thr Thr Thr Pro Ala Pro
            340                 345                 350

Arg Pro Pro Thr Pro Ala Pro Thr Ile Ala Ser Gln Pro Leu Ser Leu
            355                 360                 365

Arg Pro Glu Ala Cys Arg Pro Ala Ala Gly Gly Ala Val His Thr Arg
            370                 375                 380

Gly Leu Asp Phe Ala Cys Asp Ile Tyr Ile Trp Ala Pro Leu Ala Gly
385                 390                 395                 400

Thr Cys Gly Val Leu Leu Leu Ser Leu Val Ile Thr Leu Tyr Cys Lys
            405                 410                 415

Arg Gly Arg Lys Lys Leu Leu Tyr Ile Phe Lys Gln Pro Phe Met Arg
            420                 425                 430

Pro Val Gln Thr Thr Gln Glu Glu Asp Gly Cys Ser Cys Arg Phe Pro
            435                 440                 445

Glu Glu Glu Glu Gly Gly Cys Glu Leu Arg Val Lys Phe Ser Arg Ser
450                 455                 460

Ala Asp Ala Pro Ala Tyr Gln Gln Gly Gln Asn Gln Leu Tyr Asn Glu
465                 470                 475                 480

Leu Asn Leu Gly Arg Arg Glu Glu Tyr Asp Val Leu Asp Lys Arg Arg
            485                 490                 495

Gly Arg Asp Pro Glu Met Gly Gly Lys Pro Arg Arg Lys Asn Pro Gln
            500                 505                 510

Glu Gly Leu Tyr Asn Glu Leu Gln Lys Asp Lys Met Ala Glu Ala Tyr
            515                 520                 525

Ser Glu Ile Gly Met Lys Gly Glu Arg Arg Arg Gly Lys Gly His Asp
            530                 535                 540

Gly Leu Tyr Gln Gly Leu Ser Thr Ala Thr Lys Asp Thr Tyr Asp Ala
545                 550                 555                 560

Leu His Met Gln Ala Leu Pro Pro Arg
                565

<210> SEQ ID NO 130
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10v1 CAR with 2 CD20 mimotopes

<400> SEQUENCE: 130

Met Ala Leu Pro Val Thr Ala Leu Leu Leu Pro Leu Ala Leu Leu Leu
1               5                   10                  15
```

His Ala Ala Arg Pro Glu Val Gln Leu Gln Gln Ser Gly Ala Glu Leu
                 20                  25                  30

Val Arg Pro Gly Ala Ser Val Lys Leu Ser Cys Thr Ala Ser Gly Phe
             35                  40                  45

Asn Ile Lys Asp Ser Leu Ile His Trp Val Lys Gln Arg Pro Glu Gln
         50                  55                  60

Gly Leu Glu Trp Ile Gly Trp Ile Asp Pro Glu Asp Asp Lys Thr Lys
 65                  70                  75                  80

Tyr Ala Pro Lys Phe Gln Asp Lys Ala Thr Leu Thr Ala Asp Thr Ser
                 85                  90                  95

Ser Asn Thr Ala Tyr Leu Gln Leu Ser Thr Leu Thr Ser Glu Asp Thr
            100                 105                 110

Ala Ile Tyr Tyr Cys Val Ser Arg Tyr Ile Asn Tyr Phe Ala Tyr
        115                 120                 125

Trp Gly Gln Gly Thr Thr Leu Thr Val Ser Ser Gly Gly Gly Gly Ser
        130                 135                 140

Gly Gly Gly Gly Ser Gly Gly Gly Ser Asp Ile Val Met Thr Gln
145                 150                 155                 160

Ser Pro Ser Ser Leu Thr Val Thr Ala Gly Glu Lys Val Thr Met Ser
                165                 170                 175

Cys Lys Ser Ser Gln Ser Leu Leu His Ser Gly Asn Gln Arg Asn Tyr
            180                 185                 190

Leu Thr Trp Tyr Gln Gln Lys Pro Gly Gln Pro Pro Lys Leu Leu Ile
        195                 200                 205

Tyr Trp Ala Ser Thr Arg Glu Ser Gly Val Pro Asp Arg Phe Thr Gly
        210                 215                 220

Ser Gly Ser Gly Thr Asp Phe Thr Leu Thr Ile Ser Ser Val Gln Ala
225                 230                 235                 240

Glu Asp Leu Ala Val Tyr Tyr Cys Gln Asn Asp Tyr Asp Tyr Pro Tyr
                245                 250                 255

Thr Phe Gly Gly Gly Thr Lys Leu Glu Ile Lys Ser Asp Pro Gly Ser
            260                 265                 270

Gly Gly Gly Gly Ser Cys Pro Tyr Ser Asn Pro Ser Leu Cys Ser Gly
        275                 280                 285

Gly Gly Gly Ser Cys Pro Tyr Ser Asn Pro Ser Leu Cys Ser Gly Gly
        290                 295                 300

Gly Ser Gly Leu Ala Val Ser Thr Ile Ser Ser Phe Phe Pro Pro
305                 310                 315                 320

Gly Tyr Gln Ile Tyr Ile Trp Ala Pro Leu Ala Gly Thr Cys Gly Val
            325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu
        370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Gly Arg Asp Pro
            420                 425                 430

Glu Met Gly Gly Lys Pro Arg Arg Lys Asn Pro Gln Glu Gly Leu Tyr

```
              435                 440                 445
Asn Glu Leu Gln Lys Asp Lys Met Ala Glu Ala Tyr Ser Glu Ile Gly
        450                 455                 460

Met Lys Gly Glu Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500
```

<210> SEQ ID NO 131
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 25A10v1 CAR with 2 CD20 mimotopes and 1 CD34
      epitope

<400> SEQUENCE: 131

```
Met Ala Leu Pro Val Thr Ala Leu Leu Leu Pro Leu Ala Leu Leu Leu
1               5                   10                  15

His Ala Ala Arg Pro Gly Gly Gly Gly Ser Cys Pro Tyr Ser Asn Pro
            20                  25                  30

Ser Leu Cys Ser Gly Gly Gly Gly Ser Gly Gly Gly Gly Ser Glu Val
        35                  40                  45

Gln Leu Gln Gln Ser Gly Ala Glu Leu Val Arg Pro Gly Ala Ser Val
    50                  55                  60

Lys Leu Ser Cys Thr Ala Ser Gly Phe Asn Ile Lys Asp Ser Leu Ile
65                  70                  75                  80

His Trp Val Lys Gln Arg Pro Glu Gln Gly Leu Glu Trp Ile Gly Trp
                85                  90                  95

Ile Asp Pro Glu Asp Asp Lys Thr Lys Tyr Ala Pro Lys Phe Gln Asp
                100                 105                 110

Lys Ala Thr Leu Thr Ala Asp Thr Ser Ser Asn Thr Ala Tyr Leu Gln
            115                 120                 125

Leu Ser Thr Leu Thr Ser Glu Asp Thr Ala Ile Tyr Tyr Cys Val Ser
    130                 135                 140

Arg Tyr Ile Asn Tyr Tyr Phe Ala Tyr Trp Gly Gln Gly Thr Thr Leu
145                 150                 155                 160

Thr Val Ser Ser Gly Gly Gly Gly Ser Gly Gly Gly Gly Ser Gly Gly
                165                 170                 175

Gly Gly Ser Asp Ile Val Met Thr Gln Ser Pro Ser Ser Leu Thr Val
            180                 185                 190

Thr Ala Gly Glu Lys Val Thr Met Ser Cys Lys Ser Ser Gln Ser Leu
        195                 200                 205

Leu His Ser Gly Asn Gln Arg Asn Tyr Leu Thr Trp Tyr Gln Gln Lys
    210                 215                 220

Pro Gly Gln Pro Pro Lys Leu Leu Ile Tyr Trp Ala Ser Thr Arg Glu
225                 230                 235                 240

Ser Gly Val Pro Asp Arg Phe Thr Gly Ser Gly Ser Gly Thr Asp Phe
                245                 250                 255

Thr Leu Thr Ile Ser Ser Val Gln Ala Glu Asp Leu Ala Val Tyr Tyr
            260                 265                 270
```

```
Cys Gln Asn Asp Tyr Asp Tyr Pro Tyr Thr Phe Gly Gly Thr Lys
                275                 280                 285

Leu Glu Ile Lys Gly Ser Gly Gly Gly Ser Cys Pro Tyr Ser Asn
    290                 295                 300

Pro Ser Leu Cys Ser Gly Gly Gly Ser Glu Leu Pro Thr Gln Gly
305                 310                 315                 320

Thr Phe Ser Asn Val Ser Thr Asn Val Ser Pro Ala Lys Pro Thr Thr
                325                 330                 335

Thr Ala Cys Pro Tyr Ser Asn Pro Ser Leu Cys Gly Leu Ala Val Ser
                340                 345                 350

Thr Ile Ser Ser Phe Phe Pro Pro Gly Tyr Gln Ile Tyr Ile Trp Ala
                355                 360                 365

Pro Leu Ala Gly Thr Cys Gly Val Leu Leu Leu Ser Leu Val Ile Thr
                370                 375                 380

Leu Tyr Cys Lys Arg Gly Arg Lys Lys Leu Leu Tyr Ile Phe Lys Gln
385                 390                 395                 400

Pro Phe Met Arg Pro Val Gln Thr Thr Gln Glu Glu Asp Gly Cys Ser
                405                 410                 415

Cys Arg Phe Pro Glu Glu Glu Glu Gly Gly Cys Glu Leu Arg Val Lys
                420                 425                 430

Phe Ser Arg Ser Ala Asp Ala Pro Ala Tyr Gln Gln Gly Gln Asn Gln
                435                 440                 445

Leu Tyr Asn Glu Leu Asn Leu Gly Arg Arg Glu Glu Tyr Asp Val Leu
                450                 455                 460

Asp Lys Arg Arg Gly Arg Asp Pro Glu Met Gly Gly Lys Pro Arg Arg
465                 470                 475                 480

Lys Asn Pro Gln Glu Gly Leu Tyr Asn Glu Leu Gln Lys Asp Lys Met
                485                 490                 495

Ala Glu Ala Tyr Ser Glu Ile Gly Met Lys Gly Glu Arg Arg Arg Gly
                500                 505                 510

Lys Gly His Asp Gly Leu Tyr Gln Gly Leu Ser Thr Ala Thr Lys Asp
                515                 520                 525

Thr Tyr Asp Ala Leu His Met Gln Ala Leu Pro Pro Arg
                530                 535                 540

<210> SEQ ID NO 132
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m2C2

<400> SEQUENCE: 132

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Phe Trp Val Arg Gln Thr Pro Glu Lys Arg Leu Glu Trp Val
                35                  40                  45

Ala Tyr Ile Ser Asn Gly Asp Gly Asn Thr Tyr Tyr Pro Asp Thr Leu
            50                  55                  60

Lys Gly Arg Phe Thr Ile Ser Arg Asp Asn Ala Asn Asn Thr Leu Tyr
65                  70                  75                  80
```

```
Leu Gln Met Ser Arg Leu Lys Ser Glu Asp Thr Ala Met Tyr Tyr Cys
                85                  90                  95

Ala Arg Ser Ile Ser Arg Tyr Phe Asp Val Trp Gly Ala Gly Thr Thr
            100                 105                 110

Val Thr Val Ser Ser
        115

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m2C2

<400> SEQUENCE: 133

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Phe
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Ala His Ser Phe Pro Ser
                85                  90                  95

Thr Phe Gly Gly Gly Thr Lys Leu Glu Ile Lys
            100                 105

<210> SEQ ID NO 134
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m5G9

<400> SEQUENCE: 134

Glu Ile His Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Ile Tyr Trp Val Lys Gln Ser His Gly Glu Ser Leu Glu Trp Val
        35                  40                  45

Gly Tyr Ile Asp Pro Tyr Asn Gly Gly Ala Tyr Asn Gln Lys Phe
    50                  55                  60

Lys Ala Met Ala Thr Leu Thr Val Asp Lys Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Lys Gly Val Tyr Gly Leu Ala Tyr Trp Gly Gln Gly Thr Leu
            100                 105                 110

Val Thr Val Ser Ser
        115
```

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: VL chain of m5G9

<400> SEQUENCE: 135

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ser Thr His Leu Ala Asp Gly Val Pro Ser Arg Phe Ser Gly
    50                  55                  60

Ser Gly Ser Gly Ala Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 136
<211> LENGTH: 454
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: 5G9-V1 CAR

<400> SEQUENCE: 136

Met Ala Leu Pro Val Thr Ala Leu Leu Leu Pro Leu Ala Leu Leu Leu
1               5                   10                  15

His Ala Ala Arg Pro Glu Ile His Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ser Phe Thr Asp Tyr Asn Ile Tyr Trp Val Lys Gln Ser His Gly Glu
    50                  55                  60

Ser Leu Glu Trp Val Gly Tyr Ile Asp Pro Tyr Asn Gly Gly Ala Tyr
65                  70                  75                  80

Tyr Asn Gln Lys Phe Lys Ala Met Ala Thr Leu Thr Val Asp Lys Ser
                85                  90                  95

Ser Ser Thr Ala Phe Met His Leu Asn Ser Leu Thr Ser Glu Asp Ser
            100                 105                 110

Ala Val Tyr Tyr Cys Ala Arg Lys Gly Val Tyr Gly Leu Ala Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Ser Asp Ile Gln Met Thr Gln Ser
145                 150                 155                 160

Pro Ala Ser Leu Ser Val Ser Val Gly Glu Thr Val Thr Ile Thr Cys

```
            165                 170                 175
Arg Ala Ser Glu Ser Ile Tyr Ser Asn Leu Ala Trp Tyr Gln Gln Lys
            180                 185                 190

Gln Gly Lys Ser Pro Gln Leu Leu Val Tyr Ala Ser Thr His Leu Ala
        195                 200                 205

Asp Gly Val Pro Ser Arg Phe Ser Gly Ser Gly Ser Gly Ala Gln Tyr
    210                 215                 220

Ser Leu Lys Ile Asn Ser Leu Gln Ser Glu Asp Phe Gly Ser Tyr Tyr
225                 230                 235                 240

Cys Gln His Phe Trp Gly Thr Pro Tyr Thr Phe Gly Gly Gly Thr Lys
                245                 250                 255

Leu Glu Ile Lys Gly Leu Ala Val Ser Thr Ile Ser Ser Phe Phe Pro
            260                 265                 270

Pro Gly Tyr Gln Ile Tyr Ile Trp Ala Pro Leu Ala Gly Thr Cys Gly
        275                 280                 285

Val Leu Leu Leu Ser Leu Val Ile Thr Leu Tyr Cys Lys Arg Gly Arg
    290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
                325                 330                 335

Glu Gly Gly Cys Glu Leu Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 137
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5G9-V2 CAR

<400> SEQUENCE: 137

Met Ala Leu Pro Val Thr Ala Leu Leu Leu Pro Leu Ala Leu Leu Leu
1               5                   10                  15

His Ala Ala Arg Pro Glu Ile His Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ser Phe Thr Asp Tyr Asn Ile Tyr Trp Val Lys Gln Ser His Gly Glu
```

```
                50              55              60
Ser Leu Glu Trp Val Gly Tyr Ile Asp Pro Tyr Asn Gly Gly Ala Tyr
65                  70                  75                  80

Tyr Asn Gln Lys Phe Lys Ala Met Ala Thr Leu Thr Val Asp Lys Ser
                85                  90                  95

Ser Ser Thr Ala Phe Met His Leu Asn Ser Leu Thr Ser Glu Asp Ser
                100                 105                 110

Ala Val Tyr Tyr Cys Ala Arg Lys Gly Val Tyr Gly Leu Ala Tyr Trp
                115                 120                 125

Gly Gln Gly Thr Leu Val Thr Val Ser Ser Gly Gly Gly Ser Gly
        130                 135                 140

Gly Gly Gly Ser Gly Gly Gly Ser Asp Ile Gln Met Thr Gln Ser
145                 150                 155                 160

Pro Ala Ser Leu Ser Val Ser Val Gly Glu Thr Val Thr Ile Thr Cys
                165                 170                 175

Arg Ala Ser Glu Ser Ile Tyr Ser Asn Leu Ala Trp Tyr Gln Gln Lys
                180                 185                 190

Gln Gly Lys Ser Pro Gln Leu Leu Val Tyr Ala Ser Thr His Leu Ala
                195                 200                 205

Asp Gly Val Pro Ser Arg Phe Ser Gly Ser Gly Ser Gly Ala Gln Tyr
210                 215                 220

Ser Leu Lys Ile Asn Ser Leu Gln Ser Glu Asp Phe Gly Ser Tyr Tyr
225                 230                 235                 240

Cys Gln His Phe Trp Gly Thr Pro Tyr Thr Phe Gly Gly Gly Thr Lys
                245                 250                 255

Leu Glu Ile Lys Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
                275                 280                 285

Pro Ala Ala Gly Gly Ala Val His Thr Arg Gly Leu Asp Phe Ala Cys
                290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
                340                 345                 350

Glu Glu Asp Gly Cys Ser Cys Arg Phe Pro Glu Glu Glu Glu Gly Gly
                355                 360                 365

Cys Glu Leu Arg Val Lys Phe Ser Arg Ser Ala Asp Ala Pro Ala Tyr
                370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
                435                 440                 445

Gly Glu Arg Arg Arg Gly Lys Gly His Asp Gly Leu Tyr Gln Gly Leu
                450                 455                 460

Ser Thr Ala Thr Lys Asp Thr Tyr Asp Ala Leu His Met Gln Ala Leu
465                 470                 475                 480
```

Pro Pro Arg

<210> SEQ ID NO 138
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5G9-V3 CAR

<400> SEQUENCE: 138

```
Met Ala Leu Pro Val Thr Ala Leu Leu Leu Pro Leu Ala Leu Leu Leu
1               5                   10                  15

His Ala Ala Arg Pro Glu Ile His Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ser Phe Thr Asp Tyr Asn Ile Tyr Trp Val Lys Gln Ser His Gly Glu
    50                  55                  60

Ser Leu Glu Trp Val Gly Tyr Ile Asp Pro Tyr Asn Gly Gly Ala Tyr
65                  70                  75                  80

Tyr Asn Gln Lys Phe Lys Ala Met Ala Thr Leu Thr Val Asp Lys Ser
                85                  90                  95

Ser Ser Thr Ala Phe Met His Leu Asn Ser Leu Thr Ser Glu Asp Ser
            100                 105                 110

Ala Val Tyr Tyr Cys Ala Arg Lys Gly Val Tyr Gly Leu Ala Tyr Trp
        115                 120                 125

Gly Gln Gly Thr Leu Val Thr Val Ser Ser Gly Gly Gly Ser Gly
130                 135                 140

Gly Gly Gly Ser Gly Gly Gly Ser Asp Ile Gln Met Thr Gln Ser
145                 150                 155                 160

Pro Ala Ser Leu Ser Val Ser Val Gly Glu Thr Val Thr Ile Thr Cys
                165                 170                 175

Arg Ala Ser Glu Ser Ile Tyr Ser Asn Leu Ala Trp Tyr Gln Gln Lys
            180                 185                 190

Gln Gly Lys Ser Pro Gln Leu Leu Val Tyr Ala Ser Thr His Leu Ala
        195                 200                 205

Asp Gly Val Pro Ser Arg Phe Ser Gly Ser Gly Ser Gly Ala Gln Tyr
    210                 215                 220

Ser Leu Lys Ile Asn Ser Leu Gln Ser Glu Asp Phe Gly Ser Tyr Tyr
225                 230                 235                 240

Cys Gln His Phe Trp Gly Thr Pro Tyr Thr Phe Gly Gly Gly Thr Lys
                245                 250                 255

Leu Glu Ile Lys Glu Pro Lys Ser Pro Asp Lys Thr His Thr Cys Pro
            260                 265                 270

Pro Cys Pro Ala Pro Pro Val Ala Gly Pro Ser Val Phe Leu Phe Pro
        275                 280                 285

Pro Lys Pro Lys Asp Thr Leu Met Ile Ala Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335
```

Glu Glu Gln Tyr Asn Ser Thr Tyr Arg Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys Ile Tyr Ile Trp Ala
                485                 490                 495

Pro Leu Ala Gly Thr Cys Gly Val Leu Leu Leu Ser Leu Val Ile Thr
            500                 505                 510

Leu Tyr Cys Lys Arg Gly Arg Lys Leu Leu Tyr Ile Phe Lys Gln
        515                 520                 525

Pro Phe Met Arg Pro Val Gln Thr Thr Gln Glu Glu Asp Gly Cys Ser
530                 535                 540

Cys Arg Phe Pro Glu Glu Glu Glu Gly Gly Cys Glu Leu Arg Val Lys
545                 550                 555                 560

Phe Ser Arg Ser Ala Asp Ala Pro Ala Tyr Gln Gln Gly Gln Asn Gln
                565                 570                 575

Leu Tyr Asn Glu Leu Asn Leu Gly Arg Arg Glu Glu Tyr Asp Val Leu
            580                 585                 590

Asp Lys Arg Arg Gly Arg Asp Pro Glu Met Gly Gly Lys Pro Arg Arg
        595                 600                 605

Lys Asn Pro Gln Glu Gly Leu Tyr Asn Glu Leu Gln Lys Asp Lys Met
    610                 615                 620

Ala Glu Ala Tyr Ser Glu Ile Gly Met Lys Gly Glu Arg Arg Arg Gly
625                 630                 635                 640

Lys Gly His Asp Gly Leu Tyr Gln Gly Leu Ser Thr Ala Thr Lys Asp
                645                 650                 655

Thr Tyr Asp Ala Leu His Met Gln Ala Leu Pro Pro Arg
            660                 665

<210> SEQ ID NO 139
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2C2-V1 CAR

<400> SEQUENCE: 139

Met Ala Leu Pro Val Thr Ala Leu Leu Leu Pro Leu Ala Leu Leu Leu
1               5                   10                  15

```
His Ala Ala Arg Pro Glu Val Lys Leu Val Glu Ser Gly Gly Gly Leu
            20                  25                  30
Val Gln Pro Gly Gly Ser Leu Lys Leu Ser Cys Ala Thr Ser Gly Phe
        35                  40                  45
Thr Phe Ser Asp Tyr Tyr Met Phe Trp Val Arg Gln Thr Pro Glu Lys
    50                  55                  60
Arg Leu Glu Trp Val Ala Tyr Ile Ser Asn Gly Asp Gly Asn Thr Tyr
65                  70                  75                  80
Tyr Pro Asp Thr Leu Lys Gly Arg Phe Thr Ile Ser Arg Asp Asn Ala
                85                  90                  95
Asn Asn Thr Leu Tyr Leu Gln Met Ser Arg Leu Lys Ser Glu Asp Thr
            100                 105                 110
Ala Met Tyr Tyr Cys Ala Arg Ser Ile Ser Arg Tyr Phe Asp Val Trp
        115                 120                 125
Gly Ala Gly Thr Thr Val Thr Val Ser Ser Gly Gly Gly Gly Ser Gly
    130                 135                 140
Gly Gly Gly Ser Gly Gly Gly Ser Asp Ile Val Met Thr Gln Ser
145                 150                 155                 160
Pro Ala Thr Leu Ser Val Thr Pro Gly Asp Arg Val Ser Leu Ser Cys
                165                 170                 175
Arg Ala Ser Gln Ser Ile Ser Asp Phe Leu His Trp Tyr Gln Gln Lys
            180                 185                 190
Ser His Glu Ser Pro Arg Leu Leu Ile Lys Tyr Val Ser Gln Ser Ile
        195                 200                 205
Ser Gly Ile Pro Ser Arg Phe Ser Gly Ser Gly Ser Gly Ser Asp Phe
    210                 215                 220
Thr Leu Ser Ile Asn Ser Val Glu Pro Glu Asp Val Gly Val Tyr Tyr
225                 230                 235                 240
Cys Gln Asn Ala His Ser Phe Pro Ser Thr Phe Gly Gly Gly Thr Lys
                245                 250                 255
Leu Glu Ile Lys Gly Leu Ala Val Ser Thr Ile Ser Ser Phe Phe Pro
            260                 265                 270
Pro Gly Tyr Gln Ile Tyr Ile Trp Ala Pro Leu Ala Gly Thr Cys Gly
        275                 280                 285
Val Leu Leu Leu Ser Leu Val Ile Thr Leu Tyr Cys Lys Arg Gly Arg
    290                 295                 300
Lys Lys Leu Leu Tyr Ile Phe Lys Gln Pro Phe Met Arg Pro Val Gln
305                 310                 315                 320
Thr Thr Gln Glu Glu Asp Gly Cys Ser Cys Arg Phe Pro Glu Glu Glu
                325                 330                 335
Glu Gly Gly Cys Glu Leu Arg Val Lys Phe Ser Arg Ser Ala Asp Ala
            340                 345                 350
Pro Ala Tyr Gln Gln Gly Gln Asn Gln Leu Tyr Asn Glu Leu Asn Leu
        355                 360                 365
Gly Arg Arg Glu Glu Tyr Asp Val Leu Asp Lys Arg Arg Gly Arg Asp
    370                 375                 380
Pro Glu Met Gly Gly Lys Pro Arg Arg Lys Asn Pro Gln Glu Gly Leu
385                 390                 395                 400
Tyr Asn Glu Leu Gln Lys Asp Lys Met Ala Glu Ala Tyr Ser Glu Ile
                405                 410                 415
Gly Met Lys Gly Glu Arg Arg Arg Gly Lys Gly His Asp Gly Leu Tyr
            420                 425                 430
Gln Gly Leu Ser Thr Ala Thr Lys Asp Thr Tyr Asp Ala Leu His Met
```

-continued

```
                 435                 440                 445
Gln Ala Leu Pro Pro Arg
    450

<210> SEQ ID NO 140
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2C2-V2 CAR

<400> SEQUENCE: 140

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Lys Leu Ser Cys Ala Thr Ser Gly Phe
        35                  40                  45

Thr Phe Ser Asp Tyr Tyr Met Phe Trp Val Arg Gln Thr Pro Glu Lys
    50                  55                  60

Arg Leu Glu Trp Val Ala Tyr Ile Ser Asn Gly Asp Gly Asn Thr Tyr
65                  70                  75                  80

Tyr Pro Asp Thr Leu Lys Gly Arg Phe Thr Ile Ser Arg Asp Asn Ala
                85                  90                  95

Asn Asn Thr Leu Tyr Leu Gln Met Ser Arg Leu Lys Ser Glu Asp Thr
            100                 105                 110

Ala Met Tyr Tyr Cys Ala Arg Ser Ile Ser Arg Tyr Phe Asp Val Trp
        115                 120                 125

Gly Ala Gly Thr Thr Val Thr Val Ser Ser Gly Gly Gly Gly Ser Gly
    130                 135                 140

Gly Gly Gly Ser Gly Gly Gly Gly Ser Asp Ile Val Met Thr Gln Ser
145                 150                 155                 160

Pro Ala Thr Leu Ser Val Thr Pro Gly Asp Arg Val Ser Leu Ser Cys
                165                 170                 175

Arg Ala Ser Gln Ser Ile Ser Asp Phe Leu His Trp Tyr Gln Gln Lys
            180                 185                 190

Ser His Glu Ser Pro Arg Leu Leu Ile Lys Tyr Val Ser Gln Ser Ile
        195                 200                 205

Ser Gly Ile Pro Ser Arg Phe Ser Gly Ser Gly Ser Gly Ser Asp Phe
    210                 215                 220

Thr Leu Ser Ile Asn Ser Val Glu Pro Glu Asp Val Gly Val Tyr Tyr
225                 230                 235                 240

Cys Gln Asn Ala His Ser Phe Pro Ser Thr Phe Gly Gly Gly Thr Lys
                245                 250                 255

Leu Glu Ile Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
```

```
            325                 330                 335
Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Gly Gly
            355                 360                 365

Cys Glu Leu Arg Val Lys Phe Ser Arg Ser Ala Asp Ala Pro Ala Tyr
            370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 141
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2C2-V3 CAR

<400> SEQUENCE: 141

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Lys Leu Ser Cys Ala Thr Ser Gly Phe
        35                  40                  45

Thr Phe Ser Asp Tyr Tyr Met Phe Trp Val Arg Gln Thr Pro Glu Lys
    50                  55                  60

Arg Leu Glu Trp Val Ala Tyr Ile Ser Asn Gly Asp Gly Asn Thr Tyr
65                  70                  75                  80

Tyr Pro Asp Thr Leu Lys Gly Arg Phe Thr Ile Ser Arg Asp Asn Ala
            85                  90                  95

Asn Asn Thr Leu Tyr Leu Gln Met Ser Arg Leu Lys Ser Glu Asp Thr
        100                 105                 110

Ala Met Tyr Tyr Cys Ala Arg Ser Ile Ser Arg Tyr Phe Asp Val Trp
    115                 120                 125

Gly Ala Gly Thr Thr Val Thr Val Ser Ser Gly Gly Gly Gly Ser Gly
        130                 135                 140

Gly Gly Gly Ser Gly Gly Gly Gly Ser Asp Ile Val Met Thr Gln Ser
145                 150                 155                 160

Pro Ala Thr Leu Ser Val Thr Pro Gly Asp Arg Val Ser Leu Ser Cys
            165                 170                 175

Arg Ala Ser Gln Ser Ile Ser Asp Phe Leu His Trp Tyr Gln Gln Lys
        180                 185                 190
```

-continued

Ser His Glu Ser Pro Arg Leu Leu Ile Lys Tyr Val Ser Gln Ser Ile
            195                 200                 205

Ser Gly Ile Pro Ser Arg Phe Ser Gly Ser Gly Ser Gly Ser Asp Phe
    210                 215                 220

Thr Leu Ser Ile Asn Ser Val Glu Pro Glu Asp Val Gly Val Tyr Tyr
225                 230                 235                 240

Cys Gln Asn Ala His Ser Phe Pro Ser Thr Phe Gly Gly Gly Thr Lys
                245                 250                 255

Leu Glu Ile Lys Glu Pro Lys Ser Pro Asp Lys Thr His Thr Cys Pro
                260                 265                 270

Pro Cys Pro Ala Pro Val Ala Gly Pro Ser Val Phe Leu Phe Pro
                275                 280                 285

Pro Lys Pro Lys Asp Thr Leu Met Ile Ala Arg Thr Pro Glu Val Thr
            290                 295                 300

Cys Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
            355                 360                 365

Asn Lys Ala Leu Pro Ala Pro Ile Glu Lys Thr Ile Ser Lys Ala Lys
        370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
                420                 425                 430

Asn Asn Tyr Lys Thr Thr Pro Pro Val Leu Asp Ser Asp Gly Ser Phe
            435                 440                 445

Phe Leu Tyr Ser Lys Leu Thr Val Asp Lys Ser Arg Trp Gln Gln Gly
        450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys Ile Tyr Ile Trp Ala
                485                 490                 495

Pro Leu Ala Gly Thr Cys Gly Val Leu Leu Leu Ser Leu Val Ile Thr
                500                 505                 510

Leu Tyr Cys Lys Arg Gly Arg Lys Lys Leu Leu Tyr Ile Phe Lys Gln
            515                 520                 525

Pro Phe Met Arg Pro Val Gln Thr Thr Gln Glu Glu Asp Gly Cys Ser
        530                 535                 540

Cys Arg Phe Pro Glu Glu Glu Glu Gly Gly Cys Glu Leu Arg Val Lys
545                 550                 555                 560

Phe Ser Arg Ser Ala Asp Ala Pro Ala Tyr Gln Gln Gly Gln Asn Gln
                565                 570                 575

Leu Tyr Asn Glu Leu Asn Leu Gly Arg Arg Glu Glu Tyr Asp Val Leu
            580                 585                 590

Asp Lys Arg Arg Gly Arg Asp Pro Glu Met Gly Gly Lys Pro Arg Arg
            595                 600                 605

```
Lys Asn Pro Gln Glu Gly Leu Tyr Asn Glu Leu Gln Lys Asp Lys Met
        610                 615                 620

Ala Glu Ala Tyr Ser Glu Ile Gly Met Lys Gly Glu Arg Arg Arg Gly
625                 630                 635                 640

Lys Gly His Asp Gly Leu Tyr Gln Gly Leu Ser Thr Ala Thr Lys Asp
                645                 650                 655

Thr Tyr Asp Ala Leu His Met Gln Ala Leu Pro Pro Arg
        660                 665

<210> SEQ ID NO 142
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m9E2

<400> SEQUENCE: 142

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Asp Tyr
                20                  25                  30

Asn Met Asn Trp Val Lys Gln Ser Asn Gly Lys Ser Leu Glu Trp Ile
            35                  40                  45

Gly Asn Ile Asp Pro Asp Tyr Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Ser Gly Tyr Arg Tyr Gly Phe Val Tyr Trp Gly Gln Gly Thr
                100                 105                 110

Leu Val Thr Val Ser Ala
        115

<210> SEQ ID NO 143
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m9E2

<400> SEQUENCE: 143

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95
```

```
Leu Glu Leu Pro Trp Thr Phe Gly Gly Gly Thr Lys Leu Glu Ile Lys
            100                 105                 110
```

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m28B9

<400> SEQUENCE: 144

```
Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Leu His Trp Met Lys Gln Arg Pro Glu Gln Gly Leu Glu Trp Ile
        35                  40                  45

Gly Arg Ile Asp Pro Ala Asn Gly Asn Thr Lys Ser Asp Pro Lys Phe
    50                  55                  60

Gln Asp Lys Ala Thr Ile Asp Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Ala Lys Gly Pro Trp Phe Pro Tyr Trp Gly Gln Gly Thr Leu Val Thr
            100                 105                 110

Val Ser Ala
        115
```

<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m28B9

<400> SEQUENCE: 145

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr His Cys Gln Gln Leu Tyr Arg Thr Pro Leu
                85                  90                  95

Thr Phe Gly Gly Gly Thr Lys Leu Glu Ile Lys
            100                 105
```

<210> SEQ ID NO 146
<211> LENGTH: 120
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m26D8

<400> SEQUENCE: 146
```

Gln Val Gln Leu Gln Gln Pro Gly Ala Glu Met Val Arg Pro Gly Ala
1               5                   10                  15

Ser Val Lys Leu Ser Cys Lys Ala Ser Gly Tyr Thr Phe Thr Asp Tyr
            20                  25                  30

Trp Met His Trp Val Lys Gln Arg Pro Gly Gln Gly Leu Glu Trp Ile
        35                  40                  45

Gly Lys Ile Asp Pro Ser Asp Ser Glu Thr His Tyr His Gln Lys Phe
    50                  55                  60

Lys Asp Lys Ala Thr Leu Thr Val Asp Lys Ser Ser Thr Ala Tyr
65                  70                  75                  80

Leu Gln Phe Lys Ser Leu Thr Ser Glu Asp Ser Ala Val His Tyr Cys
            85                  90                  95

Ala Arg Glu Gly Ile Trp Leu Arg Tyr Ala Met Asp Tyr Trp Gly Gln
        100                 105                 110

Gly Thr Ser Val Thr Val Ser Ser
    115                 120

```
<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m26D8

<400> SEQUENCE: 147
```

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Val Ser Ser Val Gln Ser
65                  70                  75                  80

Glu Asp Leu Ala Glu Tyr Phe Cys Gln Gln Tyr Asn Ser Tyr Pro Tyr
            85                  90                  95

Thr Phe Gly Gly Gly Thr Lys Leu Glu Ile Lys
        100                 105

```
<210> SEQ ID NO 148
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m15D1

<400> SEQUENCE: 148
```

Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Ser Ile Thr Asp Tyr
            20                  25                  30

Asn Met His Trp Val Lys Gln Ser His Gly Lys Ser Leu Glu Trp Ile
        35                  40                  45

Gly Tyr Ile Asp Pro Asp Asn Gly Ala Thr Asn Asn Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Glu Gly Tyr Gln Tyr Tyr Tyr Ala Met Asp Tyr Trp Gly
            100                 105                 110

Gln Gly Thr Ser Val Thr Val Ser Ser
            115                 120

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m15D1

<400> SEQUENCE: 149

Asp Ile Val Met Thr Gln Ala Ala Phe Ser Asn Pro Val Ala Leu Gly
1               5                   10                  15

Thr Ser Ala Ser Ile Ser Cys Ser Ser Ser Lys Ser Leu Leu His Ser
            20                  25                  30

Asn Gly Ile Thr Tyr Leu His Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Val Glu Arg Pro Trp Thr Phe Gly Gly Gly Thr Lys Leu Glu Ile Lys
            100                 105                 110

<210> SEQ ID NO 150
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH chain of m23F2

<400> SEQUENCE: 150

Gln Val Gln Val Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile

```
              35                  40                  45
Gly Asn Ile Tyr Pro Gly Ser Ser Thr Asn His Asn Glu Lys Phe
 50                  55                  60

Lys Ser Lys Ala Thr Leu Thr Val Asp Thr Ser Ser Thr Ala Tyr
 65                  70                  75                  80

Met Gln Leu Ser Ser Leu Thr Ser Asp Asp Ser Ala Val Tyr Tyr Cys
                 85                  90                  95

Ala Arg Arg Gly Ser Ser Pro Ser Tyr Thr Met Asp Tyr Trp Gly Gln
             100                 105                 110

Gly Thr Ser Val Thr Val Ser Ser
             115                 120

<210> SEQ ID NO 151
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL chain of m23F2

<400> SEQUENCE: 151

Asp Ile Val Leu Thr Gln Ser Pro Ala Ser Leu Ala Val Ala Leu Gly
 1               5                  10                  15

Gln Arg Ala Thr Ile Ser Cys Arg Ala Ser Lys Ser Val Ser Thr Phe
             20                  25                  30

Gly Tyr Ser Tyr Met His Trp Tyr Gln Gln Lys Pro Gly Gln Ala Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Lys Ile His
 65                  70                  75                  80

Pro Val Glu Glu Glu Asp Ala Ala Thr Tyr Tyr Cys Leu His Ser Arg
                 85                  90                  95

Glu Leu Pro Trp Thr Phe Gly Gly Gly Thr Lys Leu Glu Ile Lys
             100                 105                 110

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(7)
<223> OTHER INFORMATION: Any naturally occurring amino acid

<400> SEQUENCE: 152

Asp Xaa Gly Xaa Xaa Ser Xaa Gly Trp Ala
 1               5                  10

<210> SEQ ID NO 153
```

```
<211> LENGTH: 9
<212> TYPE: PRT
<213> ORGANISM: Unknown
<220> FEATURE:
<223> OTHER INFORMATION: Description of Unknown:
      "LAGLIDADG" family peptide motif sequence

<400> SEQUENCE: 153

Leu Ala Gly Leu Ile Asp Ala Asp Gly
1               5

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any naturally occurring amino acid
<220> FEATURE:
<221> NAME/KEY: MOD_RES
<222> LOCATION: (6)..(7)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (11)..(13)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 154

Tyr Xaa Xaa Asp His Xaa Xaa Pro Xaa Ser Xaa Xaa Xaa Asp Xaa Ser
1               5                   10                  15

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-5 "Gly Gly Gly
      Ser" repeating units

<400> SEQUENCE: 155

Gly Gly Gly Ser Gly Gly Gly Ser Gly Gly Gly Ser Gly Gly Gly Ser
1               5                   10                  15

Gly Gly Gly Ser
            20

<210> SEQ ID NO 156
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
```

-continued

<223> OTHER INFORMATION: This sequence may encompass 1-5 "Gly Gly Gly
      Gly Ser" repeating units

<400> SEQUENCE: 156

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Gly Gly Ser Gly Gly Gly Ser Gly Gly Gly Gly Ser Gly
1               5                   10                  15

Gly Gly Gly Ser
            20

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Gly Gly Ser
1

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Ser Gly Gly Ser
1               5

<210> SEQ ID NO 160
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Gly Gly
1

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 161

Ser Gly Gly Gly Gly
1               5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gly Gly Gly Ser
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Gly Gly Gly Gly Ser
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Gly Gly Gly Gly Ser
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Gly Gly Gly Gly Gly Ser
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Gly Gly Gly Gly Gly
1               5

<210> SEQ ID NO 167
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 167

Gly Ser Gly Gly Gly Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Gly Gly Gly Gly Gly Gly Ser
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Gly Gly Gly Gly Gly Gly Gly
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Gly Gly Gly Gly Gly Gly Gly Ser
1               5

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Gly Gly Gly Gly Ser Gly Gly Gly Gly Ser
1               5                   10

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Gly Ser
1
```

<210> SEQ ID NO 173
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This region may encompass 1-5 residues
<220> FEATURE:
<221> NAME/KEY: MISC_FEATURE
<222> LOCATION: (7)..(11)
<223> OTHER INFORMATION: This region may encompass 1-5 residues
<220> FEATURE:
<221> NAME/KEY: MISC_FEATURE
<222> LOCATION: (13)..(17)
<223> OTHER INFORMATION: This region may encompass 1-5 residues
<220> FEATURE:
<221> NAME/KEY: MISC_FEATURE
<222> LOCATION: (19)..(23)
<223> OTHER INFORMATION: This region may encompass 1-5 residues
<220> FEATURE:
<221> NAME/KEY: MISC_FEATURE
<222> LOCATION: (25)..(29)
<223> OTHER INFORMATION: This region may encompass 1-5 residues
<220> FEATURE:
<221> NAME/KEY: MISC_FEATURE
<222> LOCATION: (31)..(35)
<223> OTHER INFORMATION: This region may encompass 1-5 residues
<220> FEATURE:
<221> NAME/KEY: MISC_FEATURE
<222> LOCATION: (37)..(41)
<223> OTHER INFORMATION: This region may encompass 1-5 residues
<220> FEATURE:
<221> NAME/KEY: MISC_FEATURE
<222> LOCATION: (43)..(47)
<223> OTHER INFORMATION: This region may encompass 1-5 residues
<220> FEATURE:
<221> NAME/KEY: MISC_FEATURE
<222> LOCATION: (49)..(53)
<223> OTHER INFORMATION: This region may encompass 1-5 residues
<220> FEATURE:
<221> NAME/KEY: MISC_FEATURE
<222> LOCATION: (55)..(59)
<223> OTHER INFORMATION: This region may encompass 1-5 residues
<220> FEATURE:
<221> NAME/KEY: MISC_FEATURE
<222> LOCATION: (1)..(60)
<223> OTHER INFORMATION: This sequence may encompass 1-10 "(Gly)n-Ser"
      repeating units wherein n=1-5

<400> SEQUENCE: 173

Gly Gly Gly Gly Gly Ser Gly Gly Gly Gly Ser Gly Gly Gly Gly
1               5                   10                  15

Gly Ser Gly Gly Gly Gly Gly Ser Gly Gly Gly Gly Ser Gly Gly
                20                  25                  30

Gly Gly Gly Ser Gly Gly Gly Gly Ser Gly Gly Gly Gly Gly Ser
        35                  40                  45

Gly Gly Gly Gly Gly Ser Gly Gly Gly Gly Ser
    50                  55                  60

<210> SEQ ID NO 174
<211> LENGTH: 313
<212> TYPE: DNA
<213> ORGANISM: Homo sapiens

<400> SEQUENCE: 174
atggccaact gcgagttcag cccggtgtcc ggggacaaac cctgctgccg gctctctagg    60

-continued

```
agagcccaac tctgtcttgg cgtcagtatc ctggtcctga tcctcgtcgt ggtgctcgcg      120
gtggtcgtcc cgaggtggcg ccagcagtgg agcggtccgg gcaccaccaa gcgctttccc      180
gagaccgtcc tggcgcgatg cgtcaagtac actgaaattc atcctgagat gaggtgggtt      240
ggcgactaag gcgcaccggt gggcactgcg gggacagcag ggccccgcgc gcagggaagc      300
cgcccggatc gcc                                                        313
```